Figure 2:
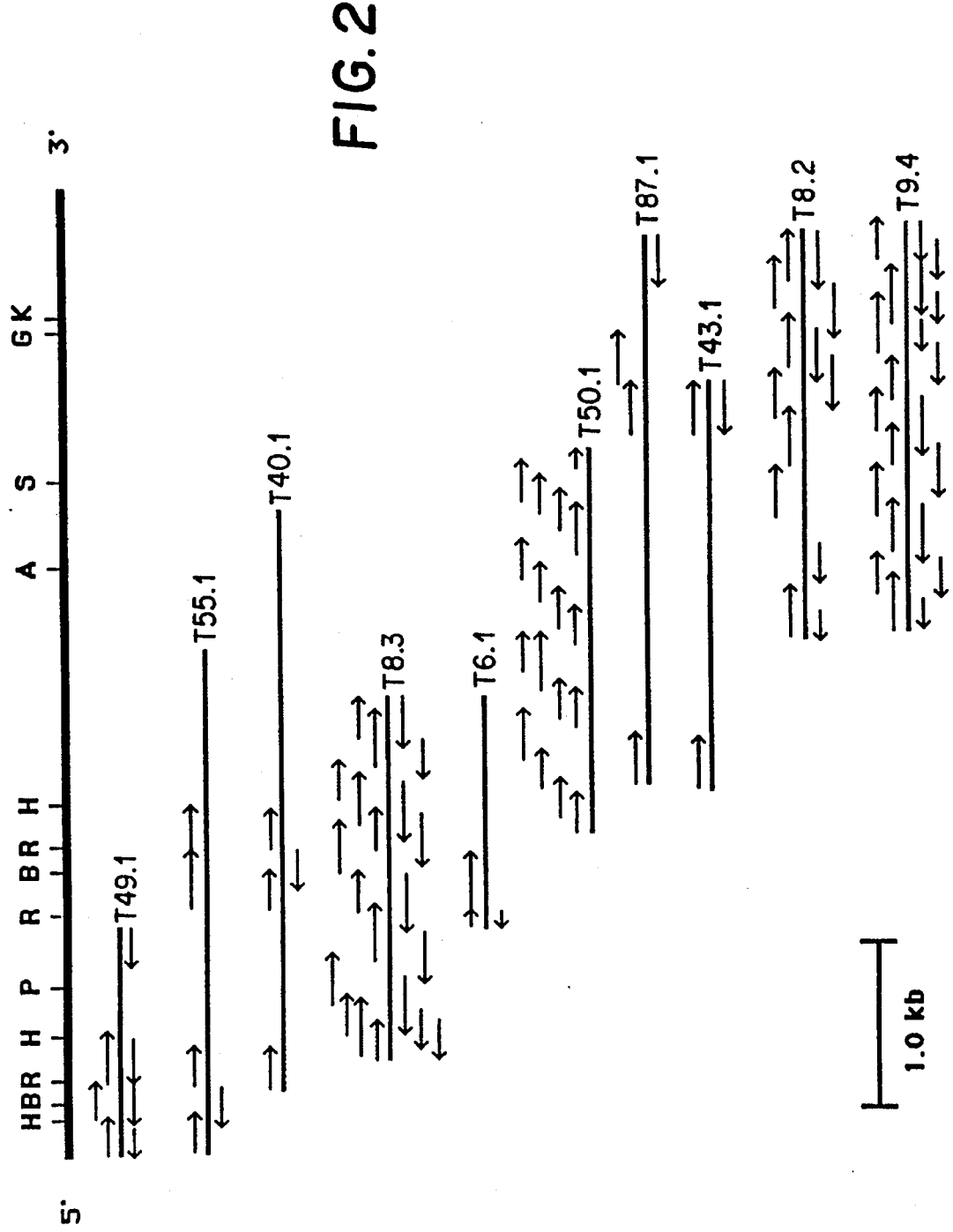

United States Patent [19]

Fearon et al.

[11] Patent Number: 5,472,939

[45] Date of Patent: Dec. 5, 1995

[54] METHOD OF TREATING COMPLEMENT MEDIATED DISORDERS

[75] Inventors: Douglas T. Fearon, Baltimore, Md.; Lloyd B. Klickstein, Brookline, Mass.; Winnie W. Wong, Newton, Mass.; Gerald R. Carson, Wellesley, Mass.; Michael F. Concino, Newton, Mass.; Stephen H. Ip, Sudbury, Mass.; Savvas C. Makrides, Bedford, Mass.; Henry C. Marsh, Jr., Reading, Mass.

[73] Assignees: The Johns Hopkins University, Baltimore, Md.; The Brigham and Women's Hospital, Boston; T Cell Sciences, Inc., Needham, both of Mass.

[21] Appl. No.: 138,825

[22] Filed: Oct. 19, 1993

Related U.S. Application Data

[60] Division of Ser. No. 588,128, Sep. 24, 1990, Pat. No. 5,256,642, which is a continuation-in-part of Ser. No. 412,745, Sep. 26, 1989, abandoned, which is a continuation-in-part of Ser. No. 332,865, Apr. 3, 1989, Pat. No. 5,212,071, which is a continuation-in-part of Ser. No. 176,532, Apr. 1, 1988, abandoned.

[51] Int. Cl.$^6$ ..................................................... A61K 37/00
[52] U.S. Cl. ........................... 514/8; 514/2; 514/12; 514/886; 514/885
[58] Field of Search ........................ 435/69.1; 514/2, 514/12, 8; 530/350

[56] References Cited

U.S. PATENT DOCUMENTS

| | | | |
|---|---|---|---|
| 4,285,932 | 8/1981 | Smith et al. | 424/94 |
| 4,642,284 | 2/1987 | Cooper et al. | 435/7 |
| 4,672,044 | 6/1987 | Schreiber | 436/501 |
| 4,713,332 | 12/1987 | Mak | 435/70 |
| 4,761,371 | 8/1988 | Bell et al. | 435/68 |
| 4,808,405 | 2/1989 | Smith et al. | 424/94.3 |
| 4,883,784 | 11/1989 | Kaneko | 514/8 |
| 4,886,743 | 12/1989 | Hood et al. | 435/5 |
| 5,163,901 | 9/1992 | Schwarz et al. | 514/2 |
| 5,212,071 | 5/1993 | Fearon et al. | 435/69.1 |

FOREIGN PATENT DOCUMENTS

WO89/09220  5/1989  WIPO.

OTHER PUBLICATIONS

Weisman et al., 1990, "Soluble human complement receptor type 1: In vivo inhibitor of complement surpressing post–ischemic myocardial inflammation and necrosis," Science 249:146–151.

Krych et al., 1989, "A secreted small form of human complement C3b/C4b receptor (CR1) that binds to C4b but not C3b," F.A.S.E.B. J. 3:A368.

Kumar et al., 1989, "Translation of the human C3b/C4b receptor mRNA in a cell–free system," Biochem., 28:4040–4046.

(List continued on next page.)

Primary Examiner—Garnette D. Draper
Assistant Examiner—John D. Ulm
Attorney, Agent, or Firm—Pennie & Edmonds

[57] ABSTRACT

The present invention relates to the C3b/C4b receptor (CR1) gene and its encoded protein. The invention also relates to CR1 nucleic acid sequences and fragments thereof comprising 70 nucleotides and their encoded peptides or proteins comprising 24 amino acids. The invention further provides for the expression of the CR1 protein and fragments thereof. The genes and proteins of the invention have uses in diagnosis and therapy of disorders involving complement activity, and various immune system or inflammatory disorders. In specific embodiments of the present invention detailed in the examples sections infra, the cloning, nucleotide sequence, and deduced amino acid sequence of a full-length CR1 cDNA and fragments thereof are described. The expression of the CR1 protein and fragments thereof is also described. Also described is the expression of a secreted CR1 molecule lacking a transmembrane region. The secreted CR1 molecule is shown to be useful in reducing damage caused by inflammation and in reducing myocardial infarct size and preventing reperfusion injury.

37 Claims, 61 Drawing Sheets

OTHER PUBLICATIONS

Glover et al., "Synthetic peptide inhibitors of complement serine proteases I. Identification of functionally equivalent protease inhibitor sequences in serpins and inhibition of C1s and D," Mol. Immunol., 25:1261–1267.

Hourcade et al., 1988, "Identification of an alternative polyadenylation site in the human C3b/C4b receptor (complement receptor type 1) transcriptional unit and prediction of a secreted form of complement receptor type 1," J. Exp. Med., 168:1255–1270.

Klickstein et al., 1988, "Identification of distinct C3b and C4b recognition sites in the human C3b/C4b receptor (CR1, CD35) by deletion mutagenesis," J. Exp. Med., 168:1699–1717.

Maillet et al., 1988, "Structure–function relationships in the inhibitory effect of heparin on complement activation: Independency of the anti–coapulant and anti–complementary sites on the heparin molecule," Mol. Immunol., 25:917–923.

Schasteen et al., 1988, "Synthetic peptide inhibitors of complement serine proteases II. Effects on hemolytic activity and production of C3a and C4a," Mol. Immunol., 25:1269–1275.

Wilson et al., 1988, "CR1 and cell membrane proteins that bind C3 and C4," Chemical Abstracts 108(1):421, abstract 4304y; 1987, Immunol. Res. 6:192–209.

Frank, 1987, "Complement in the pathiophysiology of human disease," New Eng. J. Med., 316:1525–1530.

Holers et al., 1987, "Human complement C3b/C4b receptor (CR1) mRNA polymorphism that correlates with the CR1 allelic molecular weight chromatography," Proc. Natl. Acad. Sci. U.S.A. 84:2459–2463.

Hourcade et al., 1987, "Structural analysis of the C3b/C4b receptor," Abstracts: XIIth Int. Complement Workshop, Arlaud et al. (eds.), pp. 171–172, Abstract 128.

Hourcade et al., 1987, "Alternate processing during CR1 transcription," Abstracts: XIIth Int. Complement Workshop, Arlaud et al. (eds.), p. 172, Abtract 129.

Klickstein et al., 1987, "Human C3b/C4b receptor (CR1) demonstration of long homologous repeating domains that are composed of the short consensus repeats characteristic of C3/C4 binding proteins," J. Exp. Med., 165:1095–1112.

Klickstein et al., 1987, "CR1 5' cDNA sequences contain a fourth long hemologous repeat (LHR) and identify a new B cell–specific mRNA," Abstracts: XIIth Int. Complement Workshop, Arlaud et al. (eds.), p. 180, Abstract 149.

Kristensen et al., 1987, "cDNA Structure of murine C4b–binding protein, a regulatory component of the serum complement system," Biochem., 26:4668–4674.

McLean et al., 1987, "cDNA Sequence of human apolioprotein(a) is homologous to plasminogen," Nature 330:132–137.

Smith et al., 1987, "Blocking of HIV–1 infectivity by soluble, secreted form of the CD4 antigen," Science 238:1704–1707.

Weis et al., 1987, "A complement receptor locus: Genes encoding C3b/C4b receptor and C3d/Epstein–Barr virus receptor map to 1q32," J. Immunol., 138:312–315.

Hiraki et al., 1986, "Isolation and characterization of expressible cDNA clones for mouse THY–1: A model system for cDNA expression of cell surface proteins," J. Immunol., 136:4291–4296.

Matzner et al., 1986, "Production of C5a antagonist by synovial and peritoneal tissue fibroblasts," Chemical Abstracts 106(1): Abstract 3626b; J. Cell. Physiol. 129:215–220.

Weis et al., 1986, "Identification of a partial cDNA clone for the C3d/Epstein–Barr virus receptor of human B lymphocytes: Homology with the receptor for fragments C3b and C4b of the third and fourth components of complement," Proc. Natl. Acad. Sci. U.S.A. 83:5639–5642.

Wong et al., 1986, "Analysis of multiple restriction fragment lenght polymorphisms of the gene for the human complenment receptor type 1," J. Exp. Med., 164:1531–1546.

Chung et al., 1985, "Molecular cloning and characterization of the cDNA coding for C4b–binding protein, a regulatory protein of the classical pathway of the human complement system," Biochem. J., 230:133–141.

Chung and Reid, 1985, "Structural and functional studies on C4b–binding protein, a regulatory component of the human complement system," Bioscience Reports 5:855–865.

Fries et al., 1985, "Factor I co–factor activity of CR1 overcomes the protective effect of IgG on covalently bound C3b residues," J. Immunol., 135:2673–2679.

Hood et al., 1985, "T cell antigen receptors and the immunoglobulin supergene family," Cell 40:225–229.

McCluskey et al., 1985, "Cell surface expression of an in vitro recombinant class II/class I major histocompatibility complex gene product," Cell 40:247–257.

Seya et al., 1985, "Purification and functional analysis of the polymorphic variants of the C3b/C4b receptor (CR1) and comparison with H. C4b–binding protein (C4bp), and decay accelerating factor (DAF)," J. Immunol., 135:2661–2667.

Sim et al., 1985, "Large–scale isolation of colmplement receptor type 1 (CR1) from human erythrocytes," 1985, Biochem. J., 232:883–889.

Wong et al., 1985, "Rapid purification of the human C3b/C4b receptor (CR1) by monoclonal antibody affinity chromotography," J. Immunol. Meth., 82:303–313.

Wong et al., 1985, "Identification of a partial cDNA clone for the human receptor for complement fragments C3b/C4b", Proc. Natl. Acad. Sci. USA 82:7711–7715.

Wong and Fearon, 1985, "p65: A C3b–binding protein on murine cells that shares antigenic determinants with the human C3b receptor (CR1) and is distinct from murine C3b receptor," J. Immunol., 134:4048–4056.

Yoon and Fearon, 1985, "Characterization of a soluble form of the C3b/C4b receptor (CR1) in human plasma," J. Immunol., 134:3332–3338.

Atkinson and Jones, 1984, "Biosynthesis of the human C3b/C4b receptor during differentiation of the HL–60 cell line," J. Clin. Invest., 74:1649–1657.

Patten, et al., 1984, "Structure, expression and divergence of T cell receptor beta–chain variable regions," Nature 312:40–46.

Siu et al., 1984, "The human T cell antigen receptor is encoded by variable, diversity and joining gene segments that rearrange to generate a complete v gene," Cell 37:393–401.

Dahlback et al., 1983, "Visualization of human C4b–binding protein and its complexes with vitamin K–dependent protein S and complement protein C4b," Proc. Natl. Acad. Sci. U.S.A. 80:3461–3465.

Dykman et al., 1983, "Polymorphism of human erythrocyte C3b/C4b receptor," Proc. Natl. Acad. Sci. 80:1698–1702.

Medof et al., 1983, "Role of the complement receptor CR1 in the processing of substrate–bound C3," Ann. N.Y. Acad. Sci., 421:299–306.

Stenlund et al, 1983, "Secretion of the hepatitis A virus surface antigen from mouse ells using an extra-chromosomal eucaryotic vector," EMBO J., 2:669–673.

Young et al., 1983, "Yeast RNA polymerase II genes: Isolation with antibody probes," Science 222:778–782.

Iida et al., 1982, "Complement recptor (CR1) deficiency in erythrocytes from patients with systemic lupus erythematosus," J. Exp. Med., 155:1427–1438.

Iida and Nussenzweig, 1981, "Complement receptor is an inhibitor of the complement cascade," J. Exp. Med., 153:1138–1150.

Hewick et al., 1981, "A gas–liquid solid phase peptide and protein sequenator," J. Biol. Chem., 256:7990–7997.

Suggs et al., 1981, "Use of synthetic oligonucleotides as hybridization probes: Isolation of cloned cDNA sequences for human $\beta(2)$–microglobulin," Proc. Natl. Acad. Sci. U.S.A. 78:6613–6617.

Andreatta et al., 1980, "Attempts at specific inhibition of C3–convertase," Chemical Abstracts 94(21):303, abstract 170110u, in Enzyme Inhibitors, Proc. Meet., Brodbeck, U. (ed), Verlap Chem., pp. 261–272.

Fearon, 1979, "Regulation of the amplification C3 convertase of human complement by an inhibitory protein isolated from human erythrocyte membrane," Proc. Natl. Acad. Sci. U.S.A. 76:5867–5871.

| | | | | | | | | | | | | | | | | | | | |
|---|---|---|---|---|---|---|---|---|---|---|---|---|---|---|---|---|---|---|---|
| CGT | GGT | TTG | TAG | ATG | TGC | TTG | GGG | AGA | ATG | GGG | GCC | TCT | TCT | CCA | AGA | AGC | CCG | GAG | CCT |
| | | | | | | | | | [M] | G | A | S | S | P | R | S | P | E | P |
| | | | | | | | | | 30 | | | | | | | | | | 60 |
| GTC | GGG | CCG | CCG | GCG | CCC | GGT | CTC | CCC | GGT | CTC | CCC | GGA | GGA | TCC | GAA | CTG | CTG | GCG | GTG |
| V | G | P | P | A | P | G | L | P | G | L | P | G | G | S | E | L | L | A | V |
| | | | | | | | | 90 | | | | | | | | | | | 120 |
| GTG | CTG | CTT | GCG | CCG | GTG | CTG | CCG | GTG | GCC | TGG | CAA | TGC | AAT | GCC | CCA | GAA | TGG | CTG | TTT |
| V | L | L | A | P | V | L | P | V | A | W | Q | C | N | A | P | E | W | L | F |
| | | | | | | | | | 150 | | | | | | | | | | 180 |
| GCC | AGG | CCT | ACC | AAC | CTA | ACT | GAT | GAG | TTT | CAA | TGC | AAT | GCC | CCC | ATT | GGG | ACA | CCT | CCA |
| A | R | P | T | N | L | T | D | E | F | Q | C | N | A | P | I | G | T | P | P |
| | | | | | | | | | 210 | | | | | | | | | | 240 |
| GAA | TGC | CGC | CCT | GGT | TAT | TCC | GGA | AGA | CCG | TTT | TCT | AAA | TCA | AAT | CCT | CCA | GAT | CCT | GTG |
| E | C | R | P | G | Y | S | G | R | P | F | S | K | S | N | P | P | D | P | V |
| | | | | | | | | | 270 | | | | | | | | | | 300 |
| TGG | ACT | GGT | GCT | AAG | GAC | AGG | TGC | AGA | CGT | GCC | AGA | TGC | AGA | CCT | AAT | CCT | CCA | GAT | CCT |
| W | T | G | A | K | D | R | C | R | R | A | R | C | R | P | N | P | P | D | P |
| | | | | | | | | | 330 | | | | | | | | | | 360 |
| AAT | GGC | ATG | GTT | GCT | ATC | AAA | GGC | ATC | CAG | TTC | GGA | TCC | CAA | ATT | AAA | TAT | TCT | TGT | GTG |
| N | G | M | V | A | I | K | G | I | Q | F | G | S | Q | I | K | Y | S | C | V |
| | | | | | | | | | 390 | | | | | | | | | | 420 |

FIG. 1A

```
ACT AAA GGA TAC CGA CTC ATT GGT TCC TCT GCC ACA TGC ATC ATC TCA GGT GAT ACT
 T   K   G   Y   R   L   I   G   S   S   A   T   C   I   I   S   G   D   T
                                     450                             480

GTC ATT TGG GAT AAT GAA ACA CCT ATT AGC GAC AGA ATT CCT TGT GGG CTA CCC CCC ACC
 V   I   W   D   N   E   T   P   I   S   D   R   I   P   C   G   L   P   P   T
                                     510                             540

ATC ACC AAT GGA GAT TTC ATT AGC ACC TGT GAC AGA ATT TGT GAG AAT TTT CAC TAT GGA
 I   T   N   G   D   F   I   S   T   C   D   R   I   C   E   N   F   H   Y   G
                                     570                             600

ACC TAC CGC TGC AAT CCT GGA AGC GAT GAC AAC AGA AAG GTG TTT GAG CTT GTG
 T   Y   R   C   N   P   G   S   D   D   N   R   K   V   F   E   L   V
                                     630                             660

TCC ATA TAC TGC ACC AGC AAT GAT CAA GTG GGC ATC TGG AGC CCC GCC CCT GGT GAG CCC
 S   I   Y   C   T   S   N   D   Q   V   G   I   W   S   P   A   P   G   E   P
                                     690                             720

TGC ATT ATA CCT AAC AAA TGC ACG CCT AAT GTG GAA TTT AGG TGT CAG CCT GGC TTT GAC
 C   I   I   P   N   K   C   T   P   N   V   E   F   R   C   Q   P   G   F   D
                                     750                             780

AAC AGA AGC TTA TTT TCC TTA AAT GAA GTT GTG GAG TTT AGG TGT CAG GCC CGC TTT GTC
 N   R   S   L   F   S   L   N   E   V   V   E   F   R   C   Q   A   R   F   V
                                     810                             840

ATG AAA GGA CCC CGC CGT GTG AAG TGC CAG GCC CTG AAC AAA TGG GAG CCG GAG CTA CCA
 M   K   G   P   R   R   V   K   C   Q   A   L   N   K   W   E   P   E   L   P
                                     870                             900
```

FIG. 1B

```
                                                            960                                   1020                                   1080                                   1140                                   1200                                   1260                                   1320                                   1380
AGC TGC TCC AGG GTA TGT CAG CCA CCT GAT GTC CTG CAT GCT GAG CGT ACC CAA AGG
 S   C   S   R   V   C   Q   P   P   D   V   L   H   A   E   R   T   Q   R

GAC AAG GAC AAC TTT TCA CCT GGG CAG GAA GTG TTC TAC AGC TGT GAG CCC GGC TAC GAC
 D   K   D   N   F   S   P   G   Q   E   V   F   Y   S   C   E   P   G   Y   D

CTC AGA GGG GCT GCG TCT ATG CGC TGC ACA CCC CAG GGA GAC TGG AGC CCT GCA GCC CCC
 L   R   G   A   A   S   M   R   C   T   P   Q   G   D   W   S   P   A   A   P

ACA TGT GAA GTG AAA TCC TGT GAT GAC TTC ATG GGC CAA CTT AAT GGC CGT GTG CTA
 T   C   E   V   K   S   C   D   D   F   M   G   Q   L   N   G   R   V   L

TTT CCA GTA AAT CTC CAG CTT GGA GCA AAA GTG GAT TTT GTT TGT GAT GAA GGA TTT CAA
 F   P   V   N   L   Q   L   G   A   K   V   D   F   V   C   D   E   G   F   Q

TTA AAA GGC AGC AGC TCT GCT AGT TAC TGT GTC TTG GCT GGA ATG GAA AGC CTT TGG AAT AGC
 L   K   G   S   S   S   A   S   Y   C   V   L   A   G   M   E   S   L   W   N   S

AGT GTT CCA GTG TGT GAA CAA ATC TTT TGT CCA AGT CCT CCA GTT ATT CCT AAT GGG AGA
 S   V   P   V   C   E   Q   I   F   C   P   S   P   P   V   I   P   N   G   R

CAC ACA GGA AAA CCT CTG GAA GTC TTT CCC TTT GGA AAA GCA GTA AAT TAC ACA TGC GAC
 H   T   G   K   P   L   E   V   F   P   F   G   K   A   V   N   Y   T   C   D
```

FIG. 1C

```
CCC CAC CCA GAC AGA GGG ACG AGC TTC GAC CTC ATT GGA GAG AGC ACC ATC CGC TGC ACA
 P   H   P   D   R   G   T   S   F   D   L   I   G   E   S   T   I   R   C   T
                          1410                                              1440

AGT GAC CCT CAA GGG AAT GGG GTT TGG AGC AGC CCT GCC AAG TTG AAA ACC AAT GCA TCT
 S   D   P   Q   G   N   G   V   W   S   S   P   A   K   L   K   T   N   A   S
                          1470                                              1500

CAC TGT CAA GCC CCA GAT CAT TTT CTG TTT GCC AAG TTG AAA ACC CAA ACC AAT GCA TCT
 H   C   Q   A   P   D   H   F   L   F   A   K   L   K   T   Q   T   N   A   S
```

```
                                                        1860
TCT GCT GAA TGT ATC CTC TCG GGC AAT GCT GCC CAT TGG AGC ACG AAG CCG CCA ATT TGT
 S   A   E   C   I   L   S   G   N   A   A   H   W   S   T   K   P   P   I   C
                                                        1920
CAA CGA ATT CCT TGT GGG CTA CCC CCC ATC GCC ACC AAT GGA GAT TTC ATT AGC ACC AAC
 Q   R   I   P   C   G   L   P   P   I   A   T   N   G   D   F   I   S   T   N
                                                        1980
AGA GAG AAT TTT CAC TAT GGA TCA GTG ACC TAC CGC TGC AAT CCT GGA AGC GGA GGG
 R   E   N   F   H   Y   G   S   V   T   Y   R   C   N   P   G   S   G   G
                                                        2040
AGA AAG GTG TTT GAG CTT GTG GGT GAG CCC TCC ATA TAC TGC ATT ATA CCT AAC GAT CAA
 R   K   V   F   E   L   V   G   E   P   S   I   Y   C   I   I   P   N   D   Q
                                                        2100
GTG GGC ATC TGG AGC GGC CCG GCC CCT CAG TGC ACC AGC AAA TGC ACG CCT CCA
 V   G   I   W   S   G   P   A   P   Q   C   T   S   K   C   T   P   P
                                                        2160
AAT GTG GAA AAT GGA ATA TTG GTA TCT GAC AAC AGA AGC TTA TTT TCC TTA AAT GAA GTT
 N   V   E   N   G   I   L   V   S   D   N   R   S   L   F   S   L   N   E   V
                                                        2220
GTG GAG TTT AGG TGT CAG CCT GGC TTT GTC ATG AAA GGA CCC CGC CGT GTG AAG TGC CAG
 V   E   F   R   C   Q   P   G   F   V   M   K   G   P   R   R   V   K   C   Q
```

FIG. 1E

FIG. 1F

```
                    2250                              2280
GCC CTG AAC AAA TGG GAG CCG GAG CTA CCA AGC TGC TCC AGG GTA TGT CAG CCA CCT CCA
 A   L   N   K   W   E   P   E   L   P   S   C   S   R   V   C   Q   P   P   P
                    2310                              2340
GAT GTC CTG CAT GCT GAG CGT ACC CAA AGG GAC AAG GAC AAC TTT TCA CCC GGG CAG GAA
 D   V   L   H   A   E   R   T   Q   R   D   K   D   N   F   S   P   G   Q   E
                    2370                              2400
GTG TTC TAC AGC TGT GAG CCC GGC TAT GAC CTC AGA GGG GCT GCG TCT ATG CGC TGC ACA
 V   F   Y   S   C   E   P   G   Y   D   L   R   G   A   A   S   M   R   C   T
                    2430                              2460
CCC CAG GGA GAC TGG AGC CCT GCA GCC CCC ACA TGT GAA GTG AAA TCC TGT GAT GAC TTC
 P   Q   G   D   W   S   P   A   A   P   T   C   E   V   K   S   C   D   D   F
                    2490                              2520
ATG GGA CAA CTT CTT AAT GGC CGT GTG CTA TTT CCA GTA AAT CTC CAG CTT GGA GCA AAA
 M   G   Q   L   L   N   G   R   V   L   F   P   V   N   L   Q   L   G   A   K
                    2550                              2580
GTG GAT TTT GTT TGT GAT GAA GGA TTT CAA TTA AAA GGC AGC AGC TCT GCT AGT TAT TGT GTC
 V   D   F   V   C   D   E   G   F   Q   L   K   G   S   S   S   A   S   Y   C   V
                    2610                              2640
TTG GCT GGA ATG GAA AGC CTT TGG AAT AGC AGT GTT CCA GTG TGT TGT GAA CAA ATC TTT TGT
 L   A   G   M   E   S   L   W   N   S   S   V   P   V   C   C   E   Q   I   F   C
                    2670                              2700
CCA AGT CCT CCA ATT CCT AAT GGG AGA CAC ACA GGA AAA CCT CTG GAA GTC TTT CCC
 P   S   P   P   I   P   N   G   R   H   T   G   K   P   L   E   V   F   P
```

```
TTT GGA AAA GCA GTA AAT TAC ACA TGC GAC CCC CAC AGA GGG ACG AGC TTC GAC
 F   G   K   A   V   N   Y   T   C   D   P   H   R   G   T   S   F   D
                                        2730                        2760

CTC ATT GGA GAG AGC ACC ATC CGC TGC ACA AGT GAC CCT CAA GGG AAT GGG GTT TGG AGC
 L   I   G   E   S   T   I   R   C   T   S   D   P   Q   G   N   G   V   W   S
                                        2790                        2820

AGC CCT GCC CGC TGT GGA ATT CTG GGT CAC TGT CAA GCC CCA GAT CAT TTT CTG TTT
 S   P   A   R   C   G   I   L   G   H   C   Q   A   P   D   H   F   L   F
                                        2850                        2880

GCC AAG TTG AAA ACC CAA ACC AAT GCA TCT GAC TTT CCC ATT GGG ACA TCT TTA AAG TAC
 A   K   L   K   T   Q   T   N   A   S   D   F   P   I   G   T   S   L   K   Y
                                        2910                        2940

GAA TGC CGT CCT GAG TAC TAC GGG AGG CCA TTC TCT ATC ACA TGT CTA GAT AAC CTG GTC
 E   C   R   P   E   Y   Y   G   R   P   F   S   I   T   C   L   D   N   L   V
                                        2970                        3000

TGG TCA AGT CCC AAA GAT GTC TGT AAA CGT AAA TCA TGT AAA ACT CCT CCA GAT CCA GTG
 W   S   P   K   D   V   C   K   R   K   S   C   K   T   P   P   D   P   V
                                        3030                        3060

AAT GGC ATG GTG CAT GTG ATC ACA GAC ATC CAG GTT GGA TCC AGA ATC AAC TAT TCT TGT
 N   G   M   V   H   V   I   T   D   I   Q   V   G   S   R   I   N   Y   S   C
                                        3090                        3120
```

FIG. 1G

```
ACT ACA GGG CAC CGA CTC ATT GGT CAC TCA TCT GCT GAA TGT ATC CTC TCA GGC AAT ACT
 T   T   G   H   R   L   I   G   H   S   S   A   E   C   I   L   S   G   N   T
                                        3150                                3180

GCC CAT TGG AGC ACG AAG CCG CCA ATT TGT CAA CGA ATT CCT TGT GGG CTA CCC CCA ACC
 A   H   W   S   T   K   P   P   I   C   Q   R   I   P   C   G   L   P   P   T
                                        3210                                3240

ATC GCC AAT GGA GAT TTC ATT AGC ACC AAC AGA GAG AAT TTT CAC TAT GGA TCA GTG GTG
 I   A   N   G   D   F   I   S   T   N   R   E   N   F   H   Y   G   S   V   V
                                        3270                                3300

ACC TAC CGC TGC AAT CTT GGA AGC AGA GGG AGA AAG GTG TTT GAG CTT GTG GGT GAG CCC
 T   Y   R   C   N   L   G   S   R   G   R   K   V   F   E   L   V   G   E   P
                                        3330                                3360

TCC ATA TAC TGC ACC AGC AAT GAC GAT CAA GTG GGC ATC TGG AGC GGC CCC GCC CCT CAG
 S   I   Y   C   T   S   N   D   D   Q   V   G   I   W   S   G   P   A   P   Q
                                        3390                                3420

TGC ATT ATA CCT AAC AAA TGC ACG CCT CCA AAT GTG GAA AAT GGA ATA TTG GTA TCT GAC
 C   I   I   P   N   K   C   T   P   P   N   V   E   N   G   I   L   V   S   D
                                        3450                                3480

AAC AGA AGC TTA TTT TCC TTA AAT GAA GTT GTG GAG TTT AGG TGT CAG CCT GGC TTT GTC
 N   R   S   L   F   S   L   N   E   V   V   E   F   R   C   Q   P   G   F   V
                                        3510                                3540

ATG AAA GGA CCC CGC CGT GTG AAG TGC CAG GCC CTG AAC AAA TGG GAG CCA GAG TTA CCA
 M   K   G   P   R   R   V   K   C   Q   A   L   N   K   W   E   P   E   L   P
                                        3570                                3600
```

FIG. 1H

```
AGC TGC TCC AGG GTG TGT CAG CCG CCT CCA GAA ATC CTG CAT GGT GAG CAT ACC CCA AGC
 S   C   S   R   V   C   Q   P   P   P   E   I   L   H   G   E   H   T   P   S
                       3630                                             3660

CAT CAG GAC AAC TTT TCA CCT GGG CAG GAA GTG TTC TAC AGC TGT GAG CCT TAT GAC
 H   Q   D   N   F   S   P   G   Q   E   V   F   Y   S   C   E   P   Y   D
                       3690                                             3720

CTC AGA GGG GCT GCG TCT CTG CAC TGC ACA CCC CAG GGA GAC TGG AGC CCT GAA GCC CCG
 L   R   G   A   A   S   L   H   C   T   P   Q   G   D   W   S   P   E   A   P
                       3750                                             3780

AGA TGT GCA GTG AAA TCC TGT GAT GAC TTC CTC CAA CTC CCT CAT GGC CGT GTG CTA
 R   C   A   V   K   S   C   D   D   F   L   Q   L   P   H   G   R   V   L
                       3810                                             3840

TTT CCA CTT AAT CTC CAG CTT GGG GCA AAG GTG TCC TTT GTC TGT GAT GAA GGG TTT CGC
 F   P   L   N   L   Q   L   G   A   K   V   S   F   V   C   D   E   G   F   R
                       3870                                             3900

TTA AAG GGC AGT AGT TCC GTT CAT TGT GTT TTG GTT GGA ATG AGA AGC CTT TGG AAT AAC
 L   K   G   S   S   S   V   H   C   V   L   V   G   M   R   S   L   W   N   N
                       3930                                             3960

AGT GTT CCT GTG TGT GAA CAT ATC TTT TGT CCA AAT CCT CCA GCT ATC CTT AAT GGG AGA
 S   V   P   V   C   E   H   I   F   C   P   N   P   P   A   I   L   N   G   R
                       3990                                             4020
```

FIG. 1I

```
                                                                                              4050                                                                    4080
CAC ACA GGA ACT CCC TCT GGA GAT ATT CCC TAT GGA AAA GAA ATA TCT TAC ACA TGT GAC
 H   T   G   T   P   S   G   D   I   P   Y   G   K   E   I   S   Y   T   C   D 4110                                                                    4140
CCC CAC CCA GAC AGA GGG ATG ACC TTC AAC CTC ATT GGG GAG AGC ACC ATC CGC TGC ACA
 P   H   P   D   R   G   M   T   F   N   L   I   G   E   S   T   I   R   C   T 4170                                                                    4200
AGT GAC CCT CAT GGG AAT GGG GTT TGG AGC AGC CCT GCC CCT CGC TGT GAA CTT TCT GTT
 S   D   P   H   G   N   G   V   W   S   S   P   A   P   R   C   E   L   S   V 4230                                                                    4260
CGT GCT GGT CAC TGT AAA ACC CCA GAG CAG TTT CCA TTT GCC AGT CCT ACG ATC CCA ATT
 R   A   G   H   C   K   T   P   E   Q   F   P   F   A   S   P   T   I   P   I 4290                                                                    4320
AAT GAC TTT GAG TTT CCA GTC ATC TCC GGG ACA TCT GTC TTG AAT TAT GAA CGT CCT GGG TAT TTT
 N   D   F   E   F   P   V   I   S   G   T   S   V   L   N   Y   E   R   P   G   Y   F 4350                                                                    4380
GGG AAA ATG TTC TCT ATC TCC TGC CTA GAA CCA CCA GAA CCC TTC AAT GGA ATG GTT CAT ATA AAC
 G   K   M   F   S   I   S   C   L   E   P   P   E   P   F   N   G   M   V   H   I   N 4410                                                                    4440
TGT AGA CGA AAA TCA TGT GGA CCT CCA CCA GAA CCC TTC AAT GGA ATG GTT CAT ATA AAC
 C   R   R   K   S   C   G   P   P   P   E   P   F   N   G   M   V   H   I   N 4470                                                                    4500
ACA GAT ACA CAG TTT GGA TCA ACA GTT AAT TAT TCT TGT AAT GAA GGG TTT CGA CTC ATT
 T   D   T   Q   F   G   S   T   V   N   Y   S   C   N   E   G   F   R   L   I
```

FIG. 1J

FIG. 1K

```
GGT TCC CCA TCT ACT ACT TGT CTC GTC TCA GGC AAT AAT GTC ACA TGG GAT AAG AAG GCA
 G   S   P   S   T   T   C   L   V   S   G   N   N   V   T   W   D   K   K   A
                              4530                                         4560

CCT ATT TGT GAG ATC ATA TCT TGT GAG CCA CCT CCA ACC ATA TCC AAT GGA GAC TTC TAC
 P   I   C   E   I   I   S   C   E   P   P   P   T   I   S   N   G   D   F   Y
                              4590                                         4620

AGC AAT AGA ACA TCT TTT CAC AAT GGA ACG GTG GTA ACT TAC CAG TGC CAC ACT GGA
 S   N   R   T   S   F   H   N   G   T   V   V   T   Y   Q   C   H   T   G
                              4650                                         4680

CCA GAT GGA GAA CAG CTG TTT GAG CTT GTG GGA GAA CGG TCA ATA TAT TGC ACC AGC AAA
 P   D   G   E   Q   L   F   E   L   V   G   E   R   S   I   Y   C   T   S   K
                              4710                                         4740

GAT GAT CAA GTT GGT GTT TGG AGC AGC CCT CCC CCT CGG TGT ATT TCT ACT AAT AAA TGC
 D   D   Q   V   G   V   W   S   S   P   P   P   R   C   I   S   T   N   K   C
                              4770                                         4800

ACA GCT CCA GAA AAT GCA ATT AGA GTA CCA GGA AAC AGG AGT TTC TTT TCC CTC
 T   A   P   E   N   A   I   R   V   P   G   N   R   S   F   F   S   L
                              4830                                         4860

ACT GAG ATC ATC AGA TTT AGA TGT CAG CCC GGG TTT GTC ATG GTA GGG TCC CAC ACT GTG
 T   E   I   I   R   F   R   C   Q   P   G   F   V   M   V   G   S   H   T   V
                              4890                                         4920
```

```
CAG TGC CAG ACC AAT GGC AGA TGG GGG CCC AAG CTG CCA CAC TGC TCC AGG GTG TGT CAG
 Q   C   Q   T   N   G   R   W   G   P   K   L   P   H   C   S   R   V   C   Q
                                    4950                                    4980

CCG CCT CCA GAA ATC CTG CAT GGT GAG CAT ACC CTA AGC CAT CAG GAC AAC TTT TCA CCT
 P   P   P   E   I   L   H   G   E   H   T   L   S   H   Q   D   N   F   S   P
                                    5010                                    5040

GGG CAG GAA GTG TTC TAC AGC TGT GAG CCC AGC TAT GAC CTC AGA GGG GCT GCG TCT CTG
 G   Q   E   V   F   Y   S   C   E   P   S   Y   D   L   R   G   A   A   S   L
                                    5070                                    5100

CAC TGC ACG CCC CAG GGA GAC TGG AGC CCT GAA GCC CCT AGA TGT CCA CTT AAT CTC TGT
 H   C   T   P   Q   G   D   W   S   P   E   A   P   R   C   P   L   N   L   C
                                    5130                                    5160

GAT GAC TTC CTG GGC CAA CTC CCT CAT GGC CGT GTG CTA CTT CCA AGA TGT CAG CTT
 D   D   F   L   G   Q   L   P   H   G   R   V   L   L   P   R   C   Q   L
                                    5190                                    5220

GGG GCA AAG GTG TCC TTT GTT TGC GAT GAA GGG TTC CGA TTA AAA GGC AGG TCT GCT AGT
 G   A   K   V   S   F   V   C   D   E   G   F   R   L   K   G   R   S   A   S
                                    5250                                    5280

CAT TGT GTC TTG GCT GGA ATG AAA GCC CTT TGG AAT AGC AGT GTT CCA GTG TGT GAA CAA
 H   C   V   L   A   G   M   K   A   L   W   N   S   S   V   P   V   C   E   Q
                                    5310                                    5340

ATC TTT TGT CCA AAT CCT CCA GCT ATC CTT AAT GGG AGA CAC ACA GGA ACT CCC TTT GGA
 I   F   C   P   N   P   P   A   I   L   N   G   R   H   T   G   T   P   F   G
                                    5370                                    5400
```

FIG. 1L

```
                                                    5460
GAT ATT CCC TAT GGA AAA GAA ATA TCT TAC GCA TGC GAC ACC CAC CCA GAC AGA GGG ATG
 D   I   P   Y   G   K   E   I   S   Y   A   C   D   T   H   P   D   R   G   M
                                                    5520
ACC TTC AAC CTC ATT GGG GAG AGC AGC TCC ATC CGC TGC ACA AGT GAC CCT CAA GGG AAT GGG
 T   F   N   L   I   G   E   S   S   I   R   C   T   S   D   P   Q   G   N   G
                                                    5580
GTT TGG AGC AGC CAA AAC GGG CAT TAC ATT CGC TGT GAA CTT TCT GTT CCT GCT GCC TGC CCA CAT CCA
 V   W   S   S   Q   N   G   H   Y   I   R   C   E   L   S   V   P   A   A   C   P   H   P
                                                    5640
CCC AAG ATC CAA AAC GGG CAT TAC ATT GGA GGA CAC GTA TCT CTA TAT CTT CCT GGG ATG
 P   K   I   Q   N   G   H   Y   I   G   G   H   V   S   L   Y   L   P   G   M
                                                    5700
ACA ATC AGC TAC ACT TGT GAC CCC GGC TAC CTG TTA GTG GGA AAG GGC TTC ATT TTC TGT
 T   I   S   Y   T   C   D   P   G   Y   L   L   V   G   K   G   F   I   F   C
                                                    5760
ACA GAC CAG GGA ATC TGG AGC CAA TTG GAT CAT TAT TGC AAA GAA GTA AAT TGT AGC TTC
 T   D   Q   G   I   W   S   Q   L   D   H   Y   C   K   E   V   N   C   S   F
                                                    5820
CCA CTG TTT ATG AAT GGA GAG TTA GAA ATG AAA AAA GTA TAT CAC TAT GGA
 P   L   F   M   N   G   E   L   E   M   K   K   V   Y   H   Y   G
```

FIG. 1M

```
GAT TAT GTG ACT TTG AAG TGT GAA GAT GGG TAT ACT CTG GAA GGC AGT CCC TGG AGC CAG
 D   Y   V   T   L   K   C   E   D   G   Y   T   L   E   G   S   P   W   S   Q
                                5850                                    5880

TGC CAG GCG GAT GAC AGA TGG GAC CCT CCT CTG GCC AAA TGT ACC TCT CGT GCA CAT GAT
 C   Q   A   D   D   R   W   D   P   P   L   A   K   C   T   S   R   A   H   D
                                5910                                    5940

GCT CTC ATA GTT GGC ACT TTA TCT GGT ACG ATC TTC TTT ATT TTA CTC ATC ATT TTC CTC
 A   L   I   V   G   T   L   S   G   T   I   F   F   I   L   L   I   I   F   L
                                5970                                    6000

TCT TGG ATA ATT CTA AAG CAC AGA GGC AAA AAT GCA CAT GAA AAC CCT AAA GAA GTG
 S   W   I   I   L   K   H   R   G   K   N   A   H   E   N   P   K   E   V
                                6030                                    6060

GCT ATC CAT TTA CAT TCT CAA GGA GGC AGC AGC GTT CAT CCC CGA ACT CTG CAA ACA AAT
 A   I   H   L   H   S   Q   G   G   S   S   V   H   P   R   T   L   Q   T   N
                                6090                                    6120

GAA GAA AAT AGC AGG GTC CTT CCT TGA CAA AGT ACT ATA CAG CTG AAG AAC ATC TCG AAT
 E   E   N   S   R   V   L   P   U   Q   S   T   I   Q   L   K   N   I   S   N
                                6150                                    6180

ACA ATT TTG GTG GGA AAG GAG CCA ATT GAT TTC AAC AGA ATC AGA TCT GAG CTT CAT AAA
 T   I   L   V   G   K   E   P   I   D   F   N   R   I   R   S   E   L   H   K
                                6210                                    6240

GTC TTT GAA GTG ACT TCA CAG AGA CGC AGA CAT GTG CAC TTG AAG ATG CTG CCC CTT CCC
 V   F   E   V   T   S   Q   R   R   R   H   V   H   L   K   M   L   P   L   P
                                6270                                    6300
```

FIG. 1N

```
TGG TAC CTA GCA AAG CTC CTG CCT CTT TGT GTG CGT CAC TGT GAA ACC CCC ACC CTT CTG
                                6330                                          6360
CCT CGT GCT AAA CGC ACA CAG TAT CTA GTC AGG GGA AAA GAC TGC ATT TAG GAG ATA GAA
                                6390                                          6420
AAT AGT TTG GAT TAC TTA AAG GAA TAA GGT GTT GCC TGG AAT TTC TGG TTT GTA AGG TGG
                                6450                                          6480
TCA CTG TTC TTT TTT AAA ATA TTT GTA ATA TGG AAT GGG CTC AGT AAG AAG AGC TTG GAA
                                6510                                          6540
AAT GCA GAA AGT TAT GAA AAA TAA GTC ACT TAT AAT TAT GCT ACC TAC TGA TAA CCA CTC
                                6570                                          6600
```

FIG. 10

```
CTA ATA TTT TGA TTC ATT TTC TGC CTA TCT TCT TTC ACA TAT GTG TTT TTT TAC ATA CGT
                                    6630                                    6660
ACT TTT CCC CCC TTA GTT TGT TTC CTT TTA TTT TAT AGA GCA GAA CCC TAG TCT TTT AAA
                                    6690                                    6720
CAG TTT AGA GTG AAA TAT ATG CTA TAT CAG TTT TTA CTT TCT CTA GGG AGA AAA ATT AAT
                                    6750                                    6780
TTA CTA GAA AGG CAT GAA ATG ATC ATG GGA AGA GTG GTT AAG ACT ACT GAA GAG AAA TAT
                                    6810                                    6840
TTG GAA AAT AAG ATT TCG ATA TCT TCT TTT TTT TTG AGA TGG AGT CTG GCT CTG TCT CCC
                                    6870                                    6900
AGG CTG GAG TGC AGT GGC GTA ATC TCG GCT CAC TGC AAC GTC CGC CTC CCG
                                    6930
```

FIG. 1P

| | | |
|---:|:---|---:|
| 1 | CCAAGTTGAAAACCCAAACCAATGCATCTGACTTTCCCATTGGGACATCTTTAAAGTACG | 60 |
| 61 | AATGCCGTCCTGAGTACTACGGGAGGCCATTCTCTATCACATGTCTAGATAACCTGGTCT | 120 |
| 121 | GGTCAAGTCCCAAAGATGTCTGTAAACGTAAATCATGTAAAACTCCTCCAGATCCAGTGA | 187 |
| 181 | ATGGCATGGTGCATGTGATCACAGACATCCAGGTTGGATCCAGAATCAACTATTCTTGTA | 240 |
| 241 | CTACAGGGCACCGACTCATTGGTCACTCATCTGCTGAATGTATCCTCTCGGGCAATGCTG | 300 |
| 301 | CCCATTGGAGCACGAAGCCGCCAATTTGTCAACGAATTCCTTGTGGGCTACCCCCCACCA | 360 |
| 361 | TCGCCAATGGAGATTTCATTAGCACCAACAGAGAGAATTTTCACTATGGATCAGTGGTGA | 420 |
| 421 | CCTACCGCTGCAATCCTGGAAGCGGAGGGAGAAAGGTGTTTGAGCTTGTGGGTGAGCCCT | 480 |
| 481 | CCATATACTGCACCAGCAATGACGATCAAGTGGGCATCTGGAGCGGCCCGGCCCCTCAGT | 540 |
| 541 | GCATTATACCTAACAAATGCACGCCTCCAAATGTGGAAAATGGAATATTGGTATCTGACA | 600 |
| 601 | ACAGAAGCTTATTTTCCTTAAATGAAGTTGTGGAGTTTAGGTGTCAGCCTGGCTTTGTCA | 660 |
| 661 | TGAAAGGACCCCGCCGTGTGAAGTGCCAGGCCCTGAACAAATGGGAGCCGGAGCTACCAA | 720 |
| 721 | GCTGCTCCAGGGTATGTCAGCCACCTCCAGATGTCCTGCATGCTGAGCGTACCCAAAGGG | 780 |
| 781 | ACAAGGACAACTTTTCACCCGGGCAGGAAGTGTTCTACAGCTGTGAGCCCGGCTATGACC | 840 |
| 841 | TCAGAGGGGCTGCGTCTATGCGCTGCACACCCCAGGGAGACTGGAGCCCTGCAGCCCCA | 900 |
| 901 | CATGTGAAGTGAAATCCTGTGATGACTTCATGGGCCAACTTCTTAATGGCCGTGTGCTAT | 960 |
| 961 | TTCCAGTAAATCTCCAGCTTGGAGCAAAAGTGGATTTTGTTTGTGATGAAGGATTTCAAT | 1020 |
| 1021 | TAAAAGGCAGCTCTGCTAGTTATTGTGTCTTGGCTGGAATGGAAAGCCTTTGGAATAGCA | 1080 |
| 1081 | GTGTTCCAGTGTGTGAACAAATCTTTTGTCCAAGTCCTCCAGTTATTCCTAATGGGAGAC | 1140 |
| 1141 | ACACAGGAAAACCTCTGGAAGTCTTTCCCTTTGGAAAAGCAGTAAATTACACATGCGACC | 1200 |
| 1201 | CCCACCCAGACAGAGGGACGAGCTTCGACCTCATTGGAGAGAGCACCATCCGCTGCACAA | 1260 |
| 1261 | GTGACCCTCAAGGGAATGGGGTTTGGAGCAGCCCTGCCCCTCGCTGTGGAATTCTGGGTC | 1320 |
| 1321 | ACTGTCAAGCCCCAGATCATTTTCTGTTTGCCAAGTTGAAAACCCAAACCAATGCATCTG | 1380 |
| 1381 | ACTTTCCCATTGGGACATCTTTAAAGTACGAATGCCGTCCTGAGTACTACGGGAGGCCAT | 1440 |
| 1441 | TCTCTATCACATGTCTAGATAACCTGGTCTGGTCAAGTCCCAAAGATGTCTGTAAACGTA | 1500 |

FIG. 3A

```
1501  AATCATGTAAAACTCCTCCAGATCCAGTGAATGGCATGGTGCATGTGATCACAGACATCC  1560
1561  AGGTTGGATCCAGAATCAACTATTCTTGTACTACAGGGCACCGACTCATTGGTCACTCAT  1620
1621  CTGCTGAATGTATCCTCTCAGGCAATACTGCCCATTGGAGCACGAAGCCGCCAATTTGTC  1680
1681  AACGAATTCCTTGTGGGCTACCCCCAACCATCGCCAATGGAGATTTCATTAGCACCAACA  1740
1741  GAGAGAATTTTCACTATGGATCAGTGGTGACCTACCGCTGCAATCTTGGAAGCAGAGGGA  1800
1801  GAAAGGTGTTTGAGCTTGTGGGTGAGCCCTCCATATACTGCACCAGCAATGACGATCAAG  1860
1861  TGGGCATCTGGAGCGGCCCCGCCCCTCAGTGCATTATACCTAACAAATGCACGCCTCCAA  1920
1921  ATGTGGAAAATGGAATATTGGTATCTGACAACAGAAGCTTATTTTCCTTAAATGAAGTTG  1980
1981  TGGAGTTTAGGTGTCAGCCTGGCTTTGTCATGAAAGGACCCCGCCGTGTGAAGTGCCAGG  2040
2041  CCCTGAACAAATGGGAGCCAGAGTTACCAAGCTGCTCCAGGGTGTGTCAGCCGCCTCCAG  2100
2101  AAATCCTGCATGGTGAGCATACCCCAAGCCATCAGGACAACTTTTCACCTGGGCAGGAAG  2160
2161  TGTTCTACAGCTGTGAGCCTGGCTATGACCTCAGAGGGCTGCGTCTCTGCACTGCACAC  2220
2221  CCCAGGGAGACTGGAGCCCTGAAGCCCCGAGATGTGCAGTGAAATCCTGTGATGACTTCT  2280
2281  TGGGTCAACTCCCTCATGGCCGTGTGCTATTTCCACTTAATCTCCAGCTTGGGGCAAAGG  2340
2341  TGTCCTTTGTCTGTGATGAAGGGTTTCGCTTAAAGGGCAGTTCCGTTAGTCATTGTGTCT  2400
2401  TGGTTGGAATGAGAAGCCTTTGGAATAACAGTGTTCCTGTGTGTGAACATATCTTTTGTC  2460
2461  CAAATCCTCCAGCTATCCTTAATGGGAGACACACAGGAACTCCCTCTGGAGATATTCCCT  2520
2521  ATGGAAAAGAAATATCTTACACATGTGACCCCCACCCAGACAGAGGGATGACCTTCAACC  2580
2581  TCATTGGGGAGAGCACCATCCGCTGCACAAGTGACCCTCATGGGAATGGGGTTTGGAGCA  2640
2641  GCCCTGCCCCTCGCTGTGAACTTTCTGTTCGTGCTGGTCACTGTAAAACCCCAGAGCAGT  2700
2701  TTCCATTTGCCAGTCCTACGATCCCAATTAATGACTTTGAGTTTCCAGTCGGGACATCTT  2760
2761  TGAATTATGAATGCCGTCCTGGGTATTTTGGGAAAATGTTCTCTATCTCCTGCCTAGAAA  2820
2821  ACTTGGTCTGGTCAAGTGTTGAAGACAACTGTAGACGAAAATCATGTGGACCTCCACCAG  2880
```

FIG. 3B

```
2881  AACCCTTCAATGGAATGGTGCATATAAACACAGATACACAGTTTGGATCAACAGTTAATT  2940
2941  ATTCTTGTAATGAAGGGTTTCGACTCATTGGTTCCCCATCTACTACTTGTCTCGTCTCAG  3000
3001  GCAATAATGTCACATGGGATAAGAAGGCACCTATTTGTGAGATCATATCTTGTGAGCCAC  3060
3061  CTCCAACCATATCCAATGGAGACTTCTACAGCAACAATAGAACATCTTTTCACAATGGAA  3120
3121  CGGTGGTAACTTACCAGTGCCACACTGGACCAGATGGAGAACAGCTGTTTGAGCTTGTGG  3180
3181  GAGAACGGTCAATATATTGCACCAGCAAAGATGATCAAGTTGGTGTTTGGAGCAGCCCTC  3240
3241  CCCCTCGGTGTATTTCTACTAATAAATGCACAGCTCCAGAAGTTGAAAATGCAATTAGAG  3300
3301  TACCAGGAAACAGGAGTTTCTTTTCCCTCACTGAGATCATCAGATTTAGATGTCAGCCCG  3360
3361  GGTTTGTCATGGTAGGGTCCCACACTGTGCAGTGCCAGACCAATGGCAGATGGGGCCCA  3420
3421  AGCTGCCACACTGCTCCAGGGTGTGTCAGCCGCCTCCAGAAATCCTGCATGGTGAGCATA  3480
3481  CCCTAAGCCATCAGGACAACTTTTCACCTGGGCAGGAAGTGTTCTACAGCTGTGAGCCCA  3540
3541  GCTATGACCTCAGAGGGGCTGCGTCTCTGCACTGCACGCCCCAGGGAGACTGGAGCCCTG  3600
3601  AAGCCCCTAGATGTACAGTGAAATCCTGTGATGACTTCCTGGGCCAACTCCCTCATGGCC  3660
3661  GTGTGCTACTTCCACTTAATCTCCAGCTTGGGGCAAAGGTGTCCTTTGTTTGCGATGAAG  3720
3721  GGTTCCGATTAAAAGGCAGGTCTGCTAGTCATTGTGTCTTGGCTGGAATGAAAGCCCTTT  3780
3781  GGAATAGCAGTGTTCCAGTGTGTGAACAAATCTTTTGTCCAAATCCTCCAGCTATCCTTA  3840
3841  ATGGGAGACACACAGGAACTCCCTTTGGAGATATTCCCTATGGAAAAGAAATATCTTACG  3900
3901  CATGCGACACCCACCCAGACAGAGGGATGACCTTCAACCTCATTGGGGAGAGCTCCATCC  3960
3961  GCTGCACAAGTGACCCTCAAGGGAATGGGGTTTGGAGCAGCCCTGCCCCTCGCTGTGAAC  4020
4021  TTTCTGTTCCTGCTGCCTGCCCACATCCACCCAAGATCCAAAACGGGCATTACATTGGAG  4080
4081  GACACGTATCTCTATATCTTCCTGGGATGACAATCAGCTACACTTGTGACCCCGGCTACC  4140
4141  TGTTAGTGGGAAAGGGCTTCATTTTCTGTACAGACCAGGGAATCTGGAGCCAATTGGATC  4200
4201  ATTATTGCAAAGAAGTAAATTGTAGCTTCCCACTGTTTATGAATGGAATCTCGAAGGAGT  4260
4261  TAGAAATGAAAAAAGTATATCACTATGGAGATTATGTGACTTTGAAGTGTGAAGATGGGT  4320
4321  ATACTCTGGAAGGCAGTCCCTGGAGCCAGTGCCAGGCGGATGACAGATGGGACCCTCCTC  4380
```

FIG. 3C

| | | |
|---|---|---|
| 4381 | TGGCCAAATGTACCTCTCGTGCACATGATGCTCTCATAGTTGGCACTTTATCTGGTACGA | 4440 |
| 4441 | TCTTCTTTATTTTACTCATCATTTTCCTCTCTTGGATAATTCTAAAGCACAGAAAAGGCA | 4500 |
| 4501 | ATAATGCACATGAAAACCCTAAAGAAGTGGCTATCCATTTACATTCTCAAGGAGGCAGCA | 4560 |
| 4561 | GCGTTCATCCCCGAACTCTGCAAACAAATGAAGAAAATAGCAGGGTCCTTCCTTGACAAA | 4620 |
| 4621 | GTACTATACAGCTGAAGAACATCTCGAATACAATTTTGGTGGGAAAGGAGCCAATTGATT | 4680 |
| 4681 | TCAACAGAATCAGATCTGAGCTTCATAAAGTCTTTGAAGTGACTTCACAGAGACGCAGAC | 4740 |
| 4741 | ATGTGCACTTGAAGATGCTGCCCCTTCCCTGGTACCTAGCAAAGCTCCTGCCTCTTTGTG | 4800 |
| 4801 | TGCGTCACTGTGAAACCCCCACCCTTCTGCCTCGTGCTAAACGCACACAGTATCTAGTCA | 4860 |
| 4861 | GGGGAAAAGACTGCATTTAGGAGATAGAAAATAGTTTGGATTACTTAAAGGAATAAGGTG | 4920 |
| 4921 | TTGCCTGGAATTTCTGGTTTGTAAGGTGGTCACTGTTCTTTTTTAAAATATTTGTAATAT | 4980 |
| 4981 | GGAATGGGCTCAGTAAGAAGAGCTTGGAAAATGCAGAAAGTTATGAAAAATAAGTCACTT | 5040 |
| 5041 | ATAATTATGCTACCTACTGATAACCACTCCTAATATTTTGATTCATTTCTGCCTATCTT | 5100 |
| 5101 | CTTTCACATATGTGTTTTTTTACATACGTACTTTTCCCCCCTTAGTTTGTTTCCTTTTAT | 5160 |
| 5161 | TTTATAGAGCAGAACCCTAGTCTTTTAAACAGTTTAGAGTGAAATATATGCTATATCAGT | 5220 |
| 5221 | TTTTACTTTCTCTAGGGAGAAAAATTAATTTACTAGAAAGGCATGAAATGATCATGGGAA | 5280 |
| 5281 | GAGTGGTTAAGACTACTGAAGAGAAATATTTGGAAATAAGATTTCGATATCTTCTTTTTT | 5340 |
| 5341 | TTTTGAGATGGAGTCTGGCTCTGTCTCCCAGGCTGGAGTGCAGTGGCGTAATCTCGGCTC | 5400 |
| 5401 | ACTGCAACGTCCGCCTCCCG 5420 | |

```
GTGCGTAAACTTGCGTTGGATCTTTCCCATGTCTGCAAAAGCTTCTTATGGAATTA
TTTCAAATGTGGGATATGAGAAACCTTTTCTGAAAAGTGTTCGGATAGATGGAT
```

FIG. 3D

```
B    1          KLKTQTNASDFPIGTSLKYECRPEYYGRPFSITCLDNLVWSSPKDVCK
C  439          GHCQAPDHFLFA
D  892          GHCKTPEQFPFASPTIPI  DFE V     N     G F KM   S  E        YE N R

RKSCKTPPDPVNGMVHVITDIQVGSRINYSCTTGHRLIGHSSAECILSGNAAHWSTKPPI     108
                                                           T         558
        GP  E F       IN  T F  TV    NE F      SP TT LV    NVT DK A  1011

B  109   CQRIPCGLPPTIANGDFISTNRENFHYGSVVTYRCNPGSGGRKVFELVGEPSIYCTSNDD
C  559                                L  R
D 1012   EI S EP   S     Y N  TS  N T     Q HT PD EQL      R     K

QVGIWSGPAPQCIIPNKCTPPNVENGILVSDNRSLFSLNEVVEFRCQPGFVMKGPRRVKC    228
                                                                     678
        V   SPR   ST    A E    A R PG  F    T IIR          V SHT Q   1131

B  229   QALNKWEPELPSCSRVCQPPPDVLHAERTQRDKDNFSPGQEVFYSCEPGYDLRGAASMRC
C  879                    EI  G H PSHQ                          LH
D 1132   TNGR G K  H      EI  G H LSHQ      S                   LH

TPQGDVSPAAPTCEVKSCDDFMGQLLNGRVLFPVNLQLGAKVDFVCDEGFQLKGSSASYC    348
             E  R A          L  PH   L        S        R    V H      798
             E  R T          L  PH   L L      S        R    R H     1251

B  349   VLAGHESLWNSSVPVCEQIFCPSPPVIPNGRHTGKPLEVFPFGKAVNYTCDPHPDRGTSF
C  799      V  R    N       H     N A L      T SGDI Y  EIS         MT
D 1252          KA                 N A L      T FGDI Y  EIS A T     MT

DLIGESTIRCTSDPQGNGVWSSPAPRCGIL     438
      N              H            ELSVRA 891
      N       S                   ELS    1341

1342  VPAACPHPPKIQNGHYIGGHVSLYLPGMTISYTCDPGYLLVGKGFIFCTDQGIVSQLDHY

CKEVNCSFPLFMNGISKELEMKKVYHYGDYVTLKCEDGYTLEGSPWSQCQADDRWDPPLA  1461

1462  KCTSRAHDALIVGTLSGTIFFILLIIFLSWIILKHRKGNNAHENPKEVAIHLHSQGGSSV

HPRTLQTNEENSRVLP  1537
```

FIG.5B

| SCR NO. | | | | |
|---|---|---|---|---|
| 1 | 1 | KLKTQTNASDFPIGTSLKYECRPEYY GRP F | S ITC LD N L VV SS PK DVC KR | 49 |
| 2 | 50 | KSCKTPPDPV NGMVHVIT DIQVGSRINYSCTTGHRLIGH | SSAECI LS GNA AHV STKP PICQ R | 111 |
| 3 | 112 | IP CGLPPT IANGDFIS TNRENFHYGSVVTYRCNPGSG GRKVFELVGEPS IYCTSNDD Q VGIV SG P APQCI | | 181 |
| 4 | 182 | IPNK C TPPN VENGILVS DNRSLFSLNEVVEFRCQPGFVMKGPRR | VKC QALNKVE PELPSCS R | 244 |
| 5 | 245 | V CQPPPD VLHA ERTQRDKDNFSPGQEV YSCEPGYDLRGAA | S MRC T PQ GDV S PAAPTC E | 303 |
| 6 | 304 | V KSCDDFMGQLLNGRVLFPVNL QLGAKVDFVCDEGFQLKGS | SASYCV LA GME SLVNSS YPVC EQ | 366 |
| 7 | 367 | IF CPSPPV IPNGRH TGKPLEVFPFGKAVNYTCDPHPD RGTS FDLIGE STIRCTS D PQGNGVV SSS P APRCG | | 436 |
| 8 | 437 | ILGH CQAPDHFLF AKLKTQTNASDFPIGTSLKYECRPEYY GRP F | S ITC LD N L VV SS PK DVC KR | 499 |
| 9 | 500 | KSCKTPPDPV NGMVHVIT DIQVGSRINYSCTTGHRLIGH | SSAECI LS GNT AHV STKP PICQ R | 561 |
| 10 | 562 | IP CGLPPT IANGDFIS TNRENFHYGSVVTYRCNLGS RGRKVFELVGEPS IYCTSNDD Q VGIV SG P APQCI | | 631 |
| 11 | 632 | IPNK C TPPN VENGILVS DNRSLFSLNEVVEFRCQPGFVMKGPRR | VKC QALNKVE PELPSCS R | 693 |
| 12 | 694 | V CQPPPE ILHGEH TPSHQDNFSPGQEVFYSCEPGYDLRGAA | S LHC T PQ GDV S PEAPRCA | 752 |
| 13 | 753 | V KSCDDFLGQLPHGRVLFPLNL QLGAKVSFVCDEGFRLKGS | SVSHCV LV GMR SLVNNS VPVC EH | 816 |
| 14 | 817 | IF CPNPPA ILNGRH TGTPSGDIPYGKEISYTCDPHPD RGMT FNLIGE STIRCTSDPHGN GVV SS P APRC ELSVRAG | | 892 |
| 15 | 893 | HCKTPEQFPF ASPTIPINDFEFPYGTSLNYECRPGYF GKM F | S ISC LE N L VV SS VE DNCR R | 952 |
| 16 | 953 | KSCGPPPE PFNGMVHI NTDTQF GSTVNYSCNEGFRLIGSP | STT C LVSGNNV TV DKK APIC EI | 1014 |
| 17 | 1015 | I SCEPPPT ISNGDFYS NNRTSFHNGTVVTYQCHTGP DGEQLFELVGERS IYCTSKDD Q YGVV SS P PPRC | | 1083 |
| 18 | 1084 | ISTNKCTAPE VENA IRVPGNRSFFSLTEIIRFRCQPGFVMVGSH | T VQC QTNGRV G PKLPHCS R | 1146 |
| 19 | 1147 | V CQPPPE ILHGEH TLSHQDNFSPGQEVFYSCEPSYDLRGAA | S LHC T PQ GDV S PEAPRCT | 1206 |
| 20 | 1207 | V KSCDDFLGQLPHGRVLLPLNL QLGAKVSFVCDEGFRLKGR | SASHCV LA GMK ALVNSS VPVC EQ | 1269 |
| 21 | 1270 | IF CPNPPA ILNGRH TGTPFGDIPYGKEISYACDTHPD RGMT FNLIGE SSIRCTS D PQGNGVV SS P APRC ELS | | 1341 |
| 22 | 1342 | VP AACPHPPK IQNG HYIGGHVSLYLPGMTISYTCDPGYLLVGKG | FIFC T D Q GIV SQLD HYCKE | 1404 |
| 23 | 1405 | VN CSFPLFM NGISKELEMKKVYHYGDYVTLKCEDGYTLEGSPW | SQ C QADDRVDP P LAKCTSR | 1466 |

FIG.6A

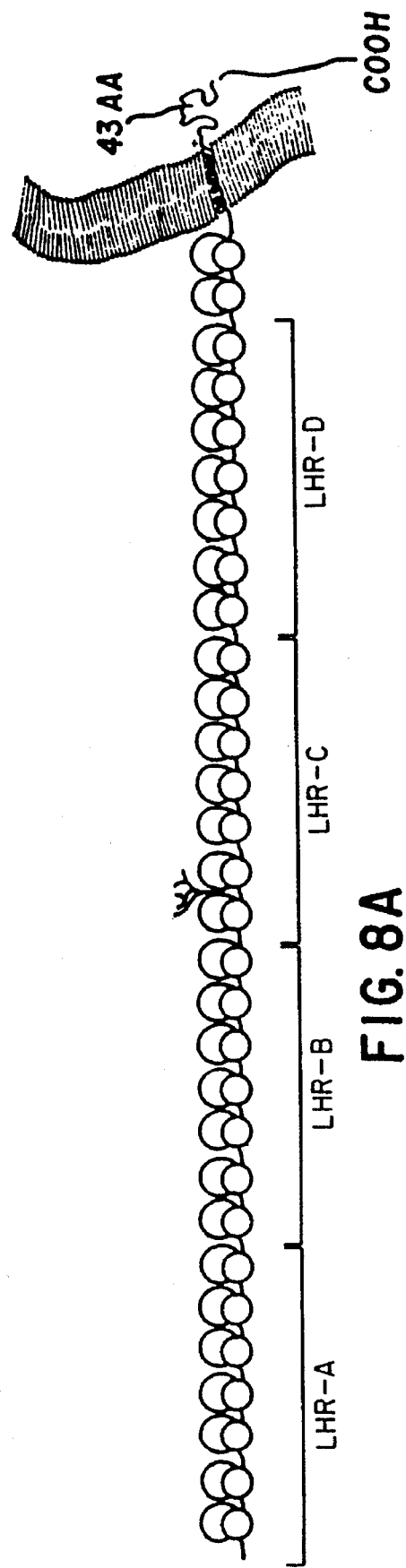
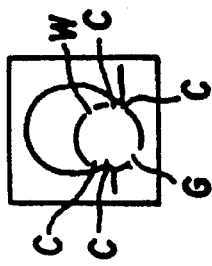
FIG. 8A
FIG. 8B

```
AA #                                                                                     LHR

1   MCLGRMGASSPRSPEPVGPPAPGLPFCCGGSLLAVVVLLALPVAWG                                     SIGNAL

47   QCNAPEWLPFARPTNLTDEFEFPIGTYLNYECRPGYSGRPFSIICLKNSVWTGAKDRCRR                       A
 497   H Q  DHFL  KLKTQ NASD      SK     E Y     T  D L  SSP  V K                        B
 947   H Q  DHFL  KLKTQ NASD      SK     E Y     T  D L  SSP  V K                        C
1400   H KT  QF   S   IPIND     V S         F KM   S E L   SSVE N                        D

107   KSCRNPPDPVNGMVHVIKGIQFGSQIKYSCTKGYRLIGSSSATCIISGDTVIVDNETPICDR                     A
 557     KT           TD  V  RN   T H     H  E L  NAAH STKP    Q                         B
1007     KT           TD  V  RN   T H     H  E L  N AH STKP    Q                         C
1460     GP  E F      INTDT    TVN  NE F     P T LV  NN T  KKA   EI                      D

169   IPCGLPPTTTNGDFISTNRENFHYGSVVTYRCNPGSGGRKVFELVGEPSIYCTSNDDQVGIVSGPAPQCI             A
 619             A                                                                       B
1069             A                           L R                                         C
1522   S EP   S    YN TS N T    Q HT PD EQL      R     K    V  S P R                     D

239   IPNKCTPPNVENGILVSDNRSLFSLNEVVEFRCQPGFVMKGPRRVKCQALNKWEPELPSCSR                     A
 689                                                                                     B
1139                                                                                     C
1592   ST    AE    A R PG   F    T IIR       V SHT Q   TNGR G K  H                       D

301   VCQPPPDVLHAERTQRDKDNFSPGQEVFYSCEPGYDLRGAASMRCTPQGDWSPAAPTCEV                       A
 751                                                                                     B
1201        EI  G H PSHQ                   LH         E R A                              C
1654        EI  G H LSHQ            S      · LH         E R T                            D

361   KSCDDFMGQQLLNGRVLFPVNLQLGAKVDFVCDEGFQLKGSSASYCVLAGMESLWNSSVPVCEQ                   A
 811                                                                                     B
1261      L  PH    L        S        R     V H  V R     N     H                          C
1714      L  PH   L L        S       R   R H      KA                                     D

424   IFCPSPPVIPNGRHTGKPLEVFPFGKAVNYTCDPHPDRGTSFDLIGESTIRCTSDPQGNGVWSSPAPRCGI            A
 874                                                                                     B
1324      N A L    T SGDI Y  EIS       MT N          H                          EL       C
1777      N A L    T FGDI Y  EIS A  T  MT N    S                                EL       D
```

FIG. 10

FIG. 30A
FIG. 30B

FIG. 31A
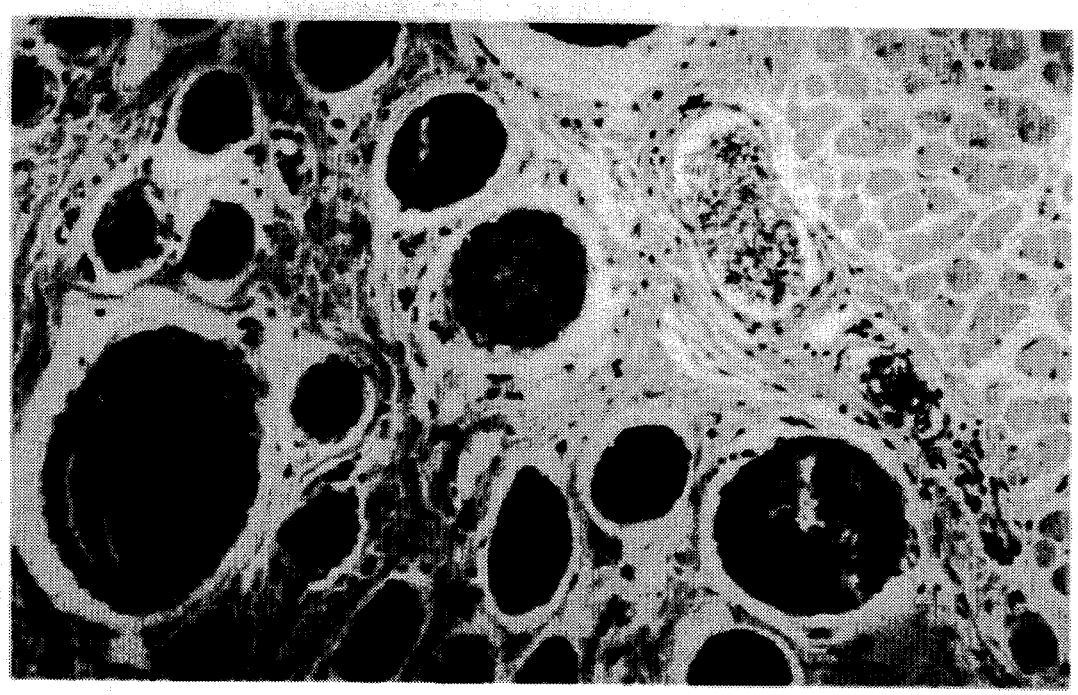
FIG. 31B

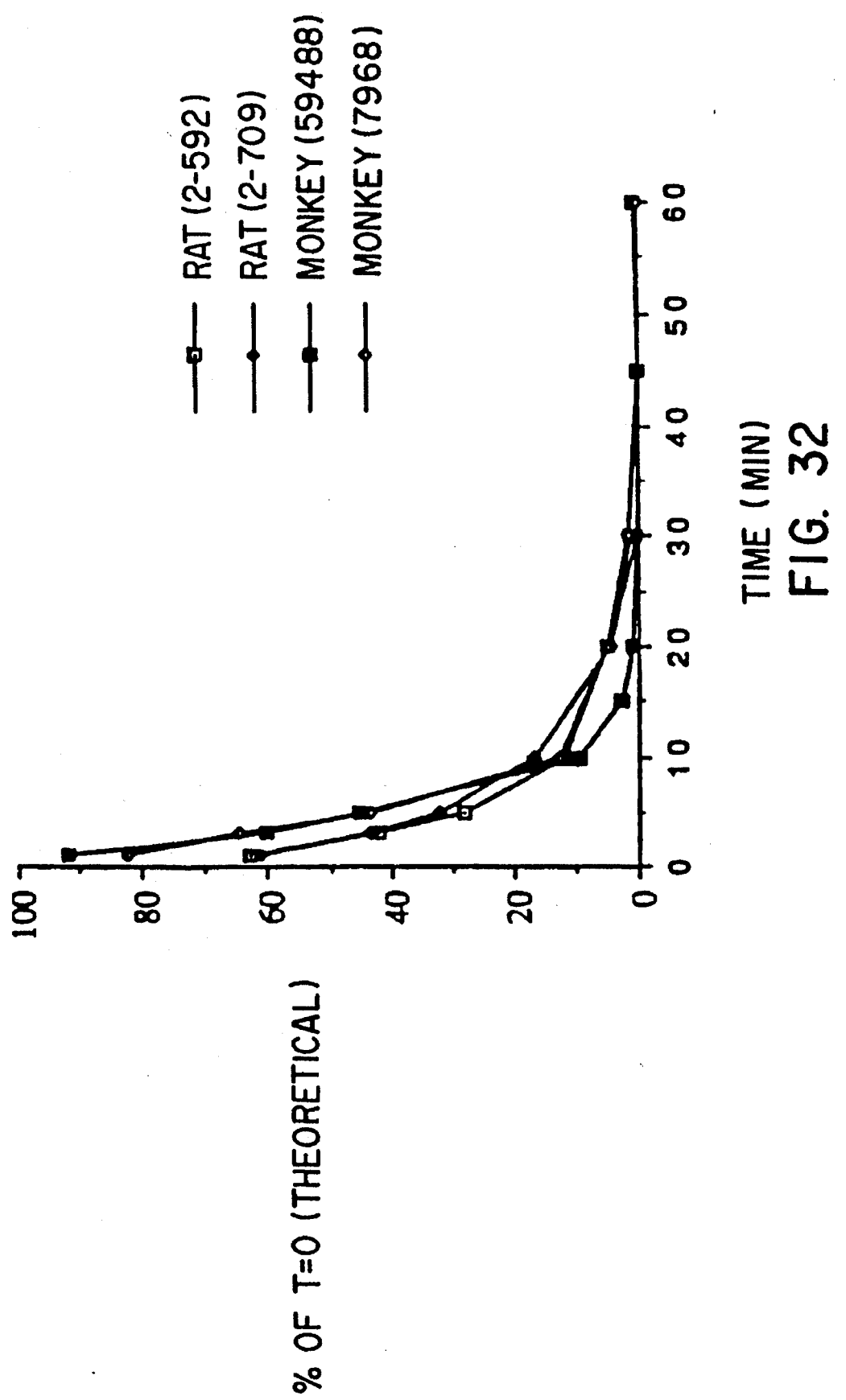

METHOD OF TREATING COMPLEMENT MEDIATED DISORDERS

Pursuant to the provisions of 35 U.S.C. §202(c), it is hereby acknowledged that the Government has certain rights in this invention, which was made in part with funds from the National Institutes of Health. This is a division of application Ser. No. 07/588,128 filed Sep. 24, 1990, now U.S. Pat. No. 5,256,642, which is a continuation-in-part of application Ser. No. 07/412,745 filed Sep. 26, 1989, now abandoned, which is a continuation-in-part of application Ser. No. 07/332,865 filed Apr. 3, 1989, now U.S. Pat. No. 5,212,071, which is a continuation-in-part of application Ser. No. 07/176,532 filed Apr. 1, 1988, now abandoned, each of which is incorporated by reference herein in its entirety.

TABLE OF CONTENTS

1. Introduction
2. Background of the Invention
   2.1. The Complement System
   2.2. The C3b/C4b Complement Receptor (CR1)
   2.3. Abnormalities of CR1 in Human Disease
3. Summary of the Invention
   3.1. Definitions
4. Description of the Figures
5. Detailed Description of the Invention
   5.1. Isolation of the CR1 Gene
   5.2. Expression of the Cloned CR1 Gene
   5.3. Identification and Purification of the Expressed Gene Product
   5.4 Structure of the CR1 Gene and Protein
      5.4.1. Genetic Analysis
      5.4.2. Protein Analysis
   5.5 CR1-Related Derivatives, Analogues, and Peptides
   5.6 Uses of CR1
      5.6.1. Assays and Diagnosis
      5.6.2. Therapy
      5.6.3. Combination Therapy
6. Example: The Cloning and Sequencing of the Human C3b/C4b Receptor (CR1)
   6.1. Materials and Methods
      6.1.1. Isolation and Sequence of CR1 Tryptic Peptides
      6.1.2. Isolation of cDNA Clones and Genomic Clones
      6.1.3. DNA Sequence Analysis
   6.2. Results
      6.2.1. Nucleotide Sequence of the CR1 Gene
      6.2.2. Analysis of the Nucleotide and Amino Acid Sequence of CR1
   6.3. Discussion
7. Example: CR1 5' cDNA Sequences Contain a Fourth Long Homologous Repeat and a Leader Sequence
   7.1. Materials and Methods
      7.1.1. Construction of a cDNA Library
      7.1.2. Isolation of Clones, Probes, and DNA Sequence Analysis
   7.2. Results
   7.3. Discussion
8. Example: Expression of Recombinant Human CR1
   8.1. Construction of pBSABCD Containing the Entire CR1 Coding Sequence
   8.2. Construction and Assay of Plasmid piABCD, a Mammalian Expression Vector Containing the Entire CR1 Coding Sequence
   8.3. Expression of CR1 Fragments
      8.3.1. Construction of Deletion Mutants piBCD, piABD, piACD, piAD, piBD, piCD and piD
      8.3.2. Construction of Deletion Mutants piP1, piE1, piE2, piE-2, piU1, piU-2 and piA/D
9. Example: Identification of C3b and C4b Binding Domains
   9.1. Assays and Results
   9.2. Discussion
10. Example: Demonstration of Factor I Cofactor Activity
11. Example: Expression of Recombinant Soluble CR1
    11.1. Materials and Methods
       11.1.1. Enzyme Digestions
       11.1.2. DNA Fragment Isolations
       11.1.3. Transfection into Mammalian Cells
       11.1.4. CHO Transfectant Cell Culture
       11.1.5. ELISA for the Detection of CR1 Levels
          11.1.5.1. CR1 Standards
          11.1.5.2. CR1 ELISA
    11.2. Genetic Modifications of CR1 Coding Sequences
       11.2.1. Construction of pBSCR1c
       11.2.2. Construction of pBSCR1s
       11.2.3. Construction of pBM-CR1c
       11.2.4. Construction of Deletion Mutants pT-CR1c1, pT-CR1c2, pT-CR1c3, pT-CR1c4, and pT-CR1c5
          11.2.4.1. pT-CR1c1
          11.2.4.2. pT-CR1c2
          11.2.4.3. pT-CR1c3
          11.2.4.4. pT-CR1c4
          11.2.4.5. pT-CR1c5
    11.3. Expression of Soluble CR1
       11.3.1. Construction of pTCS Series of Expression Vectors
          11.3.1.1. Construction of pEAXgpt
          11.3.1.2. Construction of pMLEgpt
          11.3.1.3. Construction of pTCSgpt
          11.3.1.4. Construction of pTCSdhfr
          11.3.1.5. Construction of pTCSneo
       11.3.2. Expression and Assay of Plasmids pBSCR1c, pBSCR1s and pBM-CR1c, Mammalian Expression Vectors Containing Soluble CR1 Coding Sequences
          11.3.2.1. Expression of CR1 Constructs Truncated at Different Positions Within the CR1 cDNA
          11.3.2.2. Expression of sCR1c in Two Different Expression Systems
       11.3.3. Expression and Assay of Plasmids pT-CR1c1, pT-CR1c2, pT-CR1c3, pT-CR1c4, and pT-CR1c5, Mammalian Expression Vectors Containing Soluble CR1 Coding Sequences
12. Example: Production and Purification of Soluble CR1
    12.1. Large Scale Production of Soluble CR1
       12.1.1. Production of sCR1 in Serum-Free Media
       12.1.2. Conclusions
    12.2. Purification of Soluble CR1
       12.2.1. Antibody Affinity Column Purification
          12.2.1.1. Methods
          12.2.1.2. Results
       12.2.2. CR1 Purification by HPLC
          12.2.2.1. Methods
             12.2.2.1.1. Starting Material
             12.2.2.1.2. Cation Exchange HPLC Procedure
             12.2.2.1.3. Anion Exchange HPLC Procedure
             12.2.2.1.4. Western Blot Analysis
          12.2.2.2. Results
          12.2.2.3. Characterization of Purified Soluble CR1
          12.2.2.4. Conclusions 13. Example: Demonstration of In Vitro Activity of Soluble CR1
    13.1. Inhibition of the Neutrophil Oxidative Burst
        13.1.1. Materials and Methods
            13.1.1.1. Materials
            13.1.1.2. Preparation of Neutrophils
            13.1.1.3. Preparation of Yeast Particles
            13.1.1.4. Activation of Neutrophils by Purified C5a
            13.1.1.5. Activation of Neutrophils by Purified C5a in Human Serum or Plasma
            13.1.1.6. Activation of Neutrophils by Yeast Particle-Activated Human Serum or Plasma
        13.1.2. Results
            13.1.2.1. C5a Induces an Oxygen Burst in Human Neutrophils Which Can be Measured Using DCFDA
            13.1.2.2. Human Serum Blocks the Oxygen Burst Effects of Purified C5a on Neutrophils
            13.1.2.3. Heparinized Plasma does not Block the Effects of C5a on Neutrophils
            13.1.2.4. sCR1 Present During Complement Activation Blocks C5a Generation
    13.2. Inhibition of Complement Mediated Hemolysis
        13.2.1. Methods
        13.2.2. Results
    13.3. Inhibition of C3a and C5a Production
        13.3.1. Methods
        13.3.2. Results
14. Example: Demonstration of Functional In Vivo Therapeutic Activity of Soluble CR1
    14.1. Soluble CR1 Demonstrates In Vivo Function in a Reversed Passive Arthus Reaction
        14.1.1. Materials and Methods
        14.1.2. Results
        14.1.3. Effect of Intradermal Administration of Soluble CR1
    14.2. Pharmacokinetics of In Vivo Administered sCR1
    14.3. sCR1 Reduces Infarct Size in Rats with Reperfused Infarcted Myocardium
        14.3.1. Suppression by sCR1 of Complement Activation and Myocardial Reperfusion Injury of Rats
        14.3.2. Conclusions
15. Example: Co-Formulation of Soluble Complement Receptor 1 (sCR-1) with p-Anisoylated Plasminogen, Streptokinase Activator Complex (APSAC)
16. Example: Molecular Definition of the F' Allotype of Human CR1: Loss of a C3b Binding Site is Associated with the Altered Function
    16.1. Introduction
    16.2. Materials and Methods
    16.3. Results
    16.4. Discussion
17. Deposit of Microorganisms

1. INTRODUCTION

The present invention relates to the C3b/C4b receptor (CR1) gene and its encoded protein. The invention also relates to CR1 nucleic acid sequences and fragments thereof comprising 70 nucleotides, and their encoded peptides or proteins comprising 24 amino acids. The invention also provides for the expression of the CR1 protein and fragments thereof. The CR1 nucleic acids and proteins have use in the diagnosis or therapy of disorders involving complement activity, and various inflammatory and immune disorders.

2. BACKGROUND OF THE INVENTION

2.1. The Complement System

The complement system is a group of proteins that constitutes about 10 percent of the globulins in the normal serum of humans (Hood, L. E., et al., 1984, Immunology, 2d Ed., The Benjamin/Cummings Publishing Co., Menlo Park, Calif., p. 339). Complement (C) plays an important role in the mediation of immune and allergic reactions (Rapp, H. J. and Borsos, T, 1970, Molecular Basis of Complement Action, Appleton-Century-Crofts (Meredith), N.Y.). The activation of complement components leads to the generation of a group of factors, including chemotactic peptides that mediate the inflammation associated with complement-dependent diseases. The sequential activation of the complement cascade may occur via the classical pathway involving antigen-antibody complexes, or by an alternative pathway which involves the recognition of certain cell wall polysaccharides. The activities mediated by activated complement proteins include lysis of target cells, chemotaxis, opsonization, stimulation of vascular and other smooth muscle cells, and functional aberrations such as degranulation of mast cells, increased permeability of small blood vessels, directed migration of leukocytes, and activation of B lymphocytes and macrophages (Eisen, H. N., 1974, Immunology, Harper & Row Publishers, Inc. Hagerstown, Md., p. 512).

During proteolytic cascade steps, biologically active peptide fragments, the anaphylatoxins C3a, C4a, and C5a (See WHO Scientific Group, 1977, WHO Tech. Rep. Ser. 606:5 and references cited therein), are released from the third (C3), fourth (C4), and fifth (C5) native complement components (Hugli, T. E., 1981, CRC Crit. Rev. Immunol. 1:321; Bult, H. and Herman, A. G., 1983, Agents Actions 13:405).

2.2. The C3b/C4b Complement Receptor (CR1)

The human C3b/C4b receptor, termed CR1, is present on erythrocytes, monocytes/macrophages, granulocytes, B cells, some T cells, splenic follicular dendritic cells, and glomerular podocytes (Fearon, D. T., 1980, J. Exp. Med. 152:20, Wilson, J. G., et al., 1983, J. Immunol. 131:684; Reynes, M., et al., 1985, J. Immunol. 135:2687; Gelfand, M. C., et al., 1976, N. Engl. J. Med. 295:10; Kazatchkine, M. D., et al., 1982, Clin. Immunol. Immunopathol. 27:170). CR1 specifically binds C3b, C4b, and iC3b. A soluble form of the receptor has been found in plasma that has ligand binding activity and the same molecular weight as membrane-associated CR1 (Yoon, S. H. and Fearon, D. T., 1985, J. Immunol. 134:3332). CR1 binds C3b and C4b that have covalently attached to immune complexes and other complement activators, and the consequences of these interactions depend upon the cell type bearing the receptor (Fearon, D. T. and Wong, W. W., 1983, Ann. Rev. Immunol. 1:243). Erythrocyte CR1 binds immune complexes for transport to the liver (Cornacoff, J. B., et al., 1983, J. Clin. Invest. 71:236; Medof, M. E., et al., 1982, J. Exp. Med. 156:1739) CR1 on neutrophils and monocytes internalizes bound complexes, either by adsorptive endocytosis through coated pits (Fearon, D. T., et al., 1981, J. Exp. Med. 153:1615; Abrahamson, D. R. and Fearon, D. T., 1983, Lab. Invest. 48:162) or by phagocytosis after activation of the receptor by phorbol esters, chemotactic peptides, or proteins that are present in the extracellular matrix, such as fibronectin and laminin (Newman, S. L., et al., 1980, J. Immunol. 125:2236; Wright, S. D. and Silverstein, S. C., 1982, J. Exp. Med. 156:1149; Wright, S. D., et al., 1983, J. Exp. Med. 158:1338). Phosphorylation of CR1 may have a role in the acquisition of phagocytic activity (Changelian, P. S. and Fearon, D. T., 1986, J. Exp. Med. 163:101). The function of CR1 on B lymphocytes is less defined, although treatment of these cells with antibody to CR1 enhanced their response to suboptimal doses of pokeweed mitogen (Daha, M. R., et al., 1983, Immunobiol. 164:227 (Abstr.)). CR1 on follicular dendritic cells may subserve an antigen presentation role (Klaus, G. G. B., et al., 1980, Immunol. Rev. 53:3).

CR1 can also inhibit the classical and alternative pathway C3/C5 convertases and act as a cofactor for the cleavage of C3b and C4b by factor I, indicating that CR1 also has complement regulatory functions in addition to serving as a receptor (Fearon, D. T., 1979, Proc. Natl. Acad. Sci. U.S.A. 76:5867; Iida, K. and Nussenzweig, V., 1981, J. Exp. Med. 153:1138). In the alternative pathway of complement activation, the bimolecular complex C3b,Bb is a C3 activating enzyme (convertase). CR1 (and factor H, at higher concentrations) can bind to C3b and can also promote the dissociation of C3b,Bb. Furthermore, formation of C3b,CR1 (and C3b,H) renders C3b susceptible to irreversible proteolytic inactivation by factor I, resulting in the formation of inactivated C3b (iC3b). In the classical pathway of complement activation, the complex C4b,2a is the C3 convertase. CR1 (and C4 binding protein, C4bp, at higher concentrations) can bind to C4b, and can also promote the dissociation of C4b,2a. The binding renders C4b susceptible to irreversible proteolytic inactivation by factor I through cleavage to C4c and C4d (inactivated complement proteins.)

CR1 is a glycoprotein composed of a single polypeptide chain. Four allotypic forms of CR1 have been found, differing by increments of ~40,000–50,000 daltons molecular weight. The two most common forms, the F and S allotypes, also termed the A and B allotypes, have molecular weights of 250,000 and 290,000 daltons (Dykman, T. R., et al., 1983, Proc. Natl. Acad. Sci. U.S.A. 80:1698; Wong, W. W., et al., 1983, J. Clin. Invest. 72:685), respectively, and two rarer forms have molecular weights of 210,000 and >290,000 daltons (Dykman, T. R., et al., 1984, J. Exp. Med. 159:691; Dykman, T. R., et al., 1985, J. Immunol. 134:1787). These differences apparently represent variations in the polypeptide chain of CR1, rather than glycosylation state, because they were not abolished by treatment of purified receptor protein with endoglycosidase F (Wong, W. W., et al., 1983, J. Clin. Invest. 72:685), and they were observed when receptor allotypes were biosynthesized in the presence of tunicamycin (Lublin, D. M., et al., 1986, J. Biol. Chem. 261:5736). All four CR1 allotypes have C3b-binding activity (Dykman, T. R., et al., 1983, Proc. Natl. Acad. Sci. U.S.A. 80:1698; Wong, W. W., et al., 1983, J. Clin. Invest. 72:685; Dykman, T. R., et al., 1984, J. Exp. Med. 159:691; Dykman T. R., et al., 1985, J. Immunol. 134:1787).

Two nonoverlapping restriction fragments of a CR1 cDNA were shown to crosshybridize under conditions of high stringency (Wong, W. W., et al., 1985, Proc. Natl. Acad. Sci. U.S.A. 82:7711). Both cDNA probes also hybridized to multiple restriction fragments of genomic DNA, most of which were common to both probes (id.). The existence of repetitive coding sequences within CR1 was confirmed by sequence comparisons (Klickstein, L. B., et al., 1985, Complement 2:44 (Abstr.)). In addition, the CR1 gene has been shown to have repetitive intervening sequences by the demonstration of crosshybridization of a genomic probe lacking coding sequences to several genomic restriction fragments (Wong, W. W., et al., 1986, J. Exp. Med. 164:1531). Further, DNA from an individual having the larger S allotype had an additional restriction fragment hybridizing to this genomic probe when compared with DNA from an individual having the F allotype, suggesting that duplication of genomic sequences occurred in association with the higher molecular weight CR1 allele (id.).

CR1 has been shown to have homology to complement receptor type 2 (CR2) (Weis, J. J., et al., 1986, Proc. Natl. Acad. Sci. U.S.A. 83:5639–5643).

2.3. Abnormalities of CR1 in Human Disease

Diminished expression of CR1 on erythrocytes of patients with systemic lupus erythematosus (SLE) has been reported by investigators from several geographic regions, including Japan (Miyakawa et al., 1981, Lancet 2:493–497; Minota et al., 1984, Arthr. Rheum. 27:1329–1335), the United States (Iida et al., 1982, J. Exp. Med. 155:1427–1438; Wilson et al., 1982, N. Engl. J. Med. 307:981–986) and Europe (Walport et al., 1985, Clin. Exp. Immunol. 59:547; Jouvin et al., 1986, Complement 3:88–96; Holme et al., 1986, Clin. Exp. Immunol. 63:41–48). Taken as a group, patients have an average number of receptors per cell that is 50–60% that of normal populations. An early report noted that CR1 number on erythrocytes varied inversely with disease activity, with lowest numbers occurring during periods of most severe manifestations of SLE, and higher numbers being observed during periods of remission in the same patient (Iida et al., 1982, J. Exp. Med. 155:1427–1438). CR1 number has also been found to correlate inversely with serum levels of immune complexes, with serum levels of C3d, and with the amounts of erythrocyte-bound C3dg, perhaps reflecting uptake of complement-activating immune complexes and deposition on the erythrocyte as an "innocent bystander" (Ross et al., 1985, J. Immunol. 135:2005–2014; Holme et al., 1986, Clin. Exp. Immunol. 63:41–48; Walport et al., 1985, Clin. Exp. Immunol. 59:547). A patient with SLE lacking CR1 on erythrocytes was found to have an auto-antibody to CR1 (Wilson et al., 1985, J. Clin. Invest. 76:182–190). Decreased titers of the anti-CR1 antibody coincided with improvement of the patient's clinical condition and with partial reversal of the receptor abnormality. Anti-CR1 antibody has been detected in two other SLE patients (Cook et al., 1986, Clin. Immunol. Immunopathol. 38:135–138). Recently, acquired loss of erythrocyte CR1 in the setting of active SLE and hemolytic anemia was demonstrated by observing the rapid loss of the receptor from transfused erythrocytes (Walport et al., 1987, Clin. Exp. Immunol. 69:501–507).

The relative loss of CR1 from erythrocytes has also been observed in patients with Human Immunodeficiency Virus (HIV) infections (Tausk, F. A., et al., 1986, J. Clin. Invest. 78:977–982) and with lepromatus leprosy (Tausk, F. A., et al., 1985, J. Invest. Dermat. 85:58s–61s).

Abnormalities of complement receptor expression in SLE are not limited to erythrocyte CR1. Relative deficiencies of total cellular CR1 of neutrophils and plasma membrane CR1 of B lymphocytes of the SLE patients have been shown to occur (Wilson et al., 1986, Arthr. Rheum. 29:739–747).

In patients with Type IV SLE nephritis, all detectable CR1 antigen is lost from podocytes, whereas in less severe forms of SLE nephritis and in non-SLE types of proliferative nephritis, including membranoproliferative glomerulonephritis Types I and II, CR1 expression on glomerular podocytes does not differ from normal (Kazatchkine et al., 1982, J. Clin. Invest. 69:900–912; Emancipator et al., 1983, Clin. Immunol. Immunopathol. 27:170–175). However, patients having Type IV SLE nephritis do not have fewer numbers of erythrocyte CR1 than do SLE patients having other types of renal lupus or no nephritis (Jouvin et al., 1986, Complement 3:88–96).

In vivo complement activation up-regulates CR1 expression at the plasma membrane of neutrophils (Lee, J., et al., 1984, Clin. Exp. Immunol. 56:205–214; Moore, F. D., Jr., et al., 1986, N. Engl. J. Med. 314:948–953).

Complement activation has also been associated with disease states involving inflammation. The intestinal inflammation of Crohn's disease is characterized by the lymphoid infiltration of mononuclear and polymorphonuclear leukocytes. It was found recently (Ahrenstedt et al., 1990, New Engl. J. Med. 322:1345–9) that the complement C4 concentration in the jejunal fluid of Crohn's disease patients increased compared to normal controls. Other disease states implicating the complement system in inflammation include thermal injury (burns, frostbite) (Gelfand et al., 1982, J. Clin. Invest. 70:1170; Demling et al., 1989, Surgery 106:52–9), hemodialysis (Deppisch et al., 1990, Kidney Inst. 37:696–706; Kojima et al., 1989, Nippon Jenzo Gakkai Shi 31:91–7), and post pump syndrome in cardiopulmonary bypass (Chenoweth et al., 1981, Complement Inflamm. 3:152–165; Chenoweth et al., 1986, Complement 3:152–165; Salama et al., 1988, N. Engl. J. Med. 318:408–14). Both complement and leukocytes are reported to be implicated in the pathogenesis of adult respiratory distress syndrome (Zilow et al., 1990, Clin. Exp. Immunol. 79:151–57; Langlois et al., 1989, Heart Lung 18:71–84). Activation of the complement system is suggested to be involved in the development of fatal complication in sepsis (Hack et al., 1989, Am. J. Med. 86:20–26) and causes tissue injury in animal models of autoimmune diseases such as immune-complex-induced vasculitis (Cochrane, 1984, Springer Seminar Immunopathol. 7:263), glomerulonephritis (Couser et al., 1985, Kidney Inst. 29:879), hemolytic anemia (Schreiber & Frank, 1972, J. Clin. Invest. 51:575), myasthemis gravis (Lennon et al., 1978, J. Exp. Med. 147:973; Biesecker & Gomez, 1989, J. Immunol. 142:2654), type II collagen-induced arthritis (Watson & Townes, 1985, J. Exp. Med. 162:1878), and experimental allergic neuritis (Feasby et al., 1987, Brain Res. 419:97). The complement system is also involved in hyperacute allograft and hyperacute xenograft rejection (Knechtle et al., 1985, J. Heart Transplant 4(5):541; Guttman, 1974, Transplantation 17:383; Adachi et al., 1987, Trans. Proc. 19(1):1145). Complement activation during immunotherapy with recombinant IL-2 appears to cause the severe toxicity and side effects observed from IL-2 treatment (Thijs et al., 1990, J. Immunol. 144:2419).

Complement may also play a role in diseases involving immune complexes. Immune complexes are found in many pathological states including but not limited to autoimmune diseases such as rheumatoid arthritis or SLE, hematologic malignancies such as AIDS (Tayler et al., 1983, Arthritis Rheum. 26:736–44; Inada et al., 1986, AIDS Research 2:235–247) and disorders involving autoantibodies and/or complement activation (Ross et al., 1985, J. Immunol. 135:2005–14). Inada et al. reported that erythrocyte CR1 has a functional role in the removal of circulating immune complexes in autoimmune patients and may thereby inhibit the disposition of immune complexes within body tissue (Inada et al., 1989, Ann. Rheum. Dis 4:287). A decrease in CR1 activity has been associated with clinical disease state in ARC and AIDS patients (Inada et al., 1986, AIDS Res. 2:235).

3. SUMMARY OF THE INVENTION

The present invention relates to the C3b/C4b receptor (CR1) gene and its encoded protein. The invention also relates to CR1 nucleic acid sequences and fragments thereof comprising 70 nucleotides and their encoded peptides or proteins comprising 24 amino acids. The invention further provides for the expression of the CR1 protein and fragments thereof. The genes and proteins of the invention have uses in diagnosis and therapy of disorders involving complement activity, and various immune system or inflammatory disorders.

In specific embodiments of the present invention detailed in the examples sections infra, the cloning, nucleotide sequence, and deduced amino acid sequence of a full-length CR1 cDNA and fragments thereof are described. The expression of the CR1 protein and fragments thereof is also described. Expression of the CR1 protein and its fragments which contain binding sites for C3b and/or C4b, and which exhibit factor I cofactor activity, is obtained.

Also described in the examples infra are the production and purification of soluble CR1 molecules, which molecules are shown to be therapeutically useful for the treatment of inflammatory reactions and in the reduction of myocardial infarct size and prevention of reperfusion injury.

3.1. Definitions

Ad2 MLP= adenovirus 2 major late promoter

C= complement

C3(ma)= methylamine-treated C3

C4bp= C4 binding protein

CMV= cytomegalovirus

CR1= complement receptor type 1, the C3b/C4b receptor

CR2= complement receptor, type 2

DCFDA= dichlorofluorescin diacetate

HPLC= high performance liquid chromatography iC3b= inactivated C3b

LHR= long homologous repeat mAb= monoclonal antibody

PAGE= polyacrylamide gel electrophoresis

RPAR= reverse passive Arthrus reaction

SCR= short consensus repeat sCR1= soluble CR1 molecule

4. DESCRIPTION OF THE FIGURES

FIG. 1(A through P). Nucleotide and amino acid sequence of the entire CR1 coding region. The sequence begins with the first nucleotide following the octamer EcoRI linker in clone λT109.1. Nucleotide number 1531 of this sequence is the first nucleotide 5' of nucleotide number 1 of the sequence depicted in FIGS. 3A–3D. The strand corresponding to the mRNA is shown, with the deduced amino acid sequence presented below. The putative signal sequence encoded by nucleotide numbers 28–147 is bracketed.

FIG. 2. Restriction map of 5.5 kb of human CR1 cDNA. The black bar indicates the cDNA, restriction sites are H, HindIII; B, BamHI; R, EcoRI; P, PstI; A, ApaI; S, SacI; G, BglII; K, KpnI. The cDNA clones from which the sequence was derived are shown below the map. The arrows indicate the direction and extent of sequence analysis by the dideoxynucleotide chain termination method. cDNA clones were oriented on the basis of restriction maps and overlapping sequence identity.

FIG. 3(A through D). Nucleotide sequence of 5.5 kb of human CR1 cDNA. The strand corresponding to the mRNA is shown and base number 1 (corresponding to base number 1532 of FIG. 1) is the first base after the EcoRI linker in the most 5' clone. The stop codon is underlined. The 110-bp sequence in the box was found between nucleotides 147 and 148 (arrow) and is believed to represent a portion of an intervening sequence.

Figure 4:
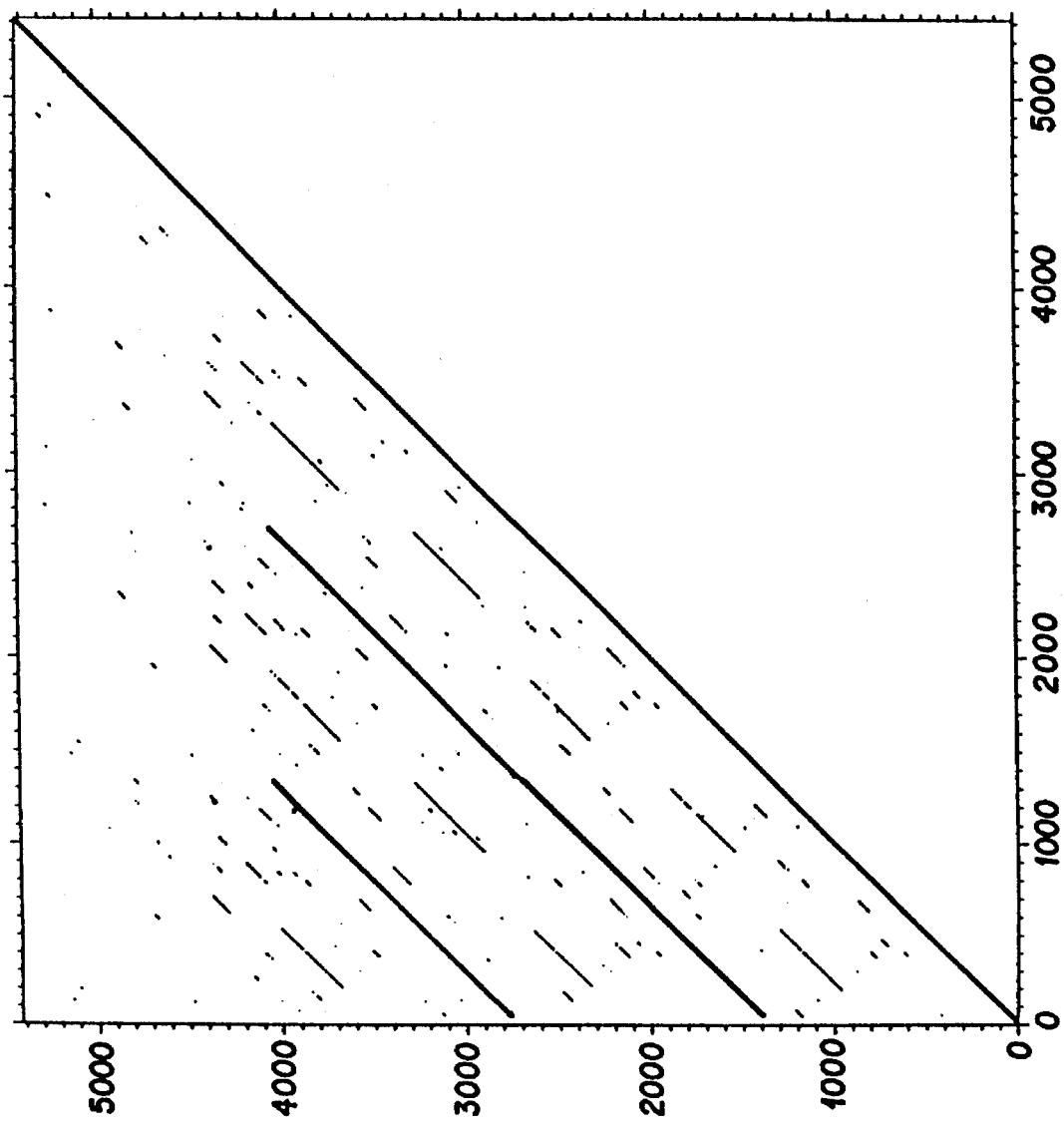

FIG. 4. Dot matrix analysis of the nucleotide sequence of 5.5 kb of human CR1 cDNA. A dot was plotted if there was at least a 40 bp of 90 bp match. The dark line bisecting the square diagonally indicates the identity of the sequence with itself. The two additional parallel dark lines 1.35 and 2.7 kb from the line of identity represent two tandem, direct long homologous repeats (LHRs) of 1.35 kb each. The six lighter, dashed lines between two LHRs correspond to short consensus repeats of ~0.2 kb. The short consensus repeats (SCRs) extend 0.4 kb beyond the long homologous repeats.

Figure 5A:
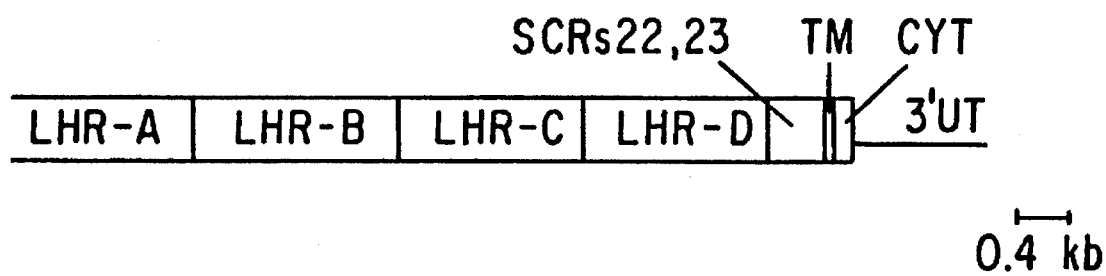

FIG. 5 (A through C). (A) A schematic diagram of the CR1 protein. (TM) transmembrane region, (Cyt) cytoplasmic region, (3'UT) 3' untranslated sequence. (B) Deduced amino acid sequence of human CR1. Each residue is shown in the one letter code (Lehninger, A. L., 1975, Biochemistry, 2d Ed., Worth Publishers, Inc., New York, p. 72). The residues in the long homologous repeats have been aligned to illustrate their homology. All the residues in LHR-B are shown, and a residue is given for LHR-C and LHR-D only where it is different from that in LHR-B. (C) A hydropathy profile is aligned under the COOH-terminus of the protein to illustrate the presumptive transmembrane region. A stretch of four positively charged residues immediately after the hydrophobic sequence is overlined. The six amino acid sequence with 67% homology to the site of protein kinase C phosphorylation in the epidermal growth factor receptor is underlined.

FIG. 6(A through B). (A) Alignment of the SCRs of CR1. The repeats are numbered 1–23 from $NH_2$-terminal to COOH-terminal. Spaces have been introduced to maximize the alignment. A residue is deemed conserved if it, or a conservative substitution, is present in at least half of the SCRs. The horizontal arrow indicates an SCR that was also sequenced from CR1 genomic clone 2.38 and is encoded by a single exon. (B) Restriction map, sequencing strategy, and partial sequence of genomic clone λ2.38. The restriction sites are: (B) BamHI, (S) SacI, (E) EcoRV, (K) KpnI, (P) PstI. The horizontal arrow indicates direction and extent of sequencing and the vertical arrows indicate the exon-intron boundaries.

Figure 7:
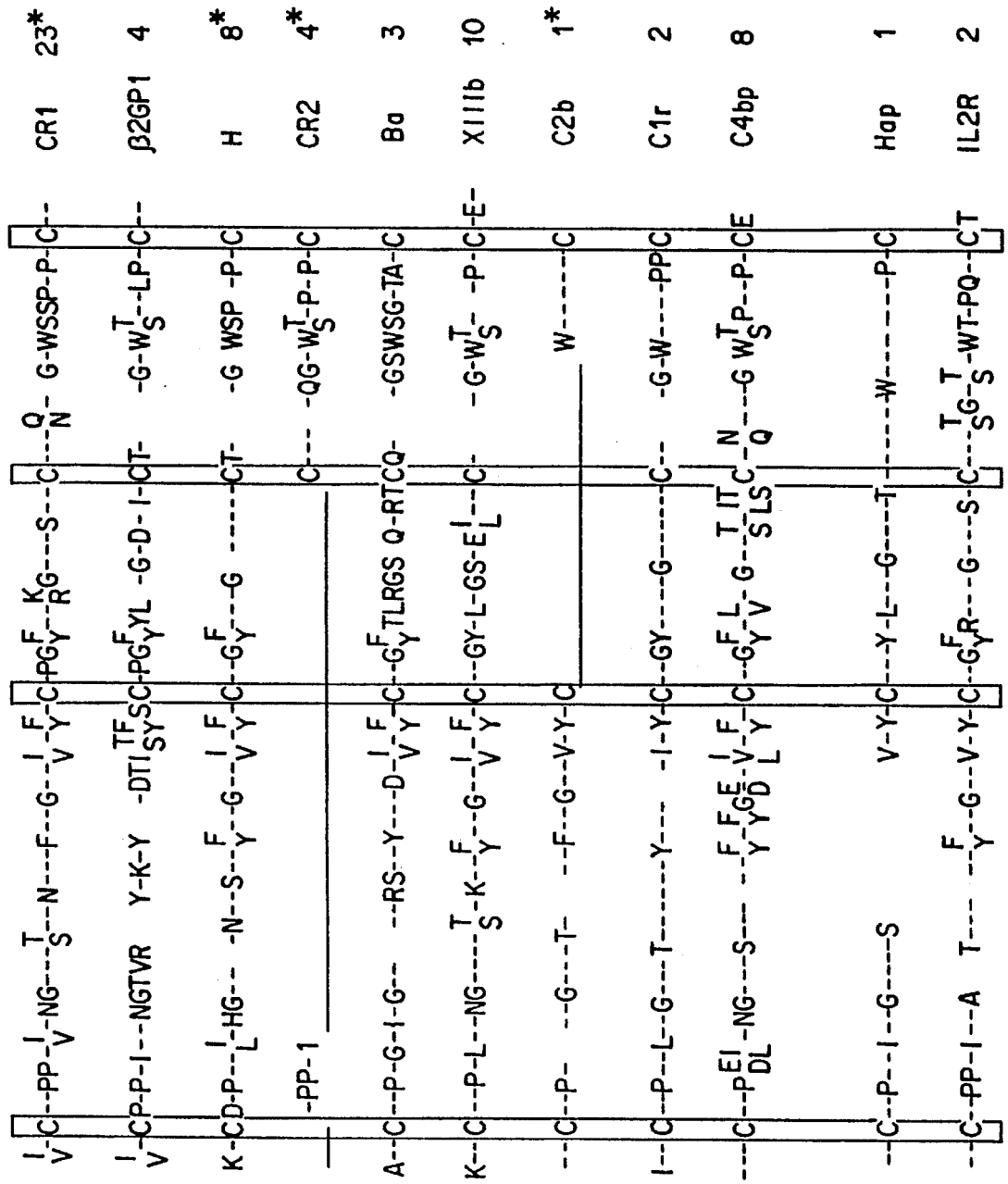

FIG. 7. Alignment of the consensus sequence of the SCRs of proteins known to have this structure. Spaces were introduced to maximize the alignment. A residue is deemed conserved as in FIG. 5, except for those proteins having only one or two SCRs, in which a residue is conserved if it is present in at least half of the other proteins. The dashes correspond to nonconserved positions. The underlined portions of CR2 and C2b indicate that no sequence information has been published in this region for these proteins. The boxes indicate the invariant half-cystines. The number to the right of the sequence represents the number of SCRs used to generate the consensus sequence. The protein abbreviations and references for the sequence data used to determine the consensus sequences are: (CR1) complement receptor type 1, (H) factor H (Kristensen, T., et al., 1986, J. Immunol. 136:3407), (C4bp) C4 binding protein (Chung, L. P., et al., 1985, Biochem. J. 230:133), (CR2) complement receptor type 2 (Weis, J. J., et al., 1986, Proc. Natl. Acad. Sci. U.S.A. 83:5639), (Ba) proteolytic fragment of factor B (Morley, B. J. and Campbell, R. D., 1984, EMBO J. 3:153), (C2b) proteolytic fragment of C2 (Gagnon, J., 1984, Philos. Trans. R. Soc. Lond. B Biol. Sci. 306:301), (C1r) r subunit of C1 (Leytus, S. P., et al., 1986, Biochemistry 25:4855), (XIIIb) b subunit of factor XIII (Ichinose, A., et al., 1986, Biochemistry 25:4633), (β2GP1) β2 glycoprotein I (Lozier, J., et al., 1984, Proc. Natl., Acad. Sci. U.S.A. 81:3640), (Hap) haptoglobin (Kurosky, A., et al., 1980, Proc. Natl. Acad. Sci. U.S.A. 77:3388), (IL-2-R) the interleukin-2 receptor (Leonard, W. J., et al., 1985, Science 230:633). Asterisk indicates that incomplete sequence is available.

FIG. 8(A through B). (A) Schematic diagram of the proposed structure of human CR1. The COOH-terminal cytoplasmic region is on the right side of the lipid bilayer. 30 SCRs are arrayed linearly on the extracellular side of the plasma membrane. The brackets indicate the LHRs. (B) The inset is an enlargement of a single SCR to illustrate the triple loop structure.

Figure 9:
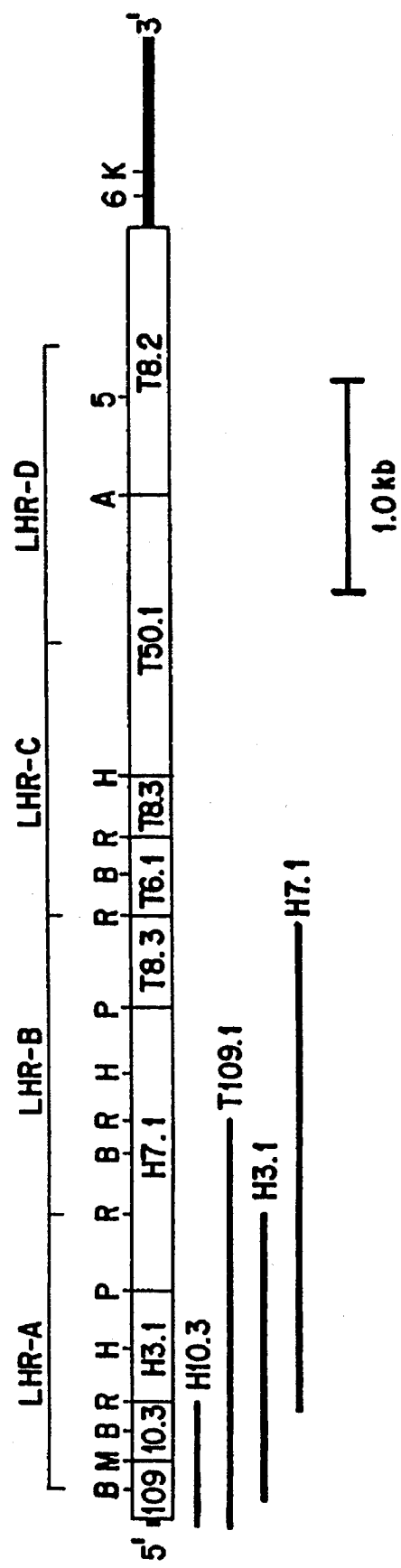

FIG. 9. Restriction map of the insert of the plasmid, pBSABCD, encoding human CR1. Indicated within the box delineating the region containing the coding sequence are the nine fragments of eight cDNA clones that were ligated to form the CR1 construct. The brackets designate the positions of LHR-A, -B, -C, and -D, respectively. The lines below the box represent the positions of the newly isolated 5' cDNA clones. The restriction sites are: A, ApaI, B, BamHI; G, BglII; H, HindIII; K, KpnI; M, BspMII; P, PstI; R, EcoRI; and S, SacI.

FIG. 10. The deduced amino acid sequence of the 5' cDNA clones encoding the seven SCRs of LHR-A, and alignment of this sequence with the corresponding SCRs of LHR-B, -C, and -D. The four cysteines that are conserved in each SCR are underlined. A residue is shown for LHR-B, -C and -D only where it is different from that in LHR-A.

FIG. 11(A through B). (A) Restriction maps of the expression plasmids, (B) piABCD and pMTABCD. $Pm_{MT}$ and $p_{CMV}$ represent the murine metallothionein and cytomegalovirus immediate early promoters, respectively.

FIG. 12(a through d). Analysis by phase contrast (panels a and c) and immunofluorescent (panels b and d) microscopy of COS cells transfected with piABCD (panels a and b) and CDM8 vector alone (panels c and d), respectively, and indirectly stained with YZ1 monoclonal anti-CR1 antibody and fluorescein-labelled goat anti-mouse F(ab')$_2$.

FIG. 13(a through d). Analysis of C3b- and C4b-binding by COS cells expressing recombinant CR1. COS cells transfected with piABCD (panels a and c) or with the CDM8 vector alone (panels b and d) were incubated with EAC4b(lim),3b (panels a and b) or with EAC4b (panels c and d) and examined for formation of rosettes by phase contrast microscopy.

Figure 14:

FIG. 14. Analysis of recombinant CR1 expressed by transfected COS cells by SDS-PAGE. COS cells transfected with the CDM8 vector alone (lanes 1 and 4) and with piABCD (lanes 2 and 5), respectively, and erythrocytes from an individual having the F and S allotypes of CR1 (lanes 3 and 6) were surface labelled with $^{125}$I. Detergent lysates of the cells were sequentially immunoadsorbed with Sepharose-UPC 10 (lanes 1–3) and Sepharose-YZ1 (lanes 4–6) and the eluates analyzed by SDS-PAGE under non-reducing conditions and autoradiography.

Figure 15:
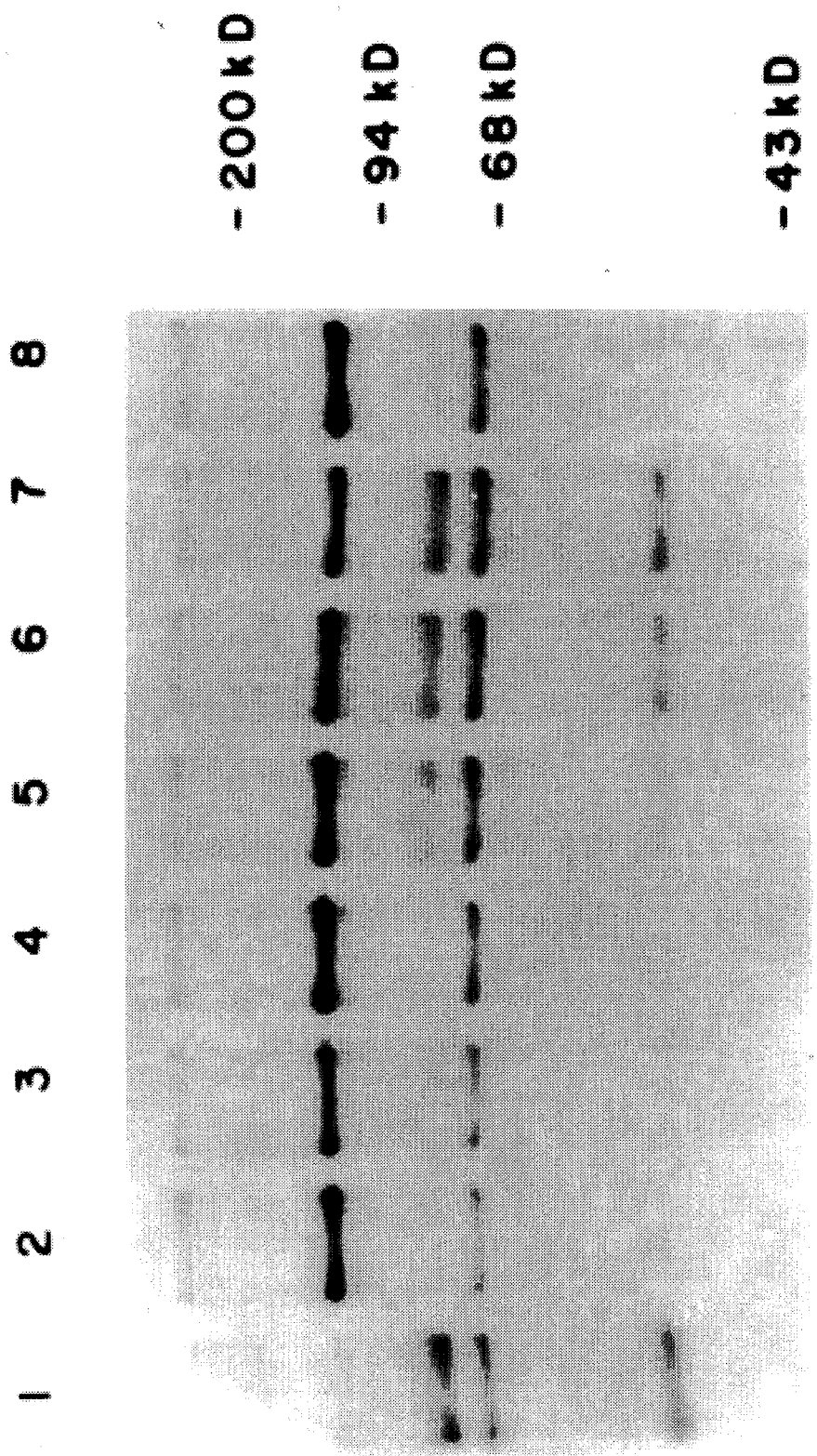

FIG. 15. Cleavage of $^{125}$I-C3(ma) by factor I in the presence of immunoimmobilized recombinant CR1. Replicate samples of $^{125}$I-C3(ma) were treated with factor I in the presence of factor H (lane 1), Sepharose-UPC10 preincubated with the lysate of COS cells transfected with the CDM8 vector alone (lane 2), Sepharose-UPC10 preincubated with the lysate of piABCD-transfected COS cells (lane 3), Sepharose-YZ1 preincubated with the lysate of CDM8-transfected COS cells (lane 4), and 6 μl (lane 5), 12 μl (lane 6) and 25 μl (lane 7) of Sepharose-YZ1 that had been preincubated with the lysate of piABCD-transfected COS cells. Samples of $^{125}$I-labelled C3(ma) were also treated in the absence of factor I with 25 µl of Sepharose-YZ1 that had been preincubated with the lysate of piABCD-transfected COS cells (lane 8). After reduction, the $^{125}$I-C3(ma) was analyzed by SDS-PAGE and autoradiography.

Figure 16:
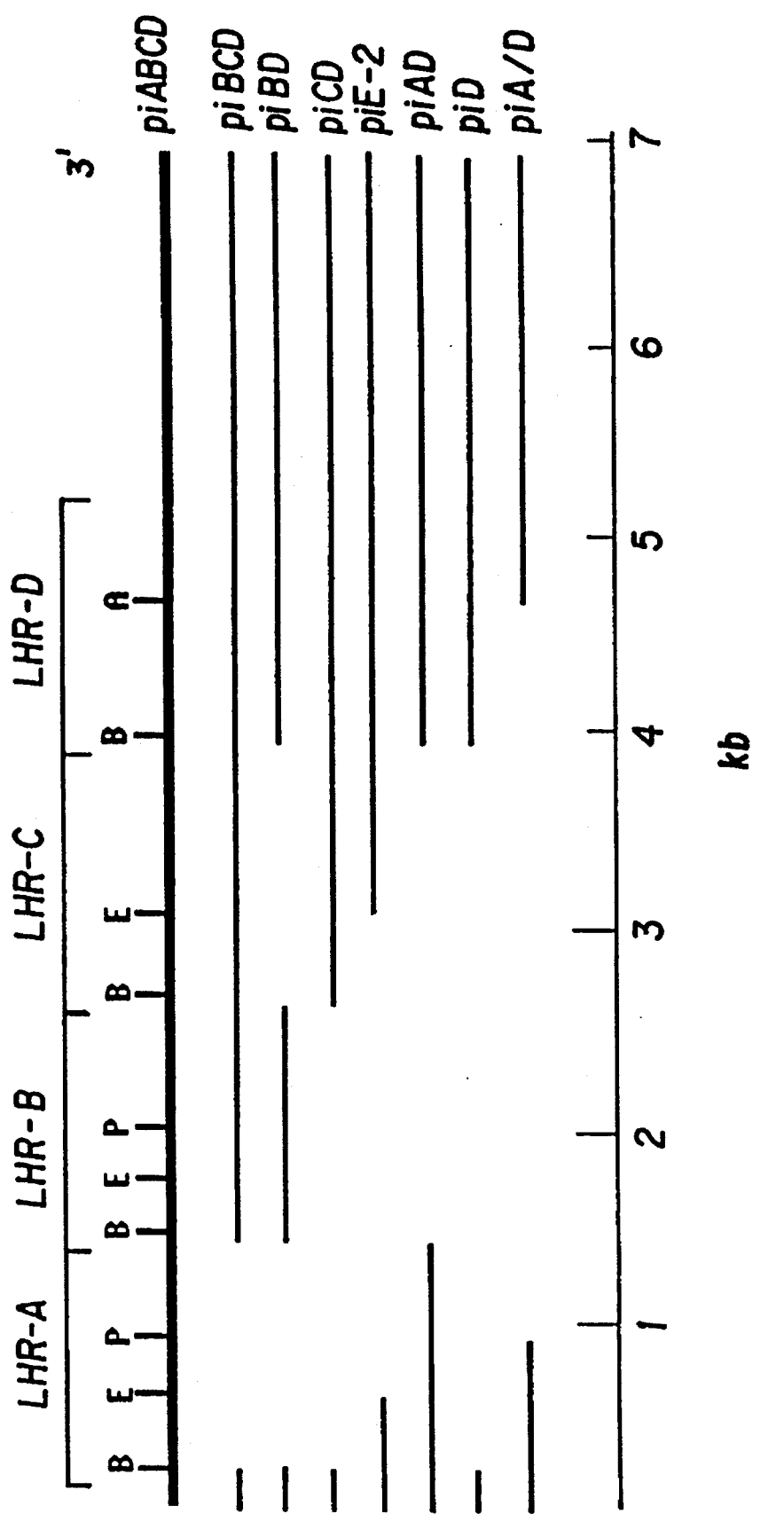

FIG. 16. The cDNA constructs encoding the CR1 deletion mutants. The positions of the cDNA segments encoding the four LHRs are indicated by the brackets above the full length piABCD construct on which are shown the restriction sites used for preparation of the deletion mutants. The cDNA restriction fragments remaining in each of the mutants are indicated by the solid lines. The restriction sites are: A, ApaI; B, BsmI; E, BstEII; and P, PstI.

Figure 17:
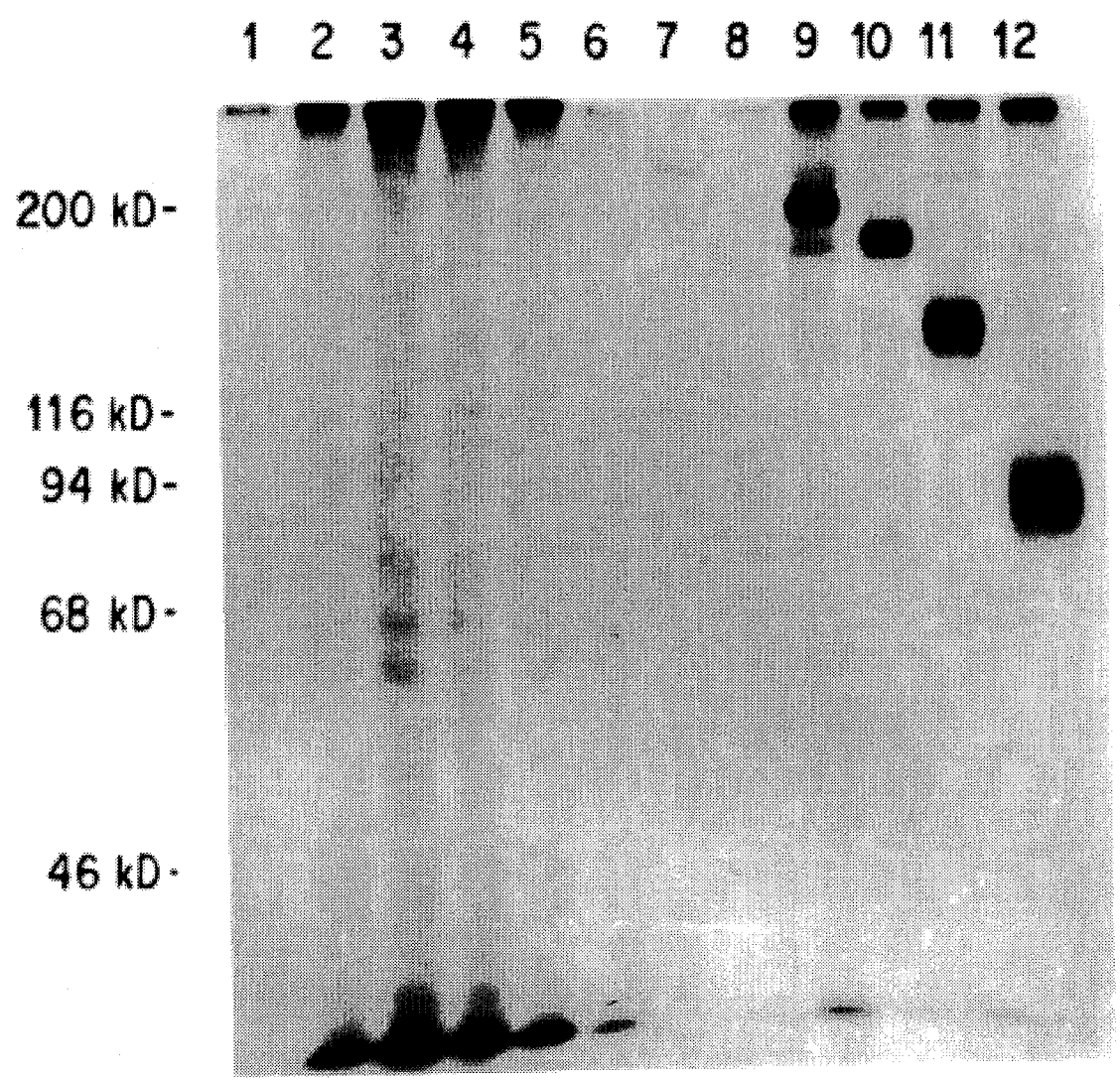

FIG. 17. Comparison of recombinant deletion mutants of CR1 with the wild type F and S allotypes of CR1. Detergent lysates of $^{125}$I-surface labelled erythrocytes (lanes 1 and 7) and COS cells transfected with CDM8 vector alone (lanes 2 and 8), piABCD (lanes 3 and 9), piBCD (lanes 4 and 10), piCD (lanes 5 and 11) and piD (lanes 6 and 12), respectively, were immunoprecipitated with Sepharose-UPC10 anti-levan antibody (lanes 1–6), Sepharose-YZ-1 anti-CR1 monoclonal antibody (lanes 7–11) and rabbit anti-CR1 antibody and Sepharose-protein A (lane 12), respectively. The eluates were subjected to SDS-PAGE under reducing conditions and autoradiography.

Figure 18:
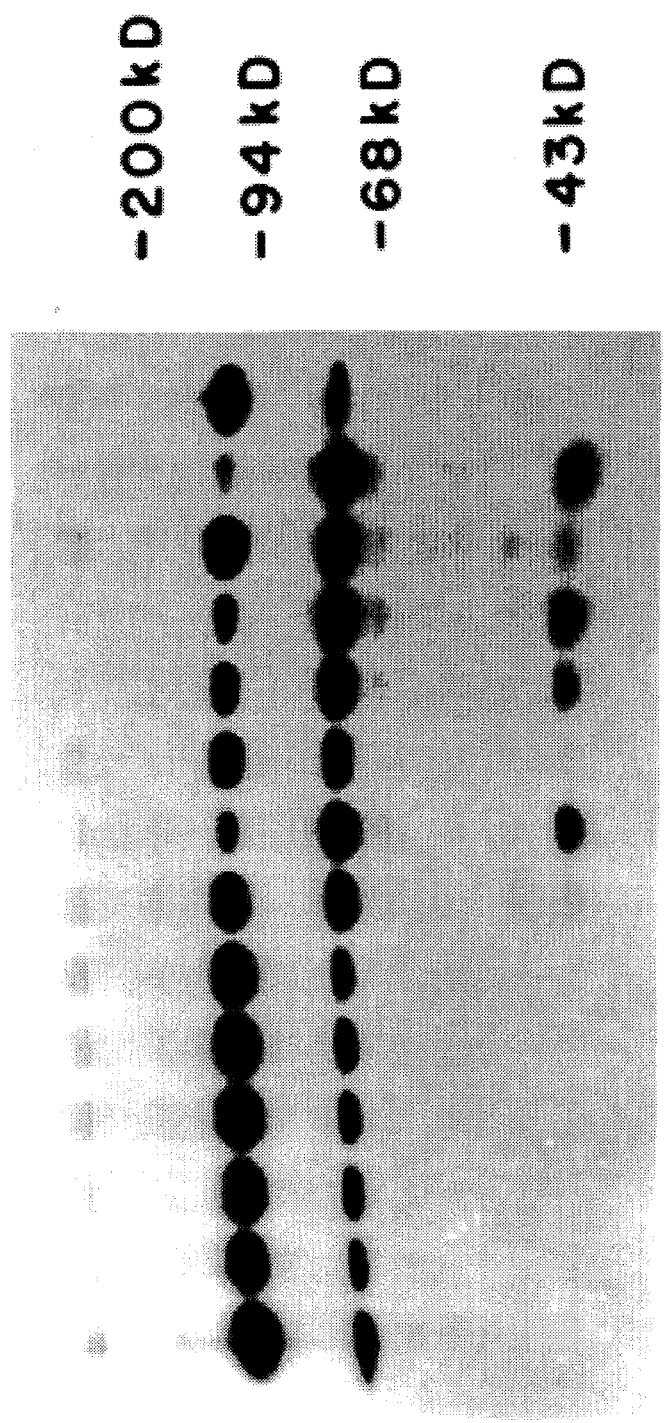

FIG. 18. Cleavage of $^{125}$I-C3(ma) by factor I in the presence of COS cells expressing full length and deletion mutants of CR1. Replicate samples of $^{125}$I-C3(ma) were incubated with COS cells transfected with the CDM8 vector alone (lanes 1 and 7), piABCD (lanes 2 and 8), piAD (lanes 3 and 9), piBD (lanes 4 and 10), piCD (lanes 5 and 11), and piD (lanes 6 and 12), respectively, in the absence (lanes 1–6) or presence (lanes 7–12) of factor I. Samples of $^{125}$I-C3(ma) also were incubated with factor H and factor I (lane 13) and with factor I alone (lane 14), respectively. After reduction, the $^{125}$I-C3(ma) was analyzed by SDS-PAGE and autoradiography.

Figure 19:
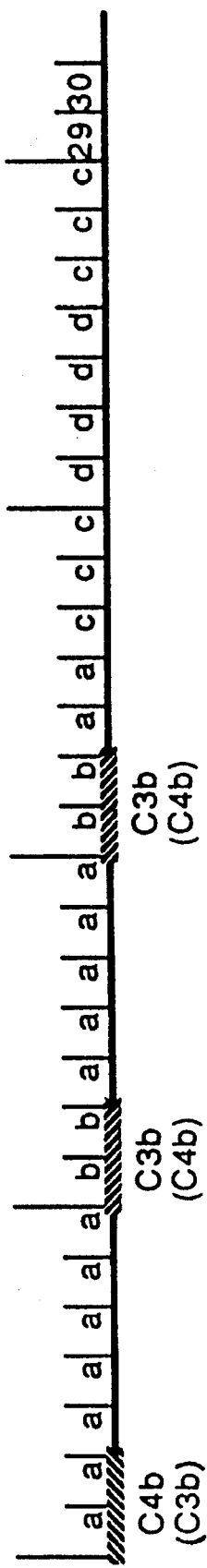

FIG. 19. Schematic model depicting the types of SCRs comprising each LHR of CR1, and the predicted sites determining the specificities of the receptor for C3b and C4b. The secondary binding specificities of these are indicated by the parentheses.

Figure 20:
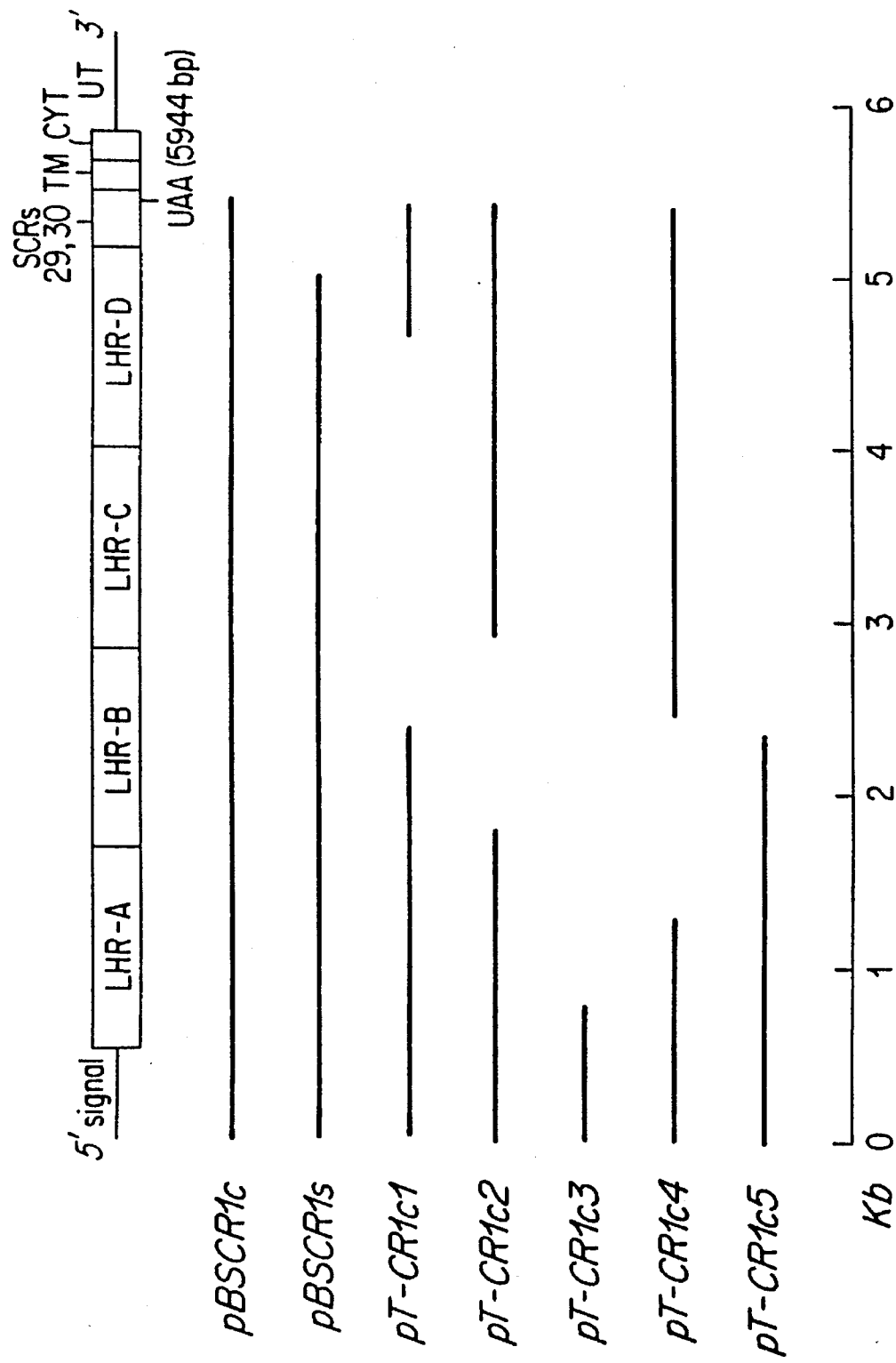

FIG. 20. A schematic diagram illustrating the DNA regions remaining in the soluble CR1 DNA constructs. The regions of the full length CR1 cDNA are indicated by the boxes along the top of the figure.

Figure 21:
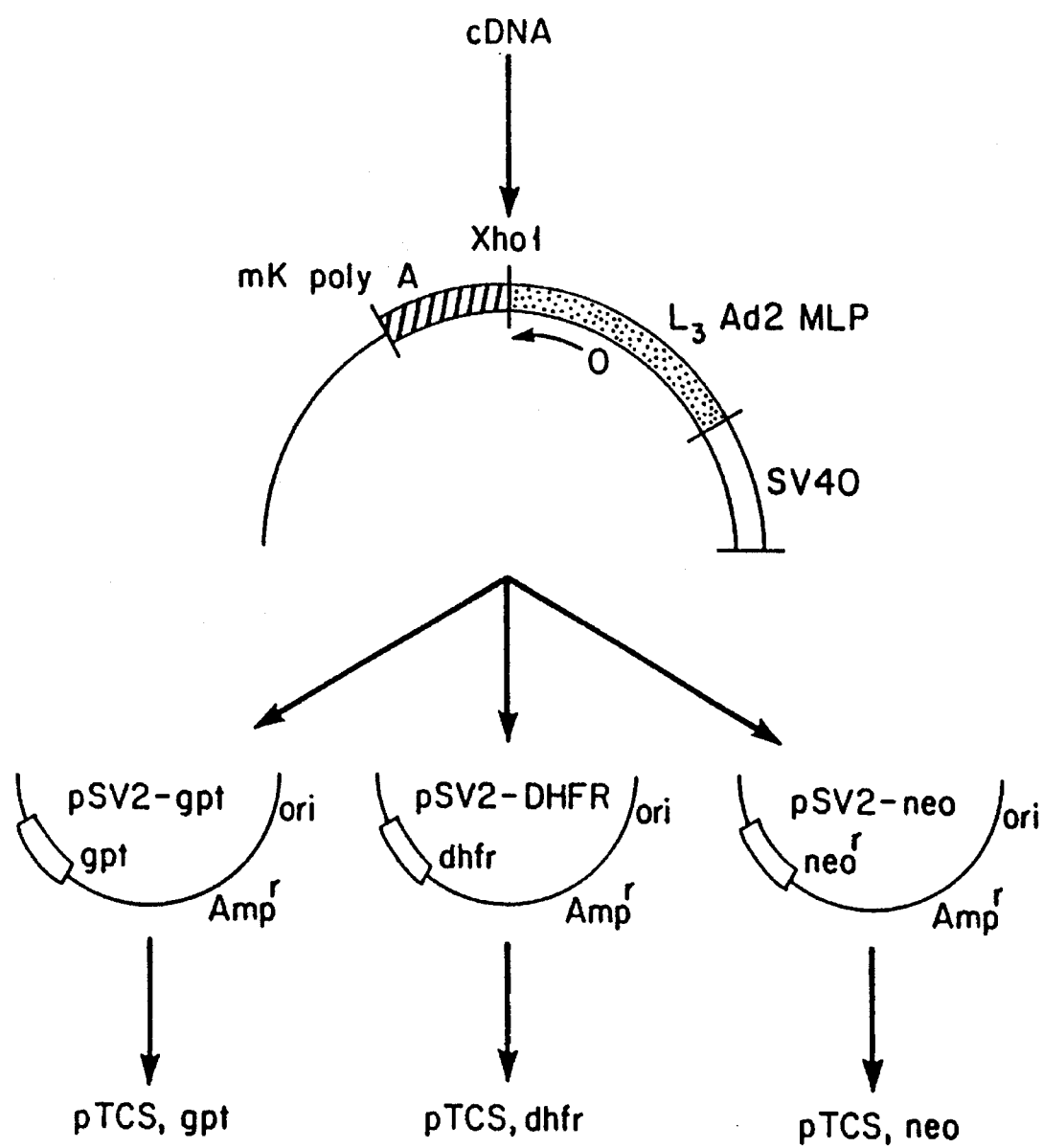

FIG. 21. A schematic diagram illustrating the major elements in the pTCS series of expression vectors.

Figure 22:
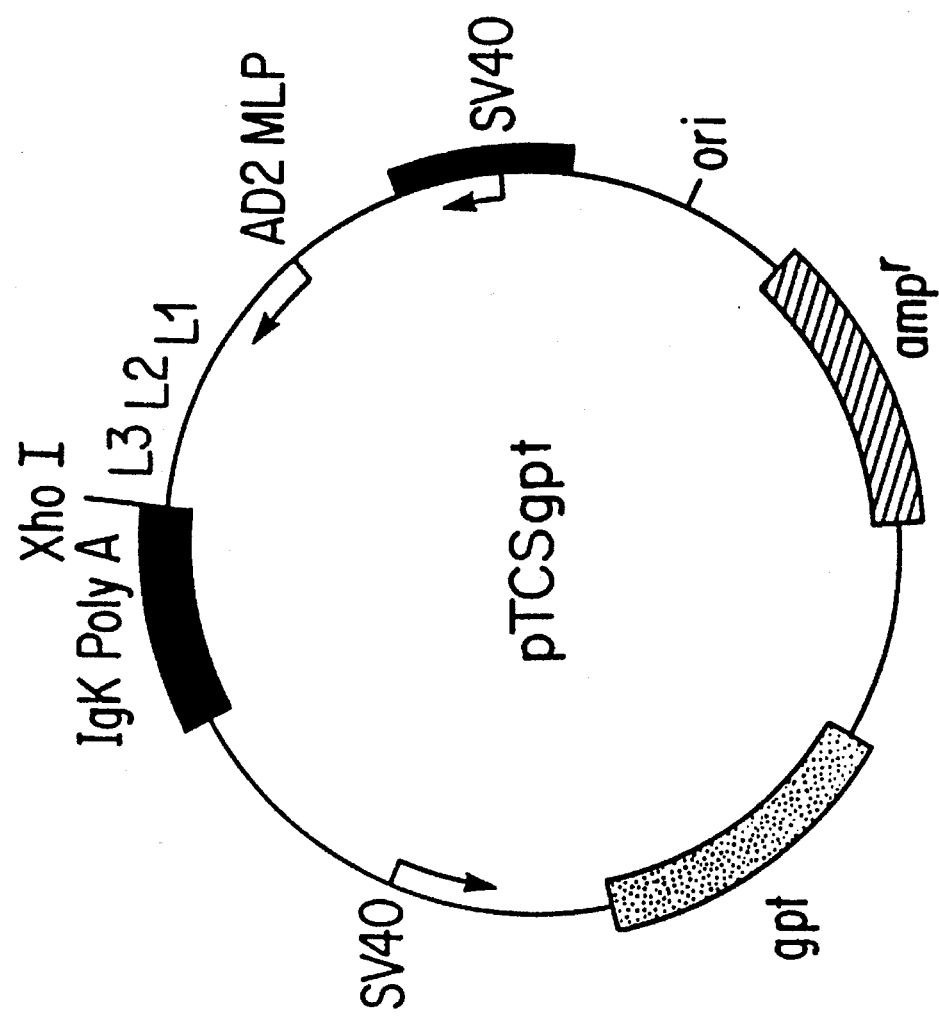

FIG. 22. A diagram of the expression vector pTCSgpt. The polyadenylation site is from the murine Ig kappa sequences (NBRF Nucleic database accession #Kcms, bp 1306–1714); the Ad2 MLP and tripartite regions are from the Ad2 sequence (NBRF Nucleic database accession #Gdad2, bp 5791–6069); the SV40 early promoter is from the SV40 genome (NBRF Nucleic Database accession #GSV40W). The gpt gene, ampicillin gene and bacterial origin of replication are from the vector pSV2gpt (ATCC Accession No. 37145).

Figure 23:
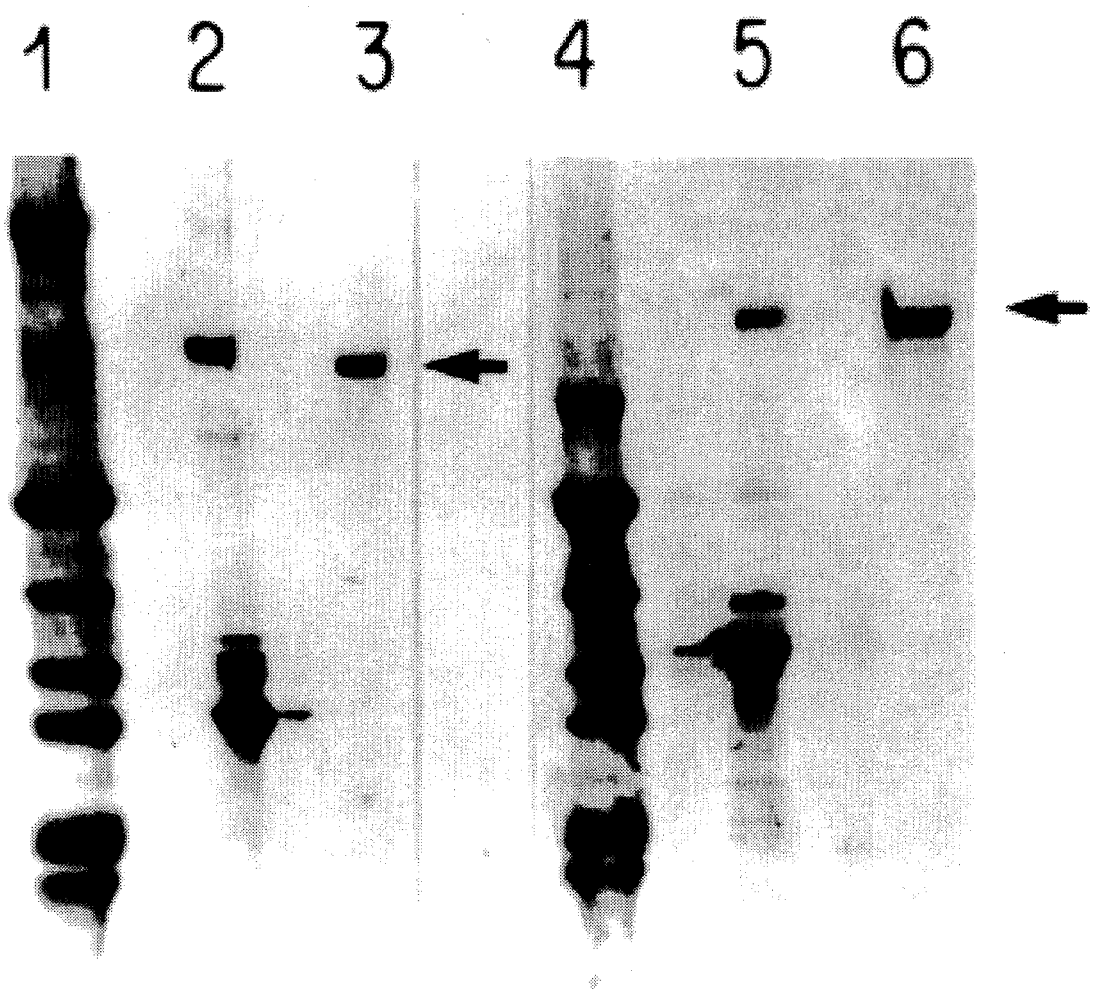

FIG. 23. 4–20% SDS-PAGE of antibody affinity purified sCR1. Non-reducing (lanes 1, 2, 3) and reducing (lanes 4, 5, 6) conditions. Lanes 1, 3: molecular weight markers; lanes 3, 5: cell culture supernatant starting material; lanes 4, 6: sCR1 purified by antibody affinity chromatography.

Figure 24:
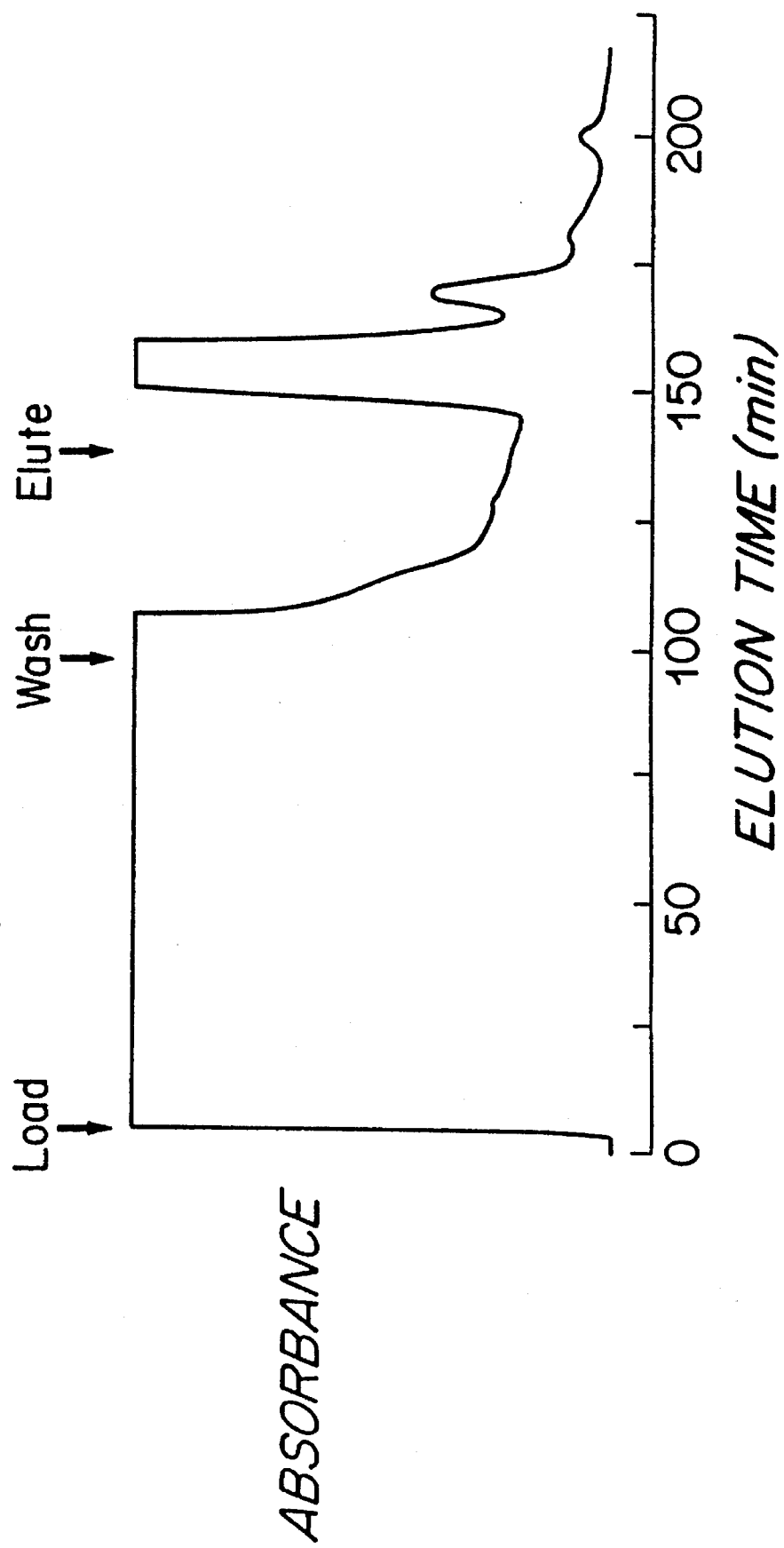

FIG. 24. Cation exchange HPLC elution profile. Eluted protein was monitored by absorbance at 280 nm (y-axis). The absorbance of both the flow-through (0–100 minutes) and the eluted sCR1 (150–165 minutes) were both offscale. The x-axis represents the elution time in minutes.

Figure 25:
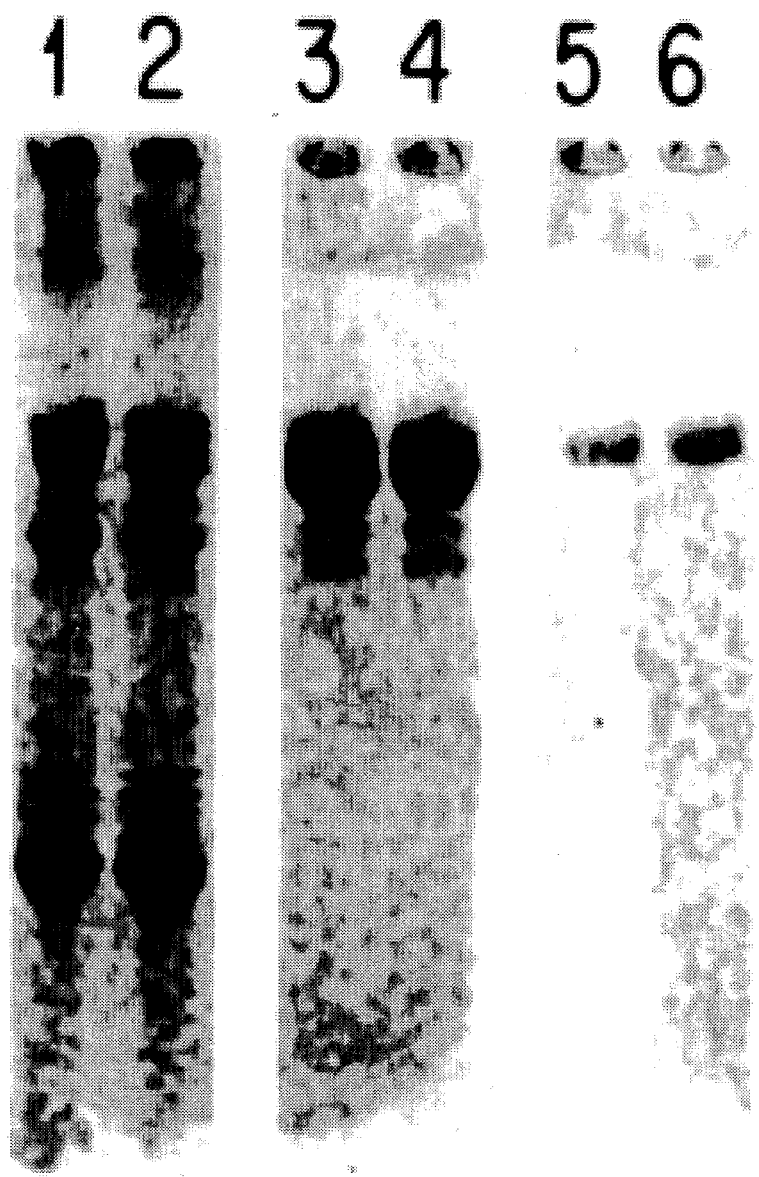
Figure 26A:
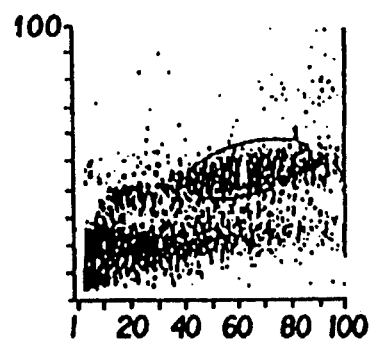
Figure 26B:
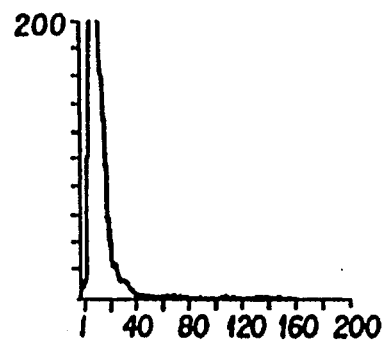
Figure 26C:
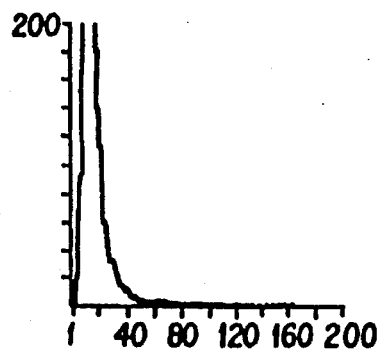
Figure 26D:
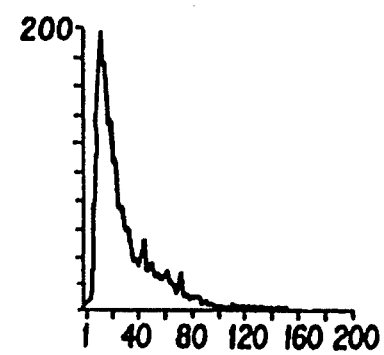
Figure 26E:
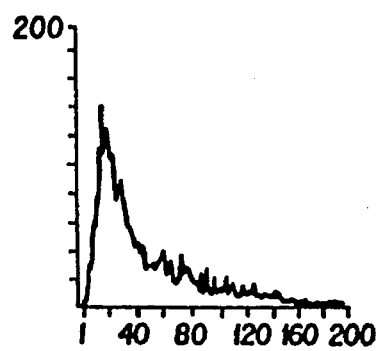
Figure 26F:
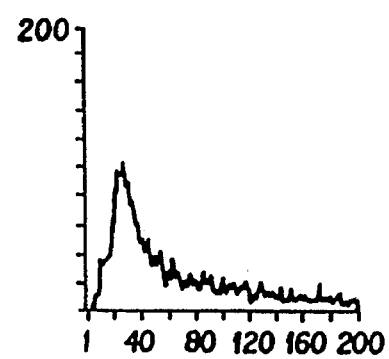
Figure 26G:
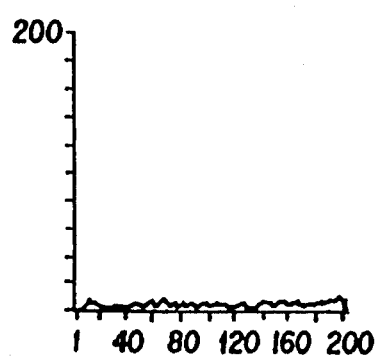

FIG. 25. 4–20% gradient SDS-PAGE of cation and anion exchange HPLC purified sCR1. SDS-polyacryamide gels were run under non-reducing conditions. Lane 1, an aliquot of bioreactor supernatant; lane 2, an aliquot of bioreactor supernatant dialyzed against cation HPLC starting buffer; lane 3, an aliquot of the eluted sCR1 peak from a cation exchange HPLC column; lane 4, an aliquot of the sCR1 peak from the cation exchange HPLC column dialyzed into starting buffer for anion HPLC; lanes 5 and 6, aliquots of two different fractions of eluted sCR1 from anion HPLC.

FIG. 26(a through g). C5a induction of an oxygen burst in human neutrophils. Following a C5a induced oxygen burst, DCFDA became oxidized and brightly fluoresced. Fluorescent intensity, as determined by flow cytometry, is measured on the x-axis and number of cells on the y-axis. Panel a, profile and gate for the cells; panel b, 0 minutes after C5a addition; panel c, 1 minute; panel d, 2 minutes; panel e, 3 minutes; panel f, 4 minutes; panel g, 20 minutes. This DCFDA assay gives a sensitive indication of C5a.

Figure 27A:
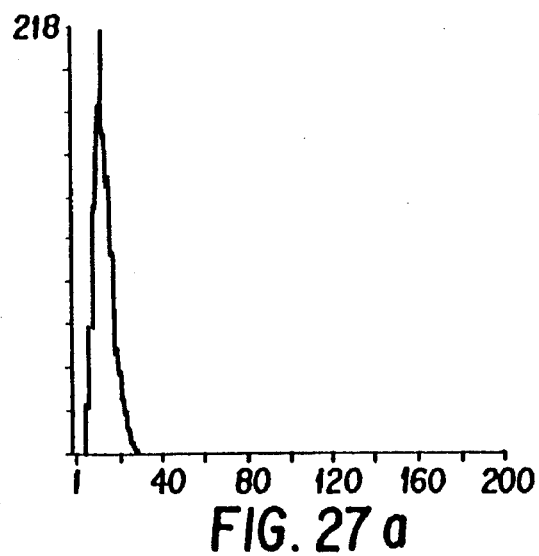
Figure 27B:
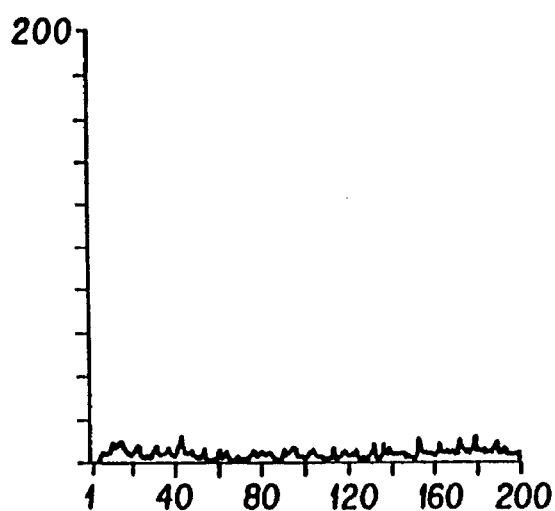
Figure 27C:
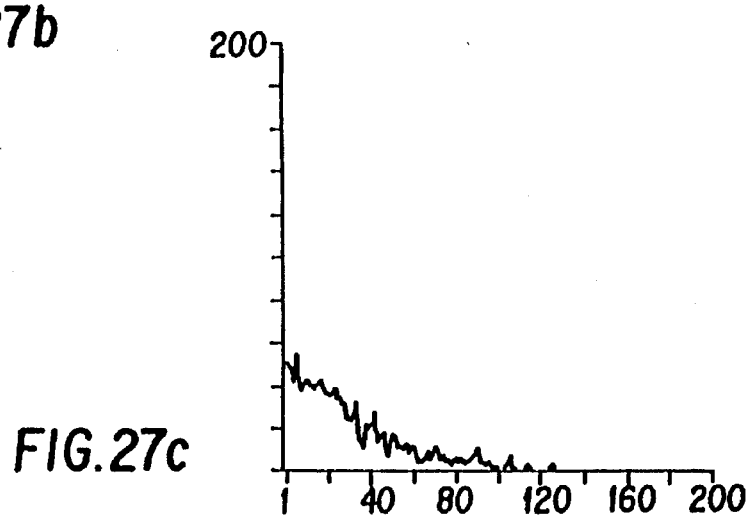

FIG. 27(a through c). Activation of human complement in the presence of sCR1 shows reduced C5a activity in the DCFDA assay. Panel a, unstimulated cells; panel b, control without sCR1 showing a high degree of fluorescence; panel c, DCFDA assay in the presence of sCR1 showing a reduction of 75% in fluorescent intensity. y-axis is number of cells and x-axis is fluorescent intensity.

Figure 28:
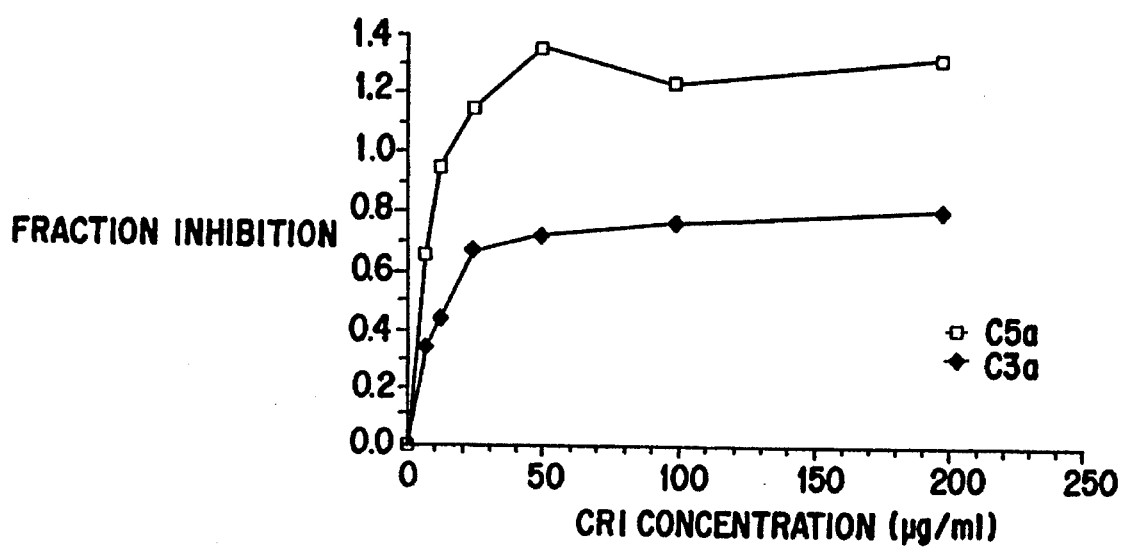

FIG. 28. Inhibition of classical pathway C5a and C3a production in human serum by sCR1. Similar profiles were observed for either antibody affinity purified or HPLC purified sCR1.

Figure 29:
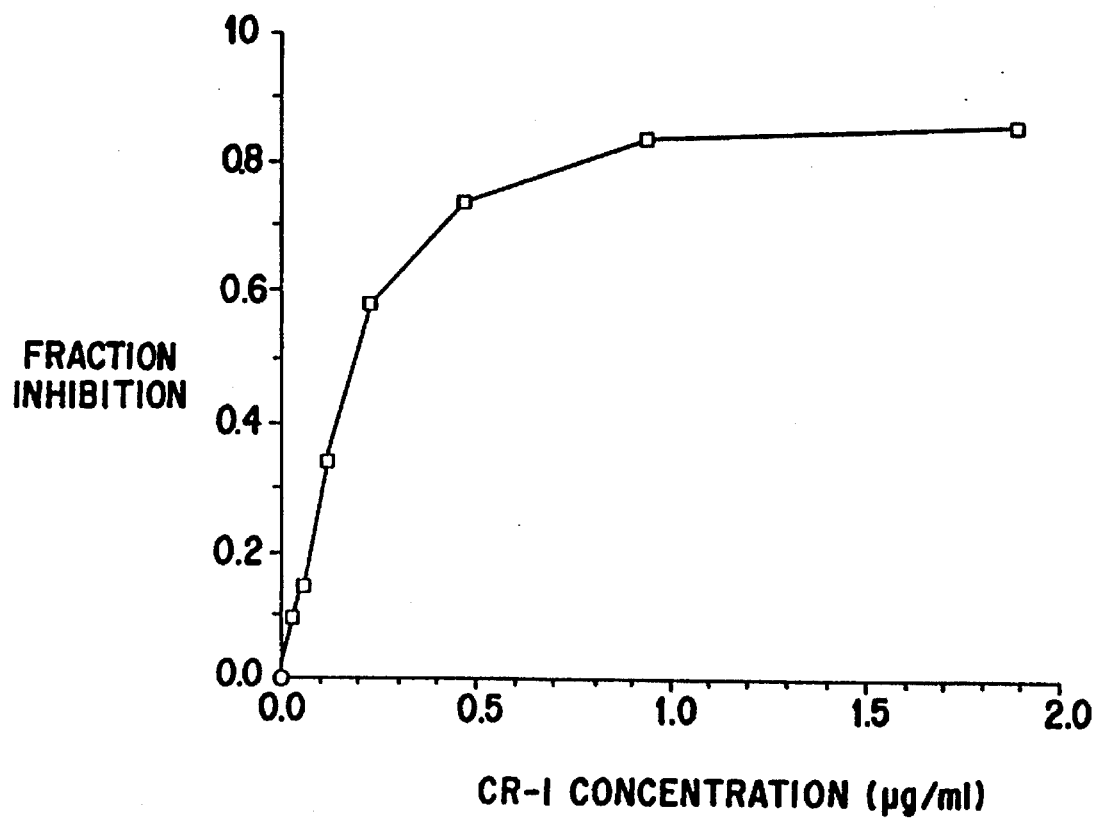

FIG. 29. Inhibition of complement-mediated hemolysis by recombinant sCR1. Similar profiles were observed for antibody affinity purified or HPLC purified sCR1.

FIG. 30(A through B). Gross morphology of RPAR in sCR1-treated (left) and untreated (right) rats. (A) Both rats received an intravenous injection of ovalbumin, followed by an intradermal injection of a mixture of either sCR1 (left rat) or PBS (right rat) with anti-ovalbumin, neat (left site); anti-ovalbumin, ½ dilution (middle site) or rabbit IgG (right site). The injections were performed in duplicate; top and bottom rows gave identical results. The rat which received sCR1 had barely visible changes, while the untreated rat developed full symptoms of RPAR. (B) The dermal surface of the skin biopsies from (A). The biopsy from the untreated rat (right) developed clearly visible lesion, while the biopsy from the sCR1-treated rat (left) showed normal morphology.

FIG. 31(A through B). Light microscopy of skin biopsies from sCR1-treated (A) and untreated (B) rats. (A) Perivascular accumulation of polymorphonuclear and mononuclear cells was observed, however, no extensive infiltration of neutrophils or extravasation of erythrocytes was seen. (B) Extensive infiltration of polymorphonuclear cells and extravasation of erythrocytes was identified.

FIG. 32. The clearance of injected sCR1 from the blood of rats and monkeys showing biphasic, α and β, clearance phases.

Figure 33:
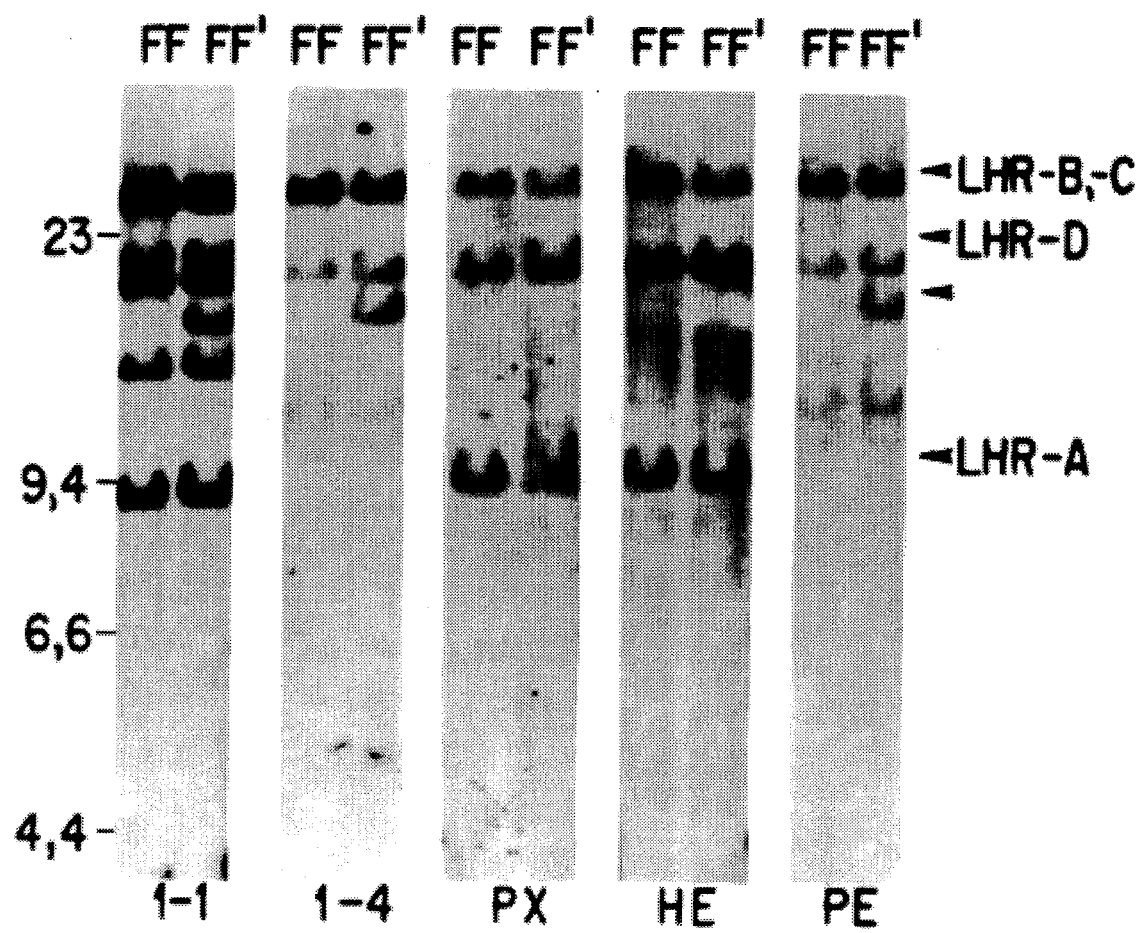

FIG. 33. Autoradiographs of the Southern blots in which the CR1 cDNA and intron probes were hybridized to the EcoRV digests of the DNA from individuals who expressed the F or the F' allotypes. The positions of the Hind III fragments of λDNA are designated in kilobases on the left. The position of the F'-specific fragment is designated by a single arrow.

Figure 34:
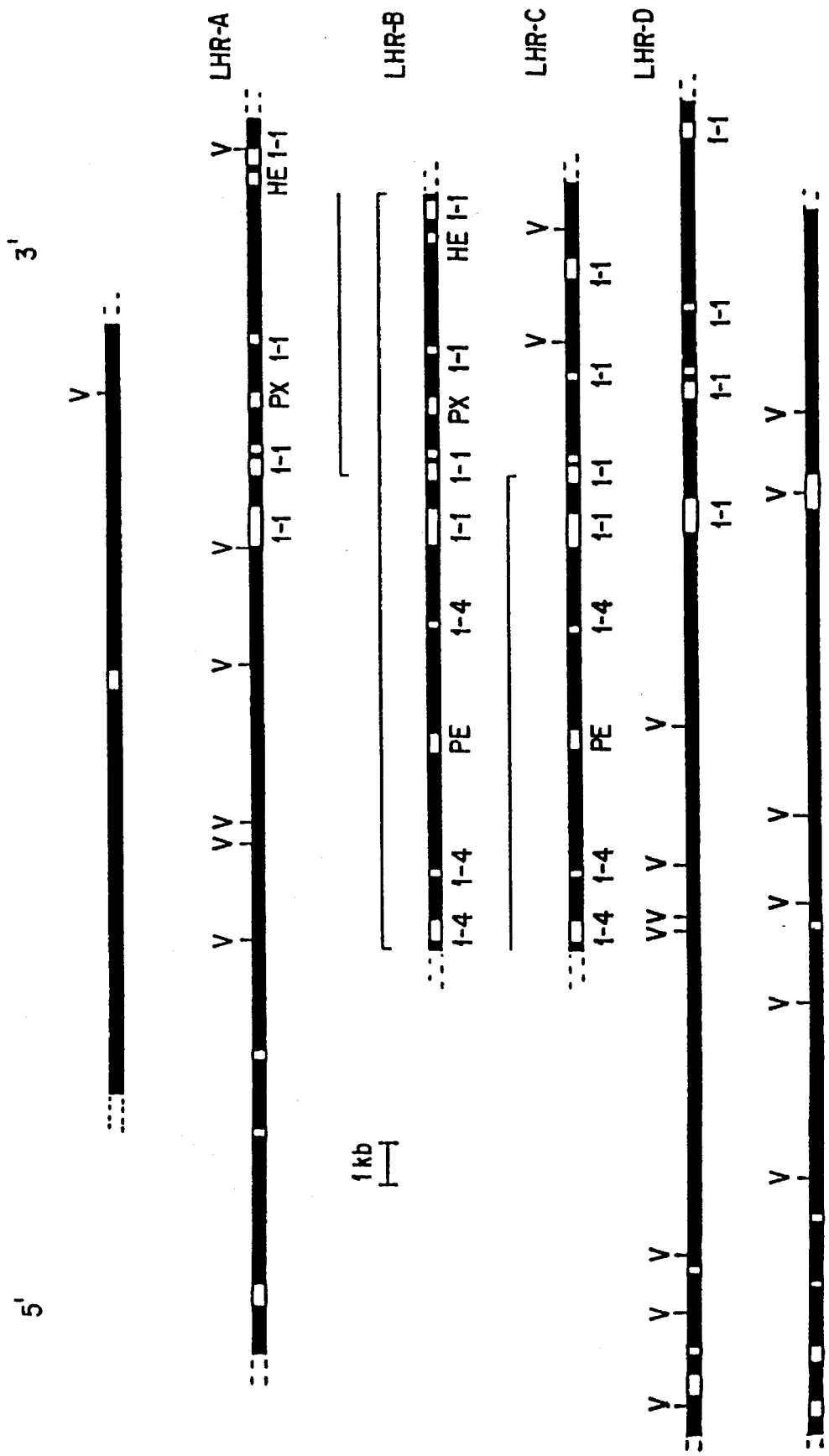

FIG. 34. EcoRV restriction map of the F allele of CR1.

The white boxes represent the positions of the exons and the stippled boxes represent the sites of hybridizations of the intron probes. The brackets over the LHR-B and -C indicate two possible regions of deletion. V represents an EcoRV site.

Figure 35:
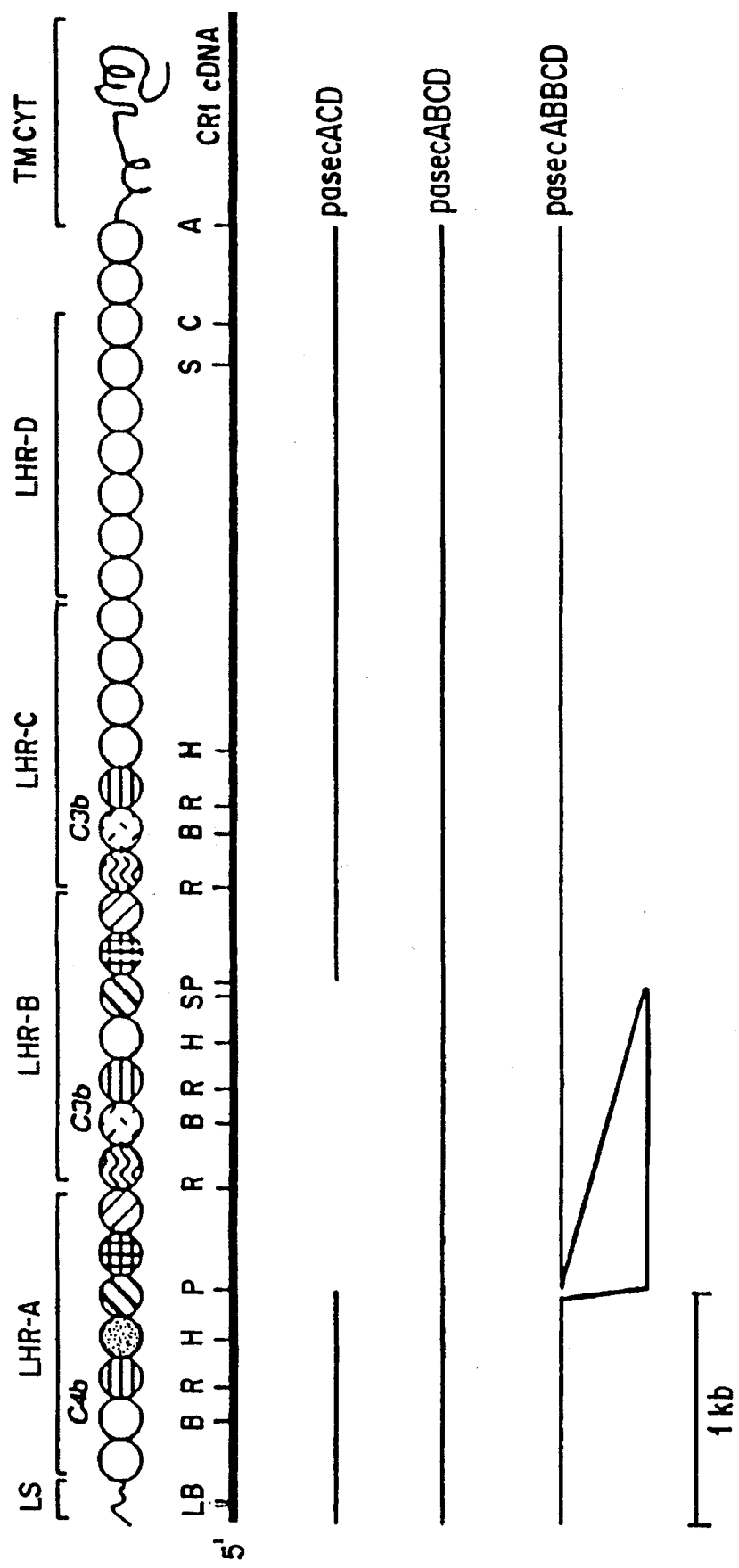

FIG. 35. The cDNA inserts for the different forms of recombinant rCR1. The restriction sites shown are: A, ApaL I; B, BamH I; C, Sac I; H, Hind III; L, Bgl I; P, Pst I; R, EcoR I; and S, Sma I. The diagram at the top represents the CR1 protein, and the SCR with identical sequences are filled in by the same patterns.

Figure 36:

FIG. 36. Coomassie Blue-stained SDS-PAGE under non-reducing conditions of recombinant sCR1 purified by absorption on YZ-1-Sepharose. Each lane contains 10 µg of recombinant sCR1 purified from the culture supernatants of COS cells that have been transfected with pasecABBCD (lane 1), pasecABCD (lane 2), or pasecACD (lane 3). The position of the $M_r$ markers are indicated on the right in kD.

Figure 37:
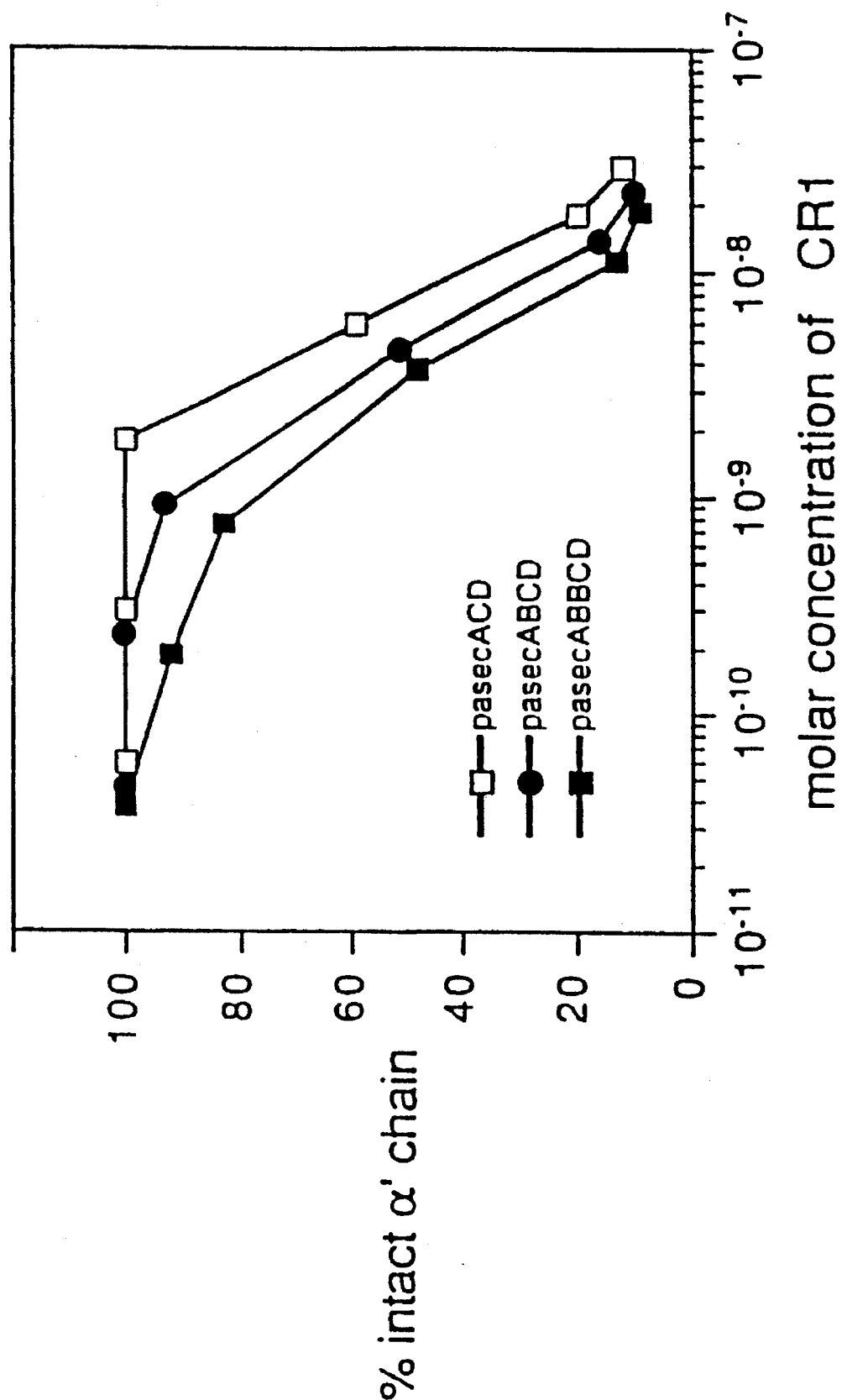

FIG. 37. Cofactor activity of recombinant sCR1. Cleavage of the α' chain of C3b was measured in the presence of increasing amounts of recombinant sCR1 derived from COS cells transfected with pasecABBCD, pasecABCD, or pasecACD.

Figure 38:
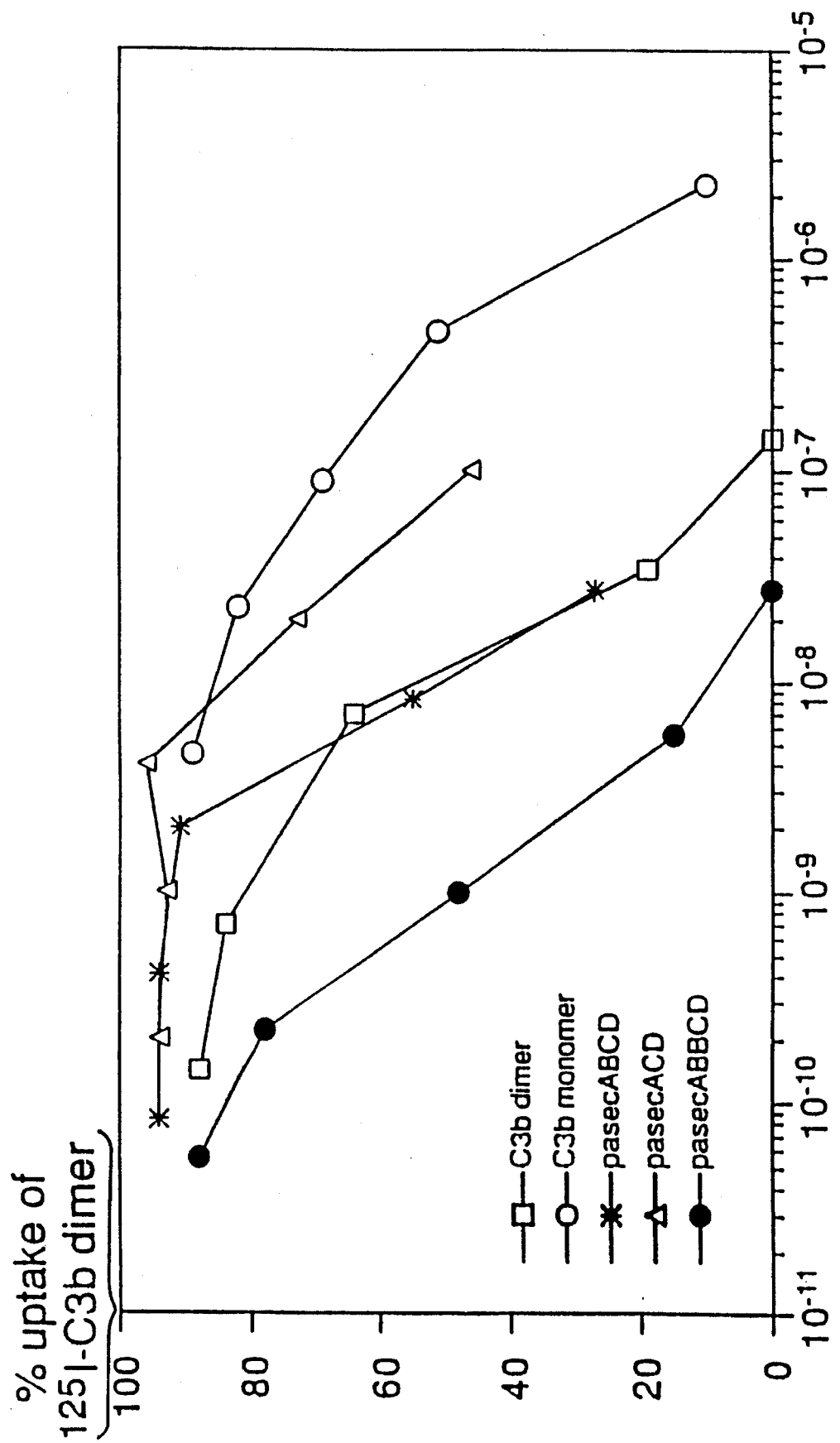

FIG. 38. Inhibition of $^{125}$I-C3b dimer uptake on erythrocytes by recombinant sCR1. Erythrocyte-bound ligand was measured in the presence of increasing concentrations of C3b dimer, C3b monomer, and recombinant sCR1 derived from COS cells transfected with pasecABBCD, pasecABCD, or pasecACD.

Figure 39:
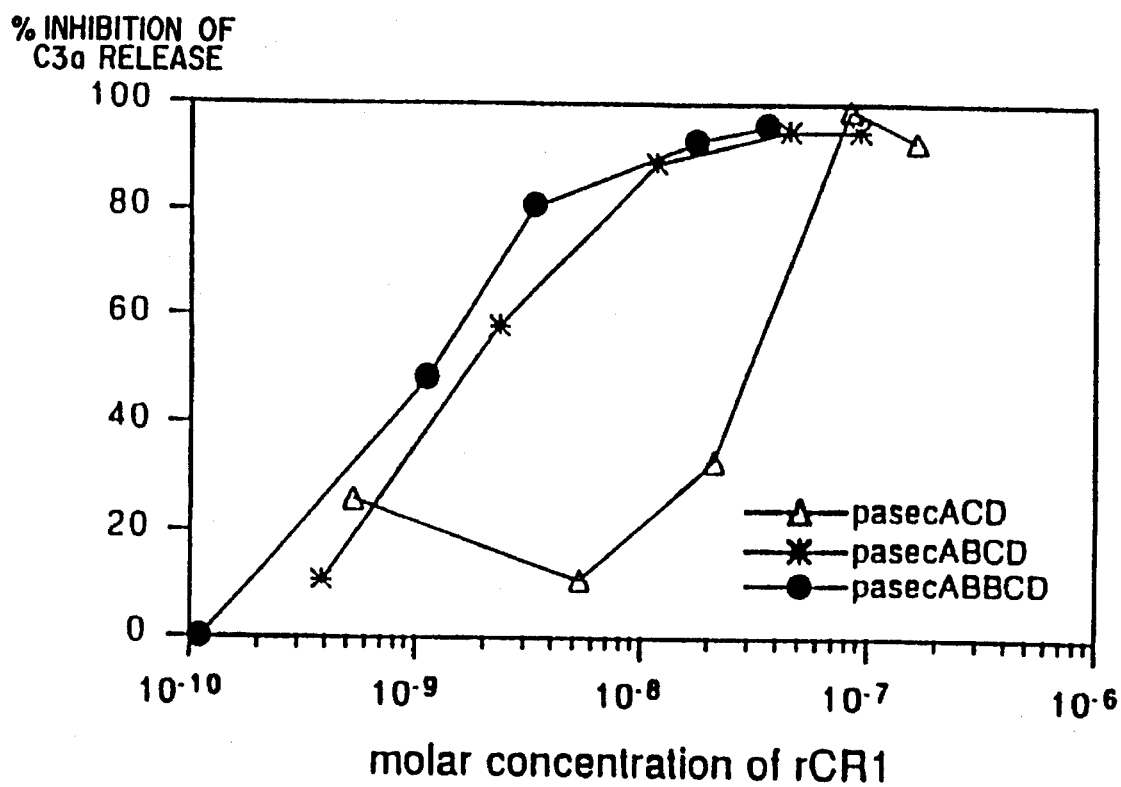
Figure 39:
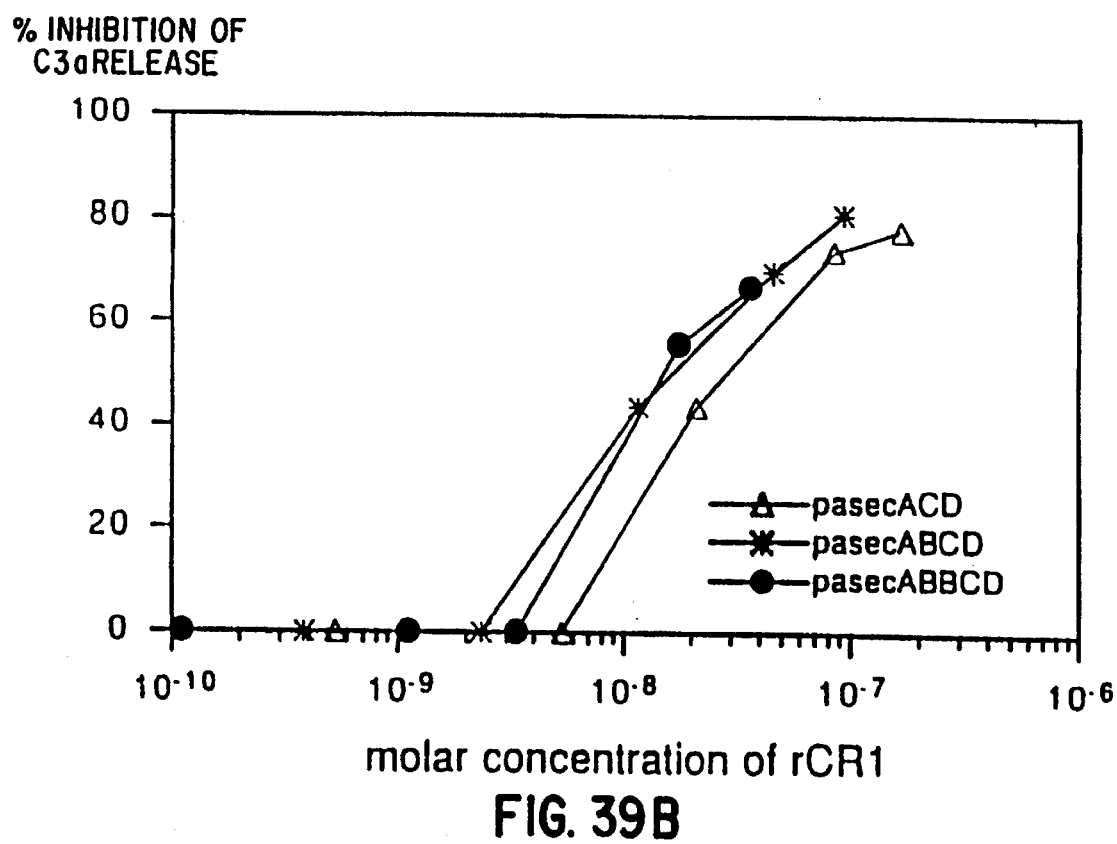

FIG. 39(A through B). Inhibition of the alternative (A) and classical (B) C3 convertases by recombinant sCR1 purified from COS cells transfected with the different plasmids encoding the CR1 variants.

FIG. 40(A through B). Inhibition of the alternative (A) and classical (B) C5 convertases by recombinant sCR1 purified from COS cells transfected with the different plasmids encoding the CR1 variants.

5. DETAILED DESCRIPTION OF THE INVENTION

The present invention is directed to the C3b/C4b receptor (CR1) gene and its encoded protein. The invention is also directed to CR1 nucleic acid sequences and fragments thereof comprising 70 nucleotides and their encoded peptides or proteins comprising 24 amino acids. The invention further provides for the expression of the CR1 protein and fragments thereof. Such CR1 sequences and proteins have value in diagnosis and therapy of inflammatory or immune system disorders, and disorders involving complement activity.

In a specific embodiment, the invention relates to soluble CR1 molecules and the expression, purification, and uses thereof. As used herein, the term "soluble CR1 molecules" shall mean portions of the CR1 protein which, in contrast to the native CR1 proteins, are not expressed on the cell surface as membrane proteins. In particular, CR1 molecules which substantially lack a transmembrane region are soluble CR1 molecules. In a preferred embodiment, the soluble CR1 molecules are secreted by a cell in which they are expressed.

In specific embodiments of the present invention detailed in the examples sections infra, the cloning and complete nucleotide and deduced amino acid sequence of the full-length CR1 cDNA, and of fragments thereof, and the expression of the encoded CR1 products, are described. The expression of CR1 and fragments thereof, with binding sites for C3b and/or C4b, and which inhibit factor I cofactor activity, is also described. The invention is further illustrated by the production and purification of soluble, truncated CR1 molecules. In specific examples, such molecules are demonstrated to be therapeutically useful in reducing inflammation, and in reducing myocardial infarct size and preventing reperfusion injury.

5.1. Isolation of the CR1 Gene

The complete coding sequence of the CR1 gene and its deduced amino acid sequence is presented in FIG. 1.

Any human cell can potentially serve as the nucleic acid source for the molecular cloning of the CR1 gene. Isolation of the CR1 gene involves the isolation of those DNA sequences which encode a protein displaying CR1-associated structure or properties, e.g., binding of C3b or C4b or immune complexes, modulating phagocytosis, immune stimulation or proliferation, and regulation of complement. The DNA may be obtained by standard procedures known in the art from cloned DNA (e.g., a DNA "library"), by chemical synthesis, by cDNA cloning, or by the cloning of genomic DNA, or fragments thereof, purified from the desired human cell. (See, for example, Maniatis et al., 1982, Molecular Cloning, A Laboratory Manual, Cold Spring Harbor Laboratory, Cold Spring Harbor, N.Y.; Glover, D. M. (ed.), 1985, DNA Cloning: A Practical Approach, MRL Press, Ltd., Oxford, U.K., Vol. I, II.) Cells which can serve as sources of nucleic acid for cDNA cloning of the CR1 gene include but are not limited to monocytes/macrophages, granulocytes, B cells, T cells, splenic follicular dendritic cells, and glomerular podocytes. Clones derived from genomic DNA may contain regulatory and intron DNA regions in addition to coding regions; clones derived from cDNA will contain only exon sequences. Whatever the source, the CR1 gene should be molecularly cloned into a suitable vector for propagation of the gene.

In the molecular cloning of the gene from genomic DNA, DNA fragments are generated, some of which will encode the desired CR1 gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the CR1 gene may be accomplished in a number of ways. For example, if an amount of a CR1 gene or its specific RNA, or a fragment thereof, is available and can be purified and labeled, the generated DNA fragments may be screened by nucleic acid hybridization to the labeled probe (Benton, W. and Davis, R., 1977, Science 196:180; Grunstein, M. and Hogness, D., 1975, Proc. Natl. Acad. Sci. U.S.A. 72:3961). Those DNA fragments with substantial homology to the probe will hybridize. If a purified CR1-specific probe is unavailable, nucleic acid fractions enriched in CR1 may be used as a probe, as an initial selection procedure. As an example, the probe representing B cell cDNA from which messages expressed by fibroblasts have been subtracted can be used. It is also possible to identify the appropriate fragment by restriction enzyme digestion(s) and comparison of fragment sizes with those expected according to a known restriction map if such is available. Further selection on the basis of the properties of the gene, or the physical, chemical, or immunological properties of its expressed product, as described infra, can be employed after the initial selection.

The CR1 gene can also be identified by mRNA selection by nucleic acid hybridization followed by in vitro translation. In this procedure, fragments are used to isolate complementary mRNAs by hybridization. Such DNA fragments may represent available, purified CR1 DNA, or DNA that has been enriched for CR1 sequences. Immunoprecipitation analysis or functional assays (e.g., for C3b or C4b binding, or promotion of phagocytosis or immune stimulation, or complement regulation, etc.) of the in vitro translation products of the isolated mRNAs identifies the mRNA and, therefore, the complementary DNA fragments that contain the CR1 sequences. In addition, specific mRNAs may be selected by adsorption of polysomes isolated from cells to immobilized antibodies specifically directed against CR1. A radiolabeled CR1 cDNA can be synthesized using the selected mRNA (from the adsorbed polysomes) as a template. The radiolabeled mRNA or cDNA may then be used as a probe to identify the CR1 DNA fragments from among other genomic DNA fragments.

Alternatives to isolating the CR1 genomic DNA include, but are not limited to, chemically synthesizing the gene sequence itself from a known sequence or making cDNA to the mRNA which encodes the CR1 gene. For example, as described supra, RNA for cDNA cloning of the CR1 gene can be isolated from cells including but not limited to monocytes/macrophages, granulocytes, B cells, T cells, dendritic cells, and podocytes. In a preferred embodiment, tonsilar cells can serve as the source of mRNA for cDNA cloning (See Section 6.1.2, infra). Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid or CDM8 plasmid (Seed, B., 1987, Nature 329:840–842) or derivatives. Recombinant molecules can be introduced into host cells via transformation, transfection, infection, electroporation, etc.

In an alternative method, the CR1 gene may be identified and isolated after insertion into a suitable cloning vector, in a "shot gun" approach. Enrichment for the CR1 gene, for example, by size fractionation, can be done before insertion into the cloning vector.

The CR1 gene is inserted into a cloning vector which can be used to transform, transfect, or infect appropriate host cells so that many copies of the gene sequences are generated. In a specific embodiment, the cloning vector can be the CDM8 vector, which can be used to achieve expression in a mammalian host cell. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CR1 gene may be modified by homopolymeric tailing.

Identification of the cloned CR1 gene can be accomplished in a number of ways based on the properties of the DNA itself, or alternatively, on the physical, immunological, or functional properties of its encoded protein. For example, the DNA itself may be detected by plaque or colony nucleic acid hybridization to labeled probes (Benton, W. and Davis, R., 1977, Science 196:180; Grunstein, M. and Hogness, D., 1975, Proc. Natl. Acad. Sci. U.S.A. 72:3961). Alternatively, the presence of the CR1 gene may be detected by assays based on properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, C3b and/or C4b and/or immune complex binding activity, complement regulatory activity, effects on phagocytosis or immune stimulation, or antigenic properties as known for CR1. Using an antibody to CR1, the CR1 protein may be identified by binding of labeled antibody to the putatively CR1-synthesizing clones, in an ELISA (enzyme-linked immunosorbent assay)-type procedure.

In specific embodiments, transformation of host cells with recombinant DNA molecules that incorporate the isolated CR1 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

In a particular embodiment, CR1 cDNA clones in a CDM8 vector can be transfected into COS (monkey kidney) cells for large-scale expression under the control of the cytomegalovirus promoter (see Section 8, infra).

If the ultimate goal is to insert the gene into virus expression vectors such as vaccinia virus or adenovirus, the recombinant DNA molecule that incorporates the CR1 gene can be modified so that the gene is flanked by virus sequences that allow for genetic recombination in cells infected with the virus so that the gene can be inserted into the viral genome.

After the CR1 DNA-containing clone has been identified, grown, and harvested, its DNA insert may be characterized as described in Section 5.4.1, infra.

When the genetic structure of the CR1 gene is known, it is possible to manipulate the structure for optimal use in the present invention. For example, promoter DNA may be ligated 5' of the CR1-coding sequence, in addition to or replacement of the native promoter to provide for increased expression of the protein. Expression vectors which express CR1 deletion mutants can also be made, to provide for expression of defined fragments of the CR1 sequence (see the example sections, infra). In a particular embodiment, deletion mutants can be constructed which encode fragments of the CR1 protein that exhibit the desired C3b and/or C4b binding activity (see Section 9, infra), e.g., LHR-A for binding of C4b, or LHR-C for binding of C3b. In a preferred embodiment, an expression vector which encodes a CR1 molecule with a deletion of the transmembrane region can be used to produce a soluble CR1 molecule (see the examples sections 11–14, infra). Many manipulations are possible, and within the scope of the present invention.

5.2. Expression of the Cloned CR1 Gene

The nucleotide sequence coding for the CR1 protein (FIG. 1) or a portion thereof, can be inserted into an appropriate expression vector, i.e., a vector which contains the necessary elements for the transcription and translation of the inserted protein-coding sequence. The necessary transcriptional and translation signals can also be supplied by the native CR1 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. The expression elements of these vectors vary in their strength and specificities. Depending on the host-vector system utilized, any one of a number of suitable transcription and translation elements may be used. For instance, when cloning in mammalian cell systems, promoters isolated from the genome of mammalian cells or from viruses that grow in these cells (e.g., adenovirus, simian virus 40, cytomegalovirus) may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where the entire CR1 gene including its own initiation codon and adjacent sequences are inserted into the appropriate expression vectors, no additional translational control signals may be needed. However, in cases where only a portion of the CR1 coding sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination).

In a specific embodiment, a soluble CR1 molecule can be expressed. Such a soluble molecule can be produced by use of recombinant DNA techniques to delete the DNA sequences encoding the CR1 transmembrane region (see Sections 11–14, infra). As demonstrated infra, the ability to express a soluble CR1 molecule is not limited to any one genetic modification of the CR1 nucleic acid sequence; as long as the nucleic acid sequence encoding a substantial portion of the CR1 transmembrane region is deleted, soluble CR1 constructs can be obtained.

Expression vectors containing CR1 gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to the inserted CR1 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes into the vector. For example, if the CR1 gene is inserted within the marker gene sequence of the vector, recombinants containing the CR1 insert can be identified by the absence of the marker gene function. In the third approach, recombinant expression vectors can be identified by assaying the foreign gene product expressed by the recombinant. Such assays can be based on the physical, immunological, or functional properties of the gene product.

Once a particular recombinant DNA molecule is identified and isolated, several methods known in the art may be used to propagate it. Once a suitable host system and growth conditions are established, recombinant expression vectors can be propagated and prepared in quantity.

In a particular embodiment detailed in the examples of the present invention, CDM8 vectors with an CR1 cDNA insert can be transfected into COS cells, in which the CR1 cDNA insert is expressed to produce the CR1 protein. In other particular embodiments detailed in the examples sections infra, CDM8 vectors with a CR1 cDNA insert corresponding to a portion of the CR1 coding region can be transfected into COS cells, where the CR1 or fragment is expressed. Per yet another example, infra, truncated, soluble CR1 molecules can be expressed in mammalian cells by use of expression vectors such as the pTCS vectors described in Section 11.3.1. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the chimeric gene product in the specific fashion desired. Expression from certain promoters can be elevated in the presence of certain inducers; thus, expression of the genetically engineered CR1 protein may be controlled. Furthermore, different host cells have characteristic and specific mechanisms for the translational and post-translational processing and modification of proteins. Appropriate cell lines or host systems can be chosen to ensure the desired modification and processing of the expressed heterologous protein. For example, in one embodiment, expression in a bacterial system can be used to produce an unglycosylated CR1 protein with the deduced amino acid sequence of FIG. 1. Expression in yeast will produce a glycosylated product. In another embodiment, mammalian COS cells can be used to ensure "native" glycosylation of the heterologous CR1 protein. Furthermore, different vector/host expression systems may effect processing reactions such as proteolytic cleavages to different extents. Many such variously processed CR1 proteins can be produced and are within the scope of the present invention.

In a preferred embodiment of the invention, large scale production of soluble CR1 molecules may be carried out as described infra in Section 12.1 et seq..

5.3. Identification and Purification of the Expressed Gene Product

Once a recombinant which expresses the CR1 gene is identified, the gene product should be analyzed. This can be achieved by assays based on the physical, immunological, or functional properties of the product.

The CR1 proteins may be isolated and purified by standard methods including chromatography (e.g., ion exchange, affinity, and sizing column chromatography, high pressure liquid chromatography), centrifugation, differential solubility, or by any other standard technique for the purification of proteins.

In a preferred aspect of the invention detailed in the examples infra, large quantities of soluble CR1 can be purified by procedures involving HPLC (see Section 12.2 et seq.). As described infra, large-scale production of purified CR1 can be achieved by using an expression system which produces soluble CR1 as starting material, thus eliminating the requirement of solubilizing membrane-bound CR1 with detergents. The reduction of fetal calf serum concentrations in the bioreactor cultures and/or the use of alternative culture medias in these cultures eliminates the need to remove high concentrations of extraneous proteins from the soluble CR1-containing starting material during subsequent purification. Either cation HPLC or a combination of cation HPLC followed by anion exchange HPLC can be used for purification in this preferred aspect. Substantially pure soluble CR1 in high yield can thus be achieved in only one or two steps.

Alternatively, once a CR1 protein produced by a recombinant is identified, the amino acid sequence of the protein can be deduced from the nucleotide sequence of the chimeric gene contained in the recombinant. As a result, the protein can be synthesized by Standard chemical methods known in the art (e.g., see Hunkapiller, M., et al., 1984, Nature 310:105–111).

In particular embodiments of the present invention, such CR1 proteins, whether produced by recombinant DNA techniques or by chemical synthetic methods, include but are not limited to those containing, as a primary amino acid sequence, all or part of the amino acid sequence substantially as depicted in FIG. 1, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Nonconservative substitutions can also result in functionally equivalent proteins.

In one embodiment, substitutes for an amino acid within the CR1 sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are CR1 proteins which are differentially modified during or after translation, e.g., by glycosylation, proteolytic cleavage, etc.

In an example of the invention detailed infra, cloned recombinant CR1 expressed by transfected cells was shown to be indistinguishable from the F allotype of erythrocytes by SDS-PAGE (FIG. 14), capable of mediating the binding of sheep erythrocytes bearing either C4b or C3b, and able to reproduce the ligand specificity of CR1 (FIG. 13), and exhibit factor I co-factor activity for cleavage of the alpha polypeptide of C3(ma) (FIG. 15).

5.4. Structure of the CR1 Gene and Protein

The structure of the CR1 gene and protein can be analyzed by various methods known in the art, including but not limited to those described infra.

5.4.1. Genetic Analysis

The cloned DNA or cDNA corresponding to the CR1 gene can be analyzed by methods including but not limited to Southern hybridization (Southern, E. M., 1975, J. Mol. Biol. 98:503–517), Northern hybridization (see e.g., Freeman et al., 1983, Proc. Natl. Acad. Sci. U.S.A. 80:4094–4098), restriction endonuclease mapping (Maniatis, T., 1982, Molecular Cloning, A Laboratory Manual, Cold Spring Harbor Laboratory, Cold Spring Harbor, N.Y.), and DNA sequence analysis. The stringency of the hybridization conditions for both Southern and Northern hybridization can be manipulated to ensure detection of nucleic acids with the desired degree of relatedness to the specific CR1 probe used. For example, hybridization under low stringency conditions with a probe containing CR1 gene sequences encoding LHR-B and LHR-C, can be used to detect CR2 nucleic acid sequences.

Restriction endonuclease mapping can be used to roughly determine the genetic structure of the CR1 gene. In a particular embodiment, cleavage with restriction enzymes can be used to derive the restriction map shown in FIG. 2, infra. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), or use of an automated DNA sequenator (e.g., Applied Biosystems, Foster City, Calif.). The cDNA sequence of the CR1 gene comprises the sequence substantially as depicted in FIG. 1, and described in Sections 6 and 7, infra.

5.4.2. Protein Analysis

The amino acid sequence of the CR1 protein can be derived by deduction from the DNA sequence, or alternatively, by direct sequencing of the protein, e.g., with an automated amino acid sequencer. The amino acid sequence of a representative CR1 protein comprises the sequence substantially as depicted in FIG. 1, and detailed in Section 6, infra. As described infra, all of the coding sequence of the F allotype CR1 has been cloned and, after cleavage of the signal peptide of 41 amino acids, the mature receptor contained 1998 amino acids including an extracellular domain of 1930 residues that forms 30 SCRs, 28 of which are organized into LHRs-A, -B, -C and -D, (FIG. 10), a single membrane spanning domain of 25 amino acids and a relatively short cytoplasmic domain of 43 amino acids.

Among the C3/C4 binding proteins that contain multiple SCRs, CR1 is unique in having groups of SCRs organized into LHRs. Comparison of the four LHRs of CR1 reveals that each is a composite of four types of SCRs: types a, b, c and d (FIG. 19). For example, the sequences of SCR-1 and -2 of LHR-A are only 62%, 62% and 57% identical to the first two SCRs of LHR-B, -C and -D, respectively. However, SCR-3 through SCR-7 differ from the corresponding SCRs of LHR-B at only a single position, and SCR-3 and -4 differ from those of LHR-C at only three positions (FIG. 10). Thus, some of the type "a" SCRs of LHR-A are also present in LHR-B and -C. The first two SCRs of LHR-B, which differ from those of LHR-A, are 99% identical with the corresponding SCRs of LHR-C, so that LHR-B and -C share the type "b" SCR at these positions. The fifth, sixth and seventh SCR of LHR-C are only 77% identical to the type "a" SCRs in LHR-A and -B at these positions, and are considered as type "c" SCRs. The first through fourth SCRs of LHR-D are relatively unique and are type "d", while the fifth through seventh SCRs are approximately 93% identical to the "c" type found in LHR-C.

The CR1 protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the CR1 protein and the corresponding regions of the gene sequence which encode such regions. A hydrophilicity profile of the COOH-terminus of the CR1 protein is depicted in FIG. 5.

Secondary structural analysis (Chou, P. and Fasman, G., 1974, Biochemistry 13:222) can also be done, to predict regions of CR1 that assume specific secondary structures.

Other methods of structural analysis can also be employed. These include but are not limited to X-ray crystallography (Engstom, A., 1974, Biochem. Exp. Biol. 11:7–13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. CR1-Related Derivatives, Analogues, and Peptides

The production and use of derivatives, analogues, and peptides related to CR1 are also envisioned, and within the scope of the present invention. Such derivatives, analogues, or peptides which have the desired immunogenicity or antigenicity can be used, for example, in immunoassays, for immunization, therapeutically, etc. Such molecules which retain, or alternatively inhibit, a desired CR1 property, e.g., binding of C3b or C4b, regulation of complement activity, or promotion of immune stimulation or phagocytosis, etc., can be used as inducers, or inhibitors, respectively, of such property.

The CR1-related derivatives, analogues, and peptides of the invention can be produced by various methods known in the art. The manipulations which result in their production can occur at the gene or protein level. For example, the cloned CR1 gene can be modified by any of numerous strategies known in the art (Maniatis, T., 1982, Molecular Cloning, A Laboratory Manual, Cold Spring Harbor Laboratory, Cold Spring Harbor, N.Y.). The CR1 sequence can be cleaved at appropriate sites with restriction endonuclease(s), followed by further enzymatic modification if desired, isolated, and ligated in vitro (see Section 8, infra). In the production of the gene encoding a derivative, analogue, or peptide related to CR1, care should be taken to ensure that the modified gene remains within the same translational reading frame as CR1, uninterrupted by translational stop signals, in the gene region where the desired CR1-specific activity is encoded. In a particular embodiment, nucleic acid sequences encoding a fusion protein, consisting of a molecule comprising a portion of the CR1 sequence plus a non-CR1 sequence, can be produced.

Additionally, the CR1 gene can be mutated in vitro or in vivo, to create and/or destroy translation initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551), use of TAB® linkers (Pharmacia), etc.

Manipulations of the CR1 sequence may also be made at the protein level. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogues and peptides related to CR1 can be chemically synthesized. For example, a peptide corresponding to a portion of CR1 which mediates the desired activity (e.g., C3b and/or C4b binding, immune stimulation, complement regulation, etc.) can be synthesized by use of a peptide synthesizer.

Specific modifications of the nucleotide sequence of CR1 can be made by recombinant DNA procedures that result in sequences encoding a protein having multiple LHR-B sequences. Such valency modifications alter the extent of C3b binding.

5.6. Uses of CR1

5.6.1. Assays and Diagnosis

CR1 proteins, analogues, derivatives, and subsequences thereof, and anti-CR1 antibodies, have uses in assays and in diagnostics. The molecules of the invention which demonstrate the desired CR1 property or function can be used to assay such property or function. For example, CR1 proteins or fragments thereof, which exhibit binding of C3b and/or C4b, in free and/or in complex forms, can be used in assays to measure the amount of such substances in a sample, e.g., a body fluid of a patient.

In a specific embodiment, full-length CR1 or a CR1 deletion mutant expressed on the cell surface (e.g., those described in Section 8, infra) having the ability to bind C3b (e.g., see Table II, Section 9, infra), iC3b or C4b (e.g., see Table II) can be used in assays to measure the levels of C3b, iC3b, or C4b, respectively, in a sample. In another embodiment, a CR1 protein or fragment thereof which is constructed by recombinant DNA technology to lack a transmembrane sequence, and is thus secreted, can be used.

In a particular embodiment, such a measurement of C3b and/or C4b can be relied on as an indication of complement activity, and can be useful in the diagnosis of inflammatory and immune system disorders. Such disorders include but are not limited to tissue damage due to burn- or myocardial infarct-induced trauma, adult respiratory distress syndrome (shock lung), autoimmune disorders such as rheumatoid arthritis, systemic lupus erythematosus, and other diseases or disorders involving undesirable or inappropriate complement activity (see, e.g., Miescher, P. A. and Muller-Eberhard, H. J., eds., 1976, Text Book of Immunopathology, 2d Ed., Vols. I and II, Grune and Stratton, New York; Sandberg, A. L., 1981, in Cellular Functions in Immunity and Inflammation, Oppenheim, J. J. et al., eds., Elsevier/North Holland, N.Y., p. 373; Conrow, R. B. et al., 1980, J. Med. Chem. 23:242; Regal, J. F. and Pickering, R. H., 1983, Int. J. Immunopharmacol. 5:71; Jacobs, H. S., 1980, Arch. Pathol. Lab. Med. 104:617).

The CR1 protein and fragments thereof containing an epitope have uses in assays including but not limited to immunoassays. The immunoassays which can be used include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectrophoresis assays, to name but a few.

CR1 genes and related nucleic acid sequences and subsequences, can be used in hybridization assays. Such hybridization assays can be used to monitor inflammatory or immune responses associated with CR1 expression, to diagnose certain disease states associated with changes in CR1 expression, to determine the CR1 allotype of a patient, and to detect the presence and/or expression of the CR1 gene and related genes (e.g., CR2).

Kits for practicing the assays for use in the present invention are also provided.

5.6.2. Therapy

The CR1 protein and fragments, derivatives, and analogues thereof can be therapeutically useful in the modulation of functions mediated by CR1. Such functions include but are not limited to binding of C3b and/or C4b, in free or in complex forms, promotion of phagocytosis, complement regulation, immune stimulation, etc. Effective doses of the CR1 proteins and related molecules of the invention have therapeutic value for many of the diseases or disorders associated with such functions, such as immune or inflammatory disorders (e.g., those described supra in Section 5.6.1). For example, full-length CR1 or fragments thereof and related molecules which exhibit the desired activity can have therapeutic uses in the inhibition of complement by their ability to act as a factor I cofactor, promoting the irreversible inactivation of complement components C3b or C4b (Fearon, D. T., 1979, Proc. Natl. Acad. Sci. U.S.A. 76:5867; Iida, K. and Nussenzweig, V., 1981, J. Exp. Med. 153:1138), and/or by the ability to inhibit the alternative or classical C3 or C5 convertases.

In a specific embodiment of the invention, an expression vector can be constructed to encode a CR1 molecule which lacks the transmembrane region (e.g., by deletion carboxy-terminal to the arginine encoded by the most C-terminal SCR), resulting in the production of a soluble CR1 fragment. In one embodiment, such a fragment can retain the ability to bind C3b and/or C4b, in free or in complex forms. In a particular embodiment, such a soluble CR1 protein may no longer exhibit factor I cofactor activity. The soluble CR1 product can be administered in vivo to a patient, so that the soluble CR1 can effectively compete out binding of the C3b and/or C4b to the native cell-surface CR1, thus blocking cell-surface CR1 factor I cofactor activity, and increasing complement activity.

After C3b has covalently attached to particles and soluble immune complexes, the inactivation of C3b by proteolytic processing into iC3b and C3dg has two biologic consequences: preventing excessive activation of the complement system via the amplification pathway, and formation of ligands that can engage receptors other than CR1. The iC3b fragment cannot bind factor B so that conversion to this state blocks additional complement activation via the alternative pathway amplification loop. However, iC3b can be bound by CR1 and CR3, the two complement receptors that mediate phagocytosis by myelomonocytic cells. Therefore, the primary biologic consequence of C3b to iC3b conversion is cessation of complement activation without interference with CR1- and CR3-mediated clearance of the C3-coated complex. In contrast, the additional conversion of iC3b to C3dg creates a fragment that interacts only with CR2 and not with CR1 and CR3. This circumstance limits complement-dependent binding of the C3dg-bearing complex to cell types expressing CR2, which include B lymphocytes, follicular dendritic cells and perhaps epithelial cells of the dermis, and diminishes or excludes interaction with phagocytic cell types. The biologic consequence of this altered pattern of cellular association would be targeting of the C3dg-bearing complexes to cells involved in the afferent phase of the immune response rather than to cells involved in clearance and degradation of particles and complexes. Therefore, CR1 molecules may be used therapeutically not only to affect the clearance process, but also in the targeting of complexes to the CR2-bearing cell types that participate in antigen presentation and antibody production.

In an alternative embodiment, a CR1 protein or fragment thereof which can bind C3b or C4b, and/or retains the ability to inhibit the alternative or classical C3 or C5 convertases, or retains factor I cofactor activity, can be used to promote complement inactivation. In such an embodiment, the CR1 protein or fragment can be valuable in the treatment of disorders which involve undesirable or inappropriate complement activity (e.g., shock lung, tissue damage due to burn or ischemic heart conditions, autoimmune disorders, inflammatory conditions, etc.).

In a specific embodiment detailed in the examples Sections 11–14 infra, a soluble CR1 molecule can be expressed which retains a desired functional activity, as demonstrated, e.g., by the ability to inhibit classical complement-mediated hemolysis, classical C5a production, classical C3a production, or neutrophil oxidative burst in vitro. In a particular embodiment, such a soluble CR1 molecule can be used to reduce inflammation and its detrimental effects, or to reduce myocardial infarct size or prevent reperfusion injury, etc. Such CR1 molecules useful for in vivo therapy may be tested in various model systems known in the art, including but not limited to the reversed passive Arthus reaction (see Section 14.1) and a rat myocardial infarct model (see Section 14.3).

In another embodiment of the invention, a fragment of CR1, or an analogue or derivative thereof, which is shown to inhibit a desired CR1 property or function, can be used to prevent or treat diseases or disorders associated with that function.

Various delivery systems are known and can be used for delivery of CR1 and related molecules, e.g., encapsulation in liposomes, microparticles, or microcapsules, expression by hematopoietic stem cell progeny in gene therapy, etc. Other methods of introduction include but are not limited to intradermal, intramuscular, intraperitoneal, intravenous, subcutaneous, intranasal, and oral routes.

The present invention also provides pharmaceutical compositions. Such compositions comprise a therapeutically effective amount of a CR1 protein, or an analogue, derivative, or fragment thereof, and a pharmaceutically acceptable carrier. Such a carrier includes but is not limited to saline, buffered saline, dextrose, and water.

5.6.3. Combination Therapy

In a further aspect there is provided a method of treating thrombotic conditions, especially acute myocardial infarction, in humans and animals, which method comprises administering to a human or animal in need thereof an effective amount of a soluble CR1 protein according to the invention and an effective amount of a thrombolytic agent.

The invention also provides the use of a soluble CR1 protein and a thrombolytic agent in the manufacture of a medicament for the treatment of thrombotic conditions in humans and animals.

In the above method, the compounds may be administered by any convenient route, for example by infusion or bolus injection, and may be administered sequentially or together. When the soluble CR1 protein according to the invention and the thrombolytic agent are administered sequentially, the soluble CR1 protein may be administered either before or after the thrombolytic agent. When the soluble CR1 protein and the thrombolytic agent are administered together they are preferably given in the form of a pharmaceutical composition comprising both agents. Thus, in a further aspect of the invention there is provided a pharmaceutical composition comprising a soluble CR1 protein and a thrombolytic agent together with a pharmaceutically acceptable carrier.

In a preferred embodiment, the composition may be formulated in accordance with routine procedures as a pharmaceutical composition adapted for intravenous administration to human beings.

Typically compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilised powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade 'Water for Injection' or saline. Where the composition is to be administered by injection, an ampoule of sterile water for injection or saline may be provided so that the ingredients may be mixed prior to administration.

A pharmaceutical pack comprising one or more containers filled with one or more of the ingredients of the pharmaceutical composition is also within the scope of the invention.

The quantity of material administered, and the ratio of thrombolytic agent to CR1 protein, will depend upon the seriousness of the thromboembolic condition and position and size of the clot. The precise dose to be employed and mode of administration must per force in view of the nature of the complaint be decided according to the circumstances by the physician supervising treatment. However, in general, a patient being treated for a thrombus will generally receive a dose of from 0.5 to 50 mg of complement inhibitor (soluble CR1 component) per standard dose of thrombolytic agent.

Particular thrombolytic agents for use in combination therapy as described above are fibrinolytic enzymes, including plasminogen activators.

The term plasminogen activator includes but is not limited to streptokinase, human tissue plasminogen activator (t-PA) and urokinase (u-PA) (both single and two-chain forms). Such enzymes are obtained from natural sources or tissues or by recombinant DNA methods where heterologous host organisms such as bacteria, yeasts, fungi or mammalian cells express genes specifying the enzymes. The term also includes:

(a) proteins disclosed in EP(European Patent Publication)-A-0155387 and EP-A-0297882 which disclose a fibrinolytically active hybrid protein which comprises one chain of a 2-chain protease linked to a chain of a different 2-chain protease, at least one of the chains in the hybrid protein being derived from a fibrinolytically active protease, such that the hybrid protein has a catalytic site essential for fibrinolytic activity which is optionally blocked by a removable blocking group;

(b) protein conjugates disclosed in EP-A- 0152736, such as urokinase linked to reversibly blocked plasmin;

(c) derivatives of fibrinolytic enzymes disclosed in EP-A-0155388 in which the catalytic site on the enzyme which is responsible for fibrinolytic activity is blocked by a human protein attached thereto by way of a reversible linking group, for example urokinase reversibly linked to the active centre of human plasmin;

(d) conjugates comprising a fibrinolytic enzyme linked to a water-soluble polymer by means of a reversible linking group as disclosed in EP-A-0183503; and (e) genetically engineered derivatives including muteins of naturally occurring plasminogen activators such as those disclosed in EP-A-0201153, EP-A-0207589, WO(PCT Publication)-8604351, EP-0041766, EP-0213794, EP-0199574, EP-A-0240334, EP-A-0241208, EP-A-0241209, EP-A-0241210, EP-A-0233013, EP-A-290118, EP-A-292326, EP-A-0213794, EP-A-0231883, WO 8704722, EP-A-0242836, EP-A-0234051, EP-A-0253582, EP-A-0253241, WO-8604351, EP-A-0236040, EP-A-0200451, EP-A-0238304, EP-A-0225286, DE(West German Publication)-3537176, EP-A-0236289, WO-8601538, EP-0227462, AU(Australian Publication)-8661804, WO-8703906 and EP-0199574, such as des($cys_{51}$-$asp_{87}$)t-PA.

In a particular aspect of the invention, the plasminogen activator is a hybrid molecule as described in EP-A-0297882 which comprises the five kringle domains of plasminogen linked to the B-chain of t-PA or u-PA via an amino acid sequence comprising, respectively, the t-PA cleavage site between residues 275 and 276 and the cysteine residue 264 of t-PA or the u-PA cleavage site between residues 158 and 159 and the cysteine residue 148 of u-PA.

Examples of such hybrids include plasminogen 1–544/t-PA 262–527 including one and two chain variants, $lys_{78}$ and $glu_1$ variants, and mixtures thereof;

plasminogen 1–544/t-PA 262–527 ($arg_{275}$ gln) including one and two chain variants, $lys_{78}$ and $glu_1$ variants, and mixtures thereof;

plasminogen 1–541/t-PA 262–527 including one and two chain variants, $lys_{78}$ and $glu_1$ variants, and mixtures thereof;

t-PA 1–50/t-PA 88–91/pro-gly-ser/plasminogen 84–544/t-PA 262–527 including one and two chain variants, $gly_{-3}$, $ser_1$ and $val_4$ variants, and mixtures thereof;

t-PA 1–91/pro-gly-ser/plasminogen 84–544/t-PA 262–527 including one and two chain variants, $gly_{-3}$, $ser_1$ and $val_4$ variants, and mixtures thereof; or plasminogen 1–546/u-PA 137–411 including one and two chain variants, $lys_{78}$ and $glu_1$ variants, and mixtures thereof.

In a preferred embodiment, the thrombolytic agent for use in combination therapy is a reversibly blocked in vivo fibrinolytic enzyme having the meaning given by Smith in U.S. Pat. No. 4,285,932, i.e., an in vivo fibrinolytic enzyme wherein the catalytic site essential for fibrinolytic activity is blocked by a group which is removable by hydrolysis at a rate such that the pseudo-first order rate constant for hydrolysis is in the range $10^{-6}$ $sec^{-1}$ to $10^{-3}$ $sec^{-1}$ in isotonic aqueous media at pH 7.4 at 37° C.

Where the fibrinolytic enzyme is a plasminogen activator comprising a serine protease domain of t-PA or urokinase, an example of a removable blocking group is a 2-aminobenzoyl group substituted in the 3- or 4-position with a halogen atom and optionally further substituted with one or more weakly electron-withdrawing or electon-donating groups, wherein the pseudo first order rate constant for hydrolysis of the derivative is in the range of $6.0 \times 10^{-5}$ to $4.0 \times 10^{-4}$ $sec^{-1}$ when measured in a buffer system consisting of 0.05M sodium phosphate, 0.1M sodium chloride, 0.01% v/v detergent comprising polyoxyethylenesorbitan monoleate having a molecular weight of approximately 1300, at pH 7.4 at 37° C.

Preferably, the reversibly blocked in vivo fibrinolytic enzyme is a binary complex between streptokinase and plasminogen, most preferably a p-anisoyl streptokinase/plasminogen complex without internal bond cleavage as described in U.S. Pat. No. 4,808,405, marketed by Beecham Group plc under the Trademark EMINASE (generic name anistreplase, hereinafter referred to as APSAC, i.e. anisoylated human plasminogen-streptokinase-activator complex; see for example J. P. Monk and R. C. Heel, 1987, Drugs 34:25–49).

In a preferred aspect, the soluble CR1 component used in combination therapy is encoded by a nucleic acid vector selected from the group consisting of pBSCR1c, pBSCR1s, pBM-CR1c, pBSCR1c/pTCSgpt and pBSCR1s/PTCSgpt and is especially that prepared from pBSCR1c/pTCSgpt as described above (see Section 12).

Particular thrombolytics for use in combination therapy (with examples of dose and method of administration) are as follows:

| | | |
|---|---|---|
| Streptokinase | 1.0–3.0 megaunits | over 30 minutes to 3 hours |
| APSAC | 30 units | 2–5 minute injection |
| t-PA (wild-type) | 50–150 mg | Infusion up to 6 hours |
| Two-chain urokinase | 40–100 mg (3–12 megaunits) | Infusion up to 6 hours |
| Single-chain urokinase | 30–100 mg | Infusion up to 5 hours |
| Hybrid plasminogen activators and acyl derivatives (as in e.g. EP-A-0155387) | 20–100 mg | Injection or infusion |
| Muteins of plasminogen activators (as in e.g. EP-A-0207589) | 10–100 mg | Injection or infusion |

6. EXAMPLE: THE CLONING AND SEQUENCING OF THE HUMAN C3b/C4b RECEPTOR (CR1)

In the examples detailed herein, we describe the cloning and nucleotide sequence of 5.5 kilobase pairs (kb) of the CR1 coding region (Klickstein, L. B., et al., 1987, J. Exp. Med. 165:1095–1112).

Ten overlapping CR1 cDNA clones that span 5.5 kb were isolated from a tonsillar library and sequenced in whole or in part. A single long open reading frame beginning at the 5' end of the clones and extending 4.7 kb downstream to a stop codon was identified. This sequence represents ~80% of the estimated 6 kb of coding sequence for the F allotype of CR1. Three tandem, direct, long homologous repeats (LHRs) of 450 amino acids were identified. Analysis of the sequences of tryptic peptides provided evidence for a fourth LHR in the F allotype of CR1. Amino acid identity between the LHRs ranged from 70% between the first and third repeats to 99% between the $NH_2$-terminal 250 amino acids of the first and second repeats. Each LHR comprises seven short consensus repeats (SCRs) of 60–70 amino acids that resemble the SCRs of other C3/C4 binding proteins, such as complement receptor type 2, factors B and H, C4 binding protein, and C2. Two additional SCRs join the LHRs to a single membrane-spanning domain of 25 amino acids: thus, the F allotype of CR1 probably contains at least 30 SCRs, 23 of which have been sequenced. Each SCR is predicted to form a triple loop structure in which the four conserved half-cystines form disulfide linkages. The linear alignment of 30 SCRs as a semi-rigid structure would extend 1,140 Angstroms from the plasma membrane and might facilitate the interaction of CR1 with C3b and C4b located within the interstices of immune complexes and microbial cell walls. The COOH-terminal cytoplasmic domain of 43 residues contains a six amino acid sequence that is homologous to the sequence in the epidermal growth factor receptor that is phosphorylated by protein kinase C.

6.1. Materials and Methods

6.1.1. Isolation and Sequence of CR1 Tryptic Peptides

CR1 was purified from washed human erythrocyte membranes by sequential Matrex Red A and YZ-1 monoclonal antibody affinity chromatography (Wong, W. W., et al., 1985, J. Immunol. Methods 82:303). Tryptic peptides were prepared and isolated by sequential gradient and isocratic reverse-phase HPLC (high performance liquid chromatography) as described (Wong, W. W., et al., 1985, Proc. Natl. Acad. Sci. U.S.A. 82:7711). Tryptic peptide analysis was performed with a 470A Protein Sequencer (Applied Biosystems, Inc., Foster City, Calif.), and analysis of each degradative cycle was achieved using a 120 PTH-amino acid analyzer (Applied Biosystems, Inc.).

6.1.2. Isolation of cDNA Clones and Genomic Clones

A cDNA library was constructed in λgt11 from human tonsilar poly(A)$^+$ RNA as described (Wong, W. W., et al., 1985, Proc. Natl. Acad. Sci. U.S.A. 82:7711). By RNA blot hybridization, the tonsil donor was homozygous for the F allele of CR1 (id.). The cDNA was selected on an agarose gel to include fractions between 2 and 7 kb before the cloning steps. The initial complexity of the library was $4.5 \times 10^6$ recombinants per 100 ng cDNA and the library was amplified in *Escherichia coli* strain Y1088. The library was screened (Maniatis, T., et al., 1982, Molecular Cloning, A Laboratory Manual, Cold Spring Harbor Laboratory, Cold Spring Harbor, N.Y.) with CR1 probes, CR1-1 (ATCC accession nos. 57330 (*E. coli* containing CR1-1 plasmid), 57331 (purified CR1-1 DNA)) and CR1-2 (Wong, W. W., et al., 1985, Proc. Natl. Acad. Sci. U.S.A. 82:7711), that had been radiolabeled to a specific activity of $2-8 \times 10^8$ cpm/μg by nick translation. Hybridization was performed in 50% formamide, 5×SSC (1×SSC: 15 mM sodium citrate, 150 mM sodium chloride) at 43° C. and filters were washed at 60° C. in 0.2×SSC, conditions that do not allow the detection of CR2 cDNA clones (Weis, J. J., et al., 1986, Proc. Natl. Acad. Sci. U.S.A. 83:5639). Positive clones were plaque-purified twice before restriction mapping and DNA sequence analysis.

A genomic library was constructed in EMBL-3 with 15–20 kb fragments produced by partial digestion of human leukocyte DNA with Sau3AI. The initial complexity was $1.2 \times 10^6$, and the library was amplified in *E. coli* strain P2392. The library was also screened with the cDNA probes CR1-1 and CR1-2 (Wong, W. W., et al., 1985, Proc. Natl. Acad. Sci. U.S.A. 82:7711).

6.1.3. DNA Sequence Analysis

Restriction fragments of the cDNA clones were subcloned in M13mp18 or M13mp19 and sequenced by the dideoxynucleotide chain termination method (Sanger, F., et al., 1977, Proc. Natl. Acad. Sci. U.S.A. 74:5463). Some clones were sequenced in whole or in part by first creating ordered deletion mutants using exonuclease III (Henikoff, S., 1984, Gene 28:351). Each region was sequenced on both strands and in most cases each region was sequenced on M13 subclones constructed from two independently isolated cDNA clones (FIG. 2). Sequence data were analyzed with the University of Wisconsin Genetics Computer Group package (Madison, Wis.).

6.2. Results

6.2.1. Nucleotide Sequence of the CR1 Gene

A size-selected tonsillar cDNA library was screened with the CR1-1 and CR1-2 probes obtained from the CR1 cDNA clone, λT8.3 (Wong, W. W., et al., 1985, Proc. Natl. Acad. Sci. U.S.A. 82:7711). Fifteen positive phage were identified out of $1.5 \times 10^6$ recombinants and 13 of these represented distinct clones. Ten were restriction mapped and sequenced in whole or in part by the dideoxynucleotide chain termination method. The cDNA clones were aligned on the basis of overlapping sequence identity (FIG. 2) and were found to span 5.5 kb (FIGS. 3A–3D). A single long open reading frame was identified beginning at the 5' end of the cDNA clones and extending 4.7 kb downstream to a stop codon. The coding sequence for CR1 in this library is expected to be 6 kb, based on an estimated 220,000 dalton molecular weight for the nonglycosylated receptor (Wong, W. W., et al., 1983, J. Clin. Invest. 72:685). Thus, these clones span ~80% of the estimated coding sequence.

Clones T49.1 and T55.1 contain coding sequence at their 5' ends, indicating that additional 5' coding and noncoding sequences remain to be identified. In the 3' region, the overlapping clones, T8.2, T43.1 and T87.1, contain the transmembrane and cytoplasmic regions encoded by an identical sequence in each clone. The clone extending most 3', T8.2, contains 807 bp of untranslated sequence without a poly(A) sequence. Clone T8.3 contains a 91-bp deletion of nucleotides 1,406–1,497 and clone T40.1 contains a 9-bp deletion of nucleotides 1,498–1,507 relative to the sequences found in clones T6.1 and T55.1. These deletions occurred in regions having sequences homologous to 5' splice sites and may represent splicing errors in the mRNA. Clones T49.1 and T55.1 contain a 110 bp insertion between nucleotides 147 and 148 of the open reading frame (FIGS. 3A–3D). This sequence is judged to be a portion of an intron because it did not hybridize to blots of tonsillar poly(A)+ RNA, it contains a 5' splice site (Breathnach, R., et al., 1978, Proc. Natl. Acad. Sci. U.S.A. 75:4853) (FIGS. 3A–3D), it is flanked by cDNA sequences in CR1 genomic clones, and it shifts the reading frame. Clone T9.4 contains 0.88 kb of intervening sequence at the 3' end that does not hybridize to blots of tonsillar poly(A)+ RNA.

6.2.2. Analysis of the Nucleotide and Amino Acid Sequence of CR1

Dot matrix analysis of the nucleotide sequence of CR1 (FIGS. 3A–3D) revealed two types of internal homologies (FIG. 4). The first type of internal homology is represented by the bold, uninterrupted lines that indicate the presence of three tandem, direct, highly homologous repeats of 1.35 kb. These nucleotide sequences encode the long homologous repeats (LHRs) of CR1. The second type of repeat is represented by the dashed parallel lines that indicate regions of lesser homology. These sequences occur every 190–210 nucleotides and encode the short consensus repeats (SCRs) of CR1.

The amino acid sequence deduced from the cDNA sequence is presented in FIG. 5B and the three LHRs, designated LHR-B, LHR-C and LHR-D, are aligned to demonstrate their homology. LHR-B extends from residue 1 through residue 438, LHR-C corresponds to residues 439–891, and LHR-D extends from residue 892 through 1,341. Residues 451–694 of LHR-C are 99% identical to residues 1–244 of LHR-B, but only 61% identical to the corresponding residues of LHR-D. In contrast, residues 695–891 of LHR-C are 91% identical to residues 1,148–1,341 of LHR-D but only 76% identical to the corresponding region of LHR-B. Thus, LHR-C appears to be a hybrid that comprises sequences most homologous to the first half of LHR-B and the second half of LHR-D. The LHRs are followed by two SCRs that are not repeated, a 25 residue hydrophobic segment and a 43 amino acid COOH-terminal region with no sequence homology to the SCRs (FIG. 5B).

The 5' 1.3 kb of the CR1 coding sequence represents a fourth LHR, LHR-A (see FIGS. 1A–1P, Supra, and Section 7, infra). This conclusion was supported by analysis of tryptic peptides of erythrocyte CR1. Ten tryptic peptides have sequences identical to the amino acid sequences derived from the cDNA clones (Table I).

TABLE I

CR1 TRYPTIC PEPTIDES FOUND IN THE DERIVED AMINO ACID SEQUENCE*

| Peptide Number | Amino acid sequence | Residue Numbers in thr Derived Sequence |
|---|---|---|
| 66 | VDFVCDEGFQLKGS–A | 330–345 |
| 28 | GAASL——QG–WSPEAP | 732–749, 1,185–1,202 |
| 49 | ——————IFC–NP–AIL | 805–826, 1,258–1,279 |
| 35 | CQALNKWEPELPSCSR | 228–243, 678–693 |
| 41c | DKDNFSPGQEVFYSCEPGYDLR | 260–281 |
| 34b | AV–YTCDPHPDRGTSFDLIGESTIR | 393–417 |
| 44d | VCQPPPEILHG | 694–704, 1,147–1,157 |
| 54d | VFELVGEPSIYCTSNDDQVGIWSGPAPQ | 152–179, 602–629 |
| 57b | YECRPEYYGRPFS | 19–31, 469–481 |
| 39b | LIGHSSAECILSGNAA | 85–100 |

*Tryptic peptides from human erythrocyte CR1 found in the derived amino acid sequence. The number ranges in the right-hand column indicate the location of the peptide in the derived amino acid sequence. Each dash in peptides 66, 28 and 49 indicates multiple residues were identified at that cycle. The dash in peptide 34b indicates no residue was identified at that cycle.

Figure 6B:
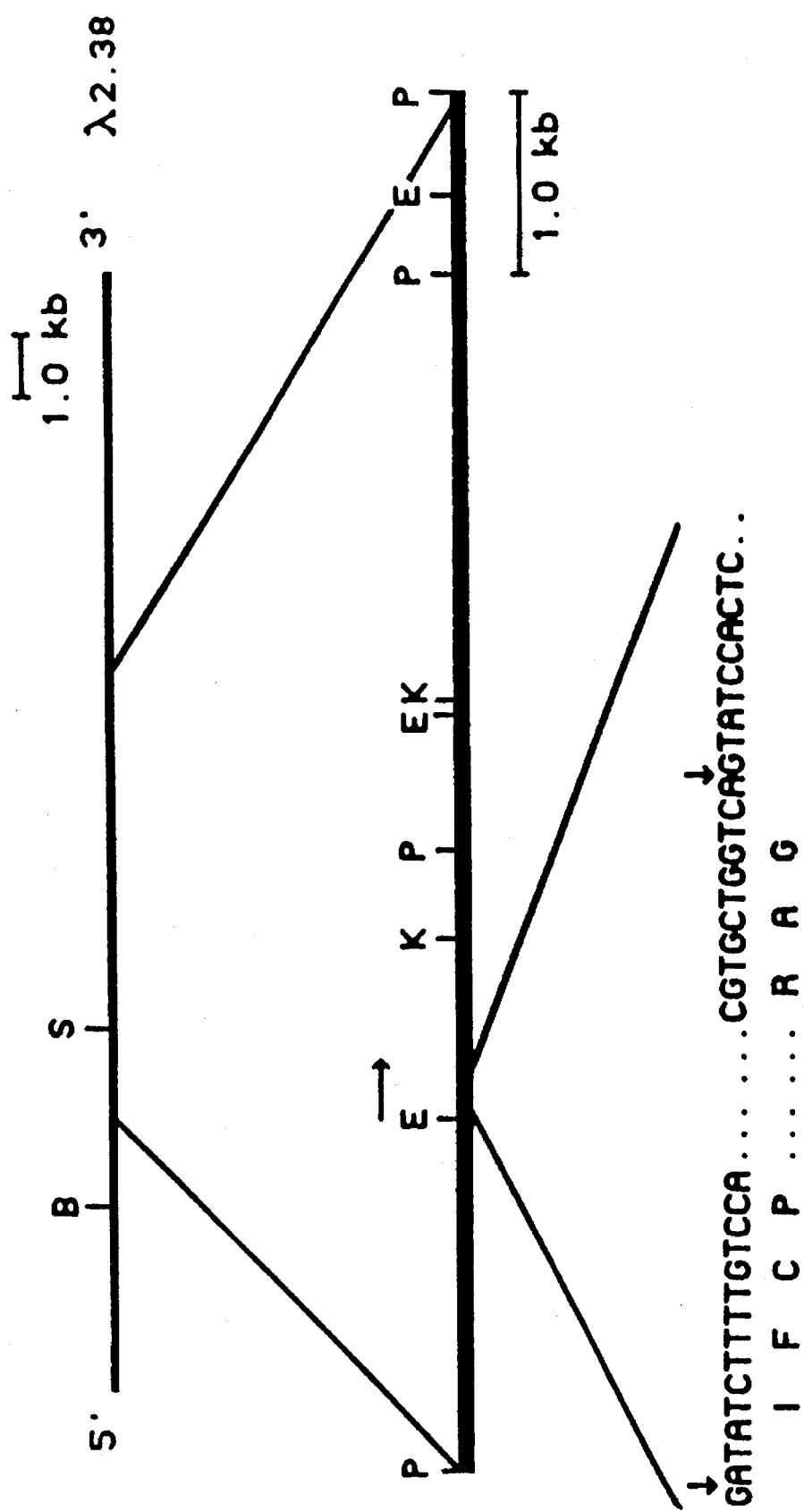

Each LHR comprises seven 60–70 amino acid SCRs that characterize the family of C3 and C4 binding proteins (C4bp) (FIG. 6A). Maximal homology between the 23 SCRs of CR1 was observed by introducing spaces in the alignment of the sequences (FIG. 6A). Altogether, 29 of the average 65 residues in each repeat are conserved. There are six residues that are present in all SCRs: the four half-cystines that are in similar relative positions suggesting that each may be involved in a critical disulfide linkage, and the tryptophan and the second glycine after the second half-cystine (FIG. 6A). Secondary structure analysis of the sequences between the invariant half-cystines using the algorithm of Chou and Fasman (Chou, P. Y. and Fasman, G. D., 1974, Biochemistry 13:222) predicted high probability β-turn formation and low probability α-helix formation. Sequence analysis of two CR1 genomic clones, 2.38 (FIG. 6B) and 2.46, indicates that SCR-14 (FIG. 6A) is encoded by a single exon and that the COOH-terminus of SCR-23 corresponds to the end of an exon. Thus, the SCRs of CR1 may be encoded by separate exons as has been shown for the SCRs of factor B (Campbell, R. D. and Bentley, D. R., 1985, Immunol. Rev. 87:19) and of the IL-2-R (Leonard, W. J., et al., 1985, Science 230:633).

The consensus sequence of the CR1 SCRs is compared with the SCRs of the other members of the superfamily having this characteristic structure (FIG. 7). These members include not only proteins having C3/C4 binding function, CR2 (Weis, J. J., et al., 1986, Proc. Natl. Acad. Sci. U.S.A. 83:5639), C4bp (Chung, L. P., et al., 1985, Biochem. J. 230:133), factor H (Kristensen, T., et al., 1986, J. Immunol. 136:3407), factor B (Morley, B. J. and Campbell, R. D., 1984, EMBO J. 3:153; Mole, J. E., et al., 1984, J. Biol. Chem. 259:3407), and C2 (Bentley, D. R. and Porter, R. R., 1984, Proc. Natl. Acad. Sci. U.S.A. 81:1212; Gagnon, J., 1984, Philos. Trans. R. Soc. Lond. B. Biol. Sci. 306:301), but also the proteins not known to have this function, such as the interleukin-2 receptor (Leonard, W. J., et al., 1985, Science 230:633), $\beta_2$-glycoprotein I (Lozier, J., et al., 1984, Proc. Natl. Acad. Sci. U.S.A. 81:3640), C1r (Leytus, S. P., et al., 1986, Biochemistry 25:4855), haptoglobin α chain (Kurosky, A., et al., 1980, Proc. Natl. Acad. Sci. U.S.A. 77:3388), and factor XIIIb (Ichinose, A., et al., 1986, Biochemistry 25:4633). The half-cystine residues are invariant in the SCRs of all proteins, except haptoglobin which lacks the third half-cystine. The tryptophan is also invariant with the exception of the fifth SCR in $\beta_2$-glycoprotein I and two of the repeats in factor XIIIb. Other residues that are conserved but not present in each SCR tend to cluster about the half-cystines. There is only one free thiol group in factor B and C2 (Christie, D. L. and Gagnon, J., 1982, Biochem. J. 201:555; Parkes, C., et al., 1983, Biochem. J. 213:201), and in the SCRs of $\beta_2$-glycoprotein I, the first half-cystine is disulfide-linked to the third and the second to the fourth (Lozier, J., et al., 1984, Proc. Natl. Acad. Sci. U.S.A. 81:3640).

In the derived amino acid sequence of CR1, there are 17 potential sites for N-linked oligosaccharides and all of them are in the extracellular region (FIG. 6A). Molecular weight differences between CR1 synthesized in the presence and absence of tunicamycin (Lublin, D. M., et al., 1986, J. Biol. Chem. 261:5736) and analysis of glucosamine content (Sim, R. B., 1985, Biochem. J. 232:883) suggest the presence of only 6–8 N-linked complex oligosaccharides, indicating that all potential sites are not used. For example, the asparagine at residue 263 of the derived amino acid sequence (FIG. 5B) was identified in peptide 41c (Table I), indicating absence of glycosylation at this site. In contrast, the unidentified amino acid in peptide 34b probably corresponds to a glycosylated asparagine at residue 395.

Figure 5C:
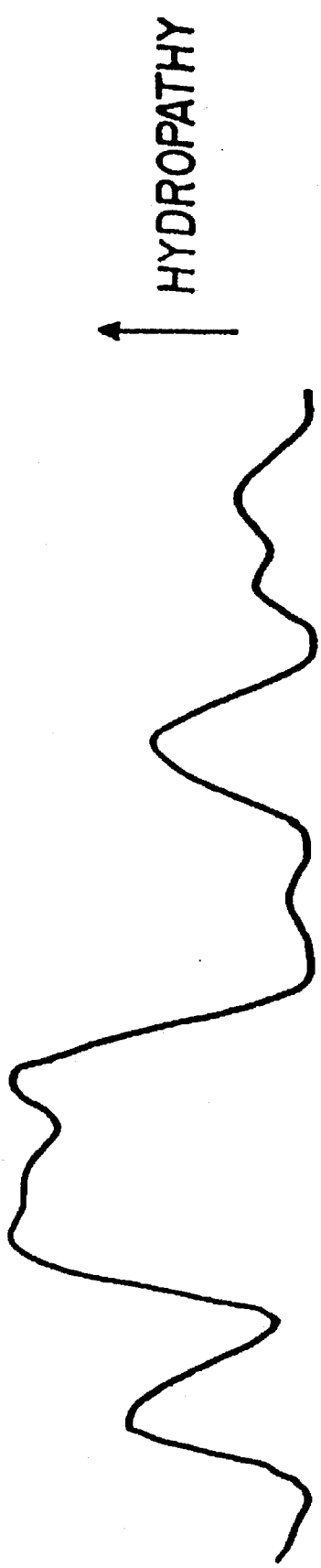

The only nonrepetitive CR1 sequences identified in the 5.5 kb of cDNA are located in the COOH-terminal region. A secondary structure analysis of this region identifies a single 25-residue putative membrane-spanning segment having strong hydrophobic character and high potential for α-helix formation (FIG. 5C). This sequence is immediately followed by four positively charged residues, a characteristic of many membrane proteins. The presumed cytoplasmic region of CR1 comprises 43 residues and contains a six amino acid sequence, VHPRTL, which is homologous to the sequence VRKRTL, a site of protein kinase C phosphorylation in the epidermal growth factor (EGF) receptor and the erbB oncogene product (Hunter, T., et al., 1984, Nature 311:480; Davis, R. J. and Czech, M. P., 1985, Proc. Natl. Acad. Sci. U.S.A. 82:1974). There are no tyrosine residues in the cytoplasmic region of tonsillar CR1.

6.3. Discussion

Approximately 80% of the primary structure of the F allotype of CR1 has been obtained by sequencing overlapping cDNA clones. The most unusual structural feature of CR1 observed in this analysis is the presence of tandem, direct LHRs of 450 amino acids, four of which are predicted to occur in the F allotype of CR1 that has an estimated polypeptide chain length of 2,000 residues (Wong, W. W., et al., 1983, J. Clin. Invest. 72:685; Sim, R. B., 1985, Biochem. J. 232:883). Three of the LHRs have been cloned and sequenced while evidence for the existence of the fourth was provided by the analysis of tryptic peptides. Each LHR is comprised of seven SCRs which are the basic structural elements of other C3/C4 binding proteins. The conservation of the four half-cystines per SCR, the probable involvement of the first and third and the second and fourth half-cystines in disulfide linkages (Lozier, J., et al., 1984, Proc. Natl. Acad. Sci. U.S.A. 81:3640) and the presence of conserved amino acids such as proline, glycine and asparagine which are frequently found in β-turns (Rose, G. D., et al., 1985, Adv. Protein Chem. 37:1) lead to the proposal that an SCR forms a triple loop structure maintained by disulfide linkages (FIG. 8B). This role for the half-cystine residues is supported by the finding that mildly trypsin-treated CR1 (Sim, R. B., 1985, Biochem. J. 232:883) and factor H (Sim, R. B. and DiScipio, R. G., 1982, Biochem. J. 205:285) migrate as intact molecules when analyzed by SDS-polyacrylamide gel electrophoresis (PAGE) under non-reducing conditions and as multiple tryptic fragments after reduction.

This series of tandemly repeated SCRs is predicted to form an elongated structure (FIG. 8A) as has been proposed for factor H and for each subunit of human C4bp (Sim, R. B. and DiScipio, R. G., 1982, Biochem. J. 205:285; Whaley, K. and Ruddy, S., 1976, J. Exp. Med. 144:1147; Dahlback, B., et al., 1983, Proc. Natl. Acad. Sci. U.S.A. 80:3461). Electron microscopic studies of the subunits of C4bp have indicated dimensions of 300×30 Angstroms (Dahlback, B., et al., 1983, Proc. Natl. Acad. Sci. U.S.A. 80:3461). As each subunit is composed of eight SCRs (Chung, L. P., et al., 1985, Biochem. J. 230:133), an individual SCR is calculated to be 38×30 Angstroms. Assuming that the SCRs of CR1 have similar dimensions and that the F allotype has 30 SCRs, the receptor could extend as much as 1,140 Angstroms from the cell membrane. Consistent with this prediction of CR1 structure is the earlier finding that ferritin-labeled antibody bound to CR1 on neutrophils was frequently 500 Angstroms from the outer leaflet of the plasma membrane (Abrahamson, D. R. and Fearon, D. T., 1983, Lab. Invest. 48:162). Such an elongated structure of CR1 would facilitate the interaction of receptor-bearing cells with C3b that has covalently bound to relatively inaccessible sites within immune complexes and microbial cell surfaces.

The finding that the SCR is the major, and perhaps only, extracytoplasmic element of CR1 provides structural evidence for a close relationship between the receptor and factor H and C4bp, two plasma proteins that are exclusively or predominantly composed of SCRs (Chung, L. P., et al., 1985, Biochem. J. 230:133; Kristensen, T., et al., 1986, J. Immunol. 136:3407). CR1 was initially isolated as an erythrocyte membrane protein having factor H-like activity after detergent solubilization (Fearon, D. T., 1979, Proc. Natl. Acad. Sci. U.S.A. 76:5867), and it was found subsequently to have the regulatory functions of factor H and C4bp when residing on the plasma membrane (Iida, K. and Nussenzweig, V., 1981, J. Exp. Med. 153:1138). By analysis of the inheritance of structural polymorphisms of CR1, factor H, and C4bp, the genes encoding these three proteins were shown to be linked (de Cordoba, R., et al., 1985, J. Exp. Med. 161:1189), and the locus for this linkage group and for the structurally related receptor, CR2, have been shown recently by in situ hybridization and by the analysis of somatic cell hybrids to be on the long arm of chromosome 1, band q32 (Weis, J. H., et al., 1987, J. Immunol. 138:312). Before the present study, the only evidence for a structural relationship between these proteins was a significant similarity in their amino acid compositions (Wong, W. W., et al., 1985, J. Immunol. Methods 82:303). Therefore, the present finding of at least 23 SCRs in CR1 constitutes the direct and formal demonstration of a structural relationship of the receptor with factor H and C4bp (Chung, L. P., et al., 1985, Biochem. J. 230:133; Kristensen, T., et al., 1986, J. Immunol. 136:3407), proteins with similar functions, and with the Ba and C2b fragments of factor B and C2 (Morley, B. J. and Campbell, R. D., 1984, EMBO J. 3:153; Mole, J. E., et al., 1984, J. Biol. Chem. 259:3407; Bentley, D. R. and Porter, R. R., 1984, Proc. Natl. Acad. Sci. U.S.A. 81:1212; Gagnon, J., 1984, Philos. Trans. R. Soc. Lond. B Biol. Sci. 306:301), components that form enzymatic complexes with C3b and C4b, respectively. However, the SCR is also found in several noncomplement proteins (Campbell, R. D., and Bentley, D. R., 1985, Immunol. Rev. 87:19; Lozier, J., et al., 1984, Proc. Natl. Acad. Sci. U.S.A. 81:3640; Leytus, S. P., et al., 1986, Biochemistry 25:4855; Kurosky, A., et al., 1980, Proc. Natl. Acad. Sci. U.S.A. 77:3388; Ichinose, A., et al., 1986, Biochemistry 25:4633) (FIG. 7), indicating that it does not necessarily represent a C3/C4 binding structure.

Among the proteins having SCRs, CR1 is unique in having organized this basic structure and genetic unit into the higher order structural unit of the LHR. Analysis of a 14.5 kb BamHI fragment of genomic DNA that is associated with expression of the S allotype has suggested that at least one repeating genomic unit in CR1 is an extended segment of DNA containing the exons encoding at least five SCRs and their flanking introns (Wong, W. W., et al., 1986, J. Exp. Med. 164:1531). These studies have also suggested that the S allele contains an additional copy of this genomic unit compared with the number present in the F allele. This observation, combined with a tryptic peptide mapping study (Nickells, M. W., et al., 1986, Mol. Immunol. 23:661) and the present finding that an LHR represents a peptide of ~40–50 kD allows us to predict the presence in the S allotype (290 kD) of an additional LHR relative to the estimate of four LHRs in the F allotype (250,000 daltons molecular weight).

In addition to providing evidence for duplication events, the sequences of the LHRs also suggest that conversion events have occurred within the CR1 gene. LHR-B and -D are 67% identical to each other throughout their length, whereas LHR-C is 99% identical to LHR-B in the $NH_2$-terminal four SCRs and 91% identical to LHR-D in the COOH-terminal three SCRs. This organization could not have occurred by a single recombinational event between identical parental alleles in the origin of this hybrid LHR. Rather, the hybrid LHR may have arisen by gene conversion (Atchison, M. and Adesnik, M., 1986, Proc. Natl. Acad. Sci. U.S.A. 83:2300) in which sequences in an LHR-C precursor were replaced by sequences present in LHR-B or LHR-D. The near complete identity and precise alignment of homologous sequences in these LHRs (FIG. 5B) also may have been maintained by a mechanism involving gene conversion. Analysis of the extent of homology between intervening sequences of those segments of the CR1 gene encoding the LHRs should determine whether gene conversion or selection based on functional constraints have strictly limited sequence divergence.

Although a previous study suggested that CR1 is monovalent (Wilson, J. G., et al., 1982, N. Engl. J. Med. 307:981), each LHR might represent a single C3b/C4b binding domain, which would make the receptor multivalent and adapted for the binding of complexes bearing multiple molecules of C3b and C4b. Alternatively, distinct LHRs might be responsible for binding C3b and C4b, respectively (see Section 9, infra), providing a structural basis for the combination of factor H and C4bp activities in CR1. Finally the LHRs of CR1 may represent structural domains that serve to extend CR1 from the plasma membrane, as suggested by the proposed structural model (FIG. 8A), and SCRs at the $NH_2$-terminal region bind C3b and C4b, as has been found for factor H (Sim, R. B. and DiScipio, R. G., 1982, Biochem. J. 205:285; Alsenz, J., et al., 1984, Biochem. J. 224:389).

Activation of protein kinase C by phorbol esters induces phosphorylation of CR1 in neutrophils, monocytes, and eosinophils (Changelian, P. S. and Fearon, D. T., 1986, J. Exp. Med. 163:101) and the CR1 cytoplasmic domain of 43 amino acids has a sequence that is homologous to a site that is phosphorylated by protein kinase C in the epidermal growth factor receptor (Hunger, T., et al., 1984, Nature 311:480; Davis, R. J. and Czech, M. P., 1985, Proc. Natl. Acad. Sci. U.S.A. 82:1974). However, this cytoplasmic sequence, which was found in three independent clones of the tonsillar library, is most likely that of B cell CR1, which is not phosphorylated after activation of protein kinase C (Changelian, P. S. and Fearon, D. T., 1986, J. Exp. Med. 163:101).

7. EXAMPLE: CR1 5' cDNA SEQUENCES CONTAIN A FOURTH LONG HOMOLOGOUS REPEAT

Analysis of a partial cDNA sequence of CR1 revealed a structure in which three LHRs, LHR-B, LHR-C, LHR-D, of 450 amino acids were each comprised of seven short consensus repeats (SCR) of 65 amino acids characteristic of C3/C4 binding proteins (see Section 6, supra). In the examples described herein, we describe the cloning and nucleotide sequence of a fourth amino-terminal LHR, LHR-A (Klickstein, L. B., et al., 1987, Complement 4:180) by the sequencing of 5' cDNA clones. Analysis of LHR-A revealed that it is 99% homologous to LHR-B in the five 3' SCRs, but only 61% homologous in the two 5' SCRs.

7.1. Materials and Methods 7.1.1. Construction of a cDNA Library

A selectively primed cDNA library, λHH, was constructed from 3 μg of poly $(A)^+$ RNA purified from DMSO-induced cells as described (Chirgwin, J. M. et al., 1979, Biochemistry 18:5290; Aviv, H. and Leder, P., 1972, Proc. Natl. Acad. Sci. U.S.A. 69:1408; Ausubel, F. M., et al., 1987, Current Protocols in Molecular Biology, John Wiley & Sons, New York) with the following modifications. LK35.1, a 35-mer oligonucleotide, 5'-TGAAGTCATC ACAGGATTTC ACTTCA-CATG TGGGG-3', was used in place of oligo$(dT)_{12-18}$ and 40 μCi of $\alpha^{32}P$-dCTP were added during second strand synthesis. One third of the cDNA was cloned in λgt11 and a cDNA library was constructed from human tonsilar poly$(A)^+$ RNA as described in Section 6.1.2, supra. 750,000 independent recombinants were obtained.

7.1.2. Isolation of Clones, Probes, and DNA Sequence Analysis

The probes used for screening cDNA libraries were CR1-1 (Wong, W. W., et al., 1985, Proc. Natl. Acad. Sci. U.S.A. 82:7711) (ATCC accession no. 57331), CR-2 (Wong, W. W., et al., supra), CR1-4 (Wong, W. W. et al., 1986, J. Exp. Med. 164:1531), and CR1-18, a 252 bp Sau3AI fragment from the 0.5 kb EcoRI fragment of cDNA clone λH3.1 corresponding to nucleotides 101–352 in FIGS. 1A–1P. Under conditions of high stringency, CR1-18 hybridizes only to cDNA clones encoding either the $NH_2$-terminal SCR of LHR-A or the signal peptide. The inserts of the cDNA clones were sequenced by the dideoxynucleotide technique (Sanger, F., et al., 1977, Proc. Natl. Acad. Sci. U.S.A. 74:5463) after subcloning fragments into M13mp18 and M13mp19 (Yanisch-Perron, C. et al., 1985, Gene 28:351).

7.2. Results

A specifically primed λgt11 cDNA library, λHH, that contained $7.5 \times 10^5$ recombinants was prepared with cDNA synthesized from poly (A)⁺ RNA from DMSO induced HL-60 cells. These cells express only the F allotype of CR1 (Lublin, D. M., et al., 1986, J. Biol. Chem. 261:5736) which is predicted to have four LHRs (Lapata, M. A., et al., 1984, Nucl. Acids Res. 12:5707). The primer, LK35.1, was an antisense 35-mer corresponding to nucleotides 896–930 of the partial cDNA sequence of CR1 presented in FIGS. 3A–3D. This oligonucleotide was shown to hybridize to LHR-B, LHR-C and LHR-D under the conditions of reverse transcription. Two hundred and fifty positive clones were identified in a plating of $3.8 \times 10^5$ unamplified recombinant phage screened with a mixture of the CR1 cDNA probes, CR1-1 and CR1-4. Thirty-eight positive clones were picked and plaque purified. Southern blots of EcoRI-digested DNA from these clones were screened with the 23-mer oligonucleotide, KS23.1, 5'-CTGAGCGTAC CCAAAGGGAC AAG-3', corresponding to nucleotides 763–785 of the partial CR1 cDNA sequence of FIG. 3. This probe hybridizes under conditions of high stringency at a single site in the sequence encoding LHR-B but not to sequences encoding LHR-C or LHR-D. The insert of clone λH7.1 (FIG. 9) contained three EcoRI fragments of 1.0 kb, 0.9 kb and 0.4 kb and the two larger fragments hybridized to KS23.1, indicating that this clone contained sequences coding for the 3' 5/7 of LHR-A and all of LHR-B. This finding confirmed that LHR-A is highly homologous to LHR-B. Clone λH3.1 (FIG. 9) contained a single KS23.1-positive EcoRI fragment of 10 kb and a 5', 0.5 kb fragment that hybridized weakly with CR1-4 at high stringency. This clone was considered to contain the additional 5' sequence completing LHR-A, including SCRs −1 and −2 and 0.1 kb of upstream sequence. None of the remaining 36 clones, all of which hybridized with CR1-1, were detected with the probe, CR1-18, a 252 bp Sau3AI fragment from the 0.5 kb EcoRI fragment of clone λH3.1 that does not hybridize to sequences encoding LHR-B, -C or -D.

DNA sequence analysis of λH3.1 revealed that the open reading frame continued to the 5' end of the cDNA, indicating that the clone did not extend to the translational start site. Therefore, the cDNA libraries, λHH and λS2T, were rescreened with the probe CR1-18 to identify one clone from each, λH10.3 and λT109.1, respectively. The EcoRI fragments of these clones that hybridized with CR1-18 were sequenced as were the inserts from the clones, λH3.1 and λH7.1. The composite sequence is presented in FIG. 1 such that the nucleotide following number 1531 in FIG. 1 is nucleotide #1 in FIGS. 3A–3D. The overlapping sequences of the cDNA clones from the HL-60 and tonsillar libraries are identical.

Immediately upstream of LHR-A, clones λH10.3 and λT109.1 contain identical putative hydrophobic leader sequences (Von Heijne, G., 1986, Nucl. Acids Res. 14:4683) encoding 41 amino acids, including an ATG matching the consensus NNA/GNNATGG proposed for eukaryotic translation initiation sites (FIG. 10) (Kozak, M., 1986, Cell 44:283). A second ATG, located six codons upstream of the chosen ATG and just downstream of an in-frame stop codon, is a poor match for this consensus sequence. The first three amino acids of this leader sequence for CR1, MGA, are the same as those reported for CR2. The sequences of these two clones diverge upstream of the ATG and that from clone λ10.3 is believed to represent a portion of an intervening sequence, as has been described for other CR1 cDNA clones in Section 6, supra.

The signal peptidase cleavage is predicted (Von Heijne, G., 1986, Nucl. Acids Res. 14:4683) to occur between glycine-46 and glutamine-47, suggesting that the blocked NH₂-terminus of CR1 (Wong., W. W., et al., 1985, J. Immunol. Methods 82:303; Holeis, V. M., et al., 1986, Complement 3:63) may be due to the presence of a pyrrolidone amide. The first two SCRs of the NH₂-terminal LHR-A contained in these clones are only 61% identical to the corresponding region of LHR-B, whereas SCRs 3–7 of LHR-A are 99% identical to the corresponding SCRs of LHR-B (FIG. 10). Comparison of LHR-A with LHR-C reveals that only the third and fourth SCRs of each are highly homologous (99% identical). LHR-A and -D have only 68% overall identity, with maximal identity of 81% between the sixth SCR of each LHR. Thus, completion of the 5' cDNA sequence of CR1 indicates that the F allotype is comprised of 2039 amino acids including a 41 amino acid signal peptide, four LHRs of seven SCRs each, two additional COOH-terminal SCRs, a 25 residue transmembrane region and a 43 amino acid cytoplasmic domain. There are 25 potential N-linked glycosylation sites.

7.3. Discussion

The primary structure of the NH₂-terminus and the signal peptide of the F allotype of CR1 has been deduced by the isolation and sequencing of 5' cDNA clones. The highly repetitive nature of the CR1 sequence made critical the development of an appropriate strategy for the preparation and identification of cDNA clones encoding this region of the receptor. A cDNA library was prepared using as a primer a 35-mer oligonucleotide known to hybridize under the conditions of reverse transcription to LHR-B, -C and -D; the possibility was considered that this primer might hybridize also to LHR-A that had been predicted to be highly homologous to LHR-B (see Section 6 supra). Appropriate cDNA clones were identified by the use of another oligonucleotide, KS23.1, that hybridizes only to LHR-B under stringent conditions, thereby increasing the probability of finding 5' cDNA clones. Two clones were found that encompassed almost all of the residual sequence of CR1, and a Sau3AI fragment of one of these, CR1-18, had sequence sufficiently unique to permit its use in the identification of the remaining 5' clones (FIGS. 9, 10).

A 250 bp probe from the 5' region of LHR-A, CR1- 18, hybridized not only to CR1 transcripts of 7.9 and 9.2 kb, but also to a 2 kb transcript in human tonsillar RNA under stringent conditions. This cross-hybridizing mRNA was not observed with CR1 cDNA probes from other LHRs or in northern blots of RNA from dimethyl sulfoxide-induced HL-60 cells and HSB-2 T lymphoblastoid cells. Thus, CR1 contains sequences homologous to two additional B cell proteins, one that is encoded by this newly recognized mRNA, and CR2.

8. EXAMPLE: EXPRESSION OF RECOMBINANT HUMAN CR1

As described supra, human CR1 cDNA clones have been isolated that span 7.0 kb and contain an open reading frame encoding 2039 amino acids (FIGS. 1A–1P). The proposed precursor form of the receptor includes a 41 amino acid signal peptide, four long homologous repeats (LHRs) of 450 amino acids with each LHR comprised of 7 short consensus repeats (SCRs), two COOH-terminal SCRs of 65 amino acids, a 25 amino acid transmembrane domain, and a 43 amino acid cytoplasmic region. Thus, the CR1 F allotype contains 30 SCRs. The NH₂-terminal LHR, LHR-A (see Section 7, supra), is 61% identical to the corresponding region of LHR-B in the first two SCRs and 99% identical in the COOH-terminal five SCRs. Restriction fragments of eight CR1 cDNA clones were spliced to form a full length construct of 6.9 kb and placed downstream of a mouse metallothionein promoter or a cytomegalovirus promoter, and transfected into L (mouse) cells or COS (monkey) cells. Recombinant cell surface CR1 was detected by indirect radioimmunoassay and immunofluorescence. No antigen was detected on cells transfected with the parental vector (CR1⁻) only. Immunoprecipitation of transfected, surface $^{125}$I-labeled, COS (monkey) cells by anti-CR1 monoclonal antibody, and analysis by non-reducing sodium dodecyl sulfate (SDS) polyacrylamide gel electrophoresis, yielded a 190,000 daltons molecular weight band which co-migrated with the F allotype from human erythrocytes. The expression of recombinant CR1 antigen of the correct molecular weight (Klickstein, L. B., et al., 1988, FASEB J. 2:A1833) provides evidence that the cDNA contains the entire coding sequence of human CR1.

8.1. Construction of Plasmid pBSABCD, Containing the Entire CR1 Coding Sequence

We describe herein the construction of plasmid pBSABCD, a vector encoding the full length (SCRs 1–30) CR1 protein.

The 2.3 kb insert from cDNA clone λT8.2 (Klickstein, L. B., et al., 1987, J. Exp. Med. 165:1095; see Section 6, supra) was subcloned into pUC18 as an EcoRI fragment, such that the 5' end was proximal to the HindIII site in the plasmid polylinker. This plasmid was named p188.2. p188.2 was cut with ApaI and HindIII, and the large 4.7 kb fragment containing CR1 sequence from SCR 26 through the 3' untranslated region plus vector sequences was gel-purified.

The insert from cDNA clone λT50.1 (Klickstein, L. B., et al., 1987, J. Exp. Med. 165:1095; see Section 6, supra) was subcloned as an EcoRI fragment into M13mp18. This phage was called 18R50.1. DNA from the replicative form of this clone was cut with HindIII and ApaI, and the 1.45 kb fragment containing CR1 SCRs 18–25 was isolated, ligated to the 4.7 kb fragment from p188.2, and the ligation transformed into E. coli DH5α. This plasmid was called p8.250.1.

The 0.75 kb and the 0.93 kb EcoRI fragments from cDNA clone λT8.3 (Wong, W. W., et al., 1985, Proc. Natl. Acad. Sci. U.S.A 22:7711) were subcloned into plasmid pBR327. These subclones were called pCR1-1 and pCR1-2, respectively, and contained SCRs 11–14 and SCRs 17–21, respectively. The EcoRI inserts were purified from each. The 0.75 kb pCR1-1 fragment was digested with SmaI, and the digest was ligated to pUC18 DNA cut with EcoRI and SmaI. A subclone, p181-1.1, with a 0.5 kb insert corresponding to SCRs 12–14, was isolated. The 0.93 kb fragment of pCR1-2 was digested with HindIII, and ligated to pUC19 cut with EcoRI and HindIII, and a subclone, p191-2.1, was isolated that contained a 0.27 kb insert containing SCR 17.

The cDNA clone λT6.1 (See Section 6, supra; Klickstein, L. B., et al., 1987, J. Exp. Med. 165:1095; Wong, W. W., et al., 1987, J. Exp. Med. 164:1531) was digested with EcoRI, and the 0.37 kb fragment corresponding to CR1 SCRs 15 and 16 was subcloned into pBR322. This clone was called pCR1-4. Clone p181-1.1 was cut with EcoRI and ScaI, and the 1.4 kb fragment was isolated. Clone p191-2.1 (Klickstein, L. B., et al., 1987, J. Exp. Med. 165:1095; see Section 6, supra) was digested with EcoRI and ScaI and the 2.0 kb fragment was isolated, ligated to the 1.4 kb fragment from p181-1.1, and the mixture was transformed into E. coli DH5α. The resulting plasmid was called p1-11-2. Plasmid p1-11-2 was digested with EcoRI, and the 0.37 kb insert fragment from pCR1-4 was inserted by ligation. The resulting plasmid was used to transform E. coli DH5α.

A subclone was chosen that contained a 0.39 kb BamHI-HindIII fragment. This plasmid was called p142 and contained CR1 SCRs 12–17. The 3.5 kb EcoRI-HindIII insert fragment from p8.250.1 was transferred to pGEM3b. This plasmid was called pG8.250.1. The 1.2 HindIII fragment from p142 was purified and ligated to pG8.250.1 that had been cut with HindIII. A subclone was chosen that contained a 2.4 kb PstI-ApaI insert, thus selecting the correct orientation. This plasmid was called pCD and contained CR1 sequences from SCR 12 through the 3' end.

The cDNA clone λ5'7.1 (Klickstein, L. B., et al., Sept. 1987, Complement 4:180; see Section 7, supra) was cut with PstI, and the 1.35 kb fragment corresponding to SCRs 6–12 was isolated and ligated to PstI-cut pCD. The mixture was transformed, and a subclone was selected which contained 1.35 kb and 1.1 kb HindIII fragments. This clone was called pBCD.

The cDNA clone λ5'3.1 (Klickstein, L. B., et al., 1987, Complement 4:180; see Section 7, supra) was cut with EcoRI, and the digest was ligated to EcoRI-cut pUC18. A subclone, p3.11-1, was isolated, that contained a 1.0 kb insert corresponding to SCRs 3–7, which insert was gel-purified. The cDNA clone λ5'10.3 (Klickstein, L. B., et al., 1987, Complement 4:180; see Section 7, supra) was cut with EcoRI, and the 0.63 kb insert containing SCRs 1 and 2 was subcloned into pUC18. This clone was called p10.3.5. Plasmid p10.3.5 was partially digested with EcoRI, and a 3.4 kb fragment corresponding to linear plasmid was isolated and ligated with the 1 kb fragment from p3.11-1. A subclone, pLA, was picked, which contained a 1.3 kb PstI fragment, in the correct site of insertion and orientation.

The cDNA clone λT109.4 (Klickstein, L. B., et al., 1987, Complement 4:180; see Section 7, supra) was digested with EcoRI, and subcloned into pUC18. A subclone was chosen that contained a 0.55 kb EcoRI fragment corresponding to the 5' untranslated region through the leader sequence and SCRs 1 and 2. The plasmid p109.4 was cut with PstI and BspMII, and a 3.0 kb fragment containing the vector, leader sequence, and SCR 1, was isolated. The fragment was ligated to a 0.81 kb PstI-BspMII fragment from pLA that contained SCRs 2–5. This new plasmid was called pNLA. The plasmid pNLA was partially digested with EcoRI and completely digested with PstI, and a 1.1 kb EcoRI-PstI fragment containing CR1 sequence from the leader sequence through SCR 5 was isolated and ligated to pBluescript KS+ (Stratagene, San Diego, Calif.) to put an XhoI site on the 5' side of the cDNA. This plasmid was called pXLA.

The plasmid pBCD was cut with EcoRV and then partially digested with PstI, and a 6.0 kb PstI-EcoRV fragment containing CR1 sequence from SCR 6 through the 3' untranslated region was isolated and ligated to PstI+SmaI-digested pXLA. The resulting bacterial expression plasmid, which contains the entire CR1 cDNA coding sequence, was called pBSABCD.

Figures 11A, 11B:
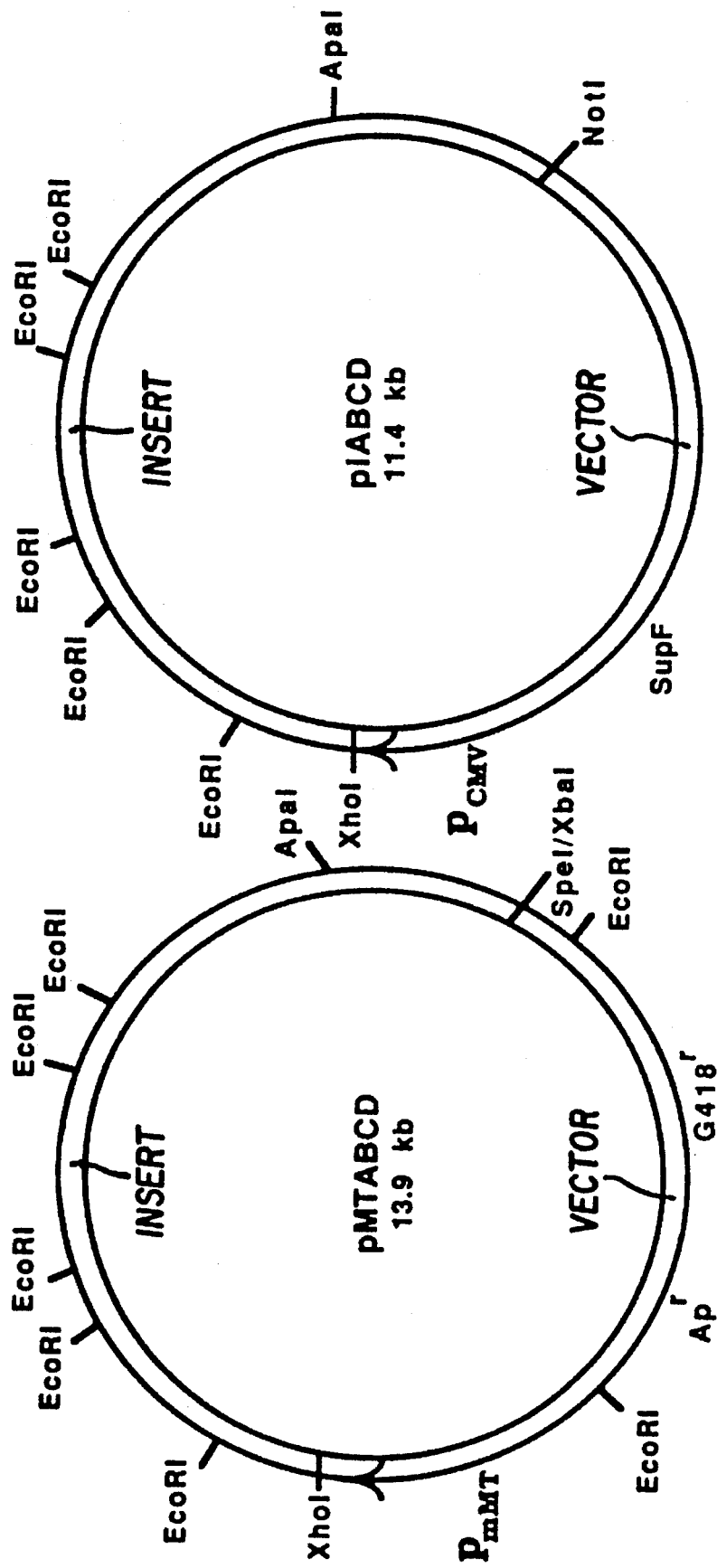
Figure 12B:
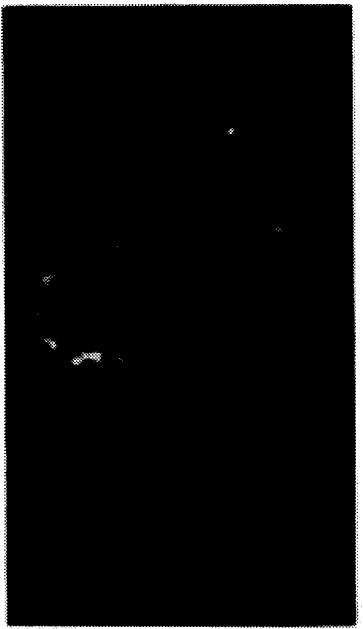
Figure 12D:
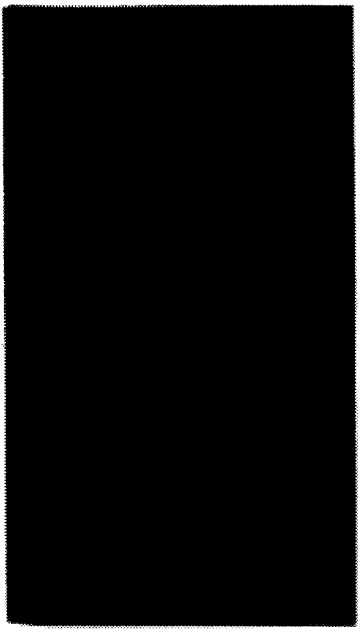
Figure 12A:
Figure 12C:
Figure 13A:
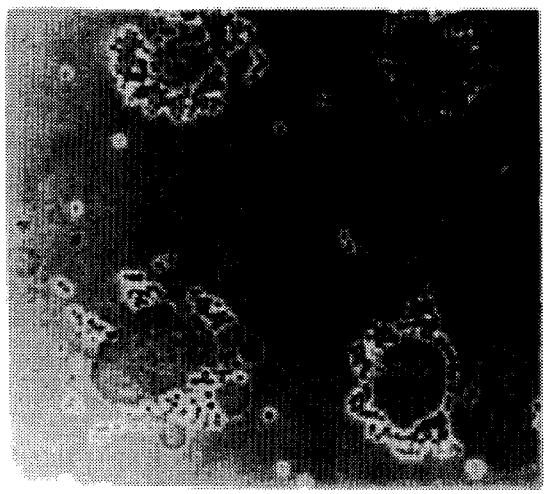
Figure 13B:
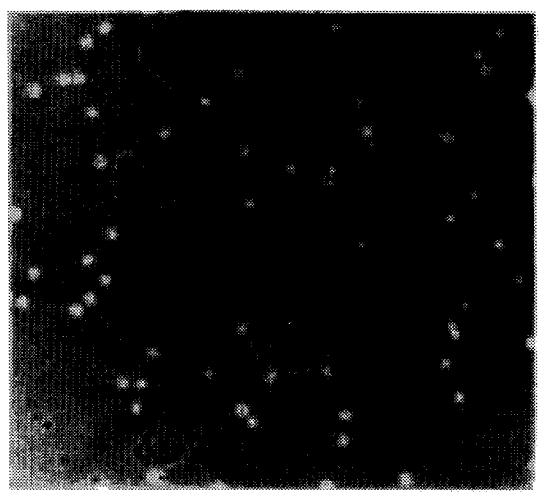
Figure 13C:
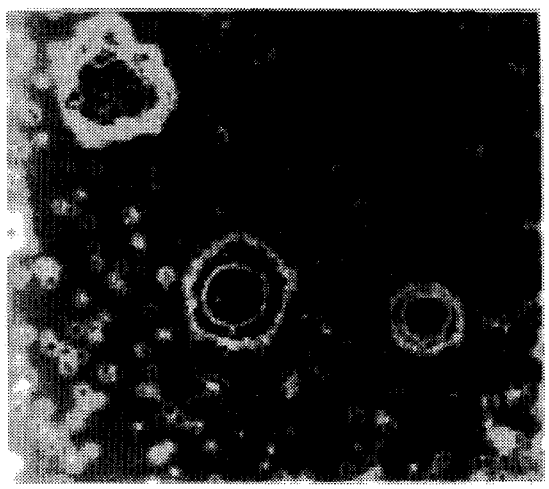
Figure 13D:

8.2. Construction and Assay of Plasmid piABCD, a Mammalian Expression Vector Containing the Entire CR1 Coding Sequence The pBSABCD plasmid was digested with XhoI and NotI, and the insert was ligated downstream from the CMV promotor in the 4.4 kb fragment of the expression vector, CDM8 (Seed, B., 1987, Nature 329:840–842), which also had been cut with these restriction enzymes. The resulting construction was termed piABCD (FIG. 11B). Alternatively, the 6.9 kb XhoI-NotI fragment was ligated downstream from the metallothionein promoter in the expression vector, pMT.neo1, which had also been cut with these restriction enzymes. The resulting construction was termed pMTABCD (FIG. 11A).

Sheep erythrocytes sensitized with rabbit antibody (EA) and limited amounts of C4b [EAC4b(lim)] and 12,000 cpm $^{125}$I-C3b per cell [EAcC4b(lim),3b] were prepared by sequential treatment of EAC4b(lim) (Diamedix) with C1, C2 and $^{125}$I-C3 followed by incubation for 60 minutes at 37° C. in gelatin veronal-buffered saline containing 40 mM EDTA. Alternatively, methylamine-treated C3 [C3(ma)] were covalently attached to sheep E (erythrocytes) treated with 3-(2-pyridyldithio) propionic acid N-hydroxysuccinimide ester (Sigma) (Lambris, J. D., et al., 1983, J. Immunol. Methods 65:277). EAC4b were prepared with purified C4 (Hammer, C. H., et al., 1981, J. Biol. Chem. 256:3995).

Both piABCD and pMTABCD were transfected by the DEAE (diethylaminoethyl)-dextran method into COS (monkey) cells. Recombinant CR1 was detected on the surface of the transfected cells by immunofluorescence using the anti-CR1 monoclonal antibody, YZ-1; and by immunoprecipitation of $^{125}$I-labeled cells followed by non-reducing SDS-PAGE, which revealed a protein having a mobility identical to that of CR1 immunoprecipitated from human erythrocytes of a donor homozygous for the F allotype (Wong, W. W., et al., 1983, J. Clin. Invest. 72:685); and by formation of rosettes with sheep erythrocytes coated with C3b (Fearon, D. T., 1980, J. Exp. Med. 152:20). The identical electrophoretic mobilities of the native and recombinant CR1 proteins confirmed that the CR1 F allotype contains SCRs 1–30.

In addition, murine L cells were co-transfected by the DEAE-dextran method (Ausubel, F. M., et al., 1987, Current Protocols in Molecular Biology, Seidman, J. G. and Struhl, K., eds., John Wiley & Sons, New York; Seed, B., 1987, Nature 329:840) in duplicate with 0, 2, or 4 µg of either piABCD or pMTABCD and 2 µg of pXGH5, a reporter plasmid that directs the expression of growth hormone (Selden, R. F., et al., 1986, Mol. Cell. Biol. 6:3173). The cells were harvested after two days and assayed for expression of CR1 by binding of YZ1 monoclonal anti-CR1 antibody. There was a dose response relationship between recombinant plasmid DNA and the expression of CR1 antigen (Table II).

TABLE II

DOSE RESPONSE OF RECOMBINANT CR1 AND HUMAN GROWTH HORMONE IN CO-TRANSFECTED L CELLS

| Plate Number | pXGH5 (µg) | pMTABCD (µg) | piABCD (µg) | YZ1 Anti-CR1 mAB RIA* (cpm) | Growth Hormone (ng/ml) |
|---|---|---|---|---|---|
| 1 | 2 | 0 | 0 | 1444 | 120 |
| 2 | 2 | 0 | 2 | 6058 | 130 |
| 3 | 2 | 0 | 2 | 6531 | 140 |
| 4 | 2 | 0 | 4 | 10620 | 180 |
| 5 | 2 | 0 | 4 | 9898 | 80 |
| 6 | 2 | 2 | 0 | 3111 | 180 |
| 7 | 2 | 2 | 0 | 2747 | 160 |
| 8 | 2 | 4 | 0 | 3547 | 160 |
| 9 | 2 | 4 | 0 | 3337 | 140 |

*For radioimmunoassay (RIA), replicate samples of $3 \times 10^5$ transfected cells in 0.1 ml phosphate-buffered saline containing 1% bovine serum albumin and 0.02% sodium azide were incubated at 0° C. for 60 minutes with 3 µg/ml YZ-1 IgG1 anti-CR1 (Changelian, P. S., et al., 1985, J. Immunol. 134:1851). The cells were washed and resuspended in 0.1 ml of buffer containing 1–2 µCi/ml of $^{125}$I-F(ab')$_2$ goat-anti-mouse IgG or $^{125}$I-protein A. After 1–2 hours at 0° C., the cells were washed and assayed for $^{125}$I.

The plasmid, piABCD, directed the expression of nearly three-fold more CR1 antigen than did pMTABCD. The growth hormone concentration in the culture medium varied by less than two-fold with the exception of plate 5. Additional experiments revealed that piABCD directed the transient expression of three-fold more CR1 antigen in COS cells than in L cells.

CR1 antigen was present in clusters on the surface of the transfected COS cells when assessed by indirect immunofluorescence of cells stained with YZ1 anti-CR 1 mAB (FIGS. 12a–12d). This distribution of recombinant CR1 on COS cells resembles that of wild type CR1 on human leukocytes (Fearon et al., 1981, J. Exp. Med. 153:1615).

The molecular weight of the recombinant CR1 was determined by surface iodination of COS cells transfected with piABCD, immunoprecipitation of cell lysates with Sepharose-YZ1, SDS-PAGE and autoradiography. The recombinant CR1 had a molecular weight of 190,000 unreduced which is equivalent to that of the F allotype and less than that of the S allotype of erythrocyte CR1 (FIG. 14).

The C3b-binding and C4b-binding function of recombinant CR1 was assayed by the formation of rosettes between the transfected COS cells and EAC4b or EAC4b(lim),3b. In 31 separate transfections, 5%–50% of COS cells transfected with the plasmid, piABCD, bound five or more EAC4b or EAC4b(lim),3b (FIGS. 13a–13d). The COS cells expressing CR1 did not form rosettes with EAC4b(lim),3bi, although this intermediate did form rosettes with Raji B lymphoblastoid cells expressing CR2.

8.3. Expression of CR1 Fragments

Expression vectors encoding part of the CR1 coding sequence (deletion mutants) were constructed as described infra, and found to express their respective CR1 inserts when transformed into COS cells. The CR1 fragments were expressed as cell-surface proteins.

8.3.1. Construction of Deletion Mutants piBCD, piABD, piACD, piAD, piBD, piCD and piD The construction of these deletion mutants was performed by taking advantage of the presence of a single BsmI site in a homologous position near the amino-terminus of each of the four CR1 long homologous repeats (LHRs), and the absence of BsmI sites elsewhere in the CR1 cDNA and Bluescript vector (Stratagene, San Diego, Calif.).

Ten micrograms of the plasmid pBSABCD were partially digested with 50 units of the restriction enzyme BsmI for 45 minutes, and the digest was fractionated by agarose gel electrophoresis. DNA fragments of 8.55 kb, 7.20 kb and 5.85 kb were purified that corresponded to linear segments of the parent plasmid that lacked one, two or three LHRs, respectively. Each of the three fragments was ligated to itself and the ligations used separately to transform competent E. coli DH5α to ampicillin resistance.

The 8.55 kb fragment was generated as the consequence of cleavage of pBSABCD at two adjacent BsmI sites, thus there are three possible product plasmids after ligation, pBCD, pACD or pABD, where the capital letters represent the LHRs that remain in the plasmid. These were distinguishable by restriction mapping with SmaI. DNA was prepared from 12 colonies, digested with SmaI, and separated by agarose gel electrophoresis. Five clones had two SmaI fragments of 2.5 kb and 6.1 kb, corresponding to deletion of the coding sequence of LHR-A, thus representing pBCD. Three clones had a single linear fragment of 8.5 kb corresponding to pACD. Four clones had two SmaI fragments of 1.2 kb and 7.4 kb, which was expected for the deletion of the coding sequence of LHR-C, producing pABD. The 5.6 kb insert of each of these three constructions was gel-purified after double digestion with XhoI and NotI, and ligated to the expression vector CDM8 that had been gel-purified after digestion with the same restriction enzymes. E. coli DK1/P3 was transformed with the ligation mixtures and DNA was prepared from five colonies of each. The presence of the deleted CR1 cDNA insert in the expression vector was shown in each case by SacI digestion, which revealed the expected two fragments of 4.20 kb and 5.75 kb. These plasmids were called piBCD, piACD and piABD.

The 7.20 kb fragment from the partial digestion of pBSABCD was a consequence of BsmI digestion at three adjacent sites or, equivalently with respect to the large fragment, at two sites with a single uncut site between them, thus there were two possible products obtainable after transformation, pAD and pCD. These were distinguished by double digestion with XhoI and PstI, which yielded two fragments of 1.0 kb and 6.2 kb in the case of pAD, and a linear fragment of 7.2 kb for pCD. The 4.2 kb insert from each of these plasmids was gel-purified after double digestion with XhoI and NotI, and subcloned into CDM8 as above. The presence of the deleted CR1 cDNA in the expression vector was shown by double digestion with PstI and BglII. The clone piAD had fragments of 2.4 kb and 6.2 kb, while piCD had a single fragment of 8.6 kb.

The 5.85 kb fragment from the BsmI digestion of pBSABCD represents a product of complete digestion and a single clone, pD, was obtained after transformation of $E.\ coli$ DH5α. This was confirmed by double digestion with HindIII and BglII which yielded the expected 3.7 kb and 2.2 kb fragments. The 2.9 kb insert of the clone was gel-purified after double digestion with XhoI and NotI and ligated to the expression vector as above. HindIII digestion of the resulting piD clone yielded the expected 7.3 kb fragment, a XhoI+ BglII double digest gave 2.2 kb and 5.1 kb fragments, and a SacI digest resulted in the expected 1.5 kb and 5.8 kb fragments.

The plasmid pBD was prepared by BsmI partial digestion of pBCD. The linear 7.2 kb fragment corresponding to cleavage of two adjacent BsmI sites was gel-purified, self-ligated as above, and $E.\ coli$ DH5α was transformed to ampicillin resistance. pBD was identified by the presence of 1.2 kb and 6.0 kb fragments upon SmaI digestion. The 4.2 kb insert was purified after double digestion with XhoI and NotI, and transferred to CDM8 as above. The clone piBD was confirmed by observation of the expected 0.8 kb and 7.8 kb fragments after HindIII digestion.

COS cells transiently expressing the piABCD, piBCD, piCD, and piD constructs, respectively, were surface-labelled with $^{125}I$, and immunoprecipitated with anti-CR1 antibody. On SDS-PAGE following reduction, the product of the piABCD construct comigrated with the F allotype of CR1, while the deletion mutants demonstrated stepwise decrements of approximately 45,000 daltons, indicative of the deletion of one, two and three LHRs, respectively (FIG. 17).

8.3.2. Construction of Deletion Mutants piE1, piE2, piE-2, piU1, piU-2 and piA/D The plasmid piABCD was completely digested with BstEII and the two fragments at 1.35 kb (a doublet) and 8.6 kb were gel-purified, mixed, and ligated, and $E.\ coli$ DK1/P3 was transformed to ampicillin and tetracycline resistance. Colonies were screened by hybridization with the CR1 cDNA probe CR1-4 (see Section 8.1, supra), and strongly positive clones were picked and further screened by digestion with SmaI. piE1 was identified by the presence of two fragments at 2.7 kb and 7.3 kb, and piE2 was identified by a single 10.0 kb linear fragment. piE-2 was identified as a weakly CR1-4 positive clone that contained a single 8.6 kb SmaI fragment.

The plasmid piP1 was obtained by complete digestion of piABCD with PstI and gel-purification of the large, 10.0 kb fragment. This fragment was ligated and $E.\ coli$ DK1/P3 was transformed with the mixture. The resulting plasmid, piP1, contained a single, 10.0 kb SmaI fragment.

The plasmids piU1 and piU-2 were prepared by first transforming the dcm⁻ strain GM271/P3 with the plasmid pXLA, and isolating DNA. This DNA was double digested with StuI and NotI, and the 3.3 kb fragment was gel-purified. The plasmid pBSABCD was partially digested with NsiI, and the resulting four base pair 3' overhangs were removed by treatment with the Klenow fragment of $E.\ coli$ DNA polymerase I. The DNA was then digested to completion with NotI, and fragments of 5.4 kb and 4.0 kb were gel-purified. These were ligated to the 3.3 kb StuI-NotI fragment from pXLA, and the ligation mixture was used to transform $E.\ coli$ DH5α to ampicillin resistance. Colonies were screened by hybridization to the CR1 cDNA probe CR1-4, and positive clones were further checked by restriction digestion with HindIII which yielded three fragments of 0.8 kb, 1.3 kb and 6.5 kb for pU1, and two fragments of 0.8 kb and 6.5 kb for pU-2. The StuI-blunted NsiI splice was confirmed to be in-frame by DNA sequencing of these plasmids. The inserts of pU1 and pU-2, 5.6 kb and 4.2 kb, respectively, were gel-purified after XhoI and NotI double digestion, and were ligated to the expression vector CDM8 as described supra. The structures of the clones, piU1 and piU-2, were confirmed by restriction digestion with XhoI+ PstI, yielding the expected two fragments of 1.2 kb and 8.8 kb for piU1 and a linear 8.7 kb fragment for piU-2.

The plasmid piA/D was prepared by first digesting piABCD with PstI to completion. The PstI digest was then partially digested with ApaI, and the 3' overhangs were removed with the Klenow fragment of $E.\ coli$ DNA polymerase I. The DNA was then fractionated by agarose gel electrophoresis and the 7.5 kb fragment was isolated, ligated, and used to transform $E.\ coli$ DK1/P3 to ampicillin and tetracycline resistance. The construction was confirmed by double digestion with KpnI+ SacI, which yielded the expected four fragments of 0.8 kb, 1.5 kb, 1.7 kb and 3.3 kb.

9. EXAMPLE: IDENTIFICATION OF C3b AND C4b BINDING DOMAINS

9.1. Assays and Results

Plasmids piABCD, piAD, piCD, and piD, containing the LHR(s) denoted by the capital letter(s) of their names, were transformed into COS cells, which were used in assays to assess the ability of their encoded CR1 fragments to bind C3b or C4b. Binding assays were carried out by observation of erythrocyte rosetting resulting from the binding of C3b or C4b-coated red cells by COS cells expressing a full-length CR1 molecule or a CR1 deletion mutant on their cell surface (transient expression). Transfected cells, $1–4 \times 10^6$/ml, were incubated with C3- or C4-bearing erythrocytes, $2–6 \times 10^8$/ml, in 0.02 ml for 60 minutes at 20° C. The percentage of transfected cells forming rosettes was evaluated microscopically with a transfected cell scored as a rosette if there were at least five adherent erythrocytes. The results are shown in Table III.

TABLE III

FORMATION OF ROSETTES BETWEEN COS CELL
TRANSFECTANTS EXPRESSING RECOMBINANT
FORMS OF CR1 AND SHEEP ERYTHROCYTES
BEARING C3 (ma) OR C4 (ma)

| COS Cell Transfectant | % Transfectants Forming Rosettes | |
|---|---|---|
| | % Transfectants Fluorescent with Anti-CR1 | |
| | EC3 (ma)* | EC4 (ma)# |
| piABCD | 109 (3)ⁿ | 62 (2) |
| piAD | 8 (3)ⁿ | 107 (2) |
| piBD | 107 (3)ⁿ | 12 (2) |
| piCD | 127 (3)ⁿ | 32 (2) |
| piD | 0 (3)ⁿ | 0 (2) |
| piA/D | 11 (2) | 83 (2) |
| piE-2 | 1 (1) | 102 (1) |

*The numbers of C3 (ma) per erythrocyte were 60,000, 350,000 and 900,000, respectively, in the three experiments using this intermediate.
The number of C4 (ma) per erythrocyte were 160,000 and 140,000, respectively, in the two experiments using this intermediate.
ⁿNumber of experiments.

In each of three separate experiments, the proportion of COS cells expressing the full length piABCD construct that formed rosettes with the EC3(ma) was similar to the fraction having detectable recombinant receptor, as assessed by immunofluorescence using either YZ1 monoclonal anti-CR1 antibody or rabbit anti-CR1 antiserum (Table III). In contrast, cells expressing piD did not form rosettes, indicating that a C3-binding site(s) must reside in or require the presence of LHR-A, -B or -C. A site was shown to be present in both LHR-B and -C by demonstrating that cells expressing either the piBD or piCD constructs formed rosettes with EC3(ma). Cells expressing piAD, piA/D, or piE-2 did not have equivalent C3-binding function. As the piE-2 construct differs from piCD only in having SCR-1 and -2 of LHR-A instead of the first two SCRs of LHR-C, the function of the C3-binding site in LHR-C must require these $NH_2$-terminal SCRS.

The proportion of COS cells expressing the full length piABCD recombinant that formed rosettes with EC4(ma) was less than the fraction rosetting with EC3(ma), perhaps reflecting fewer C4(ma) per erythrocyte (Table III) or fewer C4-binding sites per receptor. Deletion mutants having all or part of LHR-A, the piAD, piA/D and piE-2 constructs, bound EC4(ma) better than did the deletion mutants, piBD and piCD; piD lacked this function. Thus, the C4-binding site of CR1 resides primarily in LHR-A, although secondary sites may be present in LHR-B and -C. The improved rosetting capability of the piE-2 construct relative to that of piCD suggests that SCR-1 and -2 of LHR-A are involved in the C4 binding site.

Radioimmunoassay of the binding of YZ1 monoclonal anti-CR1 antibody indicated significant uptake by COS cells expressing the piABCD, piAD, piBD, and piCD constructs (Table IV). Cells transfected with piD or piA/D, which is comprised of the five $NH_2$-terminal SCRs of LHR-A and the three COOH-terminal SCRs of LHR-D, did not bind YZ1 anti-CR1 antibody, although the products of these constructs bound polyclonal anti-CR1 antiserum (Table IV). Thus, the YZ1 epitope is repeated in LHR-A, -B and -C, is not present in the $NH_2$-terminal SCRs of LHR-A, and is not present or is inaccessible in LHR-D.

TABLE IV

BINDING OF MONOCLONAL AND POLYCLONAL
ANTI-CR1 ANTIBODY TO COS CELL
TRANSFECTANTS EXPRESSING RECOMBINANT
FORMS OF CR1

| COS Cell Transfectant | Bound YZ1 Monoclonal Antibody* | Bound Rabbit Polyclonal Antibody* |
|---|---|---|
| piABCD | 2362 | 12277 |
| piAD | 2879 | 19891 |
| piBD | 3646 | 21922 |
| piCD | 2189 | 19926 |
| piA/D | 410 | 23052 |
| piD | 404 | 16386 |
| CDM8 | 428 | 4886 |

*Replicate samples of $3 \times 10^5$ transfected cells in 0.1 ml phosphate-buffered saline containing 1% bovine serum albumin and 0.02% sodium azide were incubated at 0° C. for 60 minutes with 3 μg/ml YZ1 IgG1 anti-CR1 mAb (Changelian, P. S., et al., 1985, J. Immunol. 134:1851) or with 90 μg/ml rabbit IgG anti-CR1 antibody. The cells were washed and resuspended in 0.1 ml of buffer containing 1–2 μCi/ml of $^{125}$I-F(ab')$_2$ goat-anti-mouse IgG or $^{125}$I-protein A. After 1–2 hours at 0° C., the cells were washed and assayed for $^{125}$I. Values shown are the mean of duplicate determinations, cpm per $3 \times 10^5$ COS cells.

9.2. Discussion

The conserved BsmI site found midway through the coding sequence of the first SCR in each LHR permitted the construction of a series of deletion mutants that corresponded closely to the boundaries of the LHRs, and maintained the open reading frame and the appropriate positions of the four cysteines necessary for the presumed disulfide bond formation (FIG. 16). Comparison of the C3(ma)- and C4(ma)-binding functions of these deletion mutants distinguished not only the LHRs having these specificities, but also those SCRs critical for determining the ligand specificity. Thus, the capacity of piAD, piA/D, and piE-2 forms of the receptor, but not the piD form, to mediate rosette formation between the transfected COS cells and EC4(ma) indicated that the $NH_2$-terminal two SCRs of LHR-A contained a site for interaction with this complement protein (Table III). This site was only relatively specific for C4(ma) because transfectants expressing piAD and piA/D also were capable of binding EC3(ma) (Table III). The C3(ma)-binding function of the receptors encoded by the piBD and piCD constructs, demonstrated by rosette assay and factor I-cofactor function for cleavage of C3(ma) (Table III; FIG. 18), indicated the presence of sites specific for C3(ma) in the first two SCRs of these LHRs. These sites also were capable of interacting with C4(ma) (Table III). Thus, there are preferential, but overlapping, C4- and C3- binding activities in LHR-A, -B and -C.

Alternatively, the capacity of the COS cells expressing the piBD and piCD constructs to bind EC4(ma) may have been caused by the transfer of nucleotides encoding the $NH_2$-terminal 36 amino acids from SCR-1 of LHR-A to LHR-B and -C through the ligation of the BsmI fragments. However, these 36 amino acids alone did not confer on the piD product C4-rosetting function. We cannot exclude a secondary function of LHR-D in these reactions because this LHR was present in all the constructs assayed for function. The finding of three distinct ligand recognition sites in CR1, two for C3b and one for C4b (FIG. 19), indicates that each receptor molecule may be capable of effectively binding complexes bearing multiple C4b and C3b molecules despite having a relatively low affinity for monovalent ligands (Arnaout, M. A., et al., 1983, Immunology 48:229). This finding also provides an explanation for the inability of soluble C4b to inhibit formation of rosettes between erythrocytes bearing C3b and a human B lymphoblastoid cell line (Gaither, T. A., et al., 1983, J. Immunol. 131:899). Possible ligands for which CR1 would be especially adapted may be the molecular complexes, C4b/C3b and C3b/C3b, that are generated during activation of the classical and alternative pathways, respectively. Since there are distinct binding sites in three of the four LHRs, the CR1 structural allotypes differing by their number of LHRs may have significant functional differences caused by variations in the number of ligand binding sites. Although in vitro studies have not reported differing binding activities of the F, S and F' (A, B and C, respectively) allotypes, the smaller F' allotype presumably having only three LHRs might have an impaired capability to clear immune complexes. The F' allotype has been reported possibly to be associated with systemic lupus erythematosus (van Dyne, S., et al., 1987, Clin. Exp. Immunol. 68:570).

10. EXAMPLE: DEMONSTRATION OF FACTOR I COFACTOR ACTIVITY

The recombinant CR1 protein, and specific fragments thereof, in both cell-surface and solubilized forms, were demonstrated to have C3b factor I cofactor activity.

Assays of factor I cofactor activity were carried out by modifications of a published procedure (Fearon, D. T., 1979, Proc. Natl. Acad. Sci. U.S.A. 76:5867).

For assay of factor I cofactor activity of solubilized CR1 and fragments, cell-surface CR1 protein and fragments were solubilized with Nonidet P-40, and the lysate was immunoprecipitated with anti-CR1 monoclonal antibody YZ-1 coupled to Sepharose beads. Detergent lysates of 1× 10$^6$ transfected COS cells were immunoprecipitated sequentially with Sepharose UPC10 anti-levan and Sepharose-YZ- 1. The immunoprecipitate was then assayed for factor I cofactor activity by incubation of the washed beads for 60 minutes at 37° C. with 0.5 µg of $^{125}$I-C3(ma) and 200 ng of factor I in 0.05 ml PBS, 0.5% NP-40. After incubation, the supernatant containing radiolabeled C3 (ma) was analyzed by SDS-polyacrylamide gel electrophoresis and autoradiography. Factor I cofactor activity was indicated by the appearance on the autoradiogram of lower molecular weight forms of the alpha chain of C3(ma) resulting from proteolytic cleavage by factor I.

For assay of factor I cofactor activity of cell-surface CR1 and fragments, transfected COS cells carrying a CR1 expression vector (piABCD, piAD, piBD, piCD, or piD, described supra) were incubated with 0.5 µg $^{125}$I-C3(ma) and 0.2 µg factor I (Fearon, D. T., 1977, J. Immunol. 119:1248), and analyzed as described supra.

The factor I-cofactor activity of cell-surface recombinant CR1 is shown in FIG. 15. Factor I cleaved the alpha chain of C3(ma) into fragments of molecular weights 76,000 and 46,000 only in the presence of immunoimmobilized, recombinant CR1 or factor H (FIG. 15). The regions corresponding to bands from the autoradiogram were excised from the gel and assayed for $^{125}$I to determine the amount of alpha chain cleaved. In the presence of factor H, 91% of the alpha chain was cleaved while in the presence of increasing amounts of recombinant CR1, 26%, 41%, and 55%, respectively, was cleaved. Although the COS cells transfected with the CDM8 vector alone contained some endogenous factor I-cofactor activity, an increase in this function was evident with COS cells transfected with piABCD, piBD and piCD (FIG. 18). No enhanced cleavage of $^{125}$I-C 3(ma) was seen with COS cells transfected with piAD or piD. Thus, among these constructs, only the deletion mutants, piBD and piCD, that conferred on COS cells a capacity for binding C3, also had factor I-cofactor activity for cleavage of C3.

The results of the assays for factor I cofactor activity with both cell-surface and solubilized forms of CR1 and fragments thereof are shown in Table V.

TABLE V

FACTOR I COFACTOR ACTIVITY OF CELL-SURFACE AND SOLUBILIZED FORMS OF CR1 and CR1 FRAGMENTS

| Plasmid[a] | Factor I Cofactor Activity[b] | |
|---|---|---|
| | Cell-Surface | Solubilized |
| piABCD | + | + |
| piAD | − | − |
| piBD | + | ND[c] |
| piCD | + | + |
| piD | − | ND[d] |

[a] Encoding the assayed CR1 protein or fragment, and transfected into COS cells for expression.
[b] (+) denotes an increase in cofactor activity above the endogenous level observed upon transfection with the CDM8 vector alone.
[c] Not determined.
[d] Not determined, due to the absence from LHR-D of the epitope recognized by anti-CR1 monoclonal antibody YZ-1.

As shown in Table V, expression of piABCD (encoding a full-length CR1 protein), piBD (encoding LHR-B and -D) or piCD (encoding LHR-C and -D) produced a CR1 product with C3b factor I cofactor activity. The data of Table V thus provide evidence that the CR1 protein or a fragment thereof can promote complement inactivation.

11. EXAMPLE: EXPRESSION OF RECOMBINANT SOLUBLE CR1

The CR1 cDNA was modified by recombinant DNA procedures so that a soluble form (sCR1) of CR1 or CR1 fragments was produced. The sCR1 constructs were expressed in a mammalian system where the expressed protein was secreted from the cells. Large quantities of the soluble polypeptides were produced, which, in contrast to the membrane bound form of CR1 proteins, did not have to be solubilized to obtain them in solution.

11.1. Materials and Methods

11.1.1. Enzyme Digestions

All restriction enzyme digestions, linker ligations, and T4 DNA ligase and E. coli DNA polymerase reactions were done according to the manufacturer's (New England Biolabs, Inc., Beverley, Mass.) recommendations. E. coli DH1 or DH5α were made competent by the procedure of Morrison, D. A., 1979, Meth. Enzymol 68:326–331. Competent bacterial cells were transformed with DNA according to Maniatis, T., et al., 1982, Molecular Cloning, A Laboratory Manual, Cold Spring Harbor Laboratory, Cold Spring Harbor, N.Y. Plasmids were purified by alkaline lysis or by the boiling method (Maniatis, T., et al., supra).

11.1.2. DNA Fragment Isolations

DNA fragments were purified from agarose (BioRad, Richmond, Calif.) gels as follows. The appropriate DNA band was excised from the gel using a blade, and the agarose slice was placed on a piece of parafilm, sliced into very small pieces, and transferred to a new piece of parafilm. The agarose pieces were crushed, and the agarose transferred to a 1.5 ml tube. An equal volume of phenol (Ultra pure, BRL, Gaithersburg, Md.) was added, the mixture vortexed, then frozen at −70° C. for 10 minutes, and centrifuged for 10 minutes. The aqueous phase was further extracted twice with phenol/chloroform (1:1), and twice with chloroform. The DNA was then ethanol precipitated, the pellet washed, dried in vacuo, and resuspended in 10 mM Tris-HCl, pH 7.0, 1 mM EDTA.

DNA fragments were isolated from low gelling temperature agarose (FMC, Corp., Rockland, Me.) as follows. The appropriate DNA band was excised from the agarose gel, placed in a 1.5 ml tube, and melted a 65° C. for 15 minutes. The liquified gel was extracted with phenol containing 0.1% sodium dodecyl sulfate (SDS, ultra pure, BRL, Gaithersburg, Md.). The aqueous phase was further extracted once with phenol-SDS and twice with chloroform. The DNA was then ethanol precipitated in 2.0M $NH_4$Acetate, dried, and resuspended in water.

11.1.3. Transfection into Mammalian Cells

Transfection of DNAs into mammalian cells was performed by the $CaPO_4$ precipitation and glycerol shock procedure of Graham and van der Eb (1973, Virology 52:456–467). DUX B11 CHO cells, after being incubated with the DNA-calcium phosphate preparation for 4 to 6 hours, were subjected to glycerol shock by removing the growth medium by aspiration and adding 5 ml of 20% glycerol DMEM medium for 1 minute. Cells were then washed twice in complete alpha MEM and incubated in this medium for 48 hours.

11.1.4. CHO Transfectant Cell Culture

DUX B11 CHO cell transfectants were grown in DHFR (dihydrofolate reductase) selection medium consisting of alpha MEM medium (Gibco) without nucleosides, supplemented with 10% dialyzed fetal calf serum (Gibco) and 4 mM L-glutamine. Amplification was carried out by growing cells in increasing concentrations of methotrexate (Sigma, #A- 6770, Amethopterin) (Kaufman, R. J., et al., 1985, Molec. Cell Biol. 5:1750–1759).

11.1.5. ELISA for the Detection of Soluble CR1 Levels

11.1.5.1. CR1 Standards

Detergent lysates of hemoglobin-free red blood cell (RBC) ghosts were used as a CR1 standard in the ELISA (enzyme-linked immunosorbent assay). The ghosts were prepared as previously described (Wong, W. W. and Fearon D. T., 1987, Meth. Enzymol 150:579–585). Briefly, expired whole blood was obtained from the Red Cross. The red cells were washed three times in PBS, then lysed in 6 volumes of hypotonic lysis buffer (10 mM Tris pH 8, 0.1 mM PMSF (phenyl methyl sulfonyl fluoride), 0.1 mM TPCK (tosylamidephenylethyl chloromethyl ketone), aprotonin, 2 mM EDTA). The ghosts were washed several times in lysis buffer, counted in a hemocytometer, aliquoted and frozen at −70° C. until needed. For the CR1 ELISA, ghosts were diluted to $1.6 \times 10^8$ ghosts/ml in solubilizing buffer (10 mM Tris pH 8, 50 mM KCl, 0.2% NP4O, 0.3% DOC, 6.2 mM PMSF, 0.2 mM iodacetamide, aprotonin, 0.1 mM TPCK, 2 mM EDTA, 0.2% NaN3) and serially diluted to $2.5 \times 10^6$ ghosts/ml for use as standards in the ELISA. Absorbances at 490 nm were plotted and any unknown sample run was referred to the plot to obtain ghost equivalents/ml.

11.1.5.2. CR1 ELISA

Immulon-II plates were coated with 100 µl/well of a 0.4 µg/ml concentration of an anti-CR1 monoclonal antibody (clone J3D3, AMAC IOT 17) (Cook, J., et al., 1985, Molec. Immunol. 22:531–538) in PBS and incubated overnight at 4° C. The antibody solution was then discarded and the plates were blocked by the addition of blocking buffer (1.0% BSA in PBS) at 300 µl/well and incubation at 37° C. for 2 hours. After blocking, plates were used immediately or stored at 4° C. until needed.

Plates were washed three times using PBS containing 0.05% Tween-20. Samples were added at 100 µl/well in duplicate and incubated 2 hours at 37° C. If necessary, samples were diluted in solubilizing buffer. Standard RBC ghosts were included on each plate. After sample incubation, plates were washed three times and a conjugate (Wilson, M. B. and NaKane, P. K., 1978, Immunofluorescence and Related Staining Techniques, North Holland Biomedical Press, pp. 215–224) of horseradish peroxidase (HRP) and the monoclonal antibody YZ1 (Changelian, P. S., et al., 1985, J. Immunol 184:1851–1858) was diluted 1:8000 in 50% FCS, 50% blocking buffer and added at 100 µl/well. After incubating for two hours at 37° C., the plates were again washed three times with PBS containing 0.05% Tween-20. The substrate orthophenylenediamine (OPD) was added at 0.2% concentration in substrate buffer (0.36% citric acid $H_2O$, 1.74% $Na_2HPO_4.7H_2O$, 0.1% thimerosal, 0.4% $H_2O_2$, pH 6.3) at 100 µl/well. The reaction was stopped after 20 minutes at room temperature using 50 µl/well of 2N $H_2SO_4$. Absorbances at 490 nm were read.

11.2. Genetic Modifications of CR1 Coding Sequences

CR1 cDNA is composed of approximately 6,951 nucleotide base pairs (FIGS. 1A–1P, Sections 6, 7, supra). The translational stop signal of the native cDNA is located at base pair 6145. The protein is a membrane-bound receptor molecule composed of four long homologous repeats (LHRs) which are exposed on the exterior surface of the cell membrane, plus a membrane-spanning domain of approximately 25 amino acids, followed by a carboxyl terminal region extending into the cytoplasm. This cytoplasmic domain consists of forty-three amino acids. The strategy we used to produce soluble CR1 molecules (sCR1) was to remove the transmembrane region that anchors a protein in the cell membrane and then to express the truncated constructs as secreted polypeptides.

11.2.1. Construction of pBSCR1c

Plasmid pBSABCD (Example 8, supra) contains the CR1 cDNA from nucleotides 1 to 6860 and lacks the untranslated sequences 3' to the EcoRV site at nucleotide 6860. CR1 cDNA possesses a unique BalI restriction endonuclease recognition site at base pair 5914, twenty-nine base pairs away from the start of the transmembrane domain. pBSABCD was first digested with BalI to produce a linear molecule with flush ends and was then ligated using T4 DNA ligase to a synthetic oligonucleotide consisting of two 38 nucleotide complementary strands with the following sequence:

5': CCAAATGTACCTCTCGTGCACATGATGCTtaaCTCGAG

3': GGTTTACATGGAGAGCACGTGTACTACGAATTGAGCTC

The resulting molecule had a restored BalI site and an altered sequence which reproduced the native CR1 sequence up to and including the alanine residue at the start of the transmembrane domain. In addition, a translational stop signal (in lower case and underlined above) had been introduced immediately after the alanine, followed by an XhoI restriction site to facilitate subcloning the altered cDNA.

XhoI digestion of this plasmid (designated pBSCR1c) excised the cDNA insert (designated sCR1c) by cutting at the oligonucleotide-added XhoI site in the cDNA and at the XhoI site in the pBSKS+® multiple cloning site at the 5' end of the CR1 cDNA. pBSCR1c contains the following C-terminal sequences:

Base No. 5911: CTGGCCAAATGTACCTCTCGTGCACATGATGCTTAACTCGAG
Amino Acids:  L  A  K  C  T  S  R  A  H  D  A  END XhoI site

11.2.2. Construction of pBSCR1s

A second sCR1 construct lacking a transmembrane region was generated as follows. pBSABCD was digested with SacI which cut at the unique SacI site at nucleotide base pair 5485 in the CR1 cDNA and at the SacI site in the multiple cloning site of the host plasmid, located at the 3' end of the CR1 cDNA. This digestion resulted in the excision of 1375 nucleotides of DNA sequence from the 3' end of the cDNA. This fragment was then removed electrophoretically. The exposed ends of the resulting plasmid, containing the remaining sCR1 cDNA, were made flush using T4 DNA polymerase and a blunt-end ligation was performed. The Pharmacia univeral translation terminator (catalog #27-4890-01, Pharmacia, Inc., Piscataway, N.J.), a self-complementary oligomer which contains translational stop signals in all three reading frames, was also included in the ligation. Upon ligation, the inserted oligomer provided a new translation stop signal for the sCR1 cDNA.

11.2.3. Construction of pBM-CR1c pBMT3X is a eukaryotic expression vector (Krystal, M., et al., 1986, Proc. Natl. Acad. Sci. USA 83:2709–2713) that contains the human metallothionein—1A gene, which confers to cells resistance to increased levels of heavy metals such as cadmium. The vector also contains the mouse metallothionein-1 gene that contains an engineered XhoI site preceding the initiation codon for the Mt-1 protein. The XhoI site is used as the insertion site for expression of genes under the control of the mouse Mt-I promoter.

sCR1C insert (approximately 5.9 kb) was excised from pBSCR1c using XhoI and then ligated to the unique XhoI site of vector pBMT3X. The correct orientation of the sCR1c insert in pBMT3X was determined by restriction digestion (Maniatis, T., et al., 1982, Molecular Cloning, A Laboratory Manual, Cold Spring Harbor Laboratory, Cold Spring Harbor, N.Y.). The resulting plasmid was named pBM-CR1c.

11.2.4. Construction of Deletion Mutants pT-CR1c1, pT-CR1c2, pT-CR1c3 pT-CR1c4, and pT-CR1c5

Various deletion mutants were also constructed that specifically deleted portions of the sCR1 cDNA (FIG. 20). Each deletion mutant lacked the transmembrane region of the full length cDNA so that expression of the mutants would yield soluble polypeptides.

11.2.4.1. pT-CR1c1 pBSCR1c was digested with SmaI, resulting in two fragments of size 2.56 kb and 7.3 kb. These fragments were separated by agarose gel electrophoresis, and the 7.3 kb fragment was purified and religated to itself. E. coli DH5α cells were made competent (Morrison, D. A., 1979, Meth. Enzymol. 68:326–331) and then transformed with the ligation mix. The resulting plasmid was named pBL-CR1c1. This construct removed 38% of LHR-B, 100% of LHR-C, and 51% of LHR-D of the CR1c insert. In addition, it regenerated the SmaI site at junction 2335/4894 bp and maintained the correct translational frame. pBL-CR1c1 was digested with XhoI and the CR1 insert was separated from the pBluescript® vector. The isolated CR1 fragment was then inserted into the unique XhoI site of expression vector pTCSgpt to produce plasmid pT-CR1c1.

11.2.4.2. pT-CR1C2 pBSCR1c was digested with ClaI and BalI, resulting in two fragments of size 3.96 kb and 5.9 kb. These fragments were purified from an agarose gel. Plasmid pBR322 was digested with ClaI and BalI and the 2.9 kb pBR322 fragment was purified and ligated to the 5.9 kb fragment from pBSCR1c. E. coli DH5α cells were transformed with the ligation mix and the resulting plasmid was termed pBR8.8. This plasmid was digested with XbaI, generating two fragments of size 7.45 kb and 1.35 kb. The 7.45 kb fragment was purified from an agarose gel and religated to itself. The resulting plasmid, pBR7.45, was digested with ClaI and BalI, and the isolated 4.5 kb fragment containing the sCR1 cDNA was ligated to the 3.96 kb fragment from pBSCR1c, resulting in plasmid pBL-CR1c2. This construct removed 90% of LHR-B in the sCR1 insert, regenerated the XbaI site at junction 1637/2987 bp, and maintained the correct reading frame. pBL-CR1c2 was digested with XhoI, and the sCR1 insert was separated from the pBluescript® vector. The isolated sCR1 fragment was then inserted into the unique XhoI site of expression vector pTCSgpt to produce plasmid pT-CR1c2.

11.2.4.3. pT-CR1c3 pBSCR1c was digested with NsiI resulting in three fragments of sizes 1.09 kb, 1.35 kb, and 7.46 kb. The 7.46 kb fragment was purified from an agarose gel and religated to itself, thus generating plasmid pBL-CR1c3. This construction removed 77% of LHR-A and 100% of LHR-B in the sCR1 insert. The NsiI site was regenerated at junction 463/2907 bp while maintaining the correct translation frame. pBL-CR1c3 was digested with XhoI and the sCR1 insert separated from the pBluescript® vector. The isolated sCR1 fragment was then inserted into the unique XhoI site of expression vector pTCSgpt to produce plasmid pT-CR1c3.

11.2.4.4. pT-CR1c4 pBSCR1c digested with PstI. The PstI site in the polylinker region of pBluescript® had been removed during ligation of the CR1 cDNA to this vector (Example 8.1, supra). The resulting fragments of size 1.35 kb and 8.5 kb were separated by gel electrophoresis, and the 8.5 kb fragment was purified and religated to itself, generating plasmid pBL-CR1c4. This construction removed 31% of LHR-A and 69% of LHR-B of the sCR1 insert. The PstI site was regenerated at junction 1074/2424 bp, thus maintaining the correct reading frame. pBL-CR1c4 was digested with XhoI and the sCR1 insert separated from the pBluescript® vector. The isolated sCR1 fragment was then inserted into the unique XhoI site of expression vector pTCSgpt to produce plasmid pT-CR1c4.

11.2.4.5. pT-CR1c5 pBL-CR1c1 was digested with SmaI, thus linearizing the plasmid at the unique SmaI site. The plasmid was dephosphorylated, and ligated to phosphorylated NheI linker containing a Nonsense codon (New England Biolabs, Beverley, Mass.). This type of linker contains a translational stop codon in all three possible reading frames, and it also contains an NheI restriction site, which faciliates confirming the presence of the nonsense linker in the sCR1 cDNA. The resulting plasmid was named pBL-CR1c5, and it retained LHR-A and 62% of LHR-B of the sCR1 cDNA. pBL-CR1c5 was digested with XhoI, and the sCR1 insert was separated from the pBluescript® vector. The isolated sCR1 fragment was then inserted into the unique XhoI site of expression vector pTCSgpt to produce plasmid pT-CR1c5.

11.3. Expression of Soluble CR1

As demonstrated herein, the expression of a soluble form of CR1 that can be secreted from cells in high yield is (i) not limited to one exact site in the CR1 cDNA to be used for deletion or truncation, and (ii) is also not limited to the use of a particular expression vector (see infra). The ability to produce secreted sCR1 was demonstrated in two different expression systems.

11.3.1. Construction of pTCS Series of Expression Vectors

The pTCS series of expression vectors which were used consists of three plasmids, each with a unique XhoI cloning site for insertion of cDNAs (FIG. 21). Transcription of the inserted cDNA is driven by a set of tandem promotors. The SV40 early promoter which is located upstream of the adenovirus 2 major late promotor (AD2 MLP). Between the beginning of the cDNA and the AD2 MLP is the adenovirus tripartite leader. Transcribed mRNAs are terminated at a polyadenylation signal provided by the murine immunoglobulin kappa (Igκ) sequences located downstream of the XhoI cDNA cloning site. Selectable markers xanthine-guanine phosphoribosyltransferase (gpt), dihydrofolate reductase (dhfr), or neomycin resistance (neo$^r$) were provided by the insertion of the corresponding markers from pSV2gpt, pSV2dhfr, or pSV2neo, respectively. These plasmids were also the source of the bacterial origin of replication and beta-lactamase gene for ampicillin resistance. In general, the choice of which of these vectors to use depends upon which selectable marker or combination of markers is preferred for selection of the recombinants.

The complete DNA sequences are known for adenovirus 2 (Ad2), SV40, pSV2cat (Gorman, C., 1985, DNA Cloning, Volume II, A Practical Approach, ed. D. M. Glover, IRL Press, pp. 143–190),and murine immunoglobulin kappa. Sequences are located in the GenBank® database and the National Biomedical Research annotation and references. Any of these sequences could also serve as a source for the appropriate segments of the pTCS vectors.

The vectors pTCSgpt, pTCSneo, and pTCS dhfr were constructed from the intermediate plasmids pEAXgpt and pMLEgpt as follows:

11.3.1.1. Construction of pEAXgpt

Step 1. The Ad2 MLP DNA fragment was derived from M13 mp9/MLP (Concino, M. F., et al., 1983, J. Biol. Chem. 258:8493–8496). This plasmid contains adenovirus 2 sequences of nucleotides 5778 (XhoI site) to 6231 (HindIII site) including the PvuII restriction site at nucleotide 6069 and the SacII site at nucleotide 5791 (see NBRF Nucleic database, accession #Gdad2 ). The XhoI to HindIII fragment had been cloned into the HindIII and SalI sites of M13 mp9 to generate plasmid M13 mp9/MLP.

Plasmid M13 mp9/MLP was digested with EcoRI and HindIII and the smaller MLP containing fragment isolated. A pUC plasmid (Pharmacia, Inc., Piscataway, N.J.) was also digested with EcoRI and HindIII and the larger fragment from this plasmid was then ligated to the EcoRI to HindIII MLP fragment. This resulted in a new MLP-containing plasmid with the plasmid backbone of pUC. This plasmid was digested with SmaI, ligated to SalI linkers, and recircularized. This new plasmid was then digested with PvuII which cleaved the plasmid at the PvuII site located at position #6069 within the adenovirus 2 insert sequences. The resulting linear fragment was ligated to XhoI linkers and recircularized. This plasmid was then digested with XhoI and SalI and the smaller fragment containing MLP DNA was isolated (fragment #1).

Step 2. Plasmid, pSV2gpt (American Type Culture Collection (ATCC) Accession No. 37145), was digested with PvuII, ligated to SalI linkers, and digested with SalI. The final product was a linear pSV2gpt fragment that served as the source of the gpt gene (fragment #2).

Step 3. A murine immunoglobulin Igκ fragment (Hieter, P. A., et al., 1980, Cell 22:197–207) was digested with HaeIII and AvaII and the fragment containing the polyadenylation sequences isolated. In the murine Ig kappa sequence available in the NBRF Nucleic database (accession #Kcms), the Ig stop codon is at position 1296, followed by the AvaII site at 1306, the AATAAA polyadenylation site at 1484, and the HaeIII site at 1714. The overhanging ends of this fragment were filled in with E. coli DNA polymerase, and the fragment was then ligated to XhoI linkers, and digested with XhoI. This fragment (fragment #3) served as the source of the polyadenylation site.

Step 4. Fragments 1, 2, and 3 were ligated together with T4 DNA ligase to produce a circular plasmid. The correct orientation of the fragments in this plasmid was confirmed by restriction enzyme analysis. Downstream of the XhoI cDNA cloning site was the murine kappa polyadenylation site, and further downstream from this site was the SV40 promoter and gpt gene. Upstream of the XhoI site was the MLP promoter and further upstream from this promoter was the bacterial origin of replication and ampicillin gene. This plasmid was then digested with SalI and the overhanging ends filled in with E. coli DNA polymerase. The resulting blunt end fragment was ligated to EcoRI linkers and recircularized with T4 DNA ligase. This final plasmid was designated pEAXgpt.

11.3.1.2. Construction of pMLEgpt

Step 1. Plasmid pMLP CAT (Lee, R. F., et al., 1988, Virology, 165:51–56) is an expression plasmid with a pML vector backbone and contains the adenovirus 2 MLP and tripartite leader sequences 5' to the CAT gene. pMLP CAT was digested with XhoI and SacII; the XhoI cut at a site between the CAT gene and the L3 region of the tripartite leader, and SacII cut at position #5791 within the adenovirus DNA but 5' of the MLP. The AD2 MLP and tripartite leader were thus located on this small XhoI to SacII fragment (fragment #4).

Step 2. Plasmid pEAXgpt was digested with XhoI and SacII, and the smaller MLP containing fragment was discarded. The larger fragment (fragment #5) was isolated. Fragments 4 and 5, both with SacII and XhoI ends, were ligated to produce plasmid pMLEgpt.

11.3.1.3. Construction of pTCSgpt

Step 1. pMLEgpt was digested with SacII and the ends filled in with T4 DNA polymerase to yield a blunt end fragment (fragment #6). This SacII site is located at nucleotide 5791 in the Adenovirus 2 sequence, 5' of MLP-tripartite leader.

Step 2. pSV2dhfr (ATCC Accession No. 37146) was digested with HindIII and PvuII. The smaller 342 nucleotide fragment containing the SV40 early promoter was blunt ended using the Klenow fragment of E. coli DNA polymerase (fragment #7). Fragments 6 and 7 were ligated with T4 DNA ligase. Restriction enzyme analysis confirmed that the fragments were correctly oriented to give two, tandem promoters upstream of the XhoI cDNA cloning site, each promoter able to prime RNA synthesis in the same direction. This plasmid was named pTCSgpt (FIG. 22).

11.3.1.4. Construction of pTCSdhfr

Step 1. pSV2dhfr was digested with HindIII and PvuII, and the larger fragment was then purified from an agarose gel (fragment #8). The smaller SV40 early promoter containing fragment was discarded.

Step 2. pTCSgpt was digested with EcoRI and then filled in with the Klenow fragment of E. coli DNA polymerase to generate blunt ends. This linear fragment was then digested with HindIII, and the fragment (about 1600 nucleotides) containing the pTCS transcription unit of SV40 promoter, MLP, tripartite leader, XhoI cDNA cloning site, murine Igλ sequences, and second SV40 promoter was isolated (fragment #9). This fragment had one flush end and one HindIII overhanging end. Ligation of fragments 8 and 9 generated plasmid pTCSdhfr.

11.3.1.5. Constructoin of pTCSneo

Step 1. pSV2neo (ATCC No. 37149) was digested with HindIII and BamHI, and the larger fragment (fragment #10) was isolated. This fragment contained the plasmid backbone and neo gene.

Step 2. pTCSdhfr was digested with HindIII and BamHI, and the pTCS transcription unit (fragment #11) was isolated from an agarose gel after electrophoresis of the digestion products. Ligation of fragments 10 and 11 generated plasmid pTCSneo.

11.3.2. Expression and Assay of Plasmids pBSCR1c, pBSCR1s and pBM-CR1c, Mammalian Expression Vectors Containing Soluble CR1 Coding Sequences 11.3.2.1. Expression of CR1 Constructs Truncated at Different Positions within the CR1 cDNA Plasmids pBSCR1c and pBSCR1s were constructed (Section 11.1, supra) such that most of the cDNA coding regions, except the transmembrane and cytoplasmic regions were preserved (FIG. 20). pBSCR1s is shorter than pBSCR1c since it is also missing a portion of LHR-D and SCRs 29 and 30 that are present in pBSCR1c. The sCR1 portions of these plasmids were inserted into pTCSgpt, followed by transfection and expression as described infra.

pBSCR1c/pTCSgpt construction: pBSCR1c was digested with XhoI to yield the 5.9 kb insert, sCR1c. sCR1c was inserted into the XhoI cDNA cloning site of pTCSgpt to produce pBSCR1c/pTCSgpt.

pBSCR1s/pTCSgpt construction: pBSCR1s was digested with XhoI and PvuI to release the sCR1s insert. The ends of the insert were made blunt with T4 DNA polymerase. This insert was purified from an agarose gel. Vector pTCSgpt was digested with XhoI, and the overhanging XhoI ends were filled in with E. coli DNA polymerase I. Next, the sCR1s insert was ligated to the blunt end vector to produce pBSCR1s/pTCSgpt.

Plasmids pBSCR1c/pTCSgpt and pBSCR1s/pTCSgpt were digested with FspI, and the resultant linear DNA's were transfected into Chinese Hamster Ovary cells that were mutant in the dhfr gene (CHO DUX B11 cells) via calcium phosphate coprecipitation with plasmid pSV2dhfr. Transfectants were selected by their ability to grow in DHFR selection medium. Culture supernatants of transfectant clones were assayed for secreted sCR1 by ELISA. Culture supernatants from fifty pBSCR1c/pTCSgpt recombinants were assayed and the positive recombinants were taken through the amplification process by culturing them in increasing concentrations of methotrexate. In addition, pools of transfectants were prepared by co-culturing eight pBSCR1c/pTCSgpt transfectants together per pool and carrying them through the same amplification process. Results of the amplification are presented in Table VI.

TABLE VI

EXPRESSION OF pBSCR1c/pTCSgpt

Secreted Soluble CR1 (μg/ml)

| CLONE | 0 MTX | 20 nM MTX | 50 nM MTX | 100 nM MTX | 500 nM MTX |
|---|---|---|---|---|---|
| 2* | 0.7 | 3.4 | 11 | 10.9 | |
| 4 | 0.04 | 0.1 | | | |
| 6 | 0.04 | | | | |
| 9 | 0.02 | | | | |
| 10 | 0.2 | | | | |
| 11 | 0.12 | | | | |
| 12 | 0.14 | | | | |
| 13 | 0.07 | | | | |
| 14 | 0.2 | | | | |
| 15 | 0.45 | 1.1 | 7.3 | 9.0 | |
| 21 | 0.07 | | | | |
| 30 | 0.27 | <0.02 | <0.02 | | |
| 35*† | 0.82 | 6.3 | 8.4 | 10.9 | 10.9 |
| 40 | 0.05 | | | | |
| 41 | 0.05 | | | | |
| 50 | 0.12 | | | | |
| 52 | 0.12 | | | | |
| POOL | | | | | |
| A | | 0.02 | | | |
| B | | 0.04 | | | |
| C | | 0.23 | | | |
| D | | <0.02 | <0.02 | | |
| E | | 0.27 | 1.1 | | |
| F | | 3.6 | 5.8 | 9.1 | |
| G | | 0.27 | | | |
| H | | 0.04 | | | |

*clones 2 and 35 were chosen for large scale production of sCR1.
†Clone 35 was subcloned by limiting dilution, and the production of soluble CR1 was determined for each subclone. pBSCR1c/pTCSgpt-clone 35.6 was the highest producer, showing 17.7 μg/ml sCR1.
MTX: methotrexate Twelve recombinants from pBSCR1s/pTCSgpt were assayed for production of soluble CR1 by ELISA. All twelve candidates showed detectable levels of secreted sCR1. The best producers gave levels of sCR1 which were comparable to those produced by the best pBSCR1c/pTCSgpt transfectants.

pBSCR1c/pTCSgpt and pBSCR1s/pTCSgpt recombinants produced soluble CR1 with similar levels of production. This indicated that the ability to produce a soluble CR1 polypeptide was not dependent upon an exact truncation point within the CR1 cDNA.

Initial attempts to amplify the cell line, clone 35.6 beyond 500 nm methotrexate were not successful. For this reason, alternative cell lines were sought from the panel shown in Table VI. Candidates were chosen on the basis of expression comparable to clone 35. At methotrexate levels in which the expression was beginning to plateau, lines were subcloned and screened for sCR1 concentrations in the supernatants. Cell line 15, resistant to 50 nm methotrexate, was chosen on this basis. It was subcloned, creating cell line 15.19, increasing the expression to the 35.6 level. Next, 15.19 was cultured in media containing various concentrations of methotrexate. Only 2500 nm methotrexate produced an elevated sCR1 expression level, increasing the secretion by 63% above 35.6. This cell line, designated 15.192500, was then subcloned by limited dilution, creating cell lines 15.192500.07, 15.192500.10 and 15.192500.65. These cell lines produced 143, 119, and 103 percent more sCR1 per ml respectively than 35.6.

11.3.2.2. Expression of sCR1c in Two Different Expression Systems

The truncated CR1 cDNA insert, sCR1c, was inserted into the expression vector pTCSgpt and expressed as described above. It was also inserted into the expression vector pBMT3X as described supra in Section 11.2.3, to yield pBM-CR1c. Both these expression vectors have very strong promoters. Expression of soluble CR1 was tested in both systems to determine whether one system would produce better yields of secreted polypeptide.

C127I mouse cells (ATCC Accession No. CRL 1616, Rockville, Md.) were transfected with pBM-CR1c using the calcium phosphate method (Graham, F. L. and van der Eb, A. J., 1973, Virology 52:456–467). After glycerol shock, the cells were refed with D-MEM medium containing 10% fetal bovine serum and 2 mM L-glutamine, and incubated at 37° C. for 48 hours. Thereafter, the cells were trypsinized, and split at 1:5 and 1:10 ratios into complete D-MEM medium plus 10 µM cadmium chloride. Cadmium-resistant colonies appeared within 10 days. Ten colonies were removed with the use of cloning cylinders. Each colony was transferred to a 60 mm petri dish containing complete D-MEM medium, and incubated at 37° C., 5% $CO_2$ until the cells reached confluency. Thereafter, for each dish, the cells were trypsinized and divided into three 60 mm dishes to be used for preparation of frozen cell stocks, RNA extraction, and ELISA test of the cell medium for the presence of secreted sCR1c.

When cell medium from each confluent petri dish was removed and subjected to ELISA analysis, all pBM-CR1c clones tested were positive for soluble CR1 production. The levels of secreted sCR1 from the pBM-CR1c recombinants were comparable to those from the pBSCR1c/pTCSgpt recombinants. This indicated that the ability to produce high levels of secreted sCR1 polypeptide was not dependent upon the use of only certain promoters or expression systems.

11.3.3. Expression and Assay of Plasmids pT-CR1c1, pT-CR1c2, pT-CR1c3, pT-CR1c4, and pT-CR1c5, Mammalian Expression Vectors Containing Soluble CR1 Coding Sequences The pT-CR1c series of deletion mutants were missing the transmembrane and cytoplasmic domains, as were the constructs, pBSCR1c and pBSCR1s. In addition, the deletion mutants also contained fairly large deletions of various LHR regions of the CR1 cDNA (see FIG. 20). The deletion mutants were expressed in CHO DUX B11 cells and the levels of soluble CR1 polypeptide produced were measured.

For each deletion construct, forty different pools of clones were selected for ELISA analysis to determine whether soluble CR1 polypeptides were being produced. Four of five pT-CR1c constructs were found to be secreting sCR1 into the cell culture medium, as determined either by ELISA or by the presence of functional activity in the cell culture media. Supernatants from cells transfected with three of the five pT-CR1c constructs were producing sCR1 that was functional as determined by a hemolytic assay (see Table VII and Section 13.2, infra).

TABLE VII

PRODUCTION OF FUNCTIONAL sCR1 FRAGMENTS*

| Construct | ELISA | Hemolytic Assay |
|---|---|---|
| pT-CR1c1 | − | + |
| pT-CR1c2 | + | + |
| pT-CR1c3 | − | − |
| pT-CR1c4 | + | Not determined |
| pT-CR1c5 | − | + |

*Supernatants tested for ELISA or hemolytic assays were obtained either from cultures growing in T75 flasks or in 24 well dishes. Since various amounts of soluble CR1 could have accumulated in the culture supernatants under these conditions, the results shown are qualitative. (+) indicates the production of functional sCR1 as detected by the indicated assay.

The fact that the deletion mutants were also able to produce soluble CR1, further demonstrated that the ability to express sCR1 was not dependent upon one exact genetic modification of the CR1 cDNA. As long as the transmembrane regions were deleted, all constructs were able to produce a soluble polypeptide.

12. EXAMPLE: PRODUCTION AND PURIFICATION OF SOLUBLE CR1

Large quantities of sCR1 were produced in a hollow fiber bioreactor system. The quantities of sCR1 obtained were proportional to the relative yield of the inoculated recombinant clones. For optimal purification results, a serum-free medium was chosen that resulted in high production levels of sCR1 in the absence of large quantities of exogenously added fetal calf serum polypeptides.

12.1. Large Scale Production of Soluble CR1

A Cell-Pharm™ Cell Culture System I (CD Medical, Inc., Miami Lakes, Fla.), equipped with a model IV-L hollow fiber bioreactor (30 kD molecular weight cutoff), was assembled under sterile conditions. Two clones (clone 2 and clone 35 of pBSCR1c/pTCSgpt) were expanded into eight T-225 flasks. At confluency, the cells were trypsinized, washed, pelleted, and resuspended in culture media. Approximately $5 \times 10^8$ cells of clone 2 and $10 \times 10^8$ cells of clone 35 were inoculated into two separate hollow fiber bioreactors. A 20 liter feed reservoir of alpha-MEM plus 10% fetal calf serum, 8 mM L-glutamine, 100 µg/ml penicillin-streptomycin and the appropriate concentration of methotrexate (50 nM for clone 2; 500 nM for clone 35) was used. Premixed gas (5% $CO_2$ in air) was bubbled into the reservoir medium through the oxygenator to maintain pH. Media recirculation, replacement and gas flow rates were adjusted to yield maximum production. Samples were harvested through inoculating ports, centrifuged at 1000 rpm for 10 minutes, filtered through a 0.22 µM pore size filter, and kept at 4° C. before purification. Harvest volume and frequency were increased gradually from 25 ml, three times per week at the beginning of the culture, to 40 ml, five times a week after 2–3 months. The production of sCR1 was assayed by a CR1 ELISA. The yields of clone 2 and clone 35 for the first month after inoculation were 66 µg/day and 1060 µg/day, respectively. These yields increased as the cultures became established.

12.1.1. Production of sCR1 in Serum-Free Media

Two commercially available serum-free media were tested for their ability to support cell growth and production of sCR1. A confluent T75 flask of pBSCR1c/pTCSgpt clone 35 was divided into two T75 flasks. One flask was cultured with alpha MEM, supplemented with 10% fetal calf serum, L-glutamine, antibiotics, and 500 nM methotrexate. The other flask was weaned stepwise from 5%, 1%, 0.5% and no fetal calf serum in alpha MEM plus L-glutamine, antibiotics, 500 nM methotrexate plus HB CHO growth supplement (Hana Biologics, Inc., Alameda, Calif.). The cell growth and sCR1 production levels of the two flasks were compared. The growth of the cells in the serum-free media never reached confluency. The levels of sCR1 production are given in Table VIII. In each case, the level of sCR1 production was best when cells were grown in 10% fetal calf serum. For comparison, the levels found at day 14 in serum-free media were $1.4 \times 10^{10}$ ghosts/ml as compared to $4.2 \times 10^{10}$ ghosts/ml for 10% fetal calf serum supplemented media.

TABLE VIII

PRODUCTION OF sCR1 IN SERUM-FREE MEDIA SUPPLEMENTED WITH CHO GROWTH SUPPLEMENT VERSUS 10% FETAL CALF SERUM CONTAINING MEDIA*

|  | Day 4 | Day 7 | Day 11 | Day 14 |
| --- | --- | --- | --- | --- |
| Flask 1 | 5% FCS | 1% FCS | 0.5% FCS | 0% FCS |
| CHO Growth Supplement Plus | 2.6 | 2.4 | 2.95 | 1.4 |
| Flask 2 10% FCS | 4.8 | 3.85 | 4.3 | 4.2 |

*expressed as $10^{10}$ ghosts/ml

Cell growth and sCR1 production in recombinants were tested using a second source of serum-free media (CHO-1, Ventrex Laboratories, Inc., Portland, Me.). Since it was not necessary to wean serum-grown cells into this media, cells were thawed and cultured directly in the serum-free media. This media consists of a DME-F12 base and a growth additive. Equal numbers of cells were thawed and seeded into separate wells in a 24-well plate. After the cells had attached, the media was discarded, and either 10% fetal calf serum containing media or serum-free media was added to appropriate wells. Each condition was performed in duplicate. Unlike the previously tested serum-free media, the CHO-1, Ventrex Laboratories media yielded similar levels of cell growth as did the fetal calf serum containing media.

12.1.2. Conclusions

The above-described results indicated that sCR1 producing CHO cells could be maintained in a defined serum-free media. This resulted in a savings in the cost of culture media for large scale production runs. A further advantage was that purification of sCR1 from the cell culture supernatants was simplified, since no fetal calf serum proteins had to be removed.

12.2. Purification of Soluble CR1

With the advent of specific anti-CR1 antibodies, it became possible to replace the many chromatographic steps needed to produce purified CR1 with a simplified two step procedure. This increased the yields of CR1 proteins that could be obtained to approximately 1–5 mg CR1 per $5.9 \times 10^{13}$ erythrocytes (Wong, W. W., et al., 1985, J. Immunol. Methods 82:303–313). However, since the reported purification was of membrane-bound forms of CR1, it was always necessary to solubilize the CR1 containing material in detergents.

Soluble CR1 produced by recombinant transfectants does not have to be solubilized with detergents for purification; it is already soluble. Although soluble CR1 can be purified by anti-CR1 antibody chromatography (see below), this procedure does not lend itself easily to large-scale production. The extent of scale-up is limited by the amount of anti-CR1 antibody that can be obtained for preparing the antibody matrix of the antibody purification columns. In addition, the high binding affinity of an antibody such as YZ-1 for CR1 means that rather harsh conditions, for example pH 12.2, have to be used to remove the bound sCR1 product from the antibody matrix (Wong, W. W., et al., 1985, J. Immunol. Methods 82:303–313).

To have the capacity of purifying very large quantities of soluble CR1, purification procedures involving HPLC columns were developed. These HPLC columns can easily be scaled up to produce even larger quantities of purified soluble CR1. In addition, they do not require harsh conditions for the elution and recovery of sCR1.

12.2.1. Antibody Affinity Column Purification

12.2.1.1. Methods

For antibody affinity purification of sCR1, 100 mg of monoclonal antibody YZ-1 was covalently coupled to 7 mg of AffiGel-10 (BioRad, Richmond, Calif.) according to the manufacturer's instructions. CR1 containing supernatant from cell cultures was incubated with the immobilized YZ-1 in a flask rocking at 4° C. overnight. The material was poured into a glass column and washed extensively with 10 mM Hepes, 0.1M NaCl, pH 7. The sCR1 was eluted using 20 mM sodium phosphate, 0.7M NaCl, pH 12 (Yoon, S. H. and Fearon, D. T., 1985, J. Immunol. 134:3332–3338). Eluted fractions were tested for the presence of protein using the Biorad Protein Assay (BioRad, Richmond, Calif.). Samples containing protein were immediately pooled and dialyzed in 0.1M Hepes pH 7 overnight (2×1 liters) at 4° C. The sample was then dialyzed in PBS. Presence of sCR1 was analyzed by CR1 ELISA.

12.2.1.2. Results

Cell culture supernatant containing sCR1 produced by transfectant pBSCR1c/pTCSgpt clone 2 was loaded onto the anti-CR1 antibody affinity column and the peak sCR1 fractions pooled. An aliquot of this purified material was run on a 4–20% SDS-PAGE gel (DAIICHI; Inc., polyacrylamide gels; modified procedure of Laemmli, U.K., 1970, Nature 227:680–685). Under reducing conditions, the apparent molecular weight of soluble CR1 was about 224,000 daltons (FIG. 24). This purified CR1 was also shown to be active by its ability to inhibit complement-mediated hemolysis as well as C5a and C3a production (Section 13, infra).

12.2.2. CR1 Purification by HPLC

12.2.2.1. Methods

12.2.2.1.1. Starting Material

When cultures were first established in the bioreactors, the levels of sCR1 production were lower than when the cultures had been growing for several months. Generally there was a period of several weeks before the cells in the bioreactor reached confluency and produced maximum levels of sCR1. Cell culture supernatants with low levels of sCR1 could be concentrated before purification by either ammonium sulfate precipitation or by ultrafiltration. Ammonium sulfate fractionation of supernatants over the range of 60 to 80% saturation precipitated sCR1 in essentially equivalent yields. The precipitate was dissolved in a minimum volume and dialysed into starting buffer for the cation exchange HPLC. Alternatively, the CHO cell culture supernatants could be concentrated by ultrafiltration and dialyzed into starting buffer for cation exchange chromatography.

As the bioreactors produced higher concentrations of soluble CR1, the CHO cell culture supernatants from these cultures could be dialyzed directly into starting buffer for cation exchange chromatography.

12.2.2.1.2. Cation Exchange HPLC Procedure

Samples were dialyzed into starting buffer (0.02 M sodium phosphate, 0.06N sodium chloride, pH 7.0) and then filtered through a 0.2 μm filter to remove any particulate material. The sample was then loaded onto a cation exchange high pressure liquid chromatography column (10 cm×10 mm, Hydropore-SCX HPLC column from Rainin). The column was washed and eluted with a sodium chloride gradient developed using 0.02M phosphate, 0.5N NaCl, pH 7.0. The sCR1 eluted somewhere between 0.06N and 0.25N NaCl. Elution was monitored by absorbance at 280 nm and by ELISA.

12.2.2.1.3. Anion Exchange HPLC Procedure

If desired, further purification of the cation HPLC purified sCR1 could be obtained by anion HPLC. Peak fractions from the cation HPLC were dialyzed into the starting buffer for anion HPLC. Samples were loaded and the column (Hydropore-AX from Rainin) was washed in 0.01M phosphate pH 7.5. The column was eluted with a series of steps and gradients developed using 0.01M phosphate, 0.5N NaCl, pH 7.5. The sCR1 eluted somewhere between 0.0N and 0.3N NaCl. Elution was monitored as before for cation exchange HPLC. The concentrations and pH of the cation and anion HPLC column buffers are given as examples only. Other buffer concentrations, salt conditions, or pH conditions would also work.

12.2.2.1.4. Western Blot Analysis

Western blotting was performed using a modified procedure from Towbin, H., et al., 1979, Proc. Natl. Acad. Sci. USA, 76:4350–4354. Briefly, purified sCR1 was run on a 4–20% SDS-PAGE, transferred to nitrocellulose, specifically probed with anti-CR1 (mouse mAb YZ-1 or J3D3), and detected with goat anti-mouse antibody conjugated with alkaline phosphatase.

12.2.2.2. Results

For a typical run, 50–100 ml of supernatant from a bioreactor culture were dialyzed into starting buffer and loaded onto a 10 cm×10 mm cation exchange HPLC. The peak fractions were determined by ELISA and absorbance at 280 nm, and were pooled. The protein concentration of the pool was determined by absorbance at 280 nm ($\epsilon(1\%)$ at 280 nm= 10, as estimated from the CR1c amino acid composition). Several tens of milligrams were purified from 100 ml of amplified culture supernatant.

As an example, 100 ml of culture supernatant from transfectant pBSCR1c/pTCSgpt clone 2 produced 22 mg of purified sCR1, as determined by absorbance at 280 nm, when purified by cation HPLC (FIG. 24). When monitored by CR1 ELISA, the yield was calculated to be 202% with another 13% in the flow-through or column wash fraction. The greater than 100% yield probably reflects matrix effects in the ELISA.

Given the rates that culture supernatant can be withdrawn from a bioreactor, it should be possible at this level of methotrexate amplification to produce about 100 mg of purified soluble CR1 per week per bioreactor. Some ways in which this level of production can be scaled up, include amplifying the starting cultures to a maximum extent with methotrexate prior to seeding the bioreactor, increasing the number of bioreactors in production at any one time, and using larger capacity HPLC columns.

12.2.2.3. Characterization of Purified Soluble CR1

The sCR1 containing peak fraction from the cation HPLC (FIG. 24) was further purified on an anion HPLC. The purity of the sCR1 material at the various steps was tested by SDS-PAGE (FIG. 25). The smaller bands seen in these heavily loaded gels represent fragments of sCR1 as determined by Western Blot analysis using anti-CR1 monoclonal antibodies, YZ1 or J3D3. The fragment sCR1 bands were not seen in most preparations.

The functional activity of purified sCR1 was tested by its ability to inhibit classical complement-mediated hemolysis by 50% at a purified sCR1 concentration of 0.25 µg/ml. The purified soluble CR1 was also able to inhibit classical complement C5a production by 50% at 5 µg/ml and C3a production by 50% at 13 µg/ml (see Section 13, infra).

12.2.2.4. Conclusions

As described supra, we developed an improved method for the purification of soluble CR1 that can easily be scaled up to produce the quantities of sCR1 needed for therapeutic applications. The basic elements of this procedure included a starting material that is already soluble, thus eliminating the requirement of solubilizing membrane bound CR1 with detergents. The reduction of fetal calf serum concentrations in the bioreactor cultures and/or the use of alternative culture medias in these cultures eliminated the need to remove high concentrations of extraneous proteins from the sCR1-containing starting material during subsequent purification. Furthermore, the development of an HPLC procedure for purification provided a method for large-scale purification. Either cation HPLC or a combination of cation HPLC followed by anion exchange HPLC can be used for purification. Substantially pure soluble CR1 in high yield can be achieved by this procedure in only 1 or 2 steps.

13. EXAMPLE: DEMONSTRATION OF IN VITRO ACTIVITY OF SOLUBLE CR1

13.1. Inhibition of the Neutrophil Oxidative Burst

In the reperfusion injury model of tissue damage incurred during a myocardial infarction, activated complement components induce neutrophil adhesion and activation. The activated neutrophil undergoes an oxidative burst creating highly toxic oxygen radicals. These and other potential toxins are released during neutrophil degranulation, damaging the surrounding tissue. Soluble CR1 may reduce the area of damaged tissue by preventing the generation of C3a and C5a, the complement components involved in neutrophil activation.

To monitor the ability of soluble CR1 to block the generation of C5a during complement activation in vitro, a bioassay which can quantitate the generation of oxygen radicals produced by neutrophils during a C5a induced oxygen burst was used (Bass, D. A., et al., 1983, J. Immunol. 130:1910–1917). This assay employs dichlorofluorescin diacetate (DCFDA), a lipid soluble molecule which can enter cells, become trapped, and turn highly fluorescent upon oxidation.

13.1.1. Materials and Methods 13.1.1.1. Materials

Fresh whole blood, human complement sources (Beth Israel Hospital, Boston, Mass.), dried Baker's yeast, PBS with 0.1% gelatin and 5 mM glucose, 100 mM EDTA, 10 mM DCFDA in HBSS (Kodak), Red blood cell (RBC) lysing buffer (Ortho Diagnostics), purified C5a (Sigma Chemical Co., St. Louis, Mo.), and soluble CR1 were used.

13.1.1.2. Preparation of Neutrophils

Neutrophils were prepared as described by Bass (1983, J. Immunol. 130:1910–1917). 2.0 ml of whole blood was washed 3 times in PBS-gelatin-glucose, resuspended in 5 ml of 10 µM DCFDA in HBSS plus 5 ml PBS-gelatin-glucose and incubated for 15 minutes at 37° C. Cells were then centrifuged and resuspended in 2.0 ml PBS-gelatin-glucose plus 5 mM EDTA.

13.1.1.3. Preparation of Yeast Particles

Dried baker's yeast was resuspended in $H_2O$, washed 2 times and boiled for 30 minutes. Particles were rewashed 2 times in $H_2O$ and resuspended at 0.5 grams/ml in $H_2O$ (Simpson, P. J., et al., supra).

13.1.1.4. Activation of Neutrophils by Purified C5a

100 µl of DCFDA-loaded cells were treated with RBC lysing buffer, washed one time in PBS-gelatin-glucose-EDTA and resuspended in 1.0 ml of PBS-gelatin-glucose. Fifty µl of purified C5a at 200 ng/ml or control was added to 0.5 ml of target cells at 37° C. and analyzed on the flow cytometer at various time intervals.

13.1.1.5. Activation of Neutrophils by Purified C5a in Human Serum or Plasma

100 µl of DCFDA-loaded cells were incubated with 50 µl of C5a diluted 1:1 in human serum or heparinized plasma (100 ng/ml) or control at 37° C. for 30 minutes. The RBC's were lysed out, and the neutrophils were analyzed on a flow cytometer.

13.1.1.6. Activation of Neutrophils by Yeast Particle-Activated Human Serum or Plasma 425 μl of fresh frozen serum and plasma plus 50 μl of sCR1 or control were incubated with 25 μl of yeast particles at 37° C. for 30 minutes. The complement-activated and control samples were then centrifuged to remove the yeast particles. Ten 2-fold dilutions of each of these samples were performed in PBS-gelatin-glucose-EDTA. 50 μl of each serial dilution of control and activated serum and plasma was added to 50 μl of DCFDA-loaded target cells and incubated at 37° C. for 30 minutes. The RBC's were then lysed out, and neutrophils were analyzed by flow cytometry.

13.1.2. Results 13.1.2.1. C5a Induces an Oxygen Burst in Human Neutrophils which can be Measured USING DCFDA FIGS. 26a–26g show a rapid increase in fluorescence intensity of the human neutrophils after stimulation with purified C5a. Within four minutes after addition of C5a (20 ng/ml final concentration), the neutrophils were 10-fold brighter than control DCFDA-loaded neutrophils. By 20 minutes, the neutrophils were 20-fold as bright as controls. This assay seems to be a sensitive indicator of C5a.

13.1.2.2. Human Serum Blocks the Oxygen Burst Effects of Purified C5a on Neutrophils No increase in fluorescent intensity was observed in neutrophils loaded with DCFDA and incubated with purified C5a diluted in human serum. This effect may be due to platelet derived growth factor (PDGF) released from platelets during clotting. It has been shown that low levels of PDGF can inhibit C5a-induced neutrophil activation (Wilson, E., et al., 1987, Proc. Natl. Acad. Sci. USA 84: 2213–2217).

13.1.2.3. Heparinized Plasma Does Not Block the Effects of C5a on Neutrophils

C5a diluted 1:1 in heparinized plasma induced an oxygen burst in DCFDA loaded neutrophils. Although not as dramatic as C5a in buffer, there was a ten-fold increase in fluorescent intensity after a 30 minute incubation with the neutrophils. The decreased signal may be caused by PDGF release during phlebotomy or plasma isolation. More gentle and rapid isolation of the plasma from the cellular components of blood may minimize the release of PDGF and allow for better C5a function.

13.1.2.4. sCR1 Present During Complement Activation Blocks C5a Generation

Zymosan induced activation of human complement in the presence of soluble CR1 showed reduced C5a activity as measured with the DCFDA assay. As can be seen in FIGS. 27a–27g, the 1:16 dilution of human plasma activated in the presence of sCR1 generated 70% less fluorescence intensity increase in the neutrophils as the 1:16 diluted plasma activated without sCR1 present. This implies inhibition of C5a generation by sCR1. Further optimization of the DCFDA assay and plasma collection should result in a more dynamic and sensitive assay of soluble CR1 activity.

13.2. Inhibition of Complement Mediated Hemolysis 13.2.1. Methods

The ability to inhibit complement was tested by assaying for inhibition of complement-mediated red cell lysis (hemolysis). The inhibition of hemolysis was determined as a function of soluble CR1 concentration. The sCR1 samples to be tested were diluted in 0.1M Hepes buffer (0.15N NaCl, pH 7.4), and 50 μl were added to each well of a V-bottom microtiter plate typically in triplicate. Human serum, used as the complement source, was diluted 1 to 125 in Hepes buffer, and 50 μl were added to each well. Next, commercially available sheep erythrocytes with anti-sheep antibody (Diamedix Cat. No. 789-002) were used as received and added 100 μl/well to initiate the complement pathway leading to hemolysis. The plate was incubated for 60 minutes at 37° C. and then centrifuged at 500× g for 10 minutes. The supernatants were removed and placed in a flat-bottom microtiter plate. The extent of hemolysis was measured as a function of the sample absorbance at 410 nm. The maximal absorbance (corresponding to maximal hemolysis), $A_{max}$, was obtained from the absorbance of an erythrocyte sample containing only human serum $A_S$, minus the absorbance of a sample containing only the red cells, $A_0$. Thus, $A_{max}= A_S - A_0$. The difference between the absorbance of an erythrocyte sample containing both human serum and sCR1, and the absorbance of a cell sample containing sCR1 only, was defined as $A_{sample}$. The inhibition, IH, was expressed as the fraction $(A_{max} - A_{sample}/A_{max})$, and $IH_{50}$ was defined as the concentration of sCR1 required to produce a value of IH=½. To monitor chromatography fractions, the serum-free controls were not included and anti-complement activity was monitored qualitatively as a decrease in the absorbance at 410 nm of the sample.

The hemolytic assay described above was also used to assess the capability of human recombinant sCR1 to inhibit sheep red cell lysis by complement from other species, such as guinea pig and rat. For each species, fresh-frozen serum or freshly lyophilized serum or plasma was used as a complement source. In some cases sera were obtained commercially (Sigma Chemical Company, St. Louis, Mo.).

The serum was first titered for its capacity to lyse activated red cells. The greatest dilution which yielded at least 80% maximal red cell lysis was chosen to assess the effects of added human sCR1. The assay was then performed as described above, substituting animal for human serum at the preferred dilution.

13.2.2. Results

As indicated in FIG. 28, purified sCR1 inhibited classical complement-mediated lysis by 50% at a sCR1 concentration of 0.12 μg/ml. The ability of antibody affinity purified sCR1 to inhibit the hemolytic assay was compared to that of unpurified material (sCR1 containing cell culture supernatant). The purified sCR1 had activity comparable to that of the unpurified sCR1, with both producing 50% inhibition in the hemolytic assay at $1.6 \times 10^8$ ghosts/ml. This indicated that the purification procedure was not substantially diminishing the functional activity of the final sCR1 product.

To determine if purified sCR1 could be stored frozen, an aliquot was stored at −70° C. for one week. The concentration of the frozen sCR1 was the same as the nonfrozen sCR1, as determined by absorbance at 280 nm and CR1 ELISA. The frozen sCR1 also had the same activity as the nonfrozen sCR1 as determined by inhibition of hemolysis.

The ability of human recombinant sCR1 to inhibit hemolysis mediated by complement from several species is summarized in Table IX.

TABLE IX

HEMOLYSIS OF SENSITIZED SHEEP RBC USING COMPLEMENT FROM VARIOUS ANIMAL SERA

| Animal | Final Conc. Serum Used | Inhibition by sCRI | Inhibition (IH)** (ghost/ml) | $IH_{50}$** (ghost/ml) |
|---|---|---|---|---|
| guinea | 1:500 | Yes | 66% ($2.6 \times 10^9$) | $1.0 \times 10^9$ |

TABLE IX-continued

HEMOLYSIS OF SENSITIZED SHEEP RBC USING COMPLEMENT FROM VARIOUS ANIMAL SERA

| Animal | Final Conc. Serum Used | Inhibition by sCRI | Inhibition (IH)** (ghost/ml) | IH$_{50}$** (ghost/ml) |
|---|---|---|---|---|
| pig* | | | | |
| human | 1:500 | Yes | 94% (2.5 × 10$^9$) | 2.0 × 10$^8$ |
| human | 1.312 | Yes | 94% (1.2 × 10$^9$) | 1.0 × 10$^7$ |
| rat | 1:200 | Yes | 85% (2.6 × 10$^9$) | 2.4 × 10$^8$ |
| rat* | 1:200 | Yes | 77% (3.8 × 10$^9$) | 1.0 × 10$^9$ |
| dog | 1:50 | No | | |
| rabbit* | 1:20 | No | | |
| mouse* | 1:5 | No | | |

*lyophilized sera obtained commercially (Sigma Chemical Co., St. Louis, Mo.
**as defined in text (Section 13.2)

Both guinea pig and rat complement appeared to be inhibited by human sCR1. The lack of clear inhibition for other species may reflect (a) the inappropriateness of using rabbit antibodies and sheep erythrocytes in the assay system, or (b) the high concentration of serum required for hemolysis in this system.

13.3. Inhibition of C3a and C5a Production 13.3.1. Methods

The ability to inhibit complement was also tested by assaying for specific inhibition of C3a and C5a production. For all experiments, a single human serum pool, to be used as a source of complement, was aliquoted and stored frozen at −70° C. Human IgG was heat-aggregated, aliquoted, and stored frozen at −70° C. For each experiment, serum aliquots were equilibrated at 37° C. with varying concentrations of sCR1 to be tested. The complement pathway was initiated by the addition of aggregated human IgG. Control samples containing no IgG were always included. After a fixed reaction time of 15 minutes (determined in an earlier time-course study to provide a convenient time interval during which the production of C5a or C3a is nearly complete, i.e., greater than 90%), the levels of the released complement peptides (C5a or C3a) were determined by radioimmunoassay using commercially available radioimmunoassay (RIA) kits (C5a RIA, Amersham Cat No. RPA.520; C3a RIA, Amersham Cat. No. RPA.518) in modified procedures.

Since a competitive immunoassay was used, complement peptide (C5a and C3a) concentrations varied inversely with the counts. The counts bound (CB) for a sample were defined as the total counts (in counts per minute, cpm) measured in the pellet.

The y-axis in FIG. 29 represents the fraction inhibition. The fraction inhibition is equal to the counts bound (CB) for a "sample", less the CB in the "sample with no sCR1", divided by the CB for the "no IgG control" less the CB in the "sample with no sCR1."

$$\text{INHIBITION} = \frac{[(CB \text{ sample}) - (CB \text{ no } sCR1)]}{[(CB \text{ no } IgG) - (CB \text{ no } sCR1)]}$$

13.3.2. Results

The activity of purified sCR1 was assayed by testing its ability to inhibit C5a and C3a production in an activated human serum sample.

As indicated by FIG. 29, under the conditions tested, purified sCR1 was able to maximally inhibit C5a production by 100% and C3a by 60%. Inhibition of 50% was observed at sCR1 concentrations of 5 μg/ml for C5a production and 15–20 μg/ml for C3a production. The data suggest that recombinant sCR1 inhibits the C5 convertase more efficiently than the C3 convertase.

14. EXAMPLE: DEMONSTRATION OF FUNCTIONAL IN VIVO THERAPEUTIC ACTIVITY OF SOLUBLE CR1

14.1. Soluble CR1 Demonstrates In Vivo Function in a Reversed Passive Arthus Reaction The Arthus reaction is a classic immunologically induced inflammatory response caused by injecting antigen locally that then reacts with antibodies in circulation. The major biological response is characterized by immune complex deposition, complement fixation, polymorphonuclear (PMN) leukocyte infiltration, release of lysosomal enzymes, vasoactive amine, and local tissue damage (Uriuhura, T. and Movat, H. Z., 1966, Exp. Mol. Pathol. 5:539–558; Cochrane, C. G., 1968, Adv. Immunol. 9:97–162). A modification of the direct Arthus reaction, the reversed passive Arthus reaction (RPAR), has been used as a model for identifying anti-inflammatory agents (Pflum, L. R. and Graeme, M. L., 1979, Agents and Actions 9:184–189). In a RPAR, antibody is injected locally and antigen is present in the circulation.

When tested in a rat RPAR model, soluble CR1s were able to block the local inflammatory reaction. The mechanism of the action of this soluble CR1 function in vivo may be mediated through the inhibition of complement pathway enzymes.

14.1.1. Materials and Methods

Female five week old Sprague Dawley rats (CD strain) weighing about 100–125 grams (Charles River Laboratories, Wilmington, Mass.) were anesthesized with an intraperitoneal injection of 0.1 to 0.3 ml Avertin solution. This solution was a 1:2 dilution of a stock solution made with 1 g tribromoethanol in 15 ml Amel ethanol. The fur on the backs of the animals was shaved. Next, the tail was warmed, first with warm water and then with a heat lamp. Using a 1 ml syringe, 0.35 ml of ovalbumin (Calbiochem Corp., San Diego, Calif.) at 5 mg/ml in 0.15M phosphate buffered saline (PBS) was injected intravenously into the tail vein, about 1–2 inches from the tip of the tail. Five minutes later, the rats were injected intradermally with 0.08 ml of 20 mg/ml rabbit Ig fraction of anti-ovalbumin antibody having an antibody titer of 4 mg/ml (Organon Teknika Corp., Cappel Division, West Chester, Pa.) or with 0.08 ml of 20 mg/ml rabbit IgG (Sigma Chemical Co., St. Louis, Mo.), or with PBS. Each injection was performed in duplicate and the areas around the injection were circled with a marker pen. The rats were then monitored at 1, 4, and 18 hours. After 24 hours, the rats were killed by submerging them in dry ice for 3 minutes. Skin samples were dissected from the injected sites. One of the duplicate samples was fixed in 10% formalin for paraffin embedding and the other frozen for cryostat sections. Tissue sections were prepared and stained with hematoxylin and eosin.

14.1.2. Results

A weak RPAR reaction (e.g., edema and erythema) began to be visible after 3 to 5 hours following intradermal injection of anti-ovalbumin antibody. The intensity of the reaction gradually increased until the size of the reaction reached 3–5 mm in diameter after 24 hours (FIG. 30b). No reactions were observed in the rat skin where only non-immune rabbit IgG or PBS was injected.

Under microscopic examination of the tissue sections prepared from the site of the lesion, many acute inflammatory cells were visible in the dermis, particularly around the blood vessels (FIG. 31b). This is typically recognized as vasculitis and perivasculitis. The tissue indicated a typical inflammatory condition with extensive infiltration of PMN outside of the blood vessels, the presence of erythrocytes in the connective tissue, and the loosening of collagen fibers.

14.1.3. Effect of Intradermal Administration of Soluble CR1

A mixture of purified sCR1 was prepared by combining 40 µl of 0.75 mg/ml sCR1 with an equal volume of anti-ovalbumin or normal rabbit IgG or PBS. Either the sCR1:anti-ovalbumin mixture or the sCR1:rabbit IgG mixture, or the sCR1: PBS mixture was injected intradermally into intravenously ovalbumin primed rats. Barely visible lesions developed in the injection sites that received sCR1 plus anti-ovalbumin antibody (FIG. 30a). As expected, no lesions developed in the injection sites that received sCR1: rabbit IgG or sCR1:PBS. When sections of tissue surrounding the sCR1:anti-ovalbumin injection sites were examined microscopically, clusters of PMN and mononuclear cells could be found surrounding the venules, but there was no extensive infiltration of PMN or extravasation of erythrocytes (FIG. 31a). These data indicate that soluble CR1 administration caused an inhibition of damage to the endothelial cells and an inhibition of the inflammatory reaction.

In order to determine the minimum effective dosage of sCR1 that is required to block a RPAR in the above ovalbumin rat model, ten-fold serial dilutions (neat, 1/10, 1/100, 1/1,000 and 1/10,000) of the 0.75 mg/ml sCR1 stock were tested. Each sCR1 dilution was mixed with an equal volume of neat or one-half dilution of anti-ovalbumin antibody. Each site was injected with a total of 80 µl. The ability of sCR1 to inhibit RPAR was dose dependent, with effective reduction of edema observed at 300 ng per site (Table X).

TABLE X

EFFECT OF DOSAGE ON THE INHIBITION OF RPAR BY sCR1

| sCR1 (µg/site) | Extent of Remaining RPAR |
| --- | --- |
| 30 | +/− |
| 3 | +/− |
| 0.3 | +/− |
| 0.03 | ++ |
| 0.003 | ++++ |
| 0 | ++++ |

14.2. Pharmacokinetics of In Vivo Adminstered sCR1

The biological half-life of sCR1 in vivo was determined as follows. Rats of similar age (6 weeks) and body weight (110–125 g) were injected intravenously with 250 µg of sCR1 in 0.35 ml. At 2 minutes, 5 minutes, 10 minutes, 60 minutes, and 24 hours post-injection, the rats were sacrificed and blood was obtained from vena cava puncture. 1–2 ml of sera from each rat was obtained by centrifugation at 1800 rpm for 10 minutes, and the amount of sCR1 in each sample was determined by CR1 ELISA. Two-fold dilutions of 1 µg/ml of purified sCR1 spiked into control rat serum or detergent lysates of hemoglobin-free red blood cell ghosts ($1.6 \times 10^8$ ghosts/ml) were used as CR1 standards. The results are shown in Table XI.

TABLE XI

PHARMOCOKINETIC DATA ON SERUM CONCENTRATIONS OF INJECTED sCR1 WITH TIME

| Time After Intravenous Injection | sCR1 Concentration (µg/ml) |
| --- | --- |
| Control | 0.01 |
| 2 min | 0.17 |
| 5 min | 0.80 |
| 10 min | 1.01 |
| 60 min | 0.38 |
| 24 hrs | 0.49 |

These data indicate that sCR1 can be detected 24 hours following intravenous injection. At 24 hours, the level of sCR1 in the serum was 50% of the peak level that was observed 10 minutes post-injection.

Additional studies in Sprague Dawley rats and cynomolgus monkeys (Table XII) were performed to further characterize the pharmacokinetics of in vivo administered sCR1. Each animal received a single intravenous injection of either $^{125}$I-labelled sCR1 alone (14–28 million cpm for rat, 126–153 million cpm for monkey) or a mixture of unlabelled (about 1 mg/kg) and $^{125}$I-labelled sCR1. In study 2-431, dose of 1 mg/kg or 10 mg/kg of unlabelled sCR1 were also tested in monkeys. Blood was collected from each animal at several time points within the sampling time indicated in Table XII. The clearance of sCR1 from the blood followed a biphasic pattern in rats and monkeys. The first phase ($\alpha$) had a short half-life measured in minutes. This half-life was dose dependent as shown in monkey study 2-431 where a 1 mg/kg dose gave $t_{1/2}\alpha$ of 9.13 min and a 10 mg/kg dose gave $t_{1/2}\alpha$ of 29 min. The second phase ($\beta$) showed a much longer half-life measured in hours (see Table XII and FIG. 32). The results of the monkey studies indicated that there were no clinical signs of toxicity observed in monkeys associated with the administration of a single intravenous injection at doses of 1.0 and 10 mg/kg.

TABLE XII

| | PHARMACOKINETIC STUDIES OF TP10-HD** | | | | |
| --- | --- | --- | --- | --- | --- |
| | 2-378 | 2-592 | 2-709 | 2-403 | 2-431 |
| SPECIES | Rat | Rat | Rat | Monkey | Monkey |
| Number | 12 | 4 | 4 | 2 | 2 |
| TP10-HD | Hot only | Hot + Cold | Hot + Cold | Hot + Cold | Cold only |
| Sampling Time | 5 min–72 hr | 1–30 min | 1–60 min | 1 min–24 hr | 1 min–24 hr |
| Half Life* | $t_{1/2\beta} = 3.07$ hr | $t_{1/2\alpha} = 3.9$ min | $t_{1/2\alpha} = 4.3$ min | $t_{1/2\alpha} = 6$–11 min $t_{1/2\alpha} = 4$–4.3 hr | $t_{1/2\alpha} = 9.13$ min (1 mg/kg) $t_{1/2\alpha} = 29.0$ min (10 mg/kg) |

*The half-lives were determined by y = mx + b, where y = value at $t_{1/2}$, m = slope, x = $t_{1/2}$, b = extrapolated $t_o$.
**Methods used for determining blood levels of sCR1 included measuring total radioactive counts (study 2-378), measuring TCA precipitable counts (studies 2-592, 2-709, 2-403) and reactivity in a CR1 ELISA as described in section 11.15 supra (studies 2-592, 2-709, 2-403 and 2-431).

14.3. SCR1 Reduces Infarct Size in Rats with Reperfused Infarcted Myocardium As described herein, sCR1 which was able to inhibit the activity of the complement pathway C3/C5 convertase in vitro was also able to reduce the extent of reperfusion injury in an in vivo rat myocardial infarct model.

Myocardial infarction can be induced in a rat by coronary ligation. If established within the first few hours after myocardial infarction, reperfusion has been shown to reduce the infarct size, to improve the left ventricular function, and to reduce mortality (Braunwald, E. and Kloner, R. A., 1985, J. Clin. Invest. 76:1713–1719). However, reperfusion to a myocardium that is severely ischemic but not irreversibly injured, can itself produce and extend injury. The mechanisms responsible for the reperfusion-induced injury may include injury mediated by oxygen free radicals and cellular calcium overload. Leukocytes acting either alone or in concert with microvascular endothelial cells may contribute to this injury. Complement activation may be involved in this process (Rossen, R. D., et al., 1985, Cir. Res. 57:119–130; Crawford, M. H., et al., 1988, Circulation 78:1449–1458).

14.3.1. Suppression by sCR1 of Complement Activation and Myocardial Reperfusion Injury in Rats We administered sCR1 to rats subjected to transient myocardial ischemia with subsequent reperfusion. The mechanism of injury to ischemic, but not irreversibly damaged, reperfused myocardium involves a leukocyte-dependent inflammatory reaction (Romson et al., 1983, Circulation 67:1016; Martin et al., 1988, Circ. Res. 63:483; Kraemer & Mullane, 1989, J. Pharmacol. Exp. Therap. 251:620; Litt et al., 1989, Circulation 80:1816; Ambrosio et al., 1989, Circulation 80:1846) that may require complement activation (Maroko et al., 1978, J. Clin. Invest. 61:661; Crawford et al., 1988, Circulation 78:1449). Animals were divided into groups at random and were given bolus intravenous injections of phosphate-buffered saline alone (n= 29) or containing 1 mg of sCR1 (n= 31) immediately before occlusion of the left coronary artery by suture ligation. After 35 minutes, the sutures were released, the thorax closed, and the animals were returned to their cages for 7 days, when they were killed and the myocardial infarct was measured (Weisman et al., 1988, Circulation 78:186); the 7-day interval provided a reliable assessment of infarct size and permitted analysis of possible adverse effects of sCR1 on infarct healing. The aortas of hearts that had been excised from rats under methoxyflurane anesthesia were cannulated, and the coronary arteries were perfused first with Krebs Henseleit solution and then with 30 mM KCl for diastolic arrest. After fixation by intracoronary perfusion and immersion in 10 percent buffered formalin, 2 mm transverse sections of the hearts were histologically analyzed by digitizing the areas of the normal, total infarcted and trasmurally infarcted left ventricular myocardium. The summed values of the fractional areas of all slices were used to calculate myocardial infarct size and the ratio of transmural necrosis to total necrosis. All procedures and care of the animals were in accordance with institutional guidelines. Survival rates in the group given buffer alone (24 of 29) and the sCR1-treated group (25 of 31) were similar, with deaths occurring immediately after coronary artery ligation in all but one of the control rats. Ligation of the coronary artery was judged to be successful in 22 animals in each group that met all of the following criteria: immediate electrocardiographic changes compatible with ischemia; cyanosis of the anterior left ventricular wall; and histologic evidence of myocardial necrosis post mortem. The structure was released successfully in all rats except two of the sCR1 treated animals. Analysis of all survivors, including the two rats in whom reperfusion was not achieved, demonstrated that treatment with sCR1 reduced the size of myocardial infarction from a mean of 16±2 percent of the left ventricular mass in the control rats to 9±2 percent in the sCR1 group (P<0.01). The frequency of transmural infarction also was lower in the sCR1-treated (6 of 25) than in the control rats (12 of 24) (P<0.04).

The infarct segment thickness summed over four sections of hearts from all rats treated with sCR1 was 7.8± 0.4 mm, which was not significantly different from that of all untreated animals 7.3±0.4 mm, but slightly less than that of the remote, uninfarcted interventricular septum from the hearts of these two groups of rats (sCR1 rats, 9.3±0.2 mm; untreated rats, 9.4±0.2 mm). There was also no difference in the intraventricular cavity size of these two groups (sCR1 rats, 64.9±3.6 mm$^3$; untreated rats, 68.9± 2.6 mm$^3$). Therefore, sCR1 suppresses myocardial infarct size but does not interfere with healing in a manner that causes ventricular dilation and left ventricular wall thinning, as judged from observation of hearts one week after infarction.

To determine whether suppression of tissue damage by sCR1 was associated with inhibition of complement activation by ischemic myocardium, another group of buffer-treated (n= 7) and sCR1-treated rats (n= 8) was subjected to the same ischemia-reperfusion protocol, and the animals were killed 3 hours after reperfusion. The hearts were assessed by nitroblue tetrazolium (NBT) staining (Lillie, R. D., 1965, Histopathologic Technic and Practical Histochemistry, McGraw-Hill, New York ed:3:378) to delineate regions of irreversible injury from viable myocardium, and by immunoperoxidase staining (DeLellis, in Basic Techniques of Immunohistochemistry, DeLellis, Ed., Masson, New York, 1981) with a mouse monoclonal antibody to the rat C5b-9 membrane attack complex (Schulze et al., 1989, Kidney Int. 35:60). A mouse peroxidase-antiperoxidase (PAP) system was used for the immunostaining as described. All steps of the procedure were preceded by three 10-minute washings in 0.05 M Tris-buffered saline. The sections were fixed in acetone and treated with 0.5 percent $H_2O_2$-methanol solution for 5 minutes, 4 percent heat-inactivated goat serum for 1 hour; and they were then sequentially incubated at room temperature with the primary, mouse monoclonal antibodies at 2 µg/ml for 18 hours, with affinity-purified F(ab')$_2$ goat antiserum to mouse antibody (Organon-Tecknika, West Chester, Pa.) for 60 minutes, and with mouse PAP for 60 minutes. The slides were developed with 3,3'-diaminobenzidine tetrahydrochloride and counterstained with Gill's hematoxylin 3. In the NBT-negative, infarcted areas of the control rats (n= 7), the C5b-9 complex was present primarily along the endothelium of capillaries and venules, but not in the myocardial fibers. In contrast, in rats that had received sCR1 (n= 8), the NBT-negative areas were consistently reduced in size, and little or no C5b-9 complex was detectable in these regions, as exemplified by the representative sections shown.

Quantitation of leukocytes (Ambrosio et al., 1989, Circulation 80:1846) in these serial sections revealed that within infarct zones of control rats there were 195± 28 leukocytes per square millimeter (150 high-power fields; n= 3), which were almost exclusively within capillaries and venules. Corresponding sections from the hearts of rats that had received sCR1 had only 83±3 leukocytes per square millimeter (n= 4; P= 0.006), indicating that suppression of complement activation was associated with decreased accumulation of this inflammatory cell type.

The localization of C5b-9 complexes along endothelial surfaces suggests that these cells may be the primary site of complement activation in the pathogenesis of reflow injury to ischemic myocardium, and contrasts with the more diffuse distribution of complement proteins throughout infarcted myocardium 24 hours following coronary artery occlusion (McManus et al., 1983, Lab. Invest. 48:436). While the latter may simply reflect the capacity of necrotic tissue to activate complement, the former may indicate that ischemically stressed endothelium acquires a complement-activating function. Complement activation by endothelial cells would be an especially potent stimulus for the early localization of neutrophils to ischemic myocardium, with C5a activating intravascular leukocytes and causing their rapid upregulation of cellular receptors, including CR1 and CR3 (Fearon & Collins, 1983, J. Immunol. 130:370; Arnaout et al., 1984, J. Clin. Invest. 74:1291). The latter receptor has been shown to promote the attachment of neutrophils to complement-activating endothelial cells bearing the ligand for CR3, iC3b (Marks et al., 1989, Nature 339:314). Therefore, suppression of complement activation by sCR1 may account for the decreased numbers of neutrophils apparently adherent to endothelial cells.

Reperfusion of ischemic myocardium by thrombolytic agents reduces infarct size, improves left ventricular function, and reduces mortality if established within a few hours of coronary artery occlusion (Guerci et al., 1987, N. Engl. J. Med. 317:1613; ISIS-2 Collaborative Group, 1988, Lancet ii:49; Van de Werf & Arnold, 1988, Br. Med. J. 279:1374). However, the potential benefits of reperfusion may not be fully achieved because reflow into myocardium that is severely ischemic, but not irreversibly injured, may induce necrosis (Becker & Ambrosio, 1987, Prog. Cardiovasc. Dis. 30:23; Braunwald & Kloner, 1985, J. Clin. Invest. 76:713). Two events thought to be causally related to necrosis are intravascular accumulation of neutrophils and microvascular endothelial cell injury (VanBenthuysen et al., 1987, J. Clin. Invest. 79:265), both of which may be a consequence of complement activation. The present finding of a myocardial protective effect of sCR1 supports the possibility of a central role for complement, extending earlier studies in which complement was depleted with cobra venom factor, and offers a means by which the tissue-sparing potential of thrombolytic therapy may be enhanced.

14.3.2. Conclusions

The results indicate that sCR1 treatment is effective in reducing reperfusion injury in vivo and in ameliorating the effects of myocardial infarction. To the extent that reperfusion injury can be ameliorated, the absolute amount of salvaged myocardium can be increased and the time window for which reperfusion is clinically useful can be extended. Treatment with sCR1 should be a useful concomitant therapy with thrombolytics as described in the next section or balloon coronary angioplasty during acute infarction.

15. EXAMPLE: CO-FORMULATION OF SOLUBLE COMPLEMENT RECEPTOR 1 (sCR-1) WITH p-ANISOYLATED HUMAN PLASMINOGEN-STREPTOKINASE-ACTIVATOR COMPLEX (APSAC)

Purified sCR-1 prepared as described in section 12.2 [0.93 mg in sterile Dulbecco's phosphate-buffered saline, 1.0 ml], was added to a vial of APSAC which had been reconstituted in sterile water (4.0 ml). The APSAC preparation contained the following:

| APSAC: | 30 units |
| --- | --- |
| D-Mannitol | 100 mg |
| Human Serum Albumin E.P. | 30 mg |
| p-Amidinophenyl p'-anisate.HCl | 0.15 mg |
| L-Lysine.HCl | 35 mg |
| 6-Aminohexanoic acid | 1.4 mg |

(all figures are subject to normal analytical variances)

The solutions were mixed well and the vial frozen at $-78°$ C. using solid $CO_2$. The product was lyophilised at 2–3 mbar/$-60°$ C. (condenser temp) for 24 hours and the vial restoppered and stored at $-70°$ C. On reconstitution, the vial was dissolved in 0.1M Hepes, 0.15M NaCl pH 7.4 (1.0 ml) and held on ice. Assays dilutions were made into this Hepes buffer. As controls, a vial of APSAC alone (same batch) was reconstituted in the same way and a freshly thawed sample of sCR-1 (same batch) was also tested. The samples were assayed for inhibition of complement-mediated hemolysis according to the method described in section 13.2.1 with the results given in the Table XIII below.

TABLE XIII

COMPARATIVE ANTI-HEMOLYTIC ACTIVITY
OF sCR-1/APSAC, APSAC AND sCR-1*

| | | Percent inhibition of control hemolysis | | |
| --- | --- | --- | --- | --- |
| Dilution | Final s-CR1 conc. (ng/ml) | sCR-1/APSAC | sCR-1 | APSAC |
| 1:500 | 465 | 97.5 (1.1) | 96.8 (1.2) | 0 |
| 1:2500 | 93 | 90.9 (0.7) | 90.6 (1.3) | 0 |
| 1:5000 | 46.5 | 81.5 (2.3) | 82.6 (2.5) | ND |
| 1:12500 | 18.6 | 54.6 (2.4) | 51.4 (2.6) | 0 |
| 1:50000 | 4.65 | 11.0 (2.4) | 13.2 (0.6) | 0 |

*Figures in brackets are standard errors from quadruplicate determinations.

Curve fitting of the data in Table XII gave values for the concentration of sCR-1 which inhibited hemolysis by 50% of 15.7±3.0 mg/ml and 16.0±2.9 ng/ml for sCR-1/APSAC and SCR-1 alone. These figures are not different and the results indicate that the activity of sCR-1 is unaffected by co-formulation with an APSAC pharmaceutical dosage form.

16. EXAMPLE: MOLECULAR DEFINITION OF THE F' ALLOTYPE OF HUMAN CR1: LOSS OF A C3b BINDING SITE IS ASSOCIATED WITH ALTERED FUNCTION

Human CR1 is composed of tandem long homologous repeating (LHR) segments that encode separate binding sites for C3b or C4b. Homologous recombination with unequal crossover has been proposed as the genetic mechanism that gave rise to the CR1 alleles that differ in their total numbers of LHR. The F allotype has four LHR, maned LHR-A, -B, -C, -D, 5' to 3'. The site in LHR-A preferentially binds C4b, and those in LHR-B and -C prefer C3b. A previous study revealed the presence of a fifth LHR with sequences similar to LHR-B and a third C3b binding site in the S allotype of higher molecular weight. In the present study, an 18 kb EcoRV fragment that was associated with the expression of the lower molecular weight F' allotype hybridized with a unique pattern of cDNA and intron probes specific for LHR-C. Deletion of LHR-B and one C3b binding site was proposed as the mechanism for the appearance of this F'-specific fragment. The molecular mechanism for the association of the F' allotype with SLE was explored by functional comparisons of soluble sCR1 having one, two or three C3b binding sites. While these three variants did not exhibit any significant differences in their capacities to act as cofactors for the cleavage of monomeric C3b, their relative binding of dimeric ligand varied over 100 fold. Furthermore, the variant with only one C3b binding site was at least 10 fold less effective in the inhibition of the alternative pathway C3 and C5 convertases. These observations suggest that the F' allotype may be impaired in its capacity to bind opsonized immune complexes, to inhibit the formation of the alternative pathway C3 and C5 convertase, and perhaps to mediate other CR1-dependent cellular responses. They also demonstrate that certain functions of a CR1 molecule may be enhanced by increasing the valency of the C3b binding sites.

16.1. Introduction

Four allotypic forms of CR1 that differ in size by 30 to 50 kD increments have been described. The transcripts that are associated with each allotype also differ in increments of ~1.4 kb, indicating that their primary sequences vary in the number of LHR (Wong et al., 1983, J. Clin. Invest. 72:685; Dykman et al., 1983, Proc. Natl. Acad. Sci. U.S.A. 80:1698; Dykman et al., 1984, J. Exp. Med. 159:691; Dykman et al., 1985, J. Immunol. 134:1787; Wong et al., 1986, J. Exp. Med. 164:1531; Holers et al., 1987, Proc. Natl. Acad. Sci. U.S.A. 84:2459). There are four LHR in the F (or A) allotype of ~250 kD, termed LHR-A, -B, -C, and -D, respectively, 5' to 3' (Examples 6 and 7, supra; Wong et al., 1989, J. Exp. Med. 169:847). While the first two SCR in LHR-A determine its ability to bind C4b, the corresponding units in LHR-B and -C determine their higher affinities for C3b (Example 9, supra). Analysis of the gene encoding the larger S (or B) allotype of ~290 kd by restriction mapping of genomic phage clones revealed a fifth LHR that is a chimera of the 5' half of LHR-B and the 3' half of LHR-A and is predicted to contain a third C3b binding site (Wong et al., 1989, J. Exp. Med. 169:847). The smallest F' (or C) allotype of CR1 of ~210 kD, found in increased incidence in patients with SLE and associated with patients in multiple lupus families (Dykman et al., 1984, J. Exp. Med. 159:691; Van Dyne et al., 1987, Clin. Exp. Immunol. 68:570), may have resulted from the deletion of one LHR and may be impaired in its capacity to bind efficiently to immune complexes coated with complement fragments. The data presented infra define the molecular basis of the F' allele by using intron probes specific for each LHR to analyze an EcoRV restriction fragment length polymorphism (RFLP) of the CR1 that is present in individuals who express this allotype. To provide an explanation for the apparent association of the F' allotype with SLE, soluble sCR1 variants having one, two or three C3b recognition sites and corresponding to the predicted structures of the F', F, S allotypes, respectively, were compared for their abilities to bind dimeric ligand, to act as cofactor for the cleavage of C3b, and to inhibit the alternative and classical pathway C3 and C5 convertases.

16.2. Materials and Methods

Analysis of DNA. Genomic DNA was prepared from peripheral blood leukocytes, digested with EcoRV, electrophoresed and analysed by Southern blotting as previously described (Wong et al., 1986, J. Exp. Med. 164:1531). The CR1 cDNA probe 1-1 hybridizes to SCR-4 to -7 of all the LHR while the probe 1-4 specifically hybridizes to SCR-1 and -2 of LHR-B and -C (Klickstein et al., 1987, J. Exp. Med. 165:1095; Klickstein et al., 1988, J. Exp. Med. 168:1699; Wong et al., 1989, J. Exp. Med. 169:847). The noncoding probe PE hybridizes to the intron between the two exons that encode SCR-2 in LHR-B and -C. PX hybridizes to the intron between the two exons that encode SCR-6 in LHR-A and -B, and HE hybridizes to the intron 5' of SCR-7 in LHR-A and -B (Wong et al., 1989, J. Exp. Med. 169:847) (FIG. 34). A genomic library derived from the DNA of an individual homozygous for the F allele was screened for CR1 clones by hybridization to cDNA probes that span the entire coding sequence. Restriction mapping of the overlapping phage clones that span the F allele was performed as previously described (Wong et al., 1989, J. Exp. Med. 169:847).

Construction of the expression plasmids and purification of soluble sCR1. A Pst I fragment which extends from SCR-5 in LHR-A to a corresponding position in LHR-B was isolated from the plasmid pBSABCD that contains the complete coding sequence of the F allotype of CR1 (Example 8.1, supra). This was inserted into piABCD (Example 8.2, supra) which had been linearized by partial digestion with Pst I, resulting in the creation of a fifth LHR with coding sequences identical to that of LHR-B. A clone named piABBCD with an in-frame insertion was selected by restriction mapping, and the segment encoding the entire extracellular domain was excised by digestion with Xho I and Apa LI and treated with the Klenow DNA polymerase. The blunt ended fragment was ligated to the linkers, 5'-TGAGCTAGCTCA-3', digested with Nhe I, and inserted into the Xba I site of the expression vector Ap$^r$M8, a derivative of CDM8 (Seed, 1987, Nature 329:840). This plasmid, named pasecABBCD, has a stop codon inserted after the thirty-seventh SCR and lacks the sequences encoding the transmembrane and cytoplasmic domains. The plasmid, pasecABCD, was made by the transfer of the four LHR of the F allotype from pBSABCD into Ap$^r$M8 using a similar strategy. A third plasmid, containing only three LHR and named pasecACD, was made by an in-frame deletion of the Pst I fragment extending from SCR-5 in LHR-A to a corresponding position in LHR-B. Thirty to sixty µg of each of the above plasmids were used to transfect $2\times10^7$ COS-1 cells (American Type Culture Collection, Rockville, Md.) in the presence of 400 µg/ml DEAE-dextran, and 100 µM chloroquine for 4 hours at 37° C. in Dulbecco's modified Eagle medium with high glucose (DMEM) (Hazelton, Lenexa, Kans.) and 10% Nuserum (Collaborative Research, Bedford, Mass.). The cells were shocked for 3 minutes at room temperature with 10% DMSO in HBSS without divalent cations after removal of the transfection medium (Ausubel et al., 1987, in Current Protocols in Molecular Biology, John Wiley & Sons and Greene Assoc., New York), washed and cultured in DMEM and 10% FCS. The culture supernatants were collected every 48 hours for 10 days, clarified of cell debris by centrifugation, and frozen at −70° C. On thawing of the supernatants, PMSF and sodium azide were added to final concentrations of 5 mM and 0.2%, respectively, and sCR1 was purified by affinity chromatography on mAb YZ-1-Sepharose as described except that detergents were omitted from the eluting buffer (Wong et al., 1985, J. Immunol. Meth. 82:303; Example 12.2.1, supra). The purified proteins were dialyzed twice against 1,000 volumes of PBS and frozen in small aliquots at −70° C. This procedure routinely yielded 150–200 µg of sCR1 as determined by the Micro BCA kit (Pierce, Rockford, Ill.) using BSA as a standard. The protein was analyzed by SDS-PAGE on a gel containing a linear gradient of 5% to 15% acrylamide.

Cofactor activity of sCR1. Purified human C3 (Tack & Prahl, 1976, Biochemistry 15:4512) was treated with 0.5%

TPCK-trypsin (Sigma, St. Louis, Mo.) for 5 minutes at 37° C. and the reaction was stopped by the addition of a four fold molar excess of soy bean trypsin inhibitor. The C3b was labeled with $^{125}$I to a specific activity of $5\times10^5$ cpm/μg using Iodogen (Pierce, Rockford, Ill.). Cofactor activity of sCR1 was assessed by incubation of 200 ng of C3b, 100 ng of factor I (Fearon, 1977, J. Immunol. 119:1248) with varying amounts of sCR1 in 20 μl PBS for 1 hour at 37° C. (Wong et al., 1985, J. Immunol. Meth. 82:303; Example 11, supra). The reactions were stopped by boiling the samples in an equal volume of SDS-PAGE sample buffer containing 0.1 M dithiothreitol. After electophoresis and autoradiography, the areas of the dried gel corresponding to the position of the α' chains were excised and the amount of radioactivity measured in a Beckman gamma counter (Wong et al., 1985, J. Immunol. Meth. 82:303). The counts associated with the α' chain in the absence of CR1 were taken as the 100% control.

Capacity of sCR1 to bind dimeric C3b. C3b was crosslinked by dimethyl suberimidate (Sigma, St. Louis, Mo.) (Wilson et al., 1982, New Engl. J. Med. 307:981) or 1,6-bismaleimidohexane (Pierce, Rockford, Ill.) (Weisman et al., 1990, Science 249:146), and dimers were selected by sedimentation on a linear gradient of 4.5% to 30% sucrose in PBS (Wilson et al., 1982, New Engl. J. Med. 307:981). Either method yielded dimers that bound to erythrocyte CR1 with association constants ($K_a$) that ranged from 1 to 3× $10^8 M^{-1}$. Three hundred ng of $^{125}$I-C3b dimers ($4\times10^6$ cpm/μg) were incubated with $2\times10^8$ erythrocytes in 200 μl HBSS with 0.1% BSA in the absence or presence of incremental amounts of unlabeled monomeric or dimeric C3b, or the different soluble forms of sCR1 (Weisman et al., 1990, 249:146). After one hour on ice, cell-bound ligand was separated from unbound material by centrifugation of the erythrocytes through dibutylphthalate (Wilson et al., 1982, New Engl. J. Med. 307:981). The amount of dimeric C3b bound in the presence of excess rabbit IgG anti-CR1 was taken as the nonspecific background, and specific counts bound in the absence of any inhibitor were used as the 100% control. For all these binding studies, erythrocytes from one normal individual were utilized. These cells were homozygous for the F' allotype and had relatively high amount of CR-1 (~800 YZ-1 mAb binding sites).

Inhibition of the alternative and classical pathway convertases. For assessment of the activation of the alternative pathway, 25% human serum was incubated with $5\times10^6$ zymosan particles (gift of Dr. Joyce Czop, Harvard Medical School, Boston, Mass.) in Veronal-buffered saline with 2 mM $MgCl_2$ and 8 mM EGTA in the absence or presence of incremental amounts of sCR1. For assessment of the activation of the classical pathway, 60 μg/ml of heat aggregated rabbit IgG was substituted for zymosan, and the reactions were performed in Veronal-buffered saline with 0.5 mM $MgCl_2$ and 0.15 mM $CaCl_2$ (Weisman et al., 1990, Science 249:146). After incubation for 40 minutes at 37° C., the reactions were stopped by addition of 10 mM EDTA and assayed for the amounts of C3a and C5a cleavage using radioimmunoassay kits (Amersham, Chicago, Ill.).

16.3. Results

Structure of the F' allele of CR1. We have previously reported that when the DNA of individuals who expressed the ~210 kD F' allotype of CR1 was digested with EcoRV, an additional fragment of 18 kb was observed on probing the Southern blots with the CR1 cDNA probe 1-1 (Wong et al., 1986, J. Exp. Med. 164:1531) (FIG. 33). This probe was originally derived from SCR-3 to SCR-7 in LHR-B but its sequences were sufficiently homologous to allow hybridization to the fourth through the seventh SCR of other LHR (Examples 6 & 7, supra; Klickstein et al., 1987, J. Exp. Med. 165:1095; Klickstein et al., 1988, J. Exp. Med. 168:1699; Wong et al., 1989, J. Exp. Med. 169:847). In order to assign each fragment to an LHR, the overlapping genomic clones that spanned the entire F' allele were mapped by EcoRV (FIG. 34). Fragments of 9.4 kb and 22 kB corresponded to those expected from LHR-A and -D, respectively. This was confirmed by the hybridization of the 9.4 kb but not the 22 kb fragment to the intron probes PX and HE (FIG. 33). Since there were no EcoRV sites in LHR-B, the largest fragment at the top of the blot that hybridized to all the probes represented the ~32 kb fragment that spanned LHR-B and most of LHR-C (FIGS. 33 & 34). Restriction mapping of genomic clones that spanned the previously reported CR1-like pseudogene (Wong et al., 1989, J. Exp. Med. 169:847) indicates that the fragments of 20 kb and 15 kb are derived from this region (FIG. 33).

The 18 kb EcoRV fragment that was associated with the expression of the F' allotype hybridized to the cDNA probe 1–4 and the intron probe PE, indicating that it contained the 5' half of LHR-B or -C. This fragment did not hybridize to the intron probes PX and HE, indicating that it lacked the 3' half of LHR-B (FIG. 33). Deletion of LHR-B or another fragment of similar length from the ~32 kb EcoRV fragment would yield a fragment of 18 kb which extended from the 3' most EcoRV site of LHR-A to the 5' most EcoRV site of LHR-C (FIG. 34). Such a fragment would be expected to hybridize only with the probes 1–4, PE, and 1-1, consistent with the findings in FIG. 33. Since any ~15 kb deletion including the PX and HE sites of LHR-B necessarily includes at least one of the exons that contain the C3b binding site in either LHR-B or -C, the resulting allele of three LHR would encode only one C3b binding site.

Plasmid construction and purification of soluble sCR1. There are no direct comparisons of the affinities of the CR1 allotypes for opsonized immune complexes or multimeric ligands because individuals homozygous for the F' allotype have not been identified. The availability of complete CR1 cDNA sequences and the results of the genomic analyses enabled us to produce sCR1 with structures predicted for the different polymorphic variants. To assess the capacity of individual CR1 molecules of each allotype for bivalent interactions with C3b dimers, cDNA constructs for soluble CR1 were made by the insertion of a stop codon between the end of the 3' most SCR and the beginning of the transmembrane domain. This approach eliminates the potential for interactions between the dimeric C3b and separate, adjacent molecules of membrane-bound CR1. In addition, the use of soluble CR1 avoids possible interference with enzymatic assays from the detergents required to maintain the solubility of membrane-derived preparations. The strategy employed for the insertion or deletion of an LHR utilized the conserved restriction sites to preserve the reading frame. The Pst I fragment that was inserted or deleted encoded SCR-5, -6, -7 of LHR-A and SCR- 1, -2, -3 and -4 of LHR-B (FIG. 35). Since the amino acid sequences of the third to the seventh SCR are identical in LHR-A and -B (FIG. 35) (Examples 6 & 7, supra), these procedures would result in the insertion or deletion of sequences equivalent to an LHR-B. The plasmids pasecACD, pasecABCD, and pase-cABBCD (FIG. 35) would therefore encode proteins that have one, two or three C3b binding sites, respectively.

Soluble recombinant CR1 was isolated by chromatography on YZ-1-Sepharose from the culture supernatants of COS cells that had been transfected with the CR1 plasmids. Each sCR1 protein was greater than 95% pure and the three forms exhibited incremental $M_r$ differences of ~30 kd under nonreducing conditions on SDS-PAGE, similar to those observed for the naturally occurring allotypes (FIG. 36). Biosynthetic labeling with $^{35}$S-cysteine of the COS cells transfected with the vector Ap'M8 alone showed no absorption of CR1-like proteins to the YZ-1 Sepharose. Furthermore, the soluble sCR1 had $M_r$ that were similar to the CR1 isolated from $^{125}$I-labeled erythrocytes, consistent with deletion of only 70 amino acids from each molecule. In the lanes that contained sCR1 isolated from pasecABBCD- or pasecABCD-transfected cells, small amounts of protein with $M_r$ similar to the smaller forms were observed (FIG. 36, lanes 2 and 3). These may represent the products of homologous recombination that were spontaneously generated within the transfected COS cells.

Cofactor activity of sCR1. The functional integrity of the different forms of sCR1 was measured in a cofactor assay in which radiolabeled C3b was converted to the iC3b and C3dg fragments. The amounts of sCR1 that were required for 50% factor-I-mediated cleavage of the α' chain of C3b ranged from 3.5 nM for the pasecABBCD-derived protein to 8 nM for the pasecACD-derived protein, and differed only slightly for the three forms (FIG. 37). Furthermore, conversion of C3b to C3dg was seen with the addition of 10 nM to 20 nM of all forms of sCR1. Thus soluble recombinant CR1, irrespective of the number of C3b binding sites, retained the capacity of the native molecule to bind C3b and served as a cofactor for the factor-I cleavage.

Capacity of sCR1 to bind dimeric C3b. In order to assess the effect of having different numbers of LHR-B on the binding of C3b-coated targets, the sCR1 variants were used to inhibit the uptake of $^{125}$I-C3b dimer by erythrocyte CR1. The concentrations required for 50% inhibition reflected the relative binding of either the ligand or the cell bound receptor. In the experiment shown in FIG. 38, 10 nM of unlabeled C3b dimer was required for 50% inhibition of the interaction between $^{125}$I-C3b dimer and erythrocyte CR1. The interaction of the receptor with monomeric C3b was much weaker, requiring 1 μM, or 100 fold more of this ligand to achieve similar inhibition (FIG. 38). The low binding of this monomeric interaction suggests that cross-linking of two discrete molecules of soluble CR1 by the dimeric C3b ligand would not be favored under these conditions and that occupancy of two intramolecular binding sites is necessary for effective competition. This divalent interaction was ascertained by the requirement of 10 nM and 100 nM of the pasecABCD- and the pasecACD-derived sCR1, respectively, for 50% inhibition. Interestingly, only 1 nM of the pasecABBCD-derived sCR1 having three C3b binding sites was needed for a similar effect (FIG. 38). Thus the soluble CR1 forms with one, two or three C3b binding sites differed in their binding of dimeric C3b but not for the monomeric form of this ligand that had been used as substrate for factor I cleavage (FIG. 37).

Figure 40A:
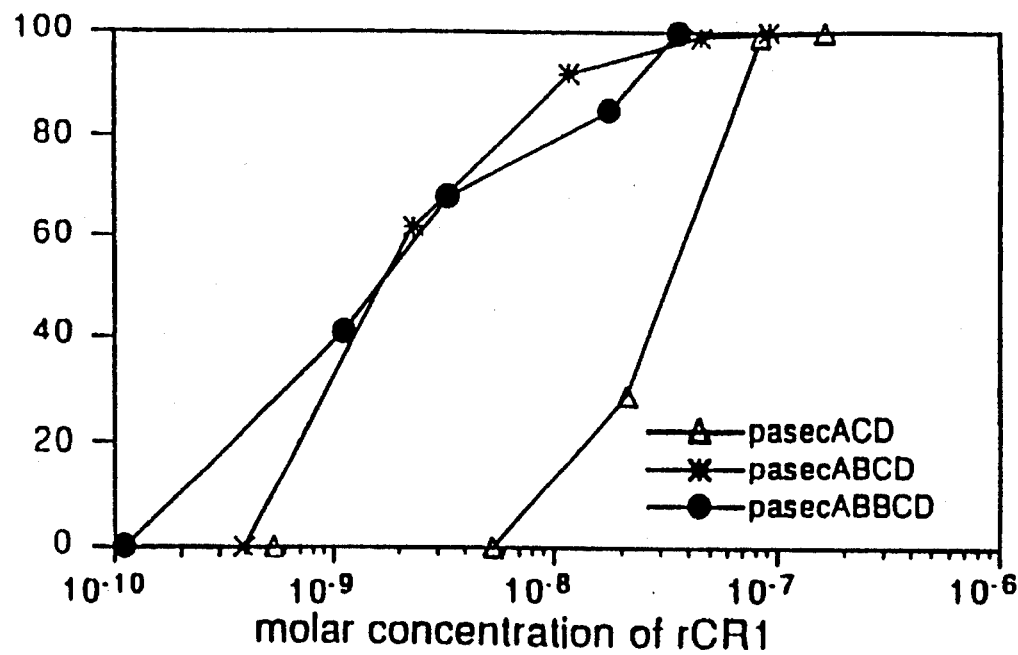
Figure 40B:
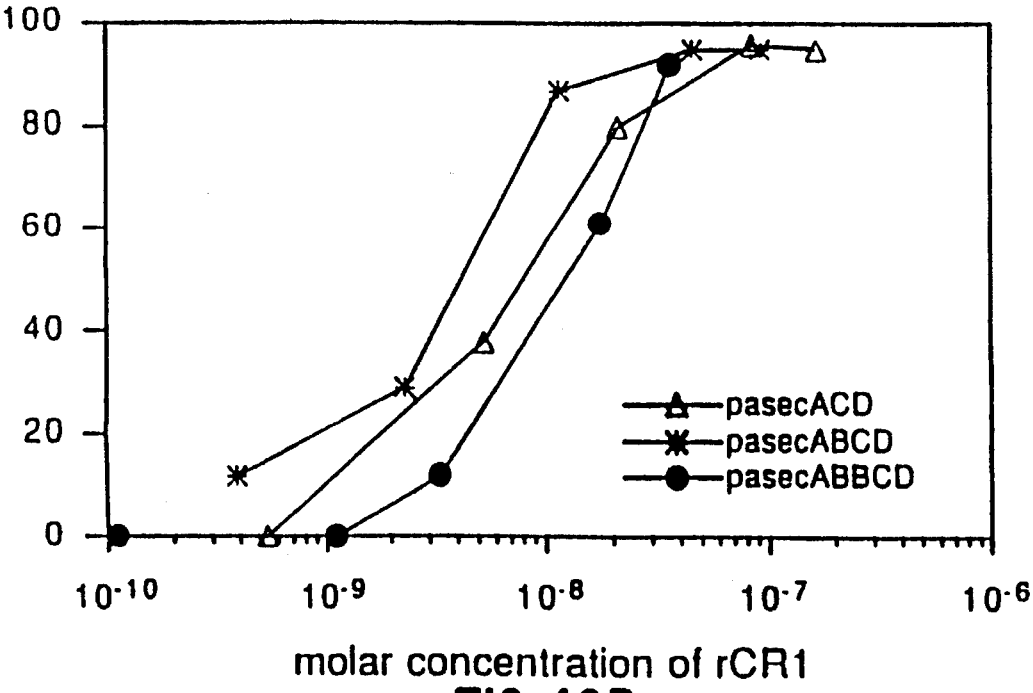

Inhibition of the alternative and classical pathway convertases. The capacities of the soluble CR1 variants to block the alternative and classical pathway convertases were compared by measurement of the C3a and C5a released on incubation of human serum with zymosan or aggregated IgG. While only 1 to 2 nM of the pasecABBCD or the pasecABCD-derived sCR1 were necessary to achieve 50% inhibition of both the alternative pathway C3 and C5 convertases, 30 fold more of the pasecACD sCR1 was required for similar effects (FIGS. 39A and 40A). This is consistent with the above predictions that the sCR1 variants would bind differently the C3b homodimers in the C5 convertases (Kinoshita et al., 1988, J. Immunol. 141:3895). That the same effect was seen with the C3 convertase indicated the presence of multiple molecules of C3b in association with the properdin-stabilized C3bBb complex. In contrast, large differences were not observed among the sCR1 variants in their capacities to inhibit the classical pathway C3 and C5 convertase (FIGS. 39B and 40B), indicating that they bound similarly the C4b molecules within the C4bC2a complex or the C4b/C3b heterodimers of the C5 convertases (Takata et al., 1987, J. Exp. Med. 165:1494). Furthermore, except for the pasecACD-derived molecule, 2 to 10 fold more recombinant CR1 was necessary to inhibit the enzymes of the classical relative to the alternative pathway, perhaps reflecting lower binding of sCR1 for the C4b-containing convertases.

16.4. Discussion

That each polymorphic variant of human CR1 is encoded by a different number of LHR is predicted by the ~1.3 kb differences in the transcripts associated with each allotype (1Wong et al., 1986, J. Exp. Med. 164:1531; Holers et al., 1987, Proc. Natl. Acad. Sci. USA 84:2459). The parallels between the homologies in the coding regions and the homologies in the corresponding noncoding regions of the different LHR of the CR1 gene enabled us to predict the coding sequences based on a restriction map of the genomic clones. Thus the fith LHR in the S allele with a 5' half that resembled LHR-B and a 3' half that resembled LHR-A was expected to encode a third binding site for C3b in the S allotype (Wong et al., 1989, J. Exp. Med. 169:847). Since EcoRV was the only restriction enzyme among nineteen others that revealed a RFLP associated with the F' allotype (Wong et al., 1986, J. Exp. Med. 164:1531), a deletion in this allele apparently involved a highly homologous region. In this study, the 18 kb EcoRV fragment associated with individuals who expressed the F' allotype (Wong et al., 1986, J. Exp. Med. 164:1531) hybridized with a combination of exon-and intron-derived probes that was specific for LHR-C (FIGS. 33 and 34). This pattern was consistent only with the deletion of LHR-B or an equivalent region resulting in the loss of one C3b binding site. We could not confirm that the appearance of the 18 kb fragment was accompanied by the disappearance on Southern blots of a ~30 kb fragment derived from LHR-B and -C because no individual homozygous for the F' allele was available for comparison. Although the smaller transcripts for this allotype might have arisen through alternative splicing (Wong et al., 1986, J. Exp. Med. 164:1531; Holers et al., 1987, Proc. Natl. Acad. Sci. USA 84:2459), these mechanisms cannot account for the observed EcoRV RFLP.

The association of the F' allotype with SLE is consistent with the suggestion that this variant may have diminished capacity to bind opsonized immune complexes (Dykman et al., 1984, J. Exp. Med. 159:691; Van Dyne et al., 1987, Clin. Exp. Immunol. 68:570). We compared the functional capabilities of sCR1 that differ in numbers of LHR-B. The effective competition of C3b dimer uptake by soluble CR1 in a recent study indicated that occupancy of tandem binding sites could occur (Weisman et al., 1990, Science 249:146), thus permitting a direct assessment of the binding of each receptor molecule for this bivalent ligand. Our strategy differed both in the site of the inserted stop codon and in the use of soluble CR1 purified from the culture supernatants of COS cells transiently transfected with plasmids that encode CR1 molecules with two, one or no LHR-B (FIG. 35). The amounts of monomeric or dimeric C3b and pasecABCD-derived recombinant CR1 necessary for 50% inhibition of binding of radiolabeled dimeric C3b to erythrocytes were very similar to those in an earlier report (Weisman et al., 1990, Science 249:146). Moreover, the binding of the purified sCR1 for dimeric C3b increased 10 fold with the addition of each C3b binding site, resulting in a 100 fold difference between sCR1 molecules derived from pasecACD or pasecABBCD (FIG. 38). Consistent with the previous observation that the C4b binding site in LHR-A retains low affinity for C3b (Klickstein et al., 1988, J. Exp. Med. 168:1699), the pasecACD-derived sCR1 with only LHR-A and -C was more effective than the C3b monomers in blocking the uptake of radiolabeled dimer (FIG. 38). The higher binding observed for the pasecABBCD-derived sCR1 relative to the pasecABCD-derived molecule similarly suggested engagement of two pairs of binding sites (FIG. 38), and confirmed the previous hypothesis that multivalent interaction was favored by such a tandem array of LHR (Klickstein et al., 1988, J. Exp. Med. 168:1699; Wong et al., 1989, J. Exp. Med. 169:847). Since the binding of CR1 for monomeric C3b is relatively low (FIG. 38), the lack of gross differences in the cofactor capacities of the different sCR1 forms in this (FIG. 37) and other studies (Seya et al., 1985, J. Immunol. 135:2661) indicated that the conditions used did not favor simultaneous occupancy of more than one active site by monomeric ligands.

Differences in the effectiveness of the soluble CR1 variants to block the alternative pathway C3 and C5 convertases is consistent with their differential affinities for the C3b homodimers (Kinoshita et al., 1988, J. Immunol. 141:3895). Indeed, in this assay, the sCR1 variants having two or more C3b binding sites were at least 30 fold more efficient than that which had only one site (FIGS. 39A and 40A). However, the pasecABBCD-derived sCR1 is not more effective than that derived from pasecABCD (FIGS. 39A and 40A) although its binding is much higher in a fluid phase assay (FIG. 38). Thus, its full capacity in this assay may be restricted by the topographical distribution of the convertase sites on the activating surface. Since all three variants studied retained one site for C4b and at least one adjacent site for C3b, their structure is consistent with their comparable capacities to inhibit the classical pathway convertases (FIGS. 39B and 40B) (Takata et al., 1987, J. Exp. Med. 165:1494). The differences between our findings and those of another study may be explained by the previous use of less stable fluid phase convertases and a mixture of the F (or A) and F' (or C) allotypes instead of purified forms (Seya et al., 1985, J. Immunol. 135:2661). An alternative explanation was that the F' variant used in that study had a different composition of LHR.

Although the efficiency of uptake of immune complexes by CR1 is enhanced by the clustering of this receptor on erythrocytes (Paccaud et al., 1988, J. Immunol. 141:3889; Chevalier & Kazatchkine, 1989, J. Immunol. 142:2031), individuals with low CR1 numbers may have fewer clusters of this receptor as well as fewer receptor molecules per cluster (Paccaud et al., 1988, J. Immunol. 141:3889). Thus the presence of the F' allotype and low amounts of CR1 in SLE patients may result in fewer total C3b and C4b binding sites and a decreased efficiency in the clearance of immune complexes from the circulation (Dykman et al., 1984, J. Exp. Med. 159:691; Van Dyne et al., 1987, Clin. Exp. Immunol. 68:570; Wilson et al., 1987, Immunol. Res. 6:192; Miyakawa et al., 1981, Lancet ii:493; Schifferli et al., 1988, J. Immunol. 140:899). The lower affinities of sCR1 observed for the classical pathway convertases (FIGS. 39 and 40) indicate that the relative amounts of C4b and C3b deposited on soluble immune complexes may be critical to the CR1-dependent uptake and processing. The absence of preclustered CR1 in neutrophils under some conditions (Paccaud et al., 1990, Eur. J. Immunol. 20:283) suggests that mechanisms that induce receptor aggregation may be essential for the triggering of biologic reactions in nucleated cells (Daha et al., 1984, J. Immunol. 132:1197; Bacle et al., 1990, J. Immunol. 144:147). A shorter CR1 allotype may further decrease the efficiencies of such interactions and lead to impairment of receptor-mediated cellular responses at tissue inflammatory sites.

17. DEPOSIT OF MICROORGANISMS

E. coli strain DK1/P3 carrying plasmid piABCD (designated pCR1-piABCD), encoding the full-length CR1 protein, was deposited with the Agricultural Research Culture Collection (NRRL), Peoria, Ill., on Mar. 31, 1988 and was assigned accession number B-18355.

Chinese hamster ovary cell line DUX B11 carrying plasmid pBSCR1c/pTCSgpt clone 35.6, encoding a soluble CR1 molecule, was deposited with the American Type Culture Collection (ATCC), Rockville, Md., on Mar. 23, 1989 and was assigned accession number CRL 10052.

The present invention is not to be limited in scope by the microorganisms deposited since the deposited embodiments are intended as single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also understood that all base pair sizes given for nucleotides are approximate and are used for the purpose of description.

Various references are cited herein, the disclosures of which are incorporated by reference in their entirety.

What is claimed is:

1. A method of treating a patient with a complement mediated immune disorder or a disorder which involves undesirable or inappropriate complement activity comprising administering to the patient a protein having an amino acid sequence as depicted in FIGS. 1A to 1P or a fragment thereof comprising at least two short consensus repeats and that has complement regulatory activity.

2. The method according to claim 1 in which the protein or fragment thereof is characterized by the ability to bind C3b.

3. The method according to claim 1 in which the protein or fragment thereof is characterized by factor I cofactor activity, an ability to inhibit C3 convertase activity or an ability to inhibit C5 convertase activity.

4. The method according to claim 1 in which the protein or fragment thereof lacks a transmembrane region.

5. The method according to claim 1 in which the patient is a non-human animal.

6. The method according to claim 1 in which the protein or fragment thereof is characterized by the ability to bind C4b.

7. The method according to claim 1 in which the protein or fragment thereof is secreted.

8. The method according to claim 1 in which the protein or fragment thereof is expressed as a cell-surface protein.

9. A method of treating a patient with a complement mediated immune disorder or a disorder which involves undesirable or inappropriate complement activity comprising administering to the patient a CR1 molecule comprising at least two short consensus repeats and that substantially lacks a transmembrane region and that has complement regulatory activity.

10. The method according to claim 9 in which the CR1 molecule is secreted by a cell in which it is expressed.

11. The method according to claim 9 in which the patient is a non-human animal.

12. A method of treating or preventing damage in a patient caused by a myocardial infarct comprising administering to the patient a protein having an amino acid sequence as depicted in FIGS. 1A to 1P or a fragment thereof comprising at least two short consensus repeats and that has complement regulatory activity.

13. The method according to claim 12 in which the patient is a non-human animal.

14. A method of treating or preventing damage in a patient caused by a myocardial infarct comprising administering to the patient a CR1 molecule comprising at least two short consensus repeats and that substantially lacks a transmembrane region and that has complement regulatory activity.

15. The method according to claim 14 in which the CR1 molecule is secreted by a cell in which it is expressed.

16. The method according to claim 14 in which the CR1 molecule is functional as detected by the ability in vitro to inhibit neutrophil oxidative burst, complement-mediated hemolysis, or C3a and C5a production.

17. The method according to claim 14 in which the molecule is encoded by a nucleic acid vector selected from the group consisting of pT-CR1c1, PT-CR1c2, pT-CR1c3, pT-CR1c4, and pT-CR 1c5.

18. The method according to claim 14 in which the patient is a non-human animal.

19. A method of treating or preventing damage in a patient caused by inflammation comprising administering to the patient a protein having an amino acid sequence as depicted in FIGS. 1A to 1P or a fragment thereof comprising at least two short consensus repeats and that has complement regulatory activity.

20. The method according to claim 19 in which the patient is a non-human animal.

21. A method of treating or preventing damage in a patient caused by inflammation comprising administering to the patient a CR1 molecule comprising at least two short consensus repeats and that substantially lacks a transmembrane region and that has complement regulatory activity.

22. The method according to claim 21 in which the CR1 molecule is secreted by a cell in which it is expressed.

23. The method according to claim 21 in which the molecule is functional as detected by the ability in vitro to inhibit neutrophil oxidative burst, complement-mediated hemolysis, or C3a and C5a production.

24. The method according to claim 21 in which the molecule is encoded by a nucleic acid vector selected from the group consisting of pT-CR1c1, pT-CR1c2, pT-CR1c3, pT-CR1c4, and pT-CR 1c5.

25. The method according to claim 21 in which the patient is a non-human animal.

26. A method of treating a patient with a complement mediated immune disorder or a disorder which involves undesirable or inappropriate complement activity comprising administering to the patient a CR1 molecule that comprises LHR-A, LHR-B, LHR-C and LHR-D, and that substantially lacks a transmembrane region and a cytoplasmic region, and that has complement regulatory activity.

27. The method according to claim 26 in which the CR1 molecule is encoded by a nucleic acid vector selected from the group consisting of pBSCR1c, pBSCR1s, pBMCR1c, pBSCR1c/pTCSgpt, and pBSCR1s/pTCSgpt.

28. The method according to claim 27 in which the CR1 molecule is expressed by a Chinese hamster ovary cell DUX B11, carrying plasmid pBSCR1c/pTCSgpt, as deposited with the ATCC and assigned accession number CRL 10052.

29. A method of treating or preventing damage in a patient caused by a myocardial infarct comprising administering to the patient a CR1 molecule that comprises LHR-A, LHR-B, LHR-C and LHR-D, and that substantially lacks a transmembrane region and a cytoplasmic region, and that has complement regulatory activity.

30. The method according to claim 29 in which the CR1 molecule is encoded by a nucleic acid vector selected from the group consisting of pBSCR1c, pBSCR1s, pBMCR1c, pBSCR1c/pTCSgpt, and pBSCR1s/pTCSgpt.

31. The method according to claim 30 in which the CR1 molecule is expressed by a Chinese hamster ovary cell DUX B11, carrying plasmid pBSCR1c/pTCSgpt, as deposited with the ATCC and assigned accession number CRL 10052.

32. A method of treating or preventing damage in a patient caused by inflammation comprising administering to the patient a CR1 molecule that comprises LHR-A, LHR-B, LHR-C and LHR-D, and that substantially lacks a transmembrane region and a cytoplasmic region, and that has complement regulatory activity.

33. The method according to claim 32 in which the CR1 molecule is encoded by a nucleic acid vector selected from the group consisting of pBSCR1c, pBSCR1s, pBMCR1c, pBSCR1c/pTCSgpt, and pBSCR1s/pTCSgpt.

34. The method according to claim 33 in which the CR1 molecule is expressed by a Chinese hamster ovary cell DUX B11, carrying plasmid pBSCR1c/pTCSgpt, as deposited with the ATCC and assigned accession number CRL 10052.

35. A method of treating a patient with a complement mediated immune disorder or a disorder which involves undesirable or inappropriate complement activity comprising administering to the patient a CR1 molecule that comprises LHR-B, LHR-C and LHR-D, and lacks LHR-A, and that substantially lacks a transmembrane region and a cytoplasmic region, and that has complement regulatory activity.

36. A method of treating or preventing damage in a patient caused by a myocardial infarct comprising administering to the patient a CR1 molecule that comprises LHR-B, LHR-C and LHR-D, and lacks LHR-A, and that substantially lacks a transmembrane region and a cytoplasmic intracellular region, and that has complement regulatory activity.

37. A method of treating or preventing damage in a patient caused by inflammation comprising administering to the patient a CR1 molecule that comprises LHR-B, LHR-C and LHR-D, and lacks LHR-A, and that substantially lacks a transmembrane region and a cytoplasmic region, and that has complement regulatory activity.

* * * * *